(12) United States Patent
Jensen et al.

(10) Patent No.: US 11,311,576 B2
(45) Date of Patent: Apr. 26, 2022

(54) METHODS OF USE FOR CAR T CELLS

(71) Applicant: Seattle Children's Hospital, Seattle, WA (US)

(72) Inventors: Michael C. Jensen, Bainbridge Island, WA (US); James Matthaei, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 354 days.

(21) Appl. No.: 16/253,572

(22) Filed: Jan. 22, 2019

(65) Prior Publication Data
US 2019/0224237 A1 Jul. 25, 2019

Related U.S. Application Data

(60) Provisional application No. 62/620,414, filed on Jan. 22, 2018, provisional application No. 62/620,706, filed on Jan. 23, 2018, provisional application No. 62/656,233, filed on Apr. 11, 2018, provisional application No. 62/724,171, filed on Aug. 29, 2018, provisional application No. 62/735,627, filed on Sep. 24, 2018, provisional application No. 62/736,727, filed on Sep. 26, 2018.

(51) Int. Cl.
| | |
|---|---|
| C12N 15/62 | (2006.01) |
| C12P 21/00 | (2006.01) |
| C07K 14/705 | (2006.01) |
| C07K 16/44 | (2006.01) |
| C07K 16/46 | (2006.01) |
| C12N 5/10 | (2006.01) |
| A61K 38/17 | (2006.01) |
| A61K 35/17 | (2015.01) |
| C07K 14/725 | (2006.01) |
| C12N 5/0783 | (2010.01) |
| A61P 35/00 | (2006.01) |
| A61K 9/00 | (2006.01) |
| A61K 31/365 | (2006.01) |
| A61K 31/519 | (2006.01) |

(52) U.S. Cl.
CPC ............ *A61K 35/17* (2013.01); *A61K 9/0019* (2013.01); *A61K 9/0053* (2013.01); *A61K 31/365* (2013.01); *A61K 31/519* (2013.01); *A61K 38/1774* (2013.01); *A61P 35/00* (2018.01); *C07K 14/7051* (2013.01); *C07K 16/44* (2013.01); *C07K 16/46* (2013.01); *C12N 5/0638* (2013.01); *C07K 2317/622* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,906,936 A | 5/1999 | Eshhar et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,005,004 A | 12/1999 | Katz et al. |

(Continued)

FOREIGN PATENT DOCUMENTS

| | | |
|---|---|---|
| CN | 102775500 | 11/2012 |
| EP | 2 614 077 | 8/2016 |

(Continued)

OTHER PUBLICATIONS

Lee et al; DOI: 10.1158/0008-5472.CAN-18-1834.*
Deng et al; Am J Cancer Res 2019;9(5):945-958.*
Li et al; Journal of Immunotherapy, 2020; 43:16-28.*
Abken, H. et al. Chimeric T-Cell Receptors: Highly Specific Tools To Target Cytotoxic T-Lymphocytes To Tumour Ceils, Cancer Treatment Reviews (1997); 23:97-112.

(Continued)

*Primary Examiner* — Bridget E Bunner
*Assistant Examiner* — Fozia M Hamud
(74) *Attorney, Agent, or Firm* — Knobbe, Martens, Olson & Bear LLP

(57) ABSTRACT

The present disclosure relates to methods of treating a patient with a cancer by administering to the patient a composition comprising CAR T cells wherein the CAR T cells comprise a CAR and the CAR comprises an E2 anti-fluorescein antibody fragment, and administering to the patient a small molecule linked to a targeting moiety by a linker. The disclosure also relates to compositions for use in such methods.

23 Claims, 67 Drawing Sheets

Specification includes a Sequence Listing.

(56) References Cited

U.S. PATENT DOCUMENTS

| | | |
|---|---|---|
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen et al. |
| 6,218,187 B1 | 4/2001 | Finer et al. |
| 6,261,787 B1 | 7/2001 | Davis et al. |
| 6,319,494 B1 | 11/2001 | Capon et al. |
| 6,392,013 B1 | 5/2002 | Seed et al. |
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Eisenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weidanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,932,830 B2 | 1/2015 | Peters et al. |
| 8,946,385 B2 | 2/2015 | Kawai |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,609 B2 | 8/2015 | Tan et al. |
| 9,133,436 B2 | 9/2015 | Riley et al. |
| 9,156,915 B2 | 10/2015 | Waldman et al. |
| 9,163,258 B2 | 10/2015 | Riddell et al. |
| 9,175,308 B2 | 11/2015 | Shiku et al. |
| 9,211,321 B2 | 12/2015 | Karlsson-Parra et al. |
| 9,212,229 B2 | 12/2015 | Schönfeld et al. |
| 9,220,728 B2 | 12/2015 | Sadelain et al. |
| 9,226,936 B2 | 1/2016 | Hu et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |

(56) References Cited

U.S. PATENT DOCUMENTS

| | | |
|---|---|---|
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra et al. |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Agerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe et al. |
| 9,862,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 2001/0031252 A1 | 10/2001 | Low et al. |
| 2002/0111474 A1 | 8/2002 | Capon et al. |
| 2003/0175288 A1 | 9/2003 | Itoh |
| 2005/0113564 A1 | 5/2005 | Campana |
| 2006/0155115 A1 | 7/2006 | Jakobsen et al. |
| 2008/0051380 A1 | 2/2008 | Auerbach et al. |
| 2009/0011984 A1 | 1/2009 | Yla-Herttuala et al. |
| 2009/0202501 A1 | 8/2009 | Zhang et al. |
| 2010/0135974 A1 | 6/2010 | Eshhar et al. |
| 2010/0278830 A1 | 11/2010 | Shoemaker et al. |
| 2011/0172254 A1 | 7/2011 | Leamon |
| 2011/0178279 A1 | 7/2011 | Williams et al. |
| 2012/0093842 A1 | 4/2012 | Eshhar et al. |
| 2012/0302466 A1 | 11/2012 | Sentman |
| 2013/0143895 A1 | 6/2013 | McAllister et al. |
| 2013/0287752 A1 | 10/2013 | Davila |
| 2013/0309267 A1 | 11/2013 | Simmons et al. |
| 2013/0309258 A1 | 12/2013 | June et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell |
| 2014/0286987 A1 | 9/2014 | Spencer et al. |
| 2014/0308259 A1 | 10/2014 | Scholler et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0378389 A1 | 12/2014 | Robbins et al. |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0225470 A1 | 8/2015 | Zhang et al. |
| 2015/0238631 A1 | 8/2015 | Kim et al. |
| 2015/0283178 A1 | 10/2015 | June et al. |
| 2015/0307564 A1 | 10/2015 | Young et al. |
| 2015/0307842 A1 | 10/2015 | Sentman |
| 2015/0314014 A1 | 11/2015 | Lauremann |
| 2015/0320799 A1 | 11/2015 | Low et al. |
| 2015/0328292 A1 | 11/2015 | Spencer et al. |
| 2015/0368342 A1 | 12/2015 | Wu et al. |
| 2016/0046700 A1 | 2/2016 | Foster et al. |
| 2016/0046724 A1 | 2/2016 | Brogdon et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0096892 A1 | 4/2016 | Brogdon et al. |
| 2016/0120907 A1 | 5/2016 | Sentman |
| 2016/0136190 A1 | 5/2016 | Weichert et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0340649 A1 | 11/2016 | Brown et al. |
| 2016/0361360 A1 | 12/2016 | Chang et al. |
| 2017/0166877 A1 | 6/2017 | Bayle et al. |
| 2017/0290900 A1 | 10/2017 | Low et al. |
| 2017/0306303 A1 | 10/2017 | Taunton et al. |
| 2017/0340672 A1 | 11/2017 | Wu et al. |
| 2017/0356010 A1 | 12/2017 | Frost et al. |
| 2020/0087399 A1 | 3/2020 | Jensen et al. |
| 2020/0354477 A1 | 11/2020 | Jensen |

FOREIGN PATENT DOCUMENTS

| | | |
|---|---|---|
| WO | WO 86/04356 | 7/1986 |
| WO | WO 92/10591 | 6/1992 |
| WO | WO 92/15671 | 9/1992 |
| WO | WO 01/091625 | 12/2001 |
| WO | WO 02/088334 | 11/2002 |
| WO | WO 06/029879 | 3/2006 |
| WO | WO 08/057437 | 5/2008 |
| WO | WO 09/091826 | 7/2009 |
| WO | WO 09/117117 | 9/2009 |
| WO | WO 10/025177 | 3/2010 |
| WO | WO 12/054825 | 4/2012 |
| WO | WO 12/082841 | 6/2012 |
| WO | WO 12/138475 | 10/2012 |
| WO | WO 13/039889 | 3/2013 |
| WO | WO 13/177247 | 11/2013 |
| WO | WO 14/011984 | 1/2014 |
| WO | WO 14/043441 | 3/2014 |
| WO | WO 14/055771 | 4/2014 |
| WO | WO 14/100615 | 6/2014 |
| WO | WO 2014/127261 A1 | 8/2014 |
| WO | WO 15/057834 | 4/2015 |
| WO | WO 2015/057852 A1 | 4/2015 |

(56) References Cited

FOREIGN PATENT DOCUMENTS

| WO | WO 2016/025322 A1 | 2/2016 |
|---|---|---|
| WO | WO 16/102965 | 6/2016 |
| WO | WO 2016/098078 A2 | 6/2016 |
| WO | WO 16/054520 | 7/2016 |
| WO | WO 16/149665 | 9/2016 |
| WO | WO 2016/168769 A1 | 10/2016 |
| WO | WO 16/201300 | 12/2016 |
| WO | WO 2016/210447 A1 | 12/2016 |
| WO | WO 17/029511 | 2/2017 |
| WO | WO 17/029512 | 2/2017 |
| WO | WO 17/068360 | 4/2017 |
| WO | WO 17/068361 | 4/2017 |
| WO | WO 17/137758 | 8/2017 |
| WO | WO 17/137759 | 8/2017 |
| WO | WO 17/143094 | 8/2017 |
| WO | WO 17/165245 | 9/2017 |
| WO | WO 17/165571 | 9/2017 |
| WO | WO 17/180587 | 10/2017 |
| WO | WO 2017/177149 A2 | 10/2017 |
| WO | WO 17/216561 | 12/2017 |
| WO | WO 17/216562 | 12/2017 |
| WO | WO 18/013797 | 1/2018 |
| WO | WO 18/111763 | 6/2018 |
| WO | WO 18/115146 | 6/2018 |
| WO | WO 2018/111834 A1 | 6/2018 |
| WO | WO 2018/148224 A1 | 8/2018 |
| WO | WO 2018/152451 A1 | 8/2018 |
| WO | WO 18/160622 | 9/2018 |
| WO | WO 2018/160622 A1 | 9/2018 |
| WO | WO 19/156795 | 8/2019 |

OTHER PUBLICATIONS

Abken, H., et al., Tuning tumor-specific T-cell activation: a matter of costimulation? TRENDS in Immunology vol. 23 No. 5 May 2002: 240-45.

Abstracts for the 26th Annual Scientific Meeting of the Society for Immunotherapy of Cancer (SITC), J Immunother., vol. 34, No. 9, Nov.-Dec. 2011 (62 pp.).

Airenne et al., Recombinant avidin and avidin-fusion proteins , Biomolecular Engineering16 (1999) 87-92.

Alcover et al., A soluble form of the human CD8 alpha chain expressed in the baculovirus system: Biochemical characterization and binding to MHC Class I , Molecular Immunology, vol. 30, No. 1, pp. 55-67, 1993.

Alexander et al., Indoleamine 2,3-Dioxygenase Expression in Transplanted NOD Islets Prolongs Graft Survival After Adoptive Transfer of Diabetogenic Splenocytes, Diabetes2002, vol. 51 pp. 356-365.

Alonso-Camino et al. CARbodies: Human Antibodies Against Cell Surface Tumor Antigens Selected From Repertoires Displayed on T Cell Chimeric Antigen Receptors. (2013) Mol Ther Nucl Acids 2, e93 (11 pages).

Altenschmidt, U. et al. Adoptive transfer of in vitro-targeted, activated T lymphocytes results in total tumor regression, J. Immunol. (1997); 159:5509-15.

Altenschmidt, U., et al., Specific cytotoxic T lymphocytes in gene therapy, J. Mol. Med. (1997); 75, 259-266.

Altschul, S. et al., Basic local alignment search tool, J. Mol. Bio., 1990, 215, 403-410.

Altvater, B., et al., 284 (CD244) Signaling by Recombinant Antigen-specific Chimeric Receptors Costimulates Natural Killer Cell Activation to Leukemia and Neuroblastoma Cells , Clin Cancer Res 2009;15(15) Aug. 1, 2009: 4857-66.

Alvarez-Vallina, L. et al., Antigen-specific targeting of CD28-mediated T cell co-stimulation using chimeric single-chain antibody variable fragment-CD28 receptors, Eur. J. Immunol, 1996, 26, 2304-2309.

An et al., IgG2m4, an engineered antibody isotype with reduced Fc function, mAbs 2009, Landes Bioscience, 1:6, 572-579.

Ang et al., Generating a Chimeric Antigen Receptor To Redirect T-Cell Specificity after Infusion , Molecular Therapy vol. 19, Supplement 1, May 2011, S137-S138.

Arch, R, et al., 4-1BB and Ox40 Are Members of a Tumor Necrosis Factor (TNF)-Nerve Growth Factor Receptor Subfamily That Bind TNF Receptor-Associated Factors and Activate Nuclear Factor kB, Molecular And Cellular Biology (1998); 558-565.

Aruffo, A, et al., Molecular cloning of a CD28 cDNA by a high-efficiency COS cell expression system, Proc. Nati. Acad. Sci. USA (1987); 84: 8573-8577.

Baba et al., N-Linked Carbohydrate on Human Leukocyte Antigen-C and Recognition by Natural Killer Cell Inhibitory Receptors, Human Immunology 61, 1202-1218 (2000).

Baniyash et al., The T Cell Antigen Receptor Zeta Chain Is Tyrosine Phosphorylated open Activation The Journal of Biological Chemistry, vol. 263, No. 34, Issue of Dec. 5, pp. 18225-18230, 1988.

Barber, et al., Chimeric NKG2D Receptor-Expressing T Cells as an Immunotherapy for Multiple Myeloma, Exp Hematol. (Oct. 2008); 36(10):1318-28.

Barocas et al., A population-based study of renal cell carcinoma and prostate cancer in the same patients, BJU International, (2006) 97(1): 33-36.

Barrett et al., Chimeric Antigen Receptor Therapy for Cancer Annual Review of Medicine vol. 65: 333-347 (2014).

Bauer et al., Activation of NK Cells and T Cells by NKG2D, a Receptor for Stress-Inducible MICA, Science 1999, vol. 285 pp. 727-729.

Bauer, A, et al., Differential signal transduction via T-cell receptor CD3'2, CD3C-,v,and CD3'q2 isoforms. Proc. Nati. Acad. Sci. USA (1991); 88: 3842-3846.

Baum et al. Retrovirus vectors: toward the plentivirus? (2006) Molecular Therapy: The Journal of the American Society of Gene Therapy. 13:1050-1063.

Becker, M. L. B., et al., Expression of a hybrid immunoglobulin-T ceil receptor protein in transgenic mice, Cell (1989); 58:911-921.

Bedzyk, WD et al., Active site structure and antigen binding properties of idiotypically cross-reactive anti-fluorescein monoclonal antibodies, J Biol Chem., 1990, 265, 133-138.

Bejcek, B, et al., Development and Characterization of Three Recombinant Single Chain Antibody Fragments (scFvs) Directed against the CD19 Antigen1, Cancer Research55, (1995); 2346-2351.

Berg et al., Section 3.2 Primary Structure: Amino Acids Are Linked by Peptide Bonds to Form Polypeptide Chains Biochemistry. 5th Ed. New York. W.H. Freeman; 2002, pp. 1-16.

Berger, C., et al., Analysis of trans gene-specific immune responses that limit the in vivopersistence of adoptively transferred HSV-TK-modified donor T cells after allogeneic hematopoietic cell transplantation. Blood, 2006. 107(6): p. 2294-302.

Bluemel, C., et al., Epitope distance to the target cell membrane and antigen size determine the potency of T cell-mediated lysis by BiTE antibodies specific for a large melanoma surface antigen. Cancer Immunol Immunother (2010); 59(8): 1197-209.

Bolhuis, R. L. et al. Preparation for a phase I/II study using autologous gene modified T lymphocytes for treatment of metastatic renal cancer patients., Adv. Exp. Med. Biol. (1998); 451:547-55.

Boomer et al., Cutting Edge: A Double-Mutant Knockin of the CD28 YMNM and PYAP Motifs Reveals a Critical Role for the YMNM Motif in Regulation of T Cell Proliferation andBcl-x L Expression The Journal of Immunology. 2014; 192, pp. 3465-3469.

Boomer, J, et al,. An Enigmatic Tail of CD28 Signaling, Washington University School of Medicine (2010); 1-20.

Boursier et al., Evidence for an Extended Structure of the T-cell Co-receptor CD8α as Deduced from the Hydrodynamic Properties of Soluble Forms of the Extracellular Region*, The Journal of Biological Chemistry 1993, vol. 268, No. 3, Issue of Jan. 25, pp. 2013-2020.

Brennan et al., Carbohydrate Recognition by a Natural Killer Cell Receptor, Ly-49C*, The Journal of Biological Chemistry 1995, vol. 270, No. 17, Issue of Apr. 28, pp. 9691-9694.

Brentjens et al., CD19-targeted T ceils rapidly induce molecular remissions in adults with chemotherapy-refractory acute lymphoblastic leukemia. Sci Transl Med. 2013 5(177)ra38 (11 pages).

Brentjens, et al., Eradication of systemic B-cell tumors by genetically targeted human T lymphocytes co-stimulated by CD80 and interleukin-15, Nat. Med. (2003); 9: 279-286.

(56) References Cited

OTHER PUBLICATIONS

Bruhns et al., Differential Roles of N- and C-Terminal Immunoreceptor Tyrosine-Based Inhibition Motifs During Inhibition of Ceil Activation by Killer Cell Inhibitory Receptors, The Journal of Immunology 1999; 162:3168-3175.
Bukczynski et al., Costimulatory ligand 4-1 BBL (CD137L) as an efficient adjuvant of human antiviral cytotoxic T cell responses, Proc. Natl. Acad. Sci. USA, 2004, 101:1291-1296.
Cambier, et al., Antigen and Fc receptor signaling. The awesome power of the immunoreceptor tyrosine-based activation motif (ITAM), J Immunol. (Oct. 1, 1995);155(7):3281-5.
Camerini, D, et al,. The T cell activation antigen CD27 is a member of the nerve growth factor/tumor necrosis factor receptor gene family, The Journal of Immunology (1991);3165-3169.
Cameron, B.J., et al., Identification of a Titin-Derived HLA-A1-Presented Peptide as a Cross-Reactive Target for Engineered MAGE A3-Directed T Cells, Sci Transl Med (Aug. 7, 2013); 5(197): 197ra103 (11 pages).
Canfield et al., The Binding Affinity of Human IgG for its High Affinity Fc Receptor Is Determined by Multiple Amino Acids in the CH2 Domain and Is Modulated by the Hinge Region, J. Exp. Med. 1991, vol. 173 pp. 1483-1491.
Cannons et al., 4-1BB ligand induces cell division, sustains survival, and enhances effector function of CD4 and CD8 T cells with similar efficacy, J Immunol. Aug. 2001, 167(3): 1313-1324.
Carlens et al. Ex vivo T lymphocyte expansion for retroviral transduction: influence of serum-free media on variations in cell expansion rates and lymphocyte subset distribution. (2000) Exp Hematol 28(10): 1137-46.
Cartellieri, M. et al., Chimeric antigen receptor-engineered T cells for immunotherapy of cancer, J. Biomedicine and Biotechnology, 2010, Article ID 956304, 13 pages.
Cavalieri et al. Human T lymphocytes transduced by lentiviral vectors in the absence of TCR activation maintain an intact immune competence. (2003) Blood. 102(2): 497-505.
Chalupny et al., T-cell activation molecule 4-1BB binds to extracellular matrix proteins, Proc. Natl. Acad. Sci., USA, 89: 103360-10364 (Nov. 1992).
Chang et al., A Chimeric Receptor with NKG2D Specificity Enhances Natural Killer Cell Activation and Killing of Tumor Cells , Cancer Res 2013;73:1777-1786. Published online Jan. 9, 2013.
Cheadle et al, Chimeric antigen receptors for T-cell based therapy Methods Mol Biol. 2012; 907:645-66.
Chen et al. Fusion protein linkers: property, design and functionality, Adv Drug Deliv Rev.(2013); 65: 1357-1369 (Epub Sep. 29, 2012).
Cho C. Rapid identification of cytokine release syndrome after haploidentical PBSC transplantation and successful therapy with tocilizumab. Bone Marrow Transplant. Dec. 2016;51(12):1620-1621, Epub Sep. 26, 2016.
Cho et al., Macromolecular versus small-molecule therapeutics: drug discovery, development and clinical considerations TIBTECH, vol. 14, May 1996, pp. 153-158.
Cohen et al. Recognition of fresh human tumor by human peripheral blood lymphocytes transduced with a bicistronic retroviral vector encoding a murine anti-p53 TCR (2005) J Immunol. 175:5799-5808.
Colcher, D. et al. In vivo tumor targeting of a recombinant single-chain antigen-binding protein., J. Nat. Cancer Inst. (1990); 82:1191-1197.
Cole et al., The molecular determinants of CD8 co-receptor function, 2012, Immunology,137, 139-148.
Common Terminology Criteria for Adverse Events (CTCAE), National Cancer Institute Common Toxicity Criteria version 4.03 (NCI-CTCAE v4.03) (2010) (196 pages).
Cooper et al. T-cell clones can be rendered specific for CD19: toward the selective augmentation of the graft-versus-B-lineage leukemia effect (2003) Blood. 101(4): 1637-1644.
Cooper et al., Enhanced antilymphoma efficacy of CD19-redirected influenza MP1-specific CTLs by cotransfer of T cells modified to present influenza MP1, Blood 2005, vol. 105 No. 4 pp. 1622-1631.
Cordaro, T. A et al. Tumor size at the time of adoptive transfer determines whether tumor rejection occurs, Eur. J. Immunol. (2000); 30: 1297-1307.
Croft, M., The role of TNF superfamily members in T-cell function and diseases Nature Reviews, Immunology, vol. 9, Apr. 2009, pp. 271-285.
Dall, Peter et al., In vivo cervical cancer growth inhibition by genetically engineered cytotoxic T cells. Cancer Immunol. Immunother. (Jan. 2005); 54(1):51-60.
Darcy, P. K. et al., Expression in cytotoxic T lymphocytes of a single-chain anti-carcinoembryonic antigen antibody. Redirected Fas ligand-mediated lysis of colon carcinoma. Eur. J. Immunol. (1998); 28:1663-72.
Davila M. L. et al: Efficacy and toxicity management of 19-28z CAR T cell therapy in B cell acute lymphoblastic leukemia Sci Transl Med. Feb. 19, 2014;6(224):224-25.
Davila Marco L. et al: CD19-Targeted T Cells for Hematologic Malignancies Clinical Experience to Date, Cancer Journal, vol. 21, No. 6, Jan. 1, 2015 (Jan. 1, 2015),pp. 470-474.
Debelouchina et al., A molecular engineering toolbox for the structural biologist Quarterly Reviews of Biophysics, 2017, 50, e7, pp. 1-41.
Diefenbach et al., The innate immune response to tumors and its role in the induction of T-cell immunity, Immunological Reviews 2002, vol. 188: 9-21.
Dotti, et al. Design and development of therapies using chimeric antigen receptor-expressing T cells. Immun Rev (Jan. 2014); 257(1): 107-126.
Dubrovska, A., et al., A chemically induced vaccine strategy for prostate cancer, ACS Chem Biol (2011); 6(11): 1223-31.
Duncan et al., Localization of the binding site for the human high-affinity Fc receptor onlg G, Nature 1998, vol. 332 pp. 563-564.
Ertl, H. C. et al., Considerations for the clinical application of chimeric antigen receptor T cells: observations from a recombinant DNA advisory committee symposium held Jun. 15, 2010, Cancer Res., 2011, 71, 3175-3181.
Eshhar, et al., Design of Cytotoxic T Lymphocytes with Antibody-Type Specificity against Tumor Cells Using Chimeric TcR, Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., Functional expression of chimeric receptor genes in human T cells, J. Immunol. Meth. (2001); 248: 67-76.
Fedorov VD, et al., PD-1- and CTLA-4-based inhibitory chimeric antigen receptors (iCARs) divert off-target immunotherapy responses, Sci Transl Med. (Dec. 11, 2013);5(215):215ra172 (12 pages).
Feng et al., Convergence on a Distinctive Assembly Mechanism by Unrelated Families of Activating Immune Receptors , Immunity, vol. 22, 427-438, Apr. 2005.
Feng et al., The Assembly of Diverse Immune Receptors Is Focused on a Polar Membrane-Embedded Interaction Site , 2006. PLoS Biol 4(5):e142.
Ferrone, S., et al., How much longer will tumor cells fool the immune system, Immunol. Today (2000); 21: 70-72.
Figini, M, et al., Conversion of murine antibodies to human antibodies and their optimization for ovarian cancer therapy targeted to the folate receptor, Cancer Immunollmmunother (Apr. 2009); 58(4):531-46 (Epub Aug. 15, 2008).
Foell et al., CD137-mediated T cell co-stimulation terminates existing autoimmune disease in SLE-prone NZB/NZW F1 mice., Ann N Y Acad Sci. Apr. 2003; 987:230-5.
Frecha et al. Advances in the field of lentivector-based transduction of T and B lymphocytes for gene therapy (2010) Molecular Therapy: The Journal of the American Society of Gene Therapy. 18:1748-1757.
Frost et al., In Vitro Evaluation of Avidin Antibody Pretargeting Using 211At-Labeled andBiotinylated Poly-L-Lysine as Effector Molecule*, Cancer 2010, Cancer Therapy With Antibodies and Immunoconjugates, Supplement to Cancer, pp. 1101-1110.

(56) References Cited

OTHER PUBLICATIONS

Fujita, K.et al., Prolonged disease-free period in patients with advanced epithelial ovarian cancer after adoptive transfer of tumor-infiltrating lymphocytes. Clin. Cancer Res., 1995, 1, 501-507.
Gargalionis et al., The molecular rationale of Src inhibition in colorectal carcinomas, Int. J.Cancer, 134:2019-2029 (2013).
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.
Gilboa, E., How tumors escape immune destruction and what we can do about it, Cancer Immunol. Immunother. (1999); 48: 382-385.
Gilham et al., CAR-T cells and solid tumors: tuning T cells to challenge an inveterate foe, Trends in Molecular Medicine (2012); 18(7): 377-384 (Epub May 19, 2012).
Gilham et al., Primary polyclonal human T lymphocytes targeted to carcino-embryonicantigens and neural cell adhesion molecule tumor antigens by CD3zeta-based chimeric immune receptors, J. Immunother, (Mar.-Apr. 2002); 25 (2): 139-151.
Gillies, S.D. et al., Targeting Human Cytotoxic T Lymphocytes to Kill Heterologous Epidermal Growth Factor Receptor-Bearing Tumor Cells, The Journal of Immunology (1991); 146(3): 1067-1071.
Gong, M. C., et al., Prostate-specific membrane antigen (PSMA)-specific monoclonal antibodies in the treatment of prostate and other cancers, Cancer Metastasis Rev. (1999); 18: 483-490.
Goverman, J. et al., Chimeric immunoglobulin-T cell receptor proteins form functional receptors: implications for T cell receptor complex formation and activation, Cell (1990); 60:929-939.
Greenfield, E. A, Nguyen, K. A & Kuchroo, V. K. CD28/B7 co-stimulation: a review. Crit. Rev. Immunol. 18, 389-41 8 (1998).
Griffiths et al., The Nature of DNA Modern Genetic Analysis. New York: W.H. Freeman; 1999, pp. 1-11.
Grosenbach et al., A recombinant vector expressing transgenes for four T-cell costimulatory molecules (OX40L, B7-1, ICAM-1, LFA-3) induces sustained CD4+ and CD8+ T-cell activation, protection from apoptosis, and enhanced cytokine production, Cellular Immunology 222 (2003) 45-57.
Gross et al., Development and study of chimeric immunoglobulin/T cell receptor molecules as functional receptors that endow T cells with antibody-type specificity, Ph.D. Thesis presented to the Feinberg Graduate School, The Wiezmann Institute of Science, Rehovot, Israel (1990); 1-70.
Gross, G. et al., Endowing T cells with antibody specific using chimeric T cell receptors, Department of Chemical Immunology, FASEB J. (Dec. 1992); 6(15):3370-8.
Gross, G. et al., Expression of immunoglobuling-T-cell receptor chimeric molecules as functional receptors with antibody-type specificity, Proc. Natl. Acad. Sci., 1989, 86, 10024-10028.
Gross, G. et al., Generation of effector T cells expressing chimeric T cell receptor with antibody type-specificity, Transplant. Proc. (1989); 21 (1 Pt 1):127-130.
Grupp Stephan A.: Advances in T-cell therapy for All, Best Practice & Research Clinical Haematology, vol. 27, No. 3-4, Sep. 1, 2014(Sep. 1, 2014), pp. 222-228.
Gruss et al., Tumor Necrosis Factor Ligand Superfamily: Involvement in the Pathology of Malignant Lymphomas Blood, vol. 85, No. 12, Jun. 15, 1995, pp. 3378-3404.
Guinn et al., 4-1BBL Cooperates with B7-1 and B7-2 in Converting a B Cell Lymphoma Cell Line into a Long-Lasting Antitumor Vaccine, The Journal of Immunology162:5003-5010 (1999).
Habib-Agahi,H., Phan,T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).
Hackett et al. A transposon and transposase system for human application (2010) Molecular Therapy: The Journal of the American Society of Gene Therapy. 18:674-683.
Hanson, H. L. et al. Eradication of established tumors by CD8+ T cell adoptive immunotherapy. Immunity 13, 265-276 (2000).
Harper et al., CTLA-4 and CD28 Activated Lymphocyte Molecules are Closely Related in Both Mouse and Human as to Sequence, Message, Expression, Gene Structure, and Chromosomal Location, The Journal of Immunology, vol. 147, 1037-1044, No. 3, Aug. 1, 1991.
Hatakeyama et al., Transmembrane Signaling of Interleukin 2 Receptor, J. Exp. Med.1987, vol. 166 pp. 362-375.
Haynes et al., Redirecting Mouse CTL Against Colon Carcinoma: Superior Signaling Efficacy of Single-Chain Variable Domain Chimeras Containing TCR-zeta vs Fcepsilon RI-gamma J Immunol 2001; 166:182-187 (Haynes 2001).
Hege et al., Safety, tumor trafficking and immunogenicity of chimeric antigen receptor (CAR)-T cells specific for TAG-72 in colorectal cancer, Journal for immunotherapy of Cancer 2017, 5:22.
Hege et al., Systemic T Cell-independent Tumor Immunity after Transplantation of Universal Receptor-modified Bone Marrow into SCID Mice , J. Exp. Med. vol. 184 Dec. 1996 pp. 2261-2269.
Herron, J.N., et al., High resolution structures of the Apr. 4, 2020 Fab-fluorescein complex in two solvent systems: effects of solvent on structure and antigen-binding affinity . Biophys J, 1994. 67(6): p. 2167-83.
Heuser, et al., T-cell activation by recombinant immunoreceptors: impact of the intracellular signalling domain on the stability of receptor expression and antigen-specific activation of grafted T-cells, Gene Therapy (2003): 10: 1408-1419.
Hombach et al., T cell activation by recombinant FcεRI γ-chain immune receptors: an extracellular spacer domain impairs antigen-dependent T cell activation but not antigen recognition, Gene Therapy (2000) 7, 1067-1075.
Hombach, et al., Adoptive Immunotherapy with Genetically Engineered T Cells: Modification of the IgG1 Fc 'Spacer' Domain in the Extracellular Moiety of Chimeric Antigen Receptors Avoids 'Off-Target' Activation and Unintended Initiation of an Innate Immune Response, Gene Ther. (Oct. 2010); 17(10):1206-13.
Huang, J., et al., Modulation by IL-2 of CD70 and CD27 expression on CD8+ T cells: importance for the therapeutic effectiveness of cell transfer immunotherapy J. Immunol. 176 (12), 7726-7735 (2006).
Hughes M. S. et al., Transfer of a TCR gene derived from a patient with a marked antitumor response conveys highly active T-cell effector functions. Hum Gene Ther Apr. 2005; 16(4):457-72).
Hunter et al., Inhibition of Fcγ Receptor-Mediated Phagocytosis by a Nonphagocvtic FcγReceptor, Blood, vol. 91, No. 5 Mar. 1, 1998: pp. 1762-1768.
Hutchins, B. et al., Site-specific coupling and sterically controlled formation of multimeric antibody fab fragments with unnatural amino acids, J. Mol. Biol., 2011, 406, 595-603.
Hutloff, A. et al., ICOS is an inducible T-cell costimulator structurally and functionally related to CD28, Nature, 1999, 397, 263-266.
Hwu, et al, The Genetic Modification of T Cells for Cancer Therapy: An Overview of Laboratory and Clinical Trials, Cancer Detection and Prevention (1994); 18(1):43-50.
Imai, C. et al., Chimeric receptors with 4-1BB signaling capacity provoke potent cytotoxicity against acute lymphoblastic leukemia, Leukemia, 2004, 18, 676-684.
Imai, K., et al., Comparing Antibody and Small-Molecule Therapies for Cancer; https://www.medscape.com/viewarticle/550008 (26 pages), 2006.
Irving, B. A., et al., The cytoplasmic domain of the T cell receptor zeta chain is sufficient to couple to receptor-associated signal transduction pathways ' Cell (1991); 64:891-901.
Isakov et al., PKC-theta-mediated signal delivery from the TCR/CD28 surface receptors , Frontiers in Immunology, T Cell Biology, Aug. 2012, vol. 3, Article 273, pp. 1-12.
Janeway et al., Appendix I. Immunologists' Toolbox Immunobiology: The Immune System in Health and Disease. 5th ed. New York: Garland Science; 2001 (101 pages).
Janeway et al., The structure of a typical antibody molecule Immunobiology: The Immune System in Health and Disease. 5th Ed. New York: Garland Science; 2001, pp. 1-11.
Jang, I, et al., Human 4-1BB (CD137) Signals Are Mediated by TRAF2 and Activate Nuclear Factor-kB, Biochemical And Biophysical Research Communications (1998);613-620.

(56) References Cited

OTHER PUBLICATIONS

Jena et al., Redirecting T-cell specificity by introducing a tumor-specific chimeric antigen Receptor, Blood 2010, vol. 116, No. 7, pp. 1035-1044.

Jensen, M et al. CD20 Is A Molecular Target For scFvFc[zeta] Receptor Redirected T Cells: Implications for Cellular Immunotherapy of CD20+ Malignancy, Biology of Blood and Marrow Transplantation (1998); 4:75-83.

Jensen, M. C., et al., Abstract #98: Targeting Pre-B Acute Lymphoblastic Leukemia With T Cell Clones Engineered To Express A CD19-Specific Chimeric Immunoreceptor, Blood (Nov. 16, 2000); 96(11):26A.

Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.

Jonnalagadda et al., Chimeric Antigen Receptors With Mutated IgG4 Fc Spacer Avoid Fc Receptor Binding and Improve T Cell Persistence and Antitumor Efficacy. Molecular Therapy 2015, vol. 23, No. 4, pp. 757-768.

Jung, S. et al., Selection for improved protein stability by phage display, J. Mol. Biol., 1999, 294, 163-180.

Kagoya, Y., et al., Transient stimulation expands superior antitumor T cells for adoptive therapy. JCI Insight, 2017. 2(2): p. e89580 (13 pages).

Kandalaft, L. et al., A phase I clinical trial of adoptive transfer of folate receptor-alpha redirected autologous T cells for recurrent ovarian cancer, Journal of Translational Medicine, 2012, 10:157, 10 pages.

Kang, S. et al: Therapeutic uses of anti-interleukin-6 receptor antibody, International Immunology, vol. 27, No. I, Aug. 20, 2014 (Aug. 20, 2014), pp. 21-29.

Karachaliou et al., Common Co-activation of AXL and CDCP1 in EGFR-mutation-positive Non-small cell Lung Cancer Associated with Poor Prognosis, EBioMedicine (2017) https://doi.org/10/1016/j.ebiom.2018.02.001.

Kariv et al., Analysis of the Site of Interaction of CD28 with Its Counterreceptors CD80 and CD86 and Correlation with Function, 157 J. IMMUNOL.29-38 (1996).

Katz et al., Recognition of HLA-Cw4 but Not HLA-Cw6 by the NK Cell Receptor Killer CellIg-Like Receptor Two-Domain Short Tail No. 4 , J Immunol 2001; 166:7260-7267.

Kennedy, M. et al., Optical imaging of metastatic tumors using a folate-targeted fluorescent probe, J. Biomed. Opt., 2003, 8, 636-641.

Kim et al., Protein conjugation with genetically encoded unnatural amino acids. Curr OpinChem Biol (2013); 17:412-419 (Epub May 9, 2013).

Kim et al., Therapeutic Potential of 4-1BB (CD137) As a Regulator for Effector CD8+ T Cells, Journal of Hematotherapy & Stem Cell Research (2001) 10:441-449.

Kintzing et al., Emerging Strategies for Developing Next-Generation Protein Therapeutics for Cancer Treatment Trends in Pharmacological Sciences, vol. 37, No. 12, Dec. 2016, pp. 993-1008.

Klotz et al., Macromolecule-Small Molecule Interactions. Strong Binding by Intramolecularly Cross-Linked Polylysine Biochemistry. vol. 10, No. 6, Mar. 16, 1971, pp. 923-926.

Kochenderfer et al., Construction and pre-clinical evaluation of an anti-CD19 chimeric antigen receptor, Journal of Immunotherapy (2009); 32(7): 689-702.

Kochenderfer et al., Treating B-cell cancer with T cells expressing anti-CD19chimeric antigen receptors 2013, Nature Reviews Clinical Oncology, 10, 267-276 (2013).

Kochenderfer, J. et al., Eradication of B-lineage cells and regression of lymphoma in a patient treated with autologous T cells genetically engineered to recognize CD19, Blood, 2010, 116, 4099-4102.

Kochenderfer, J. et al., B-cell depletion and remissions of malignancy along with cytokine-associated toxicity in a clinical trial of anti-CD19 chimeric-antigen-receptor—transduced T cells, Blood, 2012, 119, 2709-2720.

Kolmar, H. et al., Alternative binding proteins: biological activity and therapeutic potential of cystine-knot miniproteins, The FEBS Journal, 2008, 275, 26684-26690.

Love et al., ITAM-mediated Signaling by the T-Cell Antigen Receptor, Cold Spring HarbPerspect Biol 2010;2:a002485.

Lowin-Kropf et al., Cytoskeletal Polarization of T Cells is Regulated by an Immunoreceptor Tyrosine-based Activation Motif-dependent Mechanism, The Journal of Cell Biology 1998,vol. 140, No. 4, pp. 861-871.

Lu, Y. et al., Folate-targeted dinitrophenyl hapten immunotherapy: effect of linkerchemistry on antitumor activity and allergic potential, Mol. Pharm., 2007, 695-706.

Lu, Y. et al., Preclinical pharmacokinetics, tissue distribution, and antitumor activity of afolate-hapten conjugate-targeted immunotheraphy in hapten-immunized mice, Molecular Cancer Therapeutics, 2006, 5, 3258-3267.

Lueders et al., The Long Terminal Repeat of an Endogenous Intracisternal A—ParticleGene Functions as a Promoter When Introduced into Eucaryotic Cells by Transfection Molecular and Cellular Biology, vol. 4, No. 10, Oct. 1984, pp. 2128-2135.

Lustgarten, J., et al., Specific Elimination of IgE Production Using T Cell Lines Expressing Chimeric T Cell Receptor Genes, European Journal of Immunology (1995); 25(10):2985-2991.

Ma, Jennifer S.Y. et al., Versatile strategy for controlling the specificity and activity of engineered T cells PNAS, Jan. 2016, pp. 450-458, vol. 113, Issue 4.

Ma, Q. et al., Carcinoembryonic antigen-immunoglobulin Fc fusion protein (CEA-Fc) for identification and activation of anti-CEA immunoglobulin-T-cell receptor-modified T cells, representative of a new class of Ig fusion proteins, Cancer Gene Therapy (2004); 11: 297-306.

Ma, Q., et al., Genetically engineered T cells as adoptive immunotherapy of cancer, Cancer Chemother Biol Response Modif (2002); 20: 315-41.

Maeda et al., Tumor vascular permeability and the EPR effect in macromolecular therapeutics: a review, Journal of Controlled Release 65 (2000), pp. 271-284 (14 pages).

Maher, et al., Human T-lymphocyte cytotoxicity and proliferation directed by a single chimeric TCRzeta/CD28 receptor, Nature Biotechnology (2002); 20: 70-75.

Marincola, F. M., et al., Escape of human solid tumors from T cell recognition: molecular mechanisms and functional significance, Adv. Immunol. (2000); 74: 181-273.

Maude Shannon L. et al. Chimeric Antigen Receptor T Cells for Sustained Remissions in Leukemia N Engl J Med. Oct. 16, 2014;371(16):1507-17.

Maude Shannon L. et al. Managing Cytokine Release Syndrome Associated With Novel T Cell-Engaging Therapies Cancer J. Mar.-Apr. 2014;20(2):119-22.

Maus et al., Ex vivo expansion of polyclonal and antigen-specific cytotoxic T lymphocytes by artificial APCs expressing ligands for the T-cell receptor, CD28 and 4-1BB, Nature Biotechnology, Nature Publishing Group, New York, NY, US, vol. 20, No. 2, Feb. 1, 2002, pp. 143-148.

Maus, M.V., et al., T cells expressing chimeric antigen receptors can cause anaphylaxis in humans. Cancer Immunol Res, 2013. 1(1): p. 26-31.

McGuinness RP, et al., Anti-tumor activity of human T cells expressing the CC49-zeta chimeric immune receptor, Hum Gene Ther. (Jan. 20, 1999); 10(2): 165-73.

Medstrand et al., Long Terminal Repeats Are Used as Alternative Promoters for the Endothelin B Receptor and Apolipoprotein C-I Genes in Humans , The Journal of Biological Chemistry, vol. 276, No. 3, Issue of Jan. 19, pp. 1896-1903, 2001.

Melero, I, et al., Amplification of tumor immunity by gene transfer of the co-stimulatory 4-1BB ligand: synergy with the CD28 co-stimulatory pathway, Bristol-Myers Squibb Pharmaceutical Research Institute (1998); 1116-1121.

Melief, C. J. et al., Strategies for immunotherapy of cancer, Adv. Immunol. (2000); 75:235-282.

Mooney et al., Concise Review: Neural Stem Cell-Mediated Targeted Cancer Therapies Stem Cells Translational Medicine, 2018, pp. 740-747.

(56) References Cited

OTHER PUBLICATIONS

Moore et al., Characterisation of salmon and trout CD8α and CD8β Molecular Immunology 42 (2005) 1225-1234.
Moretta et al., Activating Receptors and Coreceptors Involved in Human Natural Killer Cell-Mediated Cytolysis, Annu. Rev. Immunol. 2001. 19:197-223.
Morgan RA, et al., Cancer regression in patients after transfer of genetically engineered lymphocytes, Science (Oct. 6, 2006); 314(5796): 126-9.
Morrison, C, CAR-T Field Booms as Next-Generation Platforms Attract Big Players, Nature Biotechnology (Jun. 2015); 33: 571-72.
Muller T. et al., Expression of a CD20-specific chimeric antigen receptor enhances cytotoxic activity of NK cells and overcomes NK-resistance of lymphoma and leukemia cells, Cancer Immunol. Immunother. (2008); 57: 411-423.
Mungra et al., Targeted human cytolytic fusion proteins at the cutting edge: harnessing the apoptosis-inducing properties of human enzymes for the selective elimination of tumor cells Oncotarget, vol. 10, No. 8, 2019, pp. 897-915.
Munn et al., Role of Low-Affinity Fc Receptors in Antibody-dependent Tumor Cell Phagocytosis by Human Monocyte-derived Macrophages, Cancer Research 51, 1117-1123, Feb. 15, 1991.
Nam, K, et al., Cross-Linking of 4-1BB Activates TCR-Signaling Pathways in CD8 T Lymphocytes1, The Journal of Immunology; 1898-1905, 2005.
National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 fromhttp://www.cancer.gov/cancertopics/research-updates/2013/CAR-T-Cells.
Nelson, Aaron L., Antibody fragments, mAbs 2010, Landes Bioscience, vol. 2, Issue 1, pp. 77-83.
Nieba, L. et al., Disrupting the hydrophobic patches at the antibody variable/constant domain interface: improved in vivo folding and physical characterization of an engineered scFv fragment, Protein Eng., 1997, 10, 435-444.
Oelke et al., Ex vivo induction and expansion of antigen-specific cytotoxic T cells by HLA-lg-coated artificial antigen-presenting cells, Nature Medicine (2003); 9(5):619-624.
Oelsner, S., et al., Continuously expanding CAR NK-92 cells display selective cytotoxicity against B-cell leukemia and lymphoma , Cytotherapy, 2017; 19: 235-249.
Okazaki et al., PD-1 immunoreceptor inhibits B cell receptor mediated signaling by recruiting src homology2-domain-containing tyrosine phosphatase 2 to phosphotyrosine , PNAS Nov. 20, 2001, vol. 98, No. 24, 13866-13871.
Orr, B. et al., Rapid method for measuring ScFv thermal stability by yeast surface display, Biotechnol Prog., 2003. 19, 631-638.
Pages et al., Two Distinct Intracytoplasmic Regions of the T-cell Adhesion Molecule CD28 Participate in Phosphatidylinositol 3-Kinase Association The Journal of Biological Chemistry, vol. 271, No. 16, Apr. 19, 1996, pp. 9403-9409.
Paillard, F. Immunotherapy with T cells bearing chimeric antitumor receptors, Hum. Gene Ther. (1999); 10: 151-153.
Paillasse, M, et al., Insights into the Cholecystokinin 2 Receptor Binding Site and Processes of Activation, The American Society for Pharmacology and Experimental Therapeutics (2006); 70:1935-1945.
Pameijer, C.R., et al., Conversion of a tumor-binding peptide identified by phage display to a functional chimeric T cell antigen receptor, Cancer Gene Ther., 2007, 14, 91-07.
Park et al., Treating cancer with genetically engineered T cells Trends Biotechnol. Nov. 2011 29(11): 550-557.
Parkhurst et al. Characterization of genetically modified T-cell receptors that recognize the CEA:691-699 peptide in the context of HLA-A2.1 on human colorectal cancer cells (2009) Clin Cancer Res. Jan. 1, 2009; 15(1):169-80.
Patel Jaina M et al: Cancer CARtography: charting out a new approach to cancer immunotherapy, Immunotherapy. 2014;6(6):675-8.
Pollock et al., Inducible T cell antigen 4-1BB. Analysis of expression and function,'J Immunol 1993; 150:771-781.
Porter DL, et al. Chimeric antigen receptor T cells persist and induce sustained remissions in relapsed refractory chronic lymphocytic leukemia . Science translational medicine. 2015;7(303):303-39. doi: 10.1 126/scitranslmed.aac5415. PubMed PMID:26333935.
Porter, D.L. et al., Chimeric antigen receptor-modified T cells in chronic lymphoid leukemia, N. Engl. J. Med., 2011, 365, 725-733.
Prasad et al., T-cell antigen CD28 interacts with the lipid kinase phosphatidylinositol3-kinase by a cytoplasmic Tyr(P)-Met-Xaa-Met motif, Proc. Natl. Acad. Sci. USA, vol. 91, pp. 2834-2838, Mar. 1994.
Product brochure for the Engineered Autologous Cell Therapy (eACT™) Platform, available from Kite Pharma, retrieved Oct. 25, 2015 from http://www.kitepharma.com/c/products/eact.php.
Pule et al., Virus-specific T cells engineered to coexpress tumor-specific receptors: persistence and antitumor activity in individuals with neuroblastoma, Nat. Med. (2008); 14: 1264-1270.
Qin et al., Incorporation of a hinge domain improves the expansion of chimeric antigen receptor T cells, Journal of Hematology & Oncology (2017) 10:68.
Rai et al., Expression systems for production of heterologous proteins, Current Science2001, vol. 80, No. 9, pp. 1121-1128.
Recent patent applications in chimeric antigen receptors, *Nature Biotechnology* 32(3): 239 (2014).
Reddy et al., Elimination of Fc Receptor-Dependent Effector Functions of a Modified IgG4Monoclonal Antibody to Human CD4, J Immunol 2000; 164: 1925-1933.
Redmond et al., The role of OX40-mediated co-stimulation in T cell activation and survival, Crit Rev. Immunol. 2009, 29(3): 187-201.
Reichert, J. Day 1, Emerging Disruptive Technologies and Cutting-Edge Analytical Techniques, MAbs, 2009, 1, 190-209.
Reubi, Jean Claude, Peptide Receptors as Molecular Targets for Cancer Diagnosis and Therapy, Endocrine Reviews 24(4): 389-427, 2002.
Riha et al., CD28 co-signaling in the adaptive immune response Self/Nonself 1:3,231-240; Jul./Aug./Sep. 2010.
Riley et al., The CD28 family: a T-cell rheostat for therapeutic control of T-cell activation, Blood, Jan. 1, 2005, vol. 105, No. 1, pp. 13-21.
Riviere, I., Gallardo, H. F., Hagani, A B. & Sadelain, M. Retroviral-mediated gene transfer in primary murine and human T-lymphocytes. Mol. Biotechnol. 15, 133-142 (2000).
Roberts et al., Chemistry for peptide and protein PEGylation, Advanced Drug Delivery Reviews (2002); 54:459-476.
Rodgers, D. et al., Switch-mediated activation and retargeting of CAR-T cells for B-cell malignancies, Proc. Natl. Acad. Sci., 2016, 113, E459-468.
Romeo, C. at al., Sequence requirements for induction of cytolysis by the T cell antigen/Fc receptor zeta chain, Cell (1992); 68:889-897.
Romeo, C., et al., Cellular immunity to HIV activated by CD4 fused to T cell or Fc receptor polypeptides, Cell (1991); 64:1037-1046.
Rosenberg Cell transfer immunotherapy for metastatic solid cancer—what clinicians need to know (2011) Nat Rev Clin Oncol. 8(10):577-85).
Rosenberg et al. Adoptive cell transfer: a clinical path to effective cancer immunotherapy. Nat Rev Cancer. Apr. 2008; 8(4):299-308.
Rosenberg, S. A. et al., Adoptive cell therapy for the treatment of patients with metastatic melanoma, Current Opinion in Immunology, 2009, 21, 233-240.
Rotz Seth J. et al. Severe cytokine release syndrome in a patient receivingPD-1-directed therapy Pediatr Blood Cancer. Dec. 2017;64(12). Epub May 24, 2017 (4 pages).
Rueckert S, et al., A monoclonal antibody as an effective therapeutic agent in breast cancer: trastuzumab Expert Opin Biol Ther. Jun. 2005;5(6):853-66.
Sadelain et al., Targeting Tumours with Genetically Enhanced T Lymphocytes, Nat Rev Cancer (Jan. 2003); 3(1): 35-45.
Sadelain, et al., The promise and potential pitfalls of chimeric antigen receptors, Current Opinion in Immunology (2009); 21: 215-223.

(56) References Cited

OTHER PUBLICATIONS

Sadelain, M. et al., The basic principles of chimeric antigen receptor design, Cancer Discov., 2013, 3, 388-398.
Saoulii, C, et al., CD28-independent, TRAF2-dependent Costimulation of Resting T Cells by 4-1BB Ligand, Master of Science Thesis, Department of Immunology University of Toronto (1998), 77 pp.
Saraswat et al., DNA as Therapeutics; an Update, Indian J Pharm Sci. Sep.-Oct. 2009;71(5): 488-498.
Scholler, J., et al., Decade-long safety and function of retroviral-modified chimeric antigen receptor T cells, Sci Transl Med (May 2, 2012); 4(132): 132ra53 (7 pages).
Schonfeld, K, et al., Selective Inhibition of Tumor Growth by Clonal NK Cells Expressing an Erb82/HER2-Specific Chimeric Antigen Receptor, Mol. Ther., vol. 23 No. 2, 330-338 Feb. 2015.
Schreiber, S.L., Organic synthesis toward small-molecule probes and drugs PNAS, vol. 108, No. 17, Apr. 26, 2011, pp. 6699-6702.
Scott, D., et al., Immunogenicity of biotinylated hapten-avidin complexes, Mol Immunol(1984); 21(11): 1055-60.
Sega, E. et al., Tumor detection using folate receptor-targeted imaging agents, Cancer Metastasis Rev., 2008, 27, 655-664.
Sentman Challenges of creating effective chimeric antigen receptors for cancer therapy Immunotherapy. Aug. 2013;5(8):783-5.
Serghides et al., Evaluation of OX40 Ligand as a Costimulator of Human Antiviral Memory CD8 T Cell Responses: Comparison with B7.1 and 4-1BBL, The Journal of Immunology 175:6368-6377 (2005).
Shields et al., High Resolution Mapping of the Binding Site on Human IgG1 for FcγRI, FcγRII, FcγRIII, and FcRn and Design of IgG1 Variants with Improved Binding to the FcγR*, The Journal of Biological Chemistry 2001, vol. 276, No. 9, Issue of Mar. 2, pp. 6591-6604.
Shirasu, N. et al., Construction and Molecular Characterization of Human Chimeric T-Cell Antigen Receptors Specific for Carcinoembryonic Antigen, Anticancer Research (2010); 30:2731-2738.
Sobota et al., Binding of IgG-Opsonized Particles to FcγR Is an Active Stage of Phagocytosis That Involves Receptor Clustering and Phosphorylation, The Journal of Immunology 2005; 175:4450-4457.
Stancovski et al., Targeting of T Lymphocytes to Neu/HER2-Expressing Cells Using Chimeric Single Chain Fv Receptors, J. Immunol. (1993); 151(11):6577-6582.
Stein, P, et al., The Cytoplasmic Domain of CD28 Is both Necessary and Sufficient for Costimulation of Interleukin-2 Secretion and Association with Phosphatidylinositol3'-Kinase, American Society for Microbiology (1994); 14: 3392-3402.
Stephan et al., T cell-encoded CD80 and 4-1BBL induce auto- and transcostimulation, resulting in potent tumor rejection, Nature Medicine (Dec. 2007); 13(12): 1440-1449.
Stevens et al., Generation of Tumor-Specific CTLs from Melanoma Patients by Using Peripheral Blood Stimulated with Allogeneic Melanoma Tumor Cell Lines, J. Immunol(1995); 154:762-771.
Suhoski, M.M., et al., Engineering artificial antigen-presenting cells to express a diverse array of co-stimulatory molecules. Mol Ther, 2007. 15(5): p. 981-8.
Swanson et al., The coordination of signaling during Fc receptor-mediated phagocytosis, Journal of Leukocyte Biology, vol. 76, Dec. 2004, pp. 1093-1103.
Tam et al., Functional, Biophysical, and Structural Characterization of Human IgG1 andIgG4 Fc Variants with Ablated Immune Functionality, Antibodies 2017, 6, 12.
Tanaka, Toshio et al. Immunotherapeutic implications of IL-6 blockade for cytokine storm. Immunotherapy. Jul. 2016;8(8):959-70.
Teachey D. T. et al. Cytokine release syndrome after blinalumornab treatment related to abnormal macrophage activation and ameliorated with cytokine-directed therapy Blood. Jun. 27, 2013;121(26):5154-7. doi: 10.1182/blood-2013-02-485623. Epub May 15, 2013.

Themeli, M., et al., Generation of tumor-targeted human T lymphocytes from induced pluripotent stem cells for cancer therapy, Nat Biotechnol (2013); 31(10):928-33 (Epub Aug. 11, 2013).
Tsukahara et al. CD19 target-engineered T-cells accumulate at tumor lesions in human B-cell lymphoma xenograft mouse models (2013) Biochem Biophys Res Commun 438(1): 84-9. Epub Jul. 17, 2013.
Tumor necrosis factor receptor superfamily, HUGO Gene Nomenclature Committee, 2 pp, 2021.
Turatti, F., et al., Redirected activity of human antitumor chimeric immune receptors is governed by antigen and receptor expression levels and affinity of interaction, J Immunother (2007); 30(7): 684-93.
Turtle et al., Engineered T cells for anti-cancer therapy Curr. Opin. Immunol., Oct. 2012; 24(5): 633-39. Epub Jul. 18, 2012.
Uherek, C, et al., Chimeric antigen receptors for the retargeting of cytotoxic effector cells, J. Hematother. Stem Cell Res. (2001); 10: 523-534.
UniProtKB—O43914, TYRO protein tyrosine kinase-binding protein, pp. 1-15, 2000.
UniProtKB—P01732 (CD8A_HUMAN). T-cell surface glycoprotein CD8 alpha chain; 11pages; retrieved on May 13, 2016 from http://www.uniprot.org/uniprot/P01732.
UniProtKB—P02701, AVidin Precursor—Gallus Chicken, 2007.
UniProtKB—P10747 (CD28_HUMAN), 1989.
UniProtKB—P10966 (CD8B_HUMAN), 1989.
UniProtKB—P20963 (CD3Z_HUMAN). T-cell surface glycoprotein CD3 zeta chain; 12pages; retrieved on May 13, 2016 from http://www.uniprot.org/uniprot/P20963.
UniProtKB—Q07011 (TNR9_HUMAN). Tumor necrosis factor receptor superfamily member 9; 14 pages; retrieved on May 13, 2016 from http://www.uniprot.org/uniprot/Q07011.
Urba, W.J. et al., Redirecting T cells, New Engl. J. Med., 2011, 365, 754-757.
Urbanska, K., et al., A Universal Immune Receptor Expressed by T Cells for the Targeting of Diverse and Multiple Tumor Associated Antigens IN Abstracts for the 26th Annual Scientific Meeting of the Society for Immunotherapy of Cancer (SITC), J Immunother, vol. 34, No. 9, Nov.-Dec. 2011 (62 pages), p. 381.
Uttenthal, B.J., et al., Challenges in T cell receptor gene therapy. J Gene Med (Jun. 2012); 14(6): 386-99.
Van Dam, G. et al., Intraoperative tumor-specific fluorescence imaging in ovarian cancer by folate receptor-α targeting: first in-human results, Nature Medicine, 2011, 17, 1315-1319.
Van Rhijn et al., Nov. 30, 2015, Human autoreactive T cells recognize CD1b and phospholipids, Proceedings of the National Academy of Sciences 113(2):380-385.
Verdine et al., The Challenge of Drugging Undruggable Targets in Cancer: Lessons Learned from Targeting BCL-2 Family Members Clin. Cancer Res. vol. 13, No. 24, Dec. 15, 2007, pp. 7264-7270.
Verhoeyen et al. Lentiviral vector gene transfer into human T cells (2009) Methods Mol Biol. 506: 97-114.
Wang et al. Phenotypic and functional attributes of lentivirus-modified CD19-specific human CD8+ central memory T cells manufactured at clinical scale (2012) J Immunother.35(9):689-701.
Wang et al., Current status and perspectives of chimeric antigen receptor modified T cells for cancer treatment, Protein Cell 2017, 8(12):896-925.
Wayua, C. et al., Evaluation of a Cholecystokinin 2 Receptor-Targeted Near-Infrared Dye for Fluorescence-Guided Surgery of Cancer, Molecular Pharmaceutics, 2014, 11,468-476.
Weijtens, M. E. et al., Single chain lg/gamma gene-redirected human T lymphocytes produce cytokines, specifically lyse tumor cells, and recycle lytic capacity., J. Immunol.(Jul. 15, 1996); 157(2):836-43.
Weissman et al., Molecular cloning and chromosomal localization of the human T-cell receptor zeta chain: Distinction from the molecular CD3 complex Proc. Natl. Acad. Sci. vol. 85, Dec. 1988, pp. 9709-9713.
Weissman et al., Role of the zeta chain in the expression of the T cell antigen receptor: genetic reconstitution studies The EMBO Journal, vol. 8, No. 12, 1989, pp. 3651-3656.

(56) References Cited

OTHER PUBLICATIONS

Wen, T, et al., 4-1BB Ligand-Mediated Costimulation of Human T Cells Induces CD4 andCD8 T Cell Expansion, Cytokine Production, and the Development of Cytolytic Effector Function1, 4897-4906, 2002.
Wesolowski, J, et al., Single domain antibodies: promising experimental and therapeutic tools in infection and immunity, Med Microbiol Immunol (2009) 198:157-174.
Wilkie et al., Retargeting of Human T Cells to Tumor-Associated MUC1: The Evolution of a Chimeric Antigen Receptor, The Journal of Immunology Apr. 2008, pp. 4901-4909.
Wilson, et al. DAP12 and KAP10 (DAP10)—novel transmembrane adapter proteins of the CD3zeta family, Immunol Res. (2000); 22(1):21-42.
Wu et al., Adoptive T-cell therapy using An A tumor-infiltrating lymphocytes for metastatic melanoma: current status and future outlook Cancer, Mar. 2012 18(2): 160-75.
Wu, et al., An activating immunoreceptor complex formed by NKG2D and DAP10, Science (1999): 285:730-732.
Xu et al., Cytokine release syndrome in cancer immunotherapy with chimeric antigen receptor engineered T cells Cancer Lett. Feb. 28, 2014;343(2):172-8. Epub Oct. 16, 2013.
Xu, X.J., et al., Efficacy and safety of adoptive immunotherapy using anti-CD 19 chimeric antigen receptor transduced T-cells: a systematic review of phase I clinical trials, LeukLymphoma (2013); 54(2): 255-60 (Published online: Sep. 8, 2012).
Ye, H, et al., The Structural Basis for the Recognition of Diverse Receptor Sequences by TRAF2, The Weill Medical College and Graduate School of Medical Sciences of Cornell University; v: 321-330, 1999.
Yee, C., et al., Prospects for Adoptive T Cell Therapy, Current Opinion in Immunology(1997); 9(5):702-708.
Zhang et al., Phase I Escalating-Dose Trial of CAR-T Therapy Targeting CEA + Metastatic Colorectal Cancers, Molecular Therapy (2017), 25(5): 1248-1258.
Zhang, H., et al., 4-IBB is superior to CD28 costimulation for generating CD8+ cytotoxic lymphocytes for adoptive immunotherapy. J Immunol, 2007. 179(7): p. 4910-8.
Zhao, Y. et al., A herceptin-based chimeric antigen receptor with modified signaling domains leads to enhanced survival of transduced T lymphocytes and antitumor activity, J. Immunol, 2009, 183, 5563-5574.
Zheng et al., Arming Tumor-Reactive T Ceils with Costimulator B7-1 Enhances Therapeutic Efficacy of the T Cells, Cancer Research, 2006, vol. 66, No. 13, pp. 6793-6799.
Zhong, et al., Integrated CD28 and 4-1BB Signals Strongly Potentiate CD8+ T Cell Mediated Eradication of Metastatic Prostate Cancer, Molecular Therapy (Jan. 1, 2006); 13: p. S103, Abstract.
Amin et al., "The Eighth Edition AJCC Cancer Staging Manual: Continuing to Build a Bridge From a Population-Based to a More "Personalized" Approach to Cancer Staging," CA Cancer J Clin (2017) vol. 67, No. 2, pp. 93-99.
Boder et al., "Directed evolution of antibody fragments with monovalent femtomolar antigen-binding affinity," PNAS (Sep. 26, 2000) vol. 97, No. 20, pp. 10701-10705.
Gonzalez et al., "Genetic engineering of cytolytic T lymphocytes for adoptive T-cell therapy of neuroblastoma," The Journal of Gene Medicine (Jun. 2004) vol. 6, Issue 6, 704-711.
Grupp et al., "Chimeric Antigen Receptor-Modified T Cells for Acute Lymphoid Leukemia," N. Engl. J. Med. (Apr. 18, 2013) 368(16):1509-1518.
Honegger et al., "A mutation designed to alter crystal packing permits structural analysis of a tight-binding fluorescein-scFv complex," Protein Science (2005) 14(10), 2537-2549.
Jung et al., "Improving in vivo folding and stability of a single-chain Fv antibody fragment by loop grafting," Protein Engineering (1997) vol. 10, No. 8, pp. 956-966.

Kalos et al., "T Cells with Chimeric Antigen Receptors Have Potent Antitumor Effects and Can Establish Memory in Patients with Advanced Leukemia," Sci. Transl. Med. (Aug. 10, 2011) 3(95):1-21.
Kim et al., "NMR Structural Studies of Interactions of a Small, Nonpeptidyl Tpo Mimic with the Thrombopoietin Receptor Extracellular Juxtamembrane and Transmembrane Domains," J Biol Chem (2007) 282(19):14253-14261.
Kim et al. "Redirection of Genetically Engineered CAR•T Cells Using Bifunctional Small Molecules," Journal of the American Chemical Society (Feb. 18, 2015) vol. 137, No. 8, pp. 2832-2835, with 8 page supporting document.
Kranz et al., "Partial elucidation of an anti-hapten repertoire in BALB/c mice: comparative characterization of several monoclonal antiFLuorescyl antibodies," Mol Immunol (1981) 18(10), 889-898.
Ma et al., "Versatile strategy for controlling the specificity and activity of engineered T cells," Proc. Nat. Acad. Sci. U.S.A (Jan. 12, 2016) vol. 113, No. 4, pp. 450-458.
Molecular Cloning: A Laboraory Manual, 4th Edition, Cold Spring Harbor Laboratory Press, (2012) Green and Sambrook, TOC, 34 pages.
Pule et al., "Artificial T-cell receptors," Cytotherapy (2003) 5(3):211-226.
Restifo et al., "Adoptive immunotherapy for cancer: harnessing the T cell response," Nat. Rev. Immunol. (Mar. 22, 2012) 12(4):269-281.
Schwesinger et al., "Unbinding forces of single antibody-antigen complexes correlate with their thermal dissociation rates," PNAS (2000) 97(18), 9972-9977.
Tamada et al. "Redirecting Gene-Modified T Cells toward Various Cancer Types Using Tagged Antibodies," Clinical Cancer Research (Oct. 2, 2012) vol. 18, Iss. 23, pp. 6436-6445.
Urbanska et al., "A Universal Strategy for Adoptive Immunotherapy of Cancer through Use of a Novel T-cell Antigen Receptor," Cancer Research (2012) 72(7): 1844-1852.
Van Blitterswijk et al., "Anticancer mechanisms and clinical application of alkylphopholipids," Biochimica et Biophysica Acta (2013) 1831(3):663-674.
Van der Luit et al., "A new class of anticancer alkylphospholipids uses lipid rafts as membrane gateways to induce apoptosis in lymphoma cells," Mol Cancer Ther (2007) 6(8):2337-2345.
Vaughan et al., "Human antibodies with sub-nanomolar affinitis isolate from a large non-immunized phage display library," Nature Biotechnology (1996) vol. 14(3), pp. 309-314.
Wu et al., "Remote control of therapeutic T cells through a small molecule-gated chimeric receptor," Science (2015) vol. 350, Issue 6258, p. 293 and aab4077-aab4077.
International Search Report and Written Opinion dated Mar. 27, 2019 for PCT/US2019/014478.
Krause, A., et al., Genetic approaches to sustain the function of tumor-specific T-lymphocytes, Mol. Ther. (2000); 1 (S260): 713.
Kularatne, S.A. et al., Prostate-specific membrane antigen targeted imaging and therapy of prostate cancer using a PSMA inhibitor as a homing ligand, Mol. Pharm., 2009, 6,780-789.
Kuwana, Y. et al., Expression of chimeric receptor composed of immunoglobulin-derived V regions and T-cell receptor-derived C regions, Biochem. Biophys. Res. Comm, (1987); 149:960-968.
Kwon, B, et al., cDNA sequences of two inducible T-cell genes, cDNA sequences of two inducible T-cell genes (1989); 86: 1963-1967.
Kwon, B, et al., Expression Characteristics of Two Potential T Cell Mediator Genes, Cellular Immunology (1989); 414-422.
Lafage-Pochitaloff M, Costello R, Couez D, Simonetti J, Mannoni P, Mawas C, Olive D. Human CD28 and CTLA-4 lg superfamily genes are located on chromosome 2 at bands q33-q34 Immunogenetics 1190;31(3):198-201; 1990.
Lamers et al., Immune responses to transgene and retroviral vector in patients treated withex vivo-engineered T cells, Blood (2011) 117(1): 72-82.
Lamers, C. et al., Treatment of Metastatic Renal Cell Carcinoma With Autologous T-Lymphocytes Genetically Retargeted Against Carbonic Anhydrase IX: First Clinical Experience, J. Clin. Oncol., 2006, 24, e20-22.

(56) References Cited

OTHER PUBLICATIONS

Laroche et al., Characterization of a Recombinant Single-chain Molecule Comprising the Variable Domains of a Monoclonal Antibody Specific for Human Fibrin Fragment D-dimer*, The Journal of Biological Chemistry 1991, vol. 266, No. 25, Issue of Sep. 5, pp. 16343-16349.

Latza, U. et al., The human OX40 homolog: cDNA structure, expression and chromosomal assignment of the ACT35 antigen, Eur. J. Immunol., 1994, 24, 677-683.

Lee et al., Current concepts in the diagnosis and management of cytokine release syndrome Blood. Jul. 10, 2014;124(2):188-95. doi: 10.1182/blood-2014-05-552729. Epub May 29, 2014, with errata.

Lee, D, et al., 4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells, PLOS One (2013); 8: 1-11.

Liebowitz, D. N., Lee, K. P. & June, C. H. Co-stimulatory approaches to adoptive immunotherapy. Curr. Opin. Oncol. 10, 533-541 (1998).

Lin et al., Transglutaminase-catalyzed site-specific conjugation of small-molecule probes to proteins in vitro and on the surface of living cells, J. Am. Chem. Soc. (2006);128:4542-4543.

Linenberger, CD33-directed therapy with gemtuzumab ozogamicin in acute myeloid leukemia: progress in understanding cytotoxicity and potential mechanisms of drug resistance , Leukemia (2005) 19, 176-182.

Liou et al., A chimeric mouse-human antibody that retains specificity for HIV gp 120 and mediates the lysis of HIV-infected cells, J Immunol 1989; 143: 3967-3975.

Lodish et al., Hierarchical Structure of Proteins Molecular Cell Biology. 4th Ed. New York: W.H. Freeman; 2000. pp. 1-25.

Long, A.H., et al., 4-IBB costimulation ameliorates T cell exhaustion induced by tonic signaling of chimeric antigen receptors. Nat Med, 2015. 21(6): p. 581-90.

* cited by examiner

Fixed EC17 doses
✓ 500 nmol/kg

Dose de-escalation
✓ Loading: 500 nmol/kg
✓ Maint.: 5, 20, 100 nmol/kg

ADRENAL GLAND

BONE MARROW

BREAST

CEREBELLUM TISSUE

CERVIX

COLON

ESOPHAGUS

EYE

HEART

HYPOPHYSIS

KIDNEY

LARYNX

SPLEEN

LIVER

LUNG

LYMPH NODE

NERVE

OVARY

PANCREAS

PROSTATE

SKIN

SMALL INTESTINE

STOMACH

STRIATED MUSCLE

TESTIS

THYMUS GLAND

TONGUE

UTERUS

FITC-folate

FITC-folate

FITC-DUPA

FITC-DUPA

FITC-CA9

FITC-CA9

FITC-NK1R

FITC-NK1R

| CRS Grading Scale | | | | | |
|---|---|---|---|---|---|
| 0 | 1 | 2 | 3 | 4 | 5 |
| Normal | ~pilo ~greasy still active | pilo greasy less active | pilo, greasy bunched, thin not active, unless stimulated | moribund bunched, pale lethargic | Death |

FIG. 57A

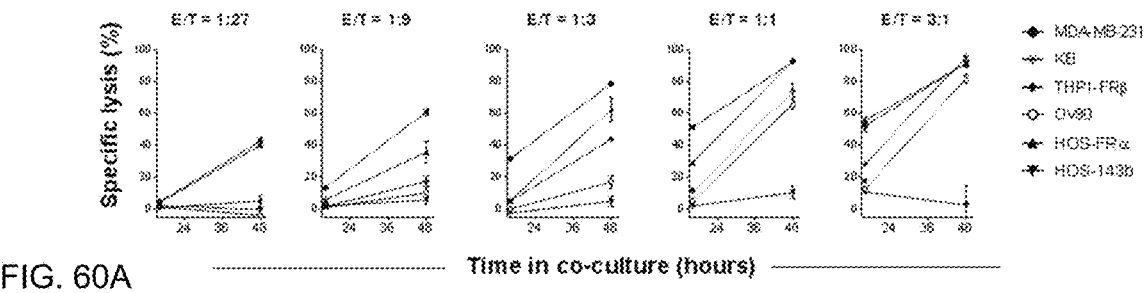
FIG. 60A
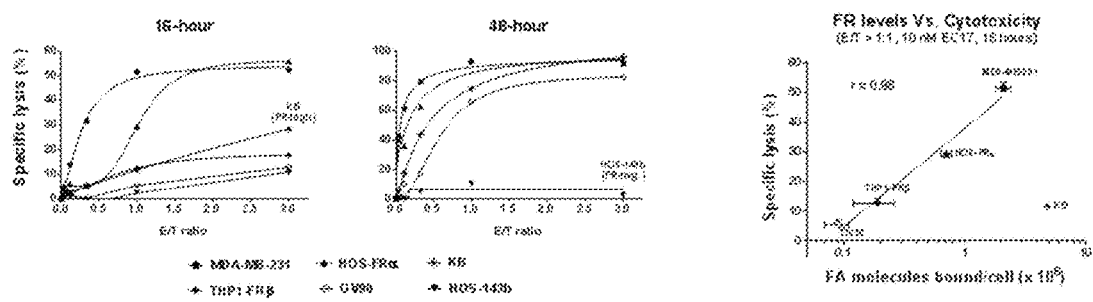
FIG. 60B
FIG. 60C
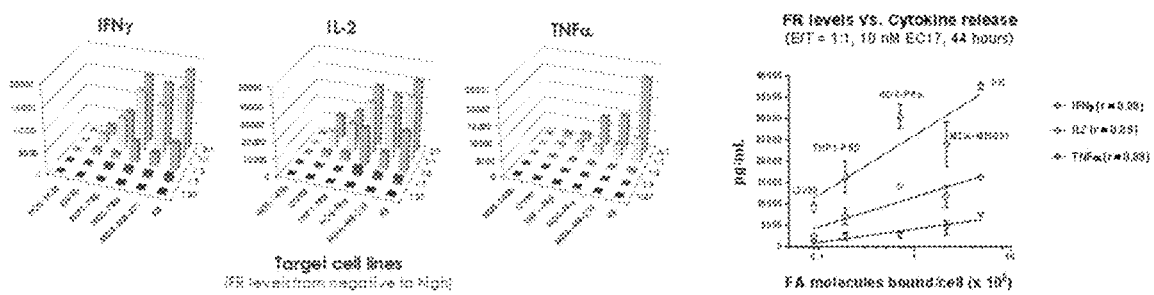
FIG. 60D
FIG. 60E

SEQUENCE LISTING

<160> NUMBER OF SEQ ID NOS: 4

<210> SEQ ID NO 1
<211> LENGTH: 3198
<212> TYPE: DNA
<213> ORGANISM: Artificial Sequence
<220> FEATURE:
<223> OTHER INFORMATION: E2 anti-fluorescein antibody fragment CAR
      nucleic acid sequence

<400> SEQUENCE: 1

```
atgcttctcc tggtgacaag ccttctgctc tgtgagttac cacacccagc attcctcctg      60
atcccaagcg tgctgacaca gcctagctcc gtgtctgccg cccctggcca gaaagtgacc     120
atcagctgta gcggcagcac cagcaacatc ggcaacaact acgtgtcctg gtatcagcag     180
caccccggca aggcccccaa gctgatgatc tacgacgtgt ccaagcggcc cagcggcgtg     240
cccgatagat ttccggcag caagagcggc aacagcgcca gctggatat cagcggcctg     300 cagtctgagg acgaggccga ctactattgc gccgcctggg acgatagcct gagcgagttc     360
```

```
ctgtttggca ccggcaccaa gctgacagtg ctgggcggag gcggaggatc tggcggcgga      420
ggaagtggcg gagggggatc tcaggtgcag ctggtgaaaa gcggcggcaa cctggtgcag      480
cctggcggat ctctgagact gagctgtgcc gccagcggct tcaccttcgg cagcttcagc      540
atgagctggg tgcgccaggc tcctggggga ggactggaat gggtggcagg actgagcgcc      600
agaagcagcc tgacccacta cgccgatagc gtgaagggcc ggttcaccat cagccgggac      660
aacgccaaga acagcgtgta cctgcagatg aacagcctgc gggtggaaga taccgccgtg      720
tactactgcg ccagacggtc ctacgacagc agcggctact ggggccactt ctacagctac      780
atggacgtgt ggggccaggg caccctcgtg acagtgtctg agagcaagta cggaccgccc      840 tgccccccctt gcctgcccc cgagttcgac ggcggaccca gcgtgttcct gttccccccc      900
aagcccaagg acaccctgat gatcagccgg acccccgagg tgacctgcgt ggtggtggac      960
gtgagccagg aagatcccga ggtccagttc aattggtacg tggacggcgt ggaagtgcac     1020
aacgccaaga ccaagcccag agaggaacag ttccagagca cctaccgggt ggtgtctgtg     1080
ctgaccgtgc tgcaccagga ctggctgaac ggcaaagaat acaagtgcaa ggtgtccaac     1140
aagggcctgc ccagcagcat cgaaaagacc atcagcaagg ccagggcca gcctcgcgag     1200 ccccaggtgt acaccctgcc tccctcccag aagagatga ccaagaacca ggtgtccctg     1260
acctgcctgg tgaagggctt ctaccccagc gacatcgccg tggagtggga gagcaacggc     1320
cagcctgaga caaactacaa gaccaccccct cccgtgctgg acagcgacgg cagcttcttc     1380
ctgtacagcc ggctgaccgt ggacaagagc cggtggcagg aaggcaacgt ctttagctgc     1440
agcgtgatgc acgaggccct gcacaaccac tacacccaga gagcctgag cctgtccctg     1500 ggcaagatgt tctgggtgct ggtggtggtg ggcggggtgc tggcctgcta cagcctgctg     1560
gtgacagtgg ccttcatcat cttttgggtg aaacggggca gaaagaaact cctgtatata     1620
ttcaaacaac catttatgag accagtacaa actactcaag aggaagatgg ctgtagctgc     1680
cgatttccag aagaagaaga aggaggatgt gaactgcggg tgaagttcag cagaagcgcc     1740
gacgcccctg cctaccagca gggccagaat cagctgtaca cgagctgaa cctgggcaga     1800 agggaagagt acgacgtcct ggataagcgg agaggccggg accctgagat gggcggcaag     1860
cctcggcgga agaaccccca ggaaggcctg tataacgaac tgcagaaaga caagatggcc     1920
gaggcctaca gcgagatcgg catgaagggc gagcggaggc ggggcaaggg ccacgacggc     1980
ctgtatcagg gcctgtccac cgccaccaag gatacctacg acgccctgca catgcaggcc     2040 ctgccccaa ggctcgaggg cggcggagag ggcagaggaa gtcttctaac atgcggtgac     2100
gtggaggaga atcccggccc taggatgctt ctcctggtga caagccttct gctctgtgag     2160
ttaccacacc cagcattcct cctgatccca cgcaaagtgt gtaacggaat aggtattggt     2220
gaatttaaag actcactctc cataaatgct acgaatatta aacacttcaa aaactgcacc     2280
tccatcagtg gcgatctcca catcctgccg gtggcattta ggggtgactc cttcacacat     2340
actcctcctc tggatccaca ggaactggat attctgaaaa ccgtaaagga aatcacaggg     2400
tttttgctga ttcaggcttg gcctgaaaac aggacggacc tccatgcctt tgagaaccta     2460
gaaatcatac gcggcaggac caagcaacat ggtcagtttt ctcttgcagt cgtcagcctg     2520
aacataacat ccttgggatt acgctccctc aaggagataa gtgatggaga tgtgataatt     2580
tcaggaaaca aaaatttgtg ctatgcaaat acaataaact ggaaaaaact gtttgggacc     2640
tccggtcaga aaaccaaaat tataagcaac agaggtgaaa acagctgcaa ggccacaggc     2700
```

-continued

```
caggtctgcc atgccttgtg ctcccccgag ggctgctggg gcccggagcc cagggactgc    2760
gtctcttgcc ggaatgtcag ccgaggcagg gaatgcgtgg acaagtgcaa ccttctggag    2820
ggtgagccaa gggagtttgt ggagaactct gagtgcatac agtgccaccc agagtgcctg    2880
cctcaggcca tgaacatcac ctgcacagga cggggaccag acaactgtat ccagtgtgcc    2940
cactacattg acggccccca ctgcgtcaag acctgcccgg caggagtcat gggagaaaac    3000
aacaccctgg tctggaagta cgcagacgcc ggccatgtgt gccacctgtg ccatccaaac    3060
tgcacctacg gatgcactgg gccaggtctt gaaggctgtc aacgaatgg gcctaagatc    3120 ccgtccatcg ccactgggat ggtgggggcc ctcctcttgc tgctggtggt ggccctgggg    3180
atcggcctct tcatgtga                                                  3198
```

<210> SEQ ID NO 2
<211> LENGTH: 1065
<212> TYPE: PRT
<213> ORGANISM: Artificial Sequence
<220> FEATURE:
<223> OTHER INFORMATION: E2 anti-fluorescein antibody fragment CAR amino acid sequence

<400> SEQUENCE: 2

```
Met Leu Leu Leu Val Thr Ser Leu Leu Cys Glu Leu Pro His Pro
1               5                   10                  15

Ala Phe Leu Leu Ile Pro Ser Val Leu Thr Gln Pro Ser Ser Val Ser
            20                  25                  30

Ala Ala Pro Gly Gln Lys Val Thr Ile Ser Cys Ser Gly Ser Thr Ser
        35                  40                  45

Asn Ile Gly Asn Asn Tyr Val Ser Trp Tyr Gln Gln His Pro Gly Lys
    50                  55                  60

Ala Pro Lys Leu Met Ile Tyr Asp Val Ser Lys Arg Pro Ser Gly Val
65                  70                  75                  80

Pro Asp Arg Phe Ser Gly Ser Lys Ser Gly Asn Ser Ala Ser Leu Asp
                85                  90                  95

Ile Ser Gly Leu Gln Ser Glu Asp Glu Ala Asp Tyr Tyr Cys Ala Ala
            100                 105                 110

Trp Asp Asp Ser Leu Ser Glu Phe Leu Phe Gly Thr Gly Thr Lys Leu
        115                 120                 125

Thr Val Leu Gly Gly Gly Gly Ser Gly Gly Gly Ser Gly Gly
    130                 135                 140

Gly Gly Ser Gln Val Gln Leu Val Glu Ser Gly Gly Asn Leu Val Gln
145                 150                 155                 160

Pro Gly Gly Ser Leu Arg Leu Ser Cys Ala Ala Ser Gly Phe Thr Phe
                165                 170                 175

Gly Ser Phe Ser Met Ser Trp Val Arg Gln Ala Pro Gly Gly Gly Leu
            180                 185                 190

Glu Trp Val Ala Gly Leu Ser Ala Arg Ser Ser Leu Thr His Tyr Ala
        195                 200                 205

Asp Ser Val Lys Gly Arg Phe Thr Ile Ser Arg Asp Asn Ala Lys Asn
    210                 215                 220

Ser Val Tyr Leu Gln Met Asn Ser Leu Arg Val Glu Asp Thr Ala Val
225                 230                 235                 240

Tyr Tyr Cys Ala Arg Arg Ser Tyr Asp Ser Ser Gly Tyr Trp Gly His
                245                 250                 255

Phe Tyr Ser Tyr Met Asp Val Trp Gly Gln Gly Thr Leu Val Thr Val
            260                 265                 270
```

```
Ser Glu Ser Lys Tyr Gly Pro Pro Cys Pro Pro Cys Pro Ala Pro Glu
        275                 280                 285

Phe Asp Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser Gln Glu Asp Pro Glu Val Gln Phe Asn Trp Tyr Val Asp Gly
                325                 330                 335

Val Glu Val His Asn Ala Lys Thr Lys Pro Arg Glu Glu Gln Phe Gln
                340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Gly Leu Pro
    370                 375                 380

Ser Ser Ile Glu Lys Thr Ile Ser Lys Ala Lys Gly Gln Pro Arg Glu
385                 390                 395                 400

Pro Gln Val Tyr Thr Leu Pro Pro Ser Gln Glu Met Thr Lys Asn
                405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
                435                 440                 445

Thr Pro Pro Val Leu Asp Ser Asp Gly Ser Phe Phe Leu Tyr Ser Arg
    450                 455                 460

Leu Thr Val Asp Lys Ser Arg Trp Gln Glu Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Leu Gly Lys Met Phe Trp Val Leu Val Val Val Gly Gly
            500                 505                 510

Val Leu Ala Cys Tyr Ser Leu Leu Val Thr Val Ala Phe Ile Ile Phe
        515                 520                 525

Trp Val Lys Arg Gly Arg Lys Lys Leu Leu Tyr Ile Phe Lys Gln Pro
530                 535                 540

Phe Met Arg Pro Val Gln Thr Thr Gln Glu Glu Asp Gly Cys Ser Cys
545                 550                 555                 560

Arg Phe Pro Glu Glu Glu Glu Gly Gly Cys Glu Leu Arg Val Lys Phe
                565                 570                 575

Ser Arg Ser Ala Asp Ala Pro Ala Tyr Gln Gln Gly Gln Asn Gln Leu
                580                 585                 590

Tyr Asn Glu Leu Asn Leu Gly Arg Arg Glu Glu Tyr Asp Val Leu Asp
        595                 600                 605

Lys Arg Arg Gly Arg Asp Pro Glu Met Gly Gly Lys Pro Arg Arg Lys
    610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
                645                 650                 655

Gly His Asp Gly Leu Tyr Gln Gly Leu Ser Thr Ala Thr Lys Asp Thr
                660                 665                 670

Tyr Asp Ala Leu His Met Gln Ala Leu Pro Pro Arg Leu Glu Gly Gly
                675                 680                 685
```

Gly Glu Gly Arg Gly Ser Leu Leu Thr Cys Gly Asp Val Glu Asn
690                 695                 700

Pro Gly Pro Arg Met Leu Leu Leu Val Thr Ser Leu Leu Leu Cys Glu
705                 710                 715                 720

Leu Pro His Pro Ala Phe Leu Leu Ile Pro Arg Lys Val Cys Asn Gly
            725                 730                 735

Ile Gly Ile Gly Glu Phe Lys Asp Ser Leu Ser Ile Asn Ala Thr Asn
            740                 745                 750

Ile Lys His Phe Lys Asn Cys Thr Ser Ile Ser Gly Asp Leu His Ile
            755                 760                 765

Leu Pro Val Ala Phe Arg Gly Asp Ser Phe Thr His Thr Pro Pro Leu
770                 775                 780

Asp Pro Gln Glu Leu Asp Ile Leu Lys Thr Val Lys Glu Ile Thr Gly
785                 790                 795                 800

Phe Leu Leu Ile Gln Ala Trp Pro Glu Asn Arg Thr Asp Leu His Ala
                805                 810                 815

Phe Glu Asn Leu Glu Ile Ile Arg Gly Arg Thr Lys Gln His Gly Gln
                820                 825                 830

Phe Ser Leu Ala Val Val Ser Leu Asn Ile Thr Ser Leu Gly Leu Arg
835                 840                 845

Ser Leu Lys Glu Ile Ser Asp Gly Asp Val Ile Ile Ser Gly Asn Lys
850                 855                 860

Asn Leu Cys Tyr Ala Asn Thr Ile Asn Trp Lys Lys Leu Phe Gly Thr
865                 870                 875                 880

Ser Gly Gln Lys Thr Lys Ile Ile Ser Asn Arg Gly Glu Asn Ser Cys
                885                 890                 895

Lys Ala Thr Gly Gln Val Cys His Ala Leu Cys Ser Pro Glu Gly Cys
                900                 905                 910

Trp Gly Pro Glu Pro Arg Asp Cys Val Ser Cys Arg Asn Val Ser Arg
                915                 920                 925

Gly Arg Glu Cys Val Asp Lys Cys Asn Leu Leu Glu Gly Glu Pro Arg
            930                 935                 940

Glu Phe Val Glu Asn Ser Glu Cys Ile Gln Cys His Pro Glu Cys Leu
945                 950                 955                 960

Pro Gln Ala Met Asn Ile Thr Cys Thr Gly Arg Gly Pro Asp Asn Cys
                965                 970                 975

Ile Gln Cys Ala His Tyr Ile Asp Gly Pro His Cys Val Lys Thr Cys
                980                 985                 990

Pro Ala Gly Val Met Gly Glu Asn Asn Thr Leu Val Trp Lys Tyr Ala
            995                 1000                1005

Asp Ala Gly His Val Cys His Leu Cys His Pro Asn Cys Thr Tyr Gly
1010                1015                1020

Cys Thr Gly Pro Gly Leu Glu Gly Cys Pro Thr Asn Gly Pro Lys Ile
1025                1030                1035                1040

Pro Ser Ile Ala Thr Gly Met Val Gly Ala Leu Leu Leu Leu Leu Val
            1045                1050                1055

Val Ala Leu Gly Ile Gly Leu Phe Met
            1060                1065

<210> SEQ ID NO 3
<211> LENGTH: 1068
<212> TYPE: PRT
<213> ORGANISM: Artificial Sequence
<220> FEATURE:
<223> OTHER INFORMATION: 4M5.3-CAR AMINO ACID SEQUENCE

<400> SEQUENCE: 3

| | | | | | | | | | | | | | | |
|---|---|---|---|---|---|---|---|---|---|---|---|---|---|---|
|Met|Leu|Leu|Leu|Val|Thr|Ser|Leu|Leu|Cys|Glu|Leu|Pro|His|Pro|
|1| | | |5| | | | |10| | | | |15|

Ala Phe Leu Leu Ile Pro Asp Val Met Thr Gln Thr Pro Leu Ser
     20       25       30

Leu Pro Val Ser Leu Gly Asp Gln Ala Ser Ile Ser Cys Arg Ser Ser
    35       40       45

Gln Ser Leu Val His Ser Asn Gly Asn Thr Tyr Leu Arg Trp Tyr Leu
  50       55       60

Gln Lys Pro Gly Gln Ser Pro Lys Val Leu Ile Tyr Lys Val Ser Asn
65       70       75      80

Arg Val Ser Gly Val Pro Asp Arg Phe Ser Gly Ser Gly Ser Gly Thr
     85       90      95

Asp Phe Thr Leu Lys Ile Asn Arg Val Glu Ala Glu Asp Leu Gly Val
     100      105      110

Tyr Phe Cys Ser Gln Ser Thr His Val Pro Trp Thr Phe Gly Gly Gly
   115      120      125

Thr Lys Leu Glu Ile Lys Ser Ser Ala Asp Asp Ala Lys Lys Asp Ala
  130      135      140

Ala Lys Lys Asp Asp Ala Lys Lys Asp Asp Ala Lys Lys Asp Gly Gly
145       150      155      160

Val Lys Leu Asp Glu Thr Gly Gly Gly Leu Val Gln Pro Gly Gly Ala
     165      170      175

Met Lys Leu Ser Cys Val Thr Ser Gly Phe Thr Phe Gly His Tyr Trp
    180      185      190

Met Asn Trp Val Arg Gln Ser Pro Glu Lys Gly Leu Glu Trp Val Ala
   195      200      205

Gln Phe Arg Asn Lys Pro Tyr Asn Tyr Glu Thr Tyr Tyr Ser Asp Ser
  210      215      220

Val Lys Gly Arg Phe Thr Ile Ser Arg Asp Asp Ser Lys Ser Ser Val
225       230      235      240

Tyr Leu Gln Met Asn Asn Leu Arg Val Glu Asp Thr Gly Ile Tyr Tyr
     245      250      255

Cys Thr Gly Ala Ser Tyr Gly Met Glu Tyr Leu Gly Gln Gly Thr Ser
   260      265      270

Val Thr Val Ser Glu Ser Lys Tyr Gly Pro Pro Cys Pro Pro Cys Pro
    275      280      285

Ala Pro Glu Phe Asp Gly Gly Pro Ser Val Phe Leu Phe Pro Pro Lys
  290      295      300

Pro Lys Asp Thr Leu Met Ile Ser Arg Thr Pro Glu Val Thr Cys Val
305       310      315      320

Val Val Asp Val Ser Gln Glu Asp Pro Glu Val Gln Phe Asn Trp Tyr
     325      330      335

Val Asp Gly Val Glu Val His Asn Ala Lys Thr Lys Pro Arg Glu Glu
    340      345      350

Gln Phe Gln Ser Thr Tyr Arg Val Val Ser Val Leu Thr Val Leu His
   355      360      365

Gln Asp Trp Leu Asn Gly Lys Glu Tyr Lys Cys Lys Val Ser Asn Lys
  370      375      380

Gly Leu Pro Ser Ser Ile Glu Lys Thr Ile Ser Lys Ala Lys Gly Gln
385       390      395      400

Pro Arg Glu Pro Gln Val Tyr Thr Leu Pro Pro Ser Gln Glu Glu Met

```
                    405                 410                 415
Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Arg Leu Thr Val Asp Lys Ser Arg Trp Gln Glu Gly Asn Val
465                 470                 475                 480

Phe Ser Cys Ser Val Met His Glu Ala Leu His Asn His Tyr Thr Gln
            485                 490                 495

Lys Ser Leu Ser Leu Ser Leu Gly Lys Met Phe Trp Val Leu Val Val
            500                 505                 510

Val Gly Gly Val Leu Ala Cys Tyr Ser Leu Leu Val Thr Val Ala Phe
            515                 520                 525

Ile Ile Phe Trp Val Lys Arg Gly Arg Lys Lys Leu Leu Tyr Ile Phe
            530                 535                 540

Lys Gln Pro Phe Met Arg Pro Val Gln Thr Thr Gln Glu Glu Asp Gly
545                 550                 555                 560

Cys Ser Cys Arg Phe Pro Glu Glu Glu Glu Gly Gly Cys Glu Leu Arg
                    565                 570                 575

Val Lys Phe Ser Arg Ser Ala Asp Ala Pro Ala Tyr Gln Gln Gly Gln
                    580                 585                 590

Asn Gln Leu Tyr Asn Glu Leu Asn Leu Gly Arg Arg Glu Glu Tyr Asp
            595                 600                 605

Val Leu Asp Lys Arg Arg Gly Arg Asp Pro Glu Met Gly Gly Lys Pro
610                 615                 620

Arg Arg Lys Asn Pro Gln Glu Gly Leu Tyr Asn Glu Leu Gln Lys Asp
625                 630                 635                 640

Lys Met Ala Glu Ala Tyr Ser Glu Ile Gly Met Lys Gly Glu Arg Arg
                    645                 650                 655

Arg Gly Lys Gly His Asp Gly Leu Tyr Gln Gly Leu Ser Thr Ala Thr
            660                 665                 670

Lys Asp Thr Tyr Asp Ala Leu His Met Gln Ala Leu Pro Pro Arg Leu
            675                 680                 685

Glu Gly Gly Gly Glu Gly Arg Gly Ser Leu Leu Thr Cys Gly Asp Val
            690                 695                 700

Glu Glu Asn Pro Gly Pro Arg Met Leu Leu Leu Val Thr Ser Leu Leu
705                 710                 715                 720

Leu Cys Glu Leu Pro His Pro Ala Phe Leu Leu Ile Pro Arg Lys Val
                    725                 730                 735

Cys Asn Gly Ile Gly Ile Gly Glu Phe Lys Asp Ser Leu Ser Ile Asn
            740                 745                 750

Ala Thr Asn Ile Lys His Phe Lys Asn Cys Thr Ser Ile Ser Gly Asp
            755                 760                 765

Leu His Ile Leu Pro Val Ala Phe Arg Gly Asp Ser Phe Thr His Thr
            770                 775                 780

Pro Pro Leu Asp Pro Gln Glu Leu Asp Ile Leu Lys Thr Val Lys Glu
785                 790                 795                 800

Ile Thr Gly Phe Leu Leu Ile Gln Ala Trp Pro Glu Asn Arg Thr Asp
                    805                 810                 815

Leu His Ala Phe Glu Asn Leu Glu Ile Ile Arg Gly Arg Thr Lys Gln
            820                 825                 830
```

```
His Gly Gln Phe Ser Leu Ala Val Val Ser Leu Asn Ile Thr Ser Leu
            835                 840                 845
Gly Leu Arg Ser Leu Lys Glu Ile Ser Asp Gly Asp Val Ile Ile Ser
    850                 855                 860
Gly Asn Lys Asn Leu Cys Tyr Ala Asn Thr Ile Asn Trp Lys Lys Leu
865                 870                 875                 880
Phe Gly Thr Ser Gly Gln Lys Thr Lys Ile Ile Ser Asn Arg Gly Glu
                885                 890                 895
Asn Ser Cys Lys Ala Thr Gly Gln Val Cys His Ala Leu Cys Ser Pro
            900                 905                 910
Glu Gly Cys Trp Gly Pro Glu Pro Arg Asp Cys Val Ser Cys Arg Asn
        915                 920                 925
Val Ser Arg Gly Arg Glu Cys Val Asp Lys Cys Asn Leu Leu Glu Gly
    930                 935                 940
Glu Pro Arg Glu Phe Val Glu Asn Ser Glu Cys Ile Gln Cys His Pro
945                 950                 955                 960
Glu Cys Leu Pro Gln Ala Met Asn Ile Thr Cys Thr Gly Arg Gly Pro
                965                 970                 975
Asp Asn Cys Ile Gln Cys Ala His Tyr Ile Asp Gly Pro His Cys Val
            980                 985                 990
Lys Thr Cys Pro Ala Gly Val Met Gly Glu Asn Asn Thr Leu Val Trp
        995                 1000                1005
Lys Tyr Ala Asp Ala Gly His Val Cys His Leu Cys His Pro Asn Cys
    1010                1015                1020
Thr Tyr Gly Cys Thr Gly Pro Gly Leu Glu Gly Cys Pro Thr Asn Gly
1025                1030                1035                1040
Pro Lys Ile Pro Ser Ile Ala Thr Gly Met Val Gly Ala Leu Leu Leu
                1045                1050                1055
Leu Leu Val Val Ala Leu Gly Ile Gly Leu Phe Met
            1060                1065

<210> SEQ ID NO 4
<211> LENGTH: 3207
<212> TYPE: DNA
<213> ORGANISM: Artificial Sequence
<220> FEATURE:
<223> OTHER INFORMATION: 4M5.3-CAR NUCLEOTIDE ACID SEQUENCE

<400> SEQUENCE: 4
atgcttctcc tggtgacaag ccttctgctc tgtgagttac cacacccagc attcctcctg      60
atcccagacg ttgtaatgac ccagaccect ctgtctctcc ccgtaagctt gggcgaccag     120
gcgagcatct cttgtcggtc ttcccagtcc ctggtccatt caaacggcaa tacttacttg     180
cggtggtact tgcagaagcc cggtcaatcc ccaaaagtgc tgatatacaa ggttagcaat     240
cgggtcagtg gagtgcccga ccgcttcagc ggaagcggat ccgggactga cttcactctg     300
aagatcaacc gggtagaagc tgaagacctg ggggtgtact tctgctctca gtcaacacac     360
gtgccatgga cctttggagg tggcaccaag ctggaaatca atcatcagc ggacgatgcc     420
aaaaagacg cggccaagaa ggacgatgcc aagaaggatg atgctaaaaa ggatggcgga     480
gtcaaattgg acgagacagg cggggactg tgcagcccg gcggtgccat gaaactgtct     540
tgtgtgacca gcggctttac cttcgggcat tattggatga actgggtgcg acagtctcca     600
gagaaagggc tcgagtgggt ggcccagttt cgaaataaac cgtacaatta tgagacctac     660
tattcagatt ctgtgaaagg gcgcttcact atttcacgcg acgacagcaa aagttccgtc     720
```

```
taccttcaga tgaacaacct tagagtggag gataccggaa tatactactg cacgggtgcc      780
agttatggca tggagtactt ggggcagggg acatctgtga ccgtttctga gagcaagtac      840
ggaccgccct gccccccttg ccctgccccc gagttcgacg gcggacccag cgtgttcctg      900
ttccccccca agcccaagga caccctgatg atcagccgga cccccgaggt gacctgcgtg      960
gtggtggacg tgagccagga agatcccgag gtccagttca attggtacgt ggacggcgtg     1020
gaagtgcaca acgccaagac caagcccaga gaggaacagt tccagagcac ctaccgggtg     1080
gtgtctgtgc tgaccgtgct gcaccaggac tggctgaacg gcaaagaata caagtgcaag     1140
gtgtccaaca agggcctgcc cagcagcatc gaaaagacca tcagcaaggc caagggccag     1200
cctcgcgagc cccaggtgta caccctgcct ccctcccagg aagagatgac caagaaccag     1260
gtgtccctga cctgcctggt gaagggcttc taccccagcg acatcgccgt ggagtgggag     1320
agcaacggcc agcctgagaa caactacaag accacccctc ccgtgctgga cagcgacggc     1380
agcttcttcc tgtacagccg gctgaccgtg gacaagagcc ggtggcagga aggcaacgtc     1440
tttagctgca gcgtgatgca cgaggccctg cacaaccact acacccagaa gagcctgagc     1500
ctgtccctgg gcaagatgtt ctgggtgctg gtggtggtgg gcggggtgct ggcctgctac     1560
agcctgctgg tgacagtggc cttcatcatc tttgggtga acgggcag aaagaaactc     1620
ctgtatatat tcaaacaacc atttatgaga ccagtacaaa ctactcaaga ggaagatggc     1680
tgtagctgcc gatttccaga agaagaagaa ggaggatgtg aactgcgggt gaagttcagc     1740
agaagcgccg acgcccctgc ctaccagcag ggccagaatc agctgtacaa cgagctgaac     1800
ctgggcagaa gggaagagta cgacgtcctg gataagcgga gaggccggga ccctgagatg     1860
ggcggcaagc ctcggcggaa gaaccccag gaaggcctgt ataacgaact gcagaaagac     1920
aagatggccg aggcctacag cgagatcggc atgaagggcg agcggaggcg gggcaagggc     1980
cacgacggcc tgtatcaggg cctgtccacc gccaccaagg ataccctacga cgccctgcac     2040
atgcaggccc tgccccaag gctcgagggc ggcggagagg gcagaggaag tcttctaaca     2100
tgcggtgacg tggaggagaa tcccggccct aggatgcttc tcctggtgac aagccttctg     2160
ctctgtgagt taccacaccc agcattcctc ctgatcccac gcaaagtgtg taacggaata     2220
ggtattggtg aatttaaaga ctcactctcc ataaatgcta cgaatattaa acacttcaaa     2280
aactgcacct ccatcagtgg cgatctccac atcctgccgg tggcatttag gggtgactcc     2340
ttcacacata ctcctcctct ggatccacag gaactggata ttctgaaaac cgtaaaggaa     2400
atcacagggt ttttgctgat tcaggcttgg cctgaaaaca ggacggacct ccatgccttt     2460
gagaacctag aaatcatacg cggcaggacc aagcaacatg gtcagttttc tcttgcagtc     2520
gtcagcctga acataacatc cttgggatta cgctccctca aggagataag tgatggagat     2580
gtgataattt caggaaacaa aaatttgtgc tatgcaaata caataaactg gaaaaaactg     2640
tttgggacct ccgtcagaa aaccaaaatt ataagcaaca gaggtgaaaa cagctgcaag     2700
gccacaggcc aggtctgcca tgccttgtgc tcccccgagg gctgctgggg cccggagccc     2760
agggactgcg tctcttgccg gaatgtcagc cgaggcaggg aatgcgtgga caagtgcaac     2820
cttctggagg gtgagccaag ggagtttgtg agaactctg agtgcataca gtgccaccca     2880
gagtgcctgc ctcaggccat gaacatcacc tgcacaggac ggggaccaga caactgtatc     2940
cagtgtgccc actacattga cggccccac tgcgtcaaga cctgcccggc aggagtcatg     3000
ggagaaaaca acaccctggt ctggaagtac gcagacgccg ccatgtgtg ccacctgtgc     3060
```

```
catccaaact gcacctacgg atgcactggg ccaggtcttg aaggctgtcc aacgaatggg    3120
cctaagatcc cgtccatcgc cactgggatg gtgggggccc tcctcttgct gctggtggtg    3180
gccctgggga tcggcctctt catgtga                                        3207
```

METHODS OF USE FOR CAR T CELLS

CROSS-REFERENCE TO RELATED APPLICATIONS

This application claims priority to U.S. Prov. App. No. 62/736,727 filed Sep. 26, 2018 entitled "METHODS OF USE FOR CAR T CELLS", U.S. Prov. App. No. 62/735,627 filed Sep. 24, 2018 entitled "METHODS OF USE FOR CAR T CELLS", U.S. Prov. App. No. 62/724,171 filed Aug. 29, 2018 entitled "METHODS OF USE FOR CAR T CELLS", U.S. Prov. App. No. 62/656,233 filed Apr. 11, 2018 entitled "METHODS OF USE FOR CAR T CELLS", U.S. Prov. App. No. 62/620,706 filed Jan. 23, 2018 entitled "METHODS OF USE FOR CAR T CELLS", and U.S. Prov. App. No. 62/620,414 filed Jan. 22, 2018 entitled "METHODS OF USE FOR CAR T CELLS", which are each incorporated by reference in its entirety.

REFERENCE TO SEQUENCE LISTING

The present application is being filed along with a Sequence Listing in electronic format. The Sequence Listing is provided as a file entitled SCRI200ASEQLIST, created Jan. 14, 2019, which is approximately 26 Kb in size. The information in the electronic format of the Sequence Listing is incorporated herein by reference in its entirety.

TECHNICAL FIELD

The present disclosure relates to methods of treating a patient with a cancer by administering to the patient a composition comprising CAR T cells wherein the CAR T cells comprise a CAR and the CAR comprises an E2 anti-fluorescein antibody fragment, and administering to the patient a small molecule linked to a targeting moiety by a linker. The disclosure also relates to compositions for use in such methods.

BACKGROUND

Immunotherapy based on adoptive transfer of lymphocytes (e.g., T cells) into a patient is a valuable therapy in the treatment of cancer and other diseases. Many important advancements have been made in the development of immunotherapies based on adoptive transfer of lymphocytes. Among the many different types of immunotherapeutic agents, one of the most promising of the immunotherapeutic agents being developed is T cells expressing chimeric antigen receptors (CAR T cells). The chimeric antigen receptor (CAR) is a genetically engineered receptor that is designed to target a specific antigen, for example, a tumor antigen. This targeting can result in cytotoxicity against the tumor, for example, such that CAR T cells expressing CARs can target and kill tumors via the specific tumor antigens.

First generation CARs are composed of a recognition region, e.g., a single chain fragment variable (scFv) region derived from an antibody for recognition and binding to the antigen expressed by the tumor, and an activation signaling domain, e.g., the CD3ζ chain of T cells can serve as a T cell activation signal in CARs. Although CAR T cells have shown positive results in vitro, they have had limited success in eliminating disease (e.g., cancer) in clinical trials. One problem has been the inability to prolong activation and expand the CAR T cell population in vivo.

To address this problem, a co-stimulation domain (e.g., CD137, CD28 or CD134) has been included in second generation CARs to achieve prolonged activation of T cells in vivo. Addition of a co-stimulation domain enhances the in vivo proliferation and survival of T cells containing CARs, and initial clinical data have shown that such constructs are promising therapeutic agents in the treatment of diseases, such as cancer.

Although improvements have been made in CAR T cell therapies, several problems remain. First, 'off-target' toxicity may occur due to normal cells that express the antigen targeted by the CAR T cells (e.g., a tumor-associated antigen). Second, unregulated CAR T cell activation may be found where the rapid and uncontrolled elimination of diseased cells (e.g., cancer cells) by CAR T cells induces a constellation of metabolic disturbances, called tumor lysis syndrome, or cytokine release syndrome (CRS), which can be fatal to patients. Tumor lysis syndrome and CRS can result due to administered CAR T cells that cannot be easily regulated, and are activated uncontrollably. Accordingly, although CAR T cells show great promise as a tool in the treatment of diseases, such as cancer, additional CAR T cell therapies are needed that provide reduced off-target toxicity, and more precise control of CAR T cell activation.

SUMMARY OF THE INVENTION

The present inventors have discovered methods of reducing off-target toxicity, and more precisely controlling CAR T cell activation, providing important advancements in CAR T cell therapy. In the various embodiments described herein, a small molecule ligand linked to a targeting moiety by a linker is used as a bridge between the cancer and CAR T cells expressing a CAR wherein the CAR comprises an E2 anti-fluorescein antibody fragment. The bridge directs the CAR T cells, expressing a CAR comprising an E2 anti-fluorescein antibody fragment, to the cancer for amelioration of the cancer. In one embodiment, the "small molecule ligand" can be, for example, a folate, DUPA, an NK-1R ligand, a CAIX ligand, a ligand of gamma glutamyl transpeptidase, an NKG2D ligand, or a CCK2R ligand, each of which is a small molecule ligand that binds specifically to cancer cells (i.e., the receptor for these ligands is overexpressed on cancers compared to normal tissues).

In one embodiment, the "small molecule ligand" is linked to a "targeting moiety" that binds to the CAR expressed by CAR T cells. In various embodiments, the "targeting moiety" can be selected, for example, from fluorescein, fluorescein isothiocyanate (FITC), NHS and/or fluorescein.

The "targeting moiety" binds to the recognition region of the genetically engineered CAR, expressing an E2 anti-fluorescein antibody fragment. Accordingly, the recognition region of the CAR (e.g., a single chain variable region (scFv) of an E2 anti-fluorescein antibody fragment, an Fab, Fv, Fc, (Fab')2 fragment, and the like) is directed to the "targeting moiety." Thus, the small molecule ligand linked to a targeting moiety by a linker acts as a bridge between the cancer and the CAR T cells, expressing an E2 anti-fluorescein antibody fragment, directing the CAR T cells to the cancer for amelioration of the cancer.

In one embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a first dose of a CAR T cell composition comprising CAR T cells wherein the CAR T cells comprise a CAR directed to the targeting moiety and wherein the CAR comprises an E2 anti-fluorescein antibody fragment, and iii)

administering to the patient a second dose of a CAR T cell composition comprising CAR T cells wherein the CAR T cells comprise the CAR directed to the targeting moiety and wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells, wherein the CAR T cells comprise a CAR directed to the targeting moiety wherein the CAR comprises an E2 anti-fluorescein antibody fragment, and wherein the CAR T cell composition comprises a mixture of the CAR T cells and non-transformed T cells.

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells wherein the CAR T cells comprise a CAR directed to the targeting moiety and wherein the CAR comprises an E2 anti-fluorescein antibody fragment; and iii) administering to the patient a folate, a conjugate comprising a folate wherein the conjugate comprising a folate does not comprise a targeting moiety, or an agent that inhibits activation of the CAR T cells.

In still another embodiment, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR directed to the targeting moiety and wherein the CAR comprises an E2 anti-fluorescein antibody fragment.

In another illustrative embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof; and iii) administering to the patient a dose of a CAR T cell composition comprising CAR T cells wherein the CAR T cells comprise a CAR directed to the targeting moiety and wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is administered at a dose of about 10 nmoles/kg of body weight of the patient to about 2500 nmoles/kg of body weight of the patient, and ii) administering to the patient a CAR T cell composition comprising CAR T cells, wherein the CAR T cells comprise a CAR, wherein the CAR comprises an E2 anti-fluorescein antibody fragment, and wherein the CAR T cells are at a dose of about 1 million of the CART cells to about 15 million of the CART cells.

In still another embodiment, a method of treatment of a cancer is provided. The method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR, wherein the CAR comprises an E2 anti-fluorescein antibody fragment, and iii) ending the continuous administration of the compound, or the pharmaceutically acceptable salt thereof, to inhibit or prevent cytokine release syndrome in the patient.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient, and ii) administering to the patient a CAR T cell composition comprising CAR T cells wherein the CAR T cells comprise a CAR, wherein the CAR comprises an E2 anti-fluorescein antibody fragment.

In still another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient before the administration of a CAR T cell composition comprising CAR T cells wherein the CAR T cells comprise a CAR directed to the targeting moiety, ii) then administering to the patient a dose of the CAR T cell composition, and iii) then administering to the patient a second dose of the compound, or the pharmaceutically acceptable salt thereof, wherein the CAR comprises an E2 anti-fluorescein antibody fragment.

Additional embodiments are also described by the following enumerated clauses. Any of the following embodiments in combination with any applicable embodiments described in the Summary section, the Detailed Description of the Illustrative Embodiments section, the Examples section, or the claims of this patent application, are also contemplated.

1. A method of treatment of a cancer, the method comprising i) administering to a patient a compound, or a pharmaceutically acceptable salt thereof, wherein the compound comprises a small molecule ligand linked to a targeting moiety by a linker; ii) administering to the patient a first dose of a CAR T cell composition comprising CAR T cells wherein the CAR T cells comprise a CAR directed to the targeting moiety and wherein the CAR comprises an E2 anti-fluorescein antibody fragment; and iii) administering to the patient a second dose of a CAR T cell composition comprising CAR T cells wherein the CAR T cells comprise the CAR directed to the targeting moiety and wherein the CAR comprises an E2 anti-fluorescein antibody fragment.

2. A method of treatment of a cancer, the method comprising i) administering to a patient a compound, or a pharmaceutically acceptable salt thereof, wherein the compound comprises a small molecule ligand linked to a targeting moiety by a linker; and ii) administering to the patient a CAR T cell composition wherein the CAR T cell composition comprises CAR T cells, wherein the CAR T cells comprise a CAR directed to the targeting moiety wherein the CAR comprises an E2 anti-fluorescein antibody fragment, and wherein the CAR T cell composition comprises a mixture of the CAR T cells and non-transformed T cells.

3. A method of treatment of a cancer, the method comprising i) administering to a patient a compound, or a pharmaceutically acceptable salt thereof, wherein the compound comprises a small molecule ligand linked to a targeting moiety by a linker; ii) administering to the patient a CAR T cell composition wherein the CAR T cell composition comprises CAR T cells wherein the CAR T cells comprise a CAR directed to the targeting moiety and wherein the CAR comprises an E2 anti-fluorescein antibody fragment; and iii) administering to the patient a folate, a conjugate comprising a folate wherein the conjugate comprising a folate does not comprise a targeting moiety, or an agent that inhibits activation of the CAR T cells.

4. The method of clause 3 wherein step iii comprises administering a folate.

5. The method of any one of clauses 3 or 4 wherein step iii comprises administering folic acid or leucovorin.

6. The method of clause 3 wherein step iii comprises administering the conjugate comprising a folate.

7. The method of clause 6 wherein the conjugate comprising a folate comprises a folate linked to one or more amino acids.

8. The method of clause 7 wherein the conjugate comprising a folate has the formula

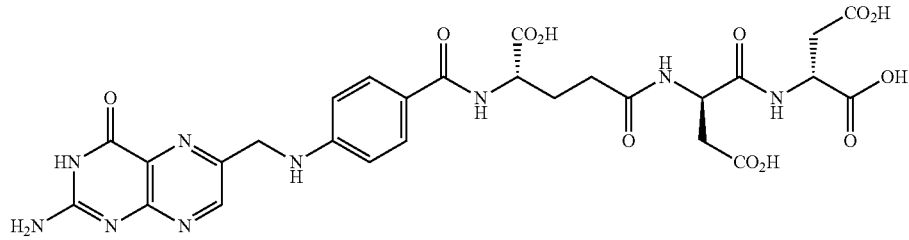 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

9. The method of any one of clauses 3 to 8 wherein the folate has the formula

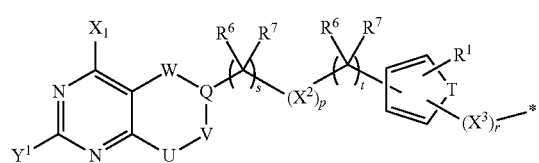

wherein $X^1$ and $Y^1$ are each independently selected from the group consisting of halo, $R^2$, $OR^2$, $SR^3$, and $NR^4R^5$; U, V, and W represent divalent moieties each independently selected from the group consisting of —$(R^{6a})C$=, —N=, —$(R^{6a})C(R^{7a})$—, and —$N(R^{4a})$—; Q is selected from the group consisting of C and CH; T is selected from the group consisting of S, O, N, and —C=C—; $X^2$ and $X^3$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, OC(Z)N($R^{4b}$)—, —N($R^{4b}$)C(Z)O—, —N($R^{4b}$)C(Z)N(R5b)-, —S(O)—, —S(O)2-, —N($R^{4a}$)S(O)2-, —C(R6b)(R7 b)-, —N(C≡CH)—, —N(CH$_2$C≡CH)—, $C_1$-$C_{12}$ alkylene, and $C_1$-$C_{12}$ alkyeneoxy, where Z is oxygen or sulfur; $R^1$ is selected from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl; $R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^h$a and $R^{7a}$ are each independently selected from the group consisting of hydrogen, halo, $C_1$-$C_{12}$ alkyl, and $C_1$-$C_{12}$ alkoxy; or $R^h$a and $R^{7a}$ are taken together to form a carbonyl group; p, r, s, and t are each independently either 0 or 1; and * represents a covalent bond to the rest of the conjugate.

10. The method of clause 3 wherein the agent that inhibits activation of the CART cells is administered and is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CAR T cell binding to the compound, or the pharmaceutically acceptable salt thereof, but does not bind to the cancer.

11. The method of clause 10 wherein the agent that inhibits activation of the CAR T cells is administered and the agent is a lymphocyte-specific protein tyrosine kinase inhibitor.

12. The method of clause 11 wherein the lymphocyte-specific protein tyrosine kinase inhibitor is Dasatinib.

13. The method of clause 10 wherein the agent that inhibits activation of the CAR T cells is administered and the agent is a PI3 kinase inhibitor.

14. The method of clause 13 wherein the PI3 kinase inhibitor is GDC0980.

15. The method of clause 10 wherein the agent that inhibits activation of the CAR T cells is administered and the agent is an IL-2 inducible T cell kinase inhibitor.

16. The method of clause 15 wherein the IL-2 inducible T cell kinase inhibitor is BMS-509744.

17. The method of clause 10 wherein the agent that inhibits activation of the CAR T cells is administered and is an agent that blocks CAR T cell binding to the compound, or the pharmaceutically acceptable salt thereof, but does not bind to the cancer.

18. The method of clause 17 wherein the agent is fluoresceinamine, FITC, or sodium fluorescein.

19. The method of clause 18 wherein the agent is FITC.

20. The method of clause 18 wherein the agent is sodium fluorescein.

21. The method of any one of clauses 17 to 20 wherein the agent that inhibits activation of the CART cells is administered at a dose of about 0.01 to about 300 umoles/kg of body weight of the patient.

22. The method of any one of clauses 17 to 20 wherein the agent that inhibits activation of the CART cells is administered at a dose of about 0.06 to about 100 umoles/kg of body weight of the patient.

23. The method of any one of clauses 17 to 20 wherein the agent that inhibits activation of the CART cells is administered at a dose of about 0.06 to about 90 umoles/kg of body weight of the patient.

24. The method of any one of clauses 17 to 20 wherein the agent that inhibits activation of the CART cells is administered at a dose of about 0.06 to about 80 umoles/kg of body weight of the patient.

25. The method of any one of clauses 17 to 20 wherein the agent that inhibits activation of the CART cells is administered at a dose of about 0.06 to about 70 umoles/kg of body weight of the patient.

26. The method of any one of clauses 17 to 20 wherein the agent that inhibits activation of the CART cells is administered at a dose of about 0.06 to about 60 umoles/kg of body weight of the patient.

27. The method of any one of clauses 17 to 20 wherein the agent that inhibits activation of the CART cells is administered at a dose of about 0.06 to about 50 umoles/kg of body weight of the patient.

28. The method of any one of clauses 17 to 20 wherein the agent that inhibits activation of the CART cells is administered at a dose of about 0.06 to about 40 umoles/kg of body weight of the patient.

29. The method of any one of clauses 17 to 20 wherein the agent that inhibits activation of the CART cells is administered at a dose of about 0.06 to about 30 umoles/kg of body weight of the patient.

30. The method of any one of clauses 17 to 20 wherein the agent that inhibits activation of the CART cells is administered at a dose of about 0.06 to about 20 umoles/kg of body weight of the patient.

31. The method of any one of clauses 17 to 20 wherein the agent that inhibits activation of the CART cells is administered at a dose of about 0.06 to about 10 umoles/kg of body weight of the patient.

32. The method of any one of clauses 17 to 20 wherein the agent that inhibits activation of the CAR T cells is administered at a dose of about 0.06 to about 8 umoles/kg of body weight of the patient.

33. The method of any one of clauses 17 to 20 wherein the agent that inhibits activation of the CAR T cells is administered at a dose of about 0.06 to about 6 umoles/kg of body weight of the patient.

34. The method of any one of clauses 3 to 33 wherein more than one dose is administered to the patient of the folate, the conjugate comprising a folate wherein the conjugate comprising a folate does not comprise a targeting moiety, or the agent that inhibits activation of the CAR T cells.

35. The method of any one of clauses 3 to 34 wherein the folate, the conjugate comprising a folate wherein the conjugate comprising a folate does not comprise a targeting moiety, or the agent that inhibits activation of the CAR T cells is administered to the patient before and/or after the compound, or the pharmaceutically acceptable salt thereof.

36. The method of any one of clauses 3 to 35 wherein administration of the folate, the conjugate comprising a folate wherein the conjugate comprising a folate does not comprise a targeting moiety, or the agent that inhibits activation of the CAR T cells causes reduction in cytokine levels in the patient.

37. The method of clause 36 wherein the reduction in cytokine levels occurs by about 3 hours after administration to the patient of the folate, the conjugate comprising a folate wherein the conjugate comprising a folate does not comprise a targeting moiety, or the agent that inhibits activation of the CAR T cells.

38. The method of clause 36 wherein the reduction in cytokine levels occurs by about 6 hours after administration to the patient of the folate, the conjugate comprising a folate wherein the conjugate comprising a folate does not comprise a targeting moiety, or the agent that inhibits activation of the CAR T cells.

39. The method of any one of clauses 36 to 38 wherein the reduction in cytokine levels is a reduction to about the cytokine levels in an untreated patient.

40. The method of any one of clauses 3 to 39 wherein the compound, or the pharmaceutically acceptable salt thereof, is administered before and subsequent to administration of the folate, the conjugate comprising a folate wherein the conjugate comprising a folate does not comprise a targeting moiety, or the agent that inhibits activation of the CAR T cells.

41. The method of any one of clauses 3 to 40 wherein CAR T cell number increases in the blood of the patient after administration of the folate, the conjugate comprising a folate wherein the conjugate comprising a folate does not comprise a targeting moiety, or the agent that inhibits activation of the CAR T cells, even though cytokine levels in the patient are reduced.

42. The method of any one of clauses 3 to 41 wherein CART cell activation is enhanced or maintained, relative to a patient not treated with a rescue agent, after administration of the folate, the conjugate comprising a folate wherein the conjugate comprising a folate does not comprise a targeting moiety, or the agent that inhibits activation of the CAR T cells, even though cytokine levels in the treated patient are reduced.

43. The method of any one of clauses 3 to 42 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

44. The method of clause 43 wherein a complete response for the tumor is obtained.

45. The method of any one of clauses 3 to 44 wherein the folate, the conjugate comprising a folate wherein the conjugate comprising a folate does not comprise a targeting moiety, or the agent that inhibits activation of the CAR T cells the agent that inhibits activation of the CAR T cells is administered to the patient when the CRS grade reaches 1, 2, 3, or 4.

46. The method of clause 45 wherein the agent that inhibits activation of the CAR T cells is administered to the patient when the CRS grade reaches 3 or 4.

47. The method of any one of clauses 3 to 46 wherein lung edema is reduced.

48. The method of any one of clauses 1 to 47 wherein the compound, or the pharmaceutically acceptable salt thereof, is administered at a dose of about 10 nmoles/kg of body weight of the patient to about 2500 nmoles/kg of body weight of the patient; and the CAR T cells are at a dose of about 1 million of the CAR T cells to about 15 million of the CAR T cells.

49. The method of clause 48 wherein the compound, or the pharmaceutically acceptable salt thereof, is administered at a dose of about 10 nmoles/kg to about 100 nmoles/kg of body weight of the patient.

50. The method of any one of clauses 48 to 49 wherein the compound, or the pharmaceutically acceptable salt thereof, is administered at a dose of about 10 nmoles/kg to about 50 nmoles/kg of body weight of the patient.

51. The method of any one of clauses 48 to 50 wherein the compound, or the pharmaceutically acceptable salt thereof, is administered at a dose of about 10 nmoles/kg to about 20 nmoles/kg of body weight of the patient.

52. The method of clause 48 wherein the compound, or the pharmaceutically acceptable salt thereof, is administered at a dose of about 10 nmoles/kg to about 600 nmoles/kg of body weight of the patient.

53. The method of clause 48 wherein the compound, or the pharmaceutically acceptable salt thereof, is administered at a dose of about 200 nmoles/kg to about 600 nmoles/kg of body weight of the patient.

54. The method of clause 48 wherein the compound, or the pharmaceutically acceptable salt thereof, is administered at a dose of about 400 nmoles/kg to about 600 nmoles/kg of body weight of the patient.

55. The method of any one of clauses 48 to 54 wherein the CAR T cells are at a dose of about 1 million of the CAR T cells to about 12.5 million of the CART cells.

56. The method of any one of clauses 48 to 55 wherein the CAR T cells are at a dose of about 1 million of the CAR T cells to about 7 million of the CAR T cells.

57. The method of any one of clauses 48 to 56 wherein the CAR T cells are at a dose of about 1 million of the CAR T cells to about 5 million of the CAR T cells.

58. The method of any one of clauses 48 to 57 wherein the CAR T cells are at a dose of about 2 million of the CAR T cells to about 5 million of the CAR T cells.

59. The method of any one of clauses 1 to 58 further comprising the step of ending continuous administration of the compound, or the pharmaceutically acceptable salt thereof, to inhibit or prevent cytokine release syndrome in the patient.

60. The method of any one of clauses 1 to 59 wherein the compound, or the pharmaceutically acceptable salt thereof, is administered continuously for at least one hour to the patient.

61. The method of any one of clauses 1 to 59 wherein the compound, or the pharmaceutically acceptable salt thereof, is administered continuously for at least four hours to the patient.

62. The method of any one of clauses 1 to 59 wherein the compound, or the pharmaceutically acceptable salt thereof, is administered continuously for at least six hours to the patient.

63. The method of any one of clauses 1 to 62 wherein the compound, or the pharmaceutically acceptable salt thereof, is administered to the patient every other day.

64. The method of any one of clauses 1 to 62 wherein the compound, or the pharmaceutically acceptable salt thereof, is administered to the patient three times weekly.

65. The method of any one of clauses 1 to 62 wherein the compound, or the pharmaceutically acceptable salt thereof, is administered to the patient two times weekly.

66. The method of any one of clauses 1 to 62 wherein the compound, or the pharmaceutically acceptable salt thereof, is administered to the patient once weekly.

67. The method of any one of clauses 1 to 62 wherein compound, or the pharmaceutically acceptable salt thereof, is administered to the patient until an unacceptable loss of body weight of the patient, a fever, a drop in blood pressure, or pulmonary edema occurs.

68. A method of treatment of a cancer, the method comprising i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof; and ii) administering to the patient a CAR T cell composition comprising CAR T cells wherein the CAR T cells comprise a CAR directed to the targeting moiety and wherein the CAR comprises an E2 anti-fluorescein antibody fragment.

69. The method of clause 68 wherein at least a first dose, a second dose, and a third dose of the compound, or the pharmaceutically acceptable salt thereof, are administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

70. The method of clause 68 wherein at least a first dose, a second dose, a third dose, and a fourth dose of the compound, or the pharmaceutically acceptable salt thereof, are administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

71. The method of clause 70 wherein the second dose of the compound, or the pharmaceutically acceptable salt thereof, is about 100-fold greater in amount than the first dose of the compound, or the pharmaceutically acceptable salt thereof, wherein the third dose of the compound, or the pharmaceutically acceptable salt thereof, is about 1000-fold greater in amount than the first dose of the compound, or the pharmaceutically acceptable salt thereof, and wherein the fourth dose of the compound, or the pharmaceutically acceptable salt thereof, is about 10000-fold greater in amount than the first dose of the compound, or the pharmaceutically acceptable salt thereof.

72. The method of clause 68 wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof.

73. A method of treatment of a cancer, the method comprising i) administering to a patient a first dose of a compound, or a pharmaceutically acceptable salt thereof, wherein the compound comprises a small molecule ligand linked to a targeting moiety by a linker; ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof and iii) administering to the patient a dose of a CAR T cell composition comprising CAR T cells wherein the CAR T cells comprise a CAR directed to the targeting moiety and wherein the CAR comprises an E2 anti-fluorescein antibody fragment.

74. The method of clause 74 wherein the second dose of the compound, or the pharmaceutically acceptable salt thereof, is at least about 60 percent lower in amount than the first dose of the compound, or the pharmaceutically acceptable salt thereof.

75. The method of clause 74 wherein the second dose of the compound, or the pharmaceutically acceptable salt thereof, is at least about 70 percent lower in amount than the first dose of the compound, or the pharmaceutically acceptable salt thereof.

76. The method of clause 74 wherein the second dose of the compound, or the pharmaceutically acceptable salt thereof, is at least about 80 percent lower in amount than the first dose of the compound, or the pharmaceutically acceptable salt thereof.

77. The method of clause 74 wherein the second dose of the compound, or the pharmaceutically acceptable salt thereof, is at least about 90 percent lower in amount than the first dose of the compound, or the pharmaceutically acceptable salt thereof.

78. The method of clause 74 wherein the second dose of the compound, or the pharmaceutically acceptable salt thereof, is at least about 95 percent lower in amount than the first dose of the compound, or the pharmaceutically acceptable salt thereof.

79. The method of clause 74 wherein the second dose of the compound, or the pharmaceutically acceptable salt thereof, is at least about 96 percent lower in amount than the first dose of the compound, or the pharmaceutically acceptable salt thereof.

80. The method of clause 74 wherein the second dose of the compound, or the pharmaceutically acceptable salt thereof, is at least about 97 percent lower in amount than the first dose of the compound, or the pharmaceutically acceptable salt thereof.

81. The method of clause 74 wherein the second dose of the compound, or the pharmaceutically acceptable salt thereof, is at least about 98 percent lower in amount than the first dose of the compound, or the pharmaceutically acceptable salt thereof.

82. The method of clause 74 wherein the second dose of the compound, or the pharmaceutically acceptable salt thereof, is at least about 99 percent lower in amount than the first dose of the compound, or the pharmaceutically acceptable salt thereof.

83. The method of clause 74 wherein the second dose of the compound, or the pharmaceutically acceptable salt thereof, is at least about 99.5 percent lower in amount than the first dose of the compound, or the pharmaceutically acceptable salt thereof.

84. The method of any one of clauses 73 to 83 wherein the first dose of the compound, or the pharmaceutically acceptable salt thereof, is about 100 nmoles/kg to about 1000 nmoles/kg of body weight of the patient.

85. The method of any one of clauses 73 to 83 wherein the first dose of the compound, or the pharmaceutically acceptable salt thereof, is about 100 nmoles/kg to about 900 nmoles/kg of body weight of the patient.

86. The method of any one of clauses 73 to 83 wherein the first dose of the compound, or the pharmaceutically acceptable salt thereof, is about 100 nmoles/kg to about 800 nmoles/kg of body weight of the patient.

87. The method of any one of clauses 73 to 83 wherein the first dose of the compound, or the pharmaceutically acceptable salt thereof, is about 100 nmoles/kg to about 700 nmoles/kg of body weight of the patient.

88. The method of any one of clauses 73 to 83 wherein the first dose of the compound, or the pharmaceutically acceptable salt thereof, is about 100 nmoles/kg to about 600 nmoles/kg of body weight of the patient.

89. The method of any one of clauses 73 to 83 wherein the first dose of the compound, or the pharmaceutically acceptable salt thereof, is about 200 nmoles/kg to about 600 nmoles/kg of body weight of the patient.

90. The method of any one of clauses 73 to 83 wherein the first dose of the compound, or the pharmaceutically acceptable salt thereof, is about 400 nmoles/kg to about 600 nmoles/kg of body weight of the patient.

91. The method of any one of clauses 73 to 83 wherein the first dose of the compound, or the pharmaceutically acceptable salt thereof, is about 500 nmoles/kg of body weight of the patient.

92. The method of clause 84 wherein the second dose of the compound, or the pharmaceutically acceptable salt thereof, is about 0.5 nmoles/kg to about 500 nmoles/kg of body weight of the patient.

93. The method of clause 85 wherein the second dose of the compound, or the pharmaceutically acceptable salt thereof, is about 0.5 nmoles/kg to about 450 nmoles/kg of body weight of the patient.

94. The method of clause 86 wherein the second dose of the compound, or the pharmaceutically acceptable salt thereof, is about 0.5 nmoles/kg to about 400 nmoles/kg of body weight of the patient.

95. The method of clause 87 wherein the second dose of the compound, or the pharmaceutically acceptable salt thereof, is about 0.5 nmoles/kg to about 350 nmoles/kg of body weight of the patient.

96. The method of clause 88 wherein the second dose of the compound, or the pharmaceutically acceptable salt thereof, is about 0.5 nmoles/kg to about 300 nmoles/kg of body weight of the patient.

97. The method of clause 89 wherein the second dose of the compound, or the pharmaceutically acceptable salt thereof, is about 1 nmole/kg to about 300 nmoles/kg of body weight of the patient.

98. The method of clause 90 wherein the second dose of the compound, or the pharmaceutically acceptable salt thereof, is about 2 nmoles/kg to about 300 nmoles/kg of body weight of the patient.

99. The method of clause 91 wherein the second dose of the compound, or the pharmaceutically acceptable salt thereof, is about 2 nmoles/kg to about 250 nmoles/kg of body weight of the patient.

100. The method of any one of clauses 92 to 99 wherein the second dose of the compound, or the pharmaceutically acceptable salt thereof, is about 5 nmoles/kg to about 40 nmoles/kg of body weight of the patient.

101. The method of any one of clauses 92 to 99 wherein the second dose of the compound, or the pharmaceutically acceptable salt thereof, is about 40 nmoles/kg to about 150 nmoles/kg of body weight of the patient.

102. The method of any one of clauses 73 to 101 further comprising administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof.

103. The method of clause 102 further comprising administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof.

104. The method of any one of clauses 73 to 103 wherein the dose(s) of the compound, or the pharmaceutically acceptable salt thereof, administered after the first dose of the compound, or the pharmaceutically acceptable salt thereof, maintain inhibition of growth of the cancer relative to the first dose of the compound, or the pharmaceutically acceptable salt thereof.

105. The method of any one of clauses 73 to 104 wherein the CART cells are administered at a dose of about 1 million of the CAR T cells to about 40 million of the CAR T cells.

106. The method of any one of clauses 73 to 105 wherein the dose(s) of the compound, or the pharmaceutically acceptable salt thereof, administered after the first dose of the compound, or the pharmaceutically acceptable salt thereof, are administered once weekly.

107. The method of any one of clauses 73 to 105 wherein the dose(s) of the compound, or the pharmaceutically acceptable salt thereof, are administered twice weekly.

108. The method of any one of clauses 1 to 107 wherein the CAR further comprises an IgG4 hinge domain, a CD3ζ activation domain, and a 4-1BB co-stimulation domain.

109. The method of any one of clauses 1 to 108 wherein the E2 anti-fluorescein antibody fragment is an scFv fragment.

110. The method of any one of clauses 1 to 109 wherein the CAR protein sequence has at least about 90% identity to SEQ ID NO:2.

111. The method of any one of clauses 1 to 10 9 wherein the CAR protein sequence has at least about 95% identity to SEQ ID NO:2.

112. The method of any one of clauses 1 to 109 wherein the CAR protein sequence has at least about 98% identity to SEQ ID NO:2.

113. The method of any one of clauses 1 to 112 wherein the CAR binds fluorescein.

114. The method of any one of clauses 1 to 109 wherein the CAR protein sequence has up to about 50 conservative amino acid substitutions and wherein the CAR binds fluorescein.

115. The method of any one of clauses 1 to 109 wherein the CAR is encoded by a polynucleotide having at least about 90% identity to SEQ ID NO:1.

116. The method of any one of clauses 1 to 109 wherein the CAR is encoded by a polynucleotide having at least about 95% identity to SEQ ID NO:1.

117. The method of any one of clauses 1 to 109 wherein the CAR is encoded by a polynucleotide having at least about 98% identity to SEQ ID NO:1.

118. The method of any one of clauses 115 to 117 wherein the CAR binds fluorescein.

119. The method of any one of clauses 1 to 118 wherein the CAR is encoded by a polynucleotide that hybridizes under high stringency conditions to a polynucleotide having SEQ ID NO:1 and wherein the CAR binds fluorescein.

120. The method of any one of clauses 1 to 119 wherein the CAR is encoded by a polynucleotide having SEQ ID NO:1, or by a degenerate variant of SEQ ID NO:1.

121. The method of any one of clauses 1 to 120 wherein the ligand is selected from the group consisting of a folate, DUPA, an NK-1R ligand, a CAIX ligand, a ligand of gamma glutamyl transpeptidase, an NKG2D ligand, and a CCK2R ligand.

122. The method of any one of clauses 1 to 121 wherein the targeting moiety is fluorescein, or a pharmaceutically acceptable salt thereof.

123. The method of any one of clauses 1 to 122 wherein the linker comprises polyethylene glycol (PEG), polyproline, a hydrophilic amino acid, a sugar, an unnatural peptidoglycan, a polyvinylpyrrolidone, pluronic F-127, or a combination thereof.

124. The method of any one of clauses 1 to 123 wherein the linker comprises PEG.

125. The method of any one of clauses 1 to 124 wherein the compound, or the pharmaceutically acceptable salt thereof, has the formula wherein B represents the small molecule ligand, L represents the linker, and T represents the targeting moiety, and wherein L comprises a structure having the formula

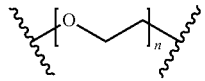

wherein n is an integer from 0 to 200.

126. The method of any one of clauses 1 to 125 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

127. The method of any one of clauses 1 to 126 wherein the cancer is a folate receptor expressing cancer.

128. The method of any one of clauses 1 to 127 wherein the cancer is an endometrial cancer.

129. The method of any one of clauses 1 to 127 wherein the cancer is a non-small cell lung cancer.

130. The method of any one of clauses 1 to 127 wherein the cancer is an ovarian cancer.

131. The method of any one of clauses 1 to 127 wherein the cancer is a triple negative breast cancer.

132. The method of any one of clauses 1 to 127 wherein the cancer is acute myelocytic leukemia.

133. The method of clause 132 wherein the cancer expresses the folate receptor-β.

134. The method of any one of clauses 1 to 133 wherein multiple doses of the CAR T cell composition are administered.

135. The method of any one of clauses 1 to 134 wherein at least two doses of the CAR T cell composition are administered.

136. The method of any one of clauses 1 to 135 wherein the patient is imaged prior to administration of the compound, or the pharmaceutically acceptable salt thereof, or prior to administration of the CAR T cell composition.

137. The method of any one of clauses 1 to 136 wherein the compound, or the pharmaceutically acceptable salt thereof, is not an antibody, and does not comprise a fragment of an antibody.

138. The method of any one of clauses 1 to 137 wherein the targeting moiety does not comprise a peptide epitope.

139. The method of any one of clauses 1 to 138 wherein cytokine release resulting in off-target toxicity in the patient does not occur and wherein CAR T cell toxicity to the cancer occurs.

140. The method of any one of clauses 1 to 138 wherein off-target tissue toxicity does not occur in the patient and wherein CAR T cell toxicity to the cancer occurs.

141. The method of any one of clauses 1 to 138 wherein the cancer comprises a tumor, wherein tumor size is reduced in the patient, and wherein off-target toxicity does not occur.

142. The method of any one of clauses 1 to 141 wherein CRS is reduced or prevented and the method results in a decrease in tumor volume in the patient.

143. The method of any one of clauses 1 to 142 wherein body weight loss due to CRS is reduced or prevented.

144. The method of any one of clauses 59 to 67 further comprising readministering the compound, or the pharmaceutically acceptable salt thereof, to the patient.

145. The method of clause 144 wherein the subsequent administration of the compound, or the pharmaceutically acceptable salt thereof, causes CAR T cell activation and an increase in cytokine levels in the patient.

146. The method of any one of clauses 1 to 145 wherein the cancer comprises a tumor and wherein a complete response for the tumor is obtained.

147. The method of any one of clauses 1 to 146 wherein the CAR T cells have a central memory/effector memory phenotype.

148. The method of any one of clauses 1 to 147 wherein the CD8:CD4 ratio of the CART cells is about 1:1.

BRIEF DESCRIPTION OF THE DRAWINGS

FIG. 11A: testing tissue section pre-incubated with DIG-E2 antibody; FIG. 11B: control tissue section without pre-incubation with DIG-E2 antibody.

FIG. 12A: testing tissue section pre-incubated with DIG-E2 antibody; FIG. 12B: control tissue section without pre-incubation with DIG-E2 antibody.

FIG. 13A: testing tissue section pre-incubated with DIG-E2 antibody; FIG. 13B: control tissue section without pre-incubation with DIG-E2 antibody.

FIG. 14A: testing tissue section pre-incubated with DIG-E2 antibody; FIG. 14B: control tissue section without pre-incubation with DIG-E2 antibody.

FIG. 15A: testing tissue section pre-incubated with DIG-E2 antibody; FIG. 15B: control tissue section without pre-incubation with DIG-E2 antibody.

FIG. 16A: testing tissue section pre-incubated with DIG-E2 antibody; FIG. 16B: control tissue section without pre-incubation with DIG-E2 antibody.

FIG. 17A: testing tissue section pre-incubated with DIG-E2 antibody; FIG. 17B: control tissue section without pre-incubation with DIG-E2 antibody.

FIG. 19A: testing tissue section pre-incubated with DIG-E2 antibody; FIG. 19B: control tissue section without pre-incubation with DIG-E2 antibody.

FIG. 20A: testing tissue section pre-incubated with DIG-E2 antibody; FIG. 20B: control tissue section without pre-incubation with DIG-E2 antibody.

FIG. 21A: testing tissue section pre-incubated with DIG-E2 antibody; FIG. 21B: control tissue section without pre-incubation with DIG-E2 antibody.

FIG. 22A: testing tissue section pre-incubated with DIG-E2 antibody; FIG. 22B: control tissue section without pre-incubation with DIG-E2 antibody.

FIG. 23A: testing tissue section pre-incubated with DIG-E2 antibody; FIG. 23B: control tissue section without pre-incubation with DIG-E2 antibody.

FIG. 24A: testing tissue section pre-incubated with DIG-E2 antibody; FIG. 24B: control tissue section without pre-incubation with DIG-E2 antibody.

FIG. 25A: testing tissue section pre-incubated with DIG-E2 antibody; FIG. 25B: control tissue section without pre-incubation with DIG-E2 antibody.

FIG. 26A: testing tissue section pre-incubated with DIG-E2 antibody; FIG. 26B: control tissue section without pre-incubation with DIG-E2 antibody.

FIG. 27A: testing tissue section pre-incubated with DIG-E2 antibody; FIG. 27B: control tissue section without pre-incubation with DIG-E2 antibody.

FIG. 28A: testing tissue section pre-incubated with DIG-E2 antibody; FIG. 28B: control tissue section without pre-incubation with DIG-E2 antibody.

FIG. 29A: testing tissue section pre-incubated with DIG-E2 antibody; FIG. 29B: control tissue section without pre-incubation with DIG-E2 antibody.

FIG. 30A A: testing tissue section pre-incubated with DIG-E2 antibody; FIG. 30B: control tissue section without pre-incubation with DIG-E2 antibody.

FIG. 31A: testing tissue section pre-incubated with DIG-E2 antibody; FIG. 31B: control tissue section without pre-incubation with DIG-E2 antibody.

FIG. 32A: testing tissue section pre-incubated with DIG-E2 antibody; FIG. 32B: control tissue section without pre-incubation with DIG-E2 antibody.

FIG. 33A: testing tissue section pre-incubated with DIG-E2 antibody; FIG. 33B: control tissue section without pre-incubation with DIG-E2 antibody.

FIG. 34A: testing tissue section pre-incubated with DIG-E2 antibody; FIG. 34B: control tissue section without pre-incubation with DIG-E2 antibody.

FIG. 35A: testing tissue section pre-incubated with DIG-E2 antibody; FIG. 35B: control tissue section without pre-incubation with DIG-E2 antibody.

FIG. 36A: testing tissue section pre-incubated with DIG-E2 antibody; FIG. 36B: control tissue section without pre-incubation with DIG-E2 antibody.

FIG. 37A: testing tissue section pre-incubated with DIG-E2 antibody; FIG. 37B: control tissue section without pre-incubation with DIG-E2 antibody.

FIG. 38A: testing tissue section pre-incubated with DIG-E2 antibody; FIG. 38B: control tissue section without pre-incubation with DIG-E2 antibody.

FIG. 43 (right panel) is a chart showing FACS analysis CAR-T expansion in mice bearing MDA-MB-231 tumors and no detectable CAR-T cell expansion in naïve mice.

FIG. 44 (middle panel) is a chart showing cytokine (IFN-γ) production from Mock T-Cells and anti-FLCAR T-cells at quantitatively similar levels in co-culture with the positive control cell line K562-OKT3 (left pair of bars, where Mock is the left bar and anti-FLCAR T-cells is the right bar); no cytokine was produced by either Mock or anti-FLCAR Tcells upon co-culture with K562 (middle); and anti-FLCAR T-cells were the only cells able to elicit secretion of the cytokine IFN-γ, but only with pretreatment of EC-17 (right, where only anti-FLCAR T-cells show a result). FIG. 44 (bottom panel) is a chart showing cytokine (TNF-α) production from Mock T-Cells and anti-FLCAR T-cells at quantitatively similar levels in co-culture with the positive control cell line K562-OKT3 (left pair of bars, where Mock is the left bar and anti-FLCAR T-cells is the right bar); no cytokine was produced by either Mock or anti-FLCAR T-cells upon co-culture with K562 (middle); and anti-FLCAR T-cells were the only cells able to elicit secretion of the cytokine TNF-α, but only with pretreatment of EC-17 (right, where only anti-FLCAR T-cells show a result).

FIG. 45 (upper right) is a chart showing percentage lysis when CD8+Mock T cells and anti-FLCAR T-cells are co-cultured with K562+OKT3 target cells at a ratio of 30:1, 10:1, 3:1, or 1:1. FIG. 45 (lower left) is a chart showing percentage lysis when CD8+Mock T cells and anti-FLCAR T-cells are co-cultured with unlabeled MDA-MB-231 cells at a ratio of 30:1, 10:1, 3:1, or 1:1. FIG. 45 (lower right) is a chart showing percentage lysis when CD8+Mock T cells and anti-FLCAR T-cells are co-cultured with EC17 labeled MDA-MB-231 cells at a ratio of 30:1, 10:1, 3:1, or 1:1. In all charts, (x) CD8+Mock T cells; (○)anti-FLCAR T-cells.

FIG. 46 (top) shows the chemical structure of FITC-folate.

FIG. 47 (top) shows the chemical structure of FITC-DUPA.

FIG. 48 (top) shows the chemical structure of FITC-CA9.

FIG. 49 (top) shows the chemical structure of FITC-NK1R.

FIG. 57A and FIG. 57B show CRS grading scale and experimental conditions applied to sodium fluorescein rescue in HOS-FRa tumor-bearing mice. Shown are changes in T cell-derived cytokines with and without rescue. p-values were calculated by Student's t-test.

FIG. 60A, FIG. 60B, FIG. 60C, FIG. 60D, and FIG. 60E show the correlation of CAR-T cell activity with FR levels and tumor cells' natural sensitivity. FIG. 60A: Kinetics of specific lysis (%) at varying E/T ratios in FR+(MDA-MB-231, KB, THP1-FRb, OV90, HOS-FRa) and FR-negative (HOS-143b) cell lines after 16 and 48 hours of co-culture in the presence of 10 nM EC17. FIG. 60B: Specific lysis (%) of target cells plotted against a linear scale of E/T ratios. High FR+KB cells demonstrated an early resistance at 16 hours while FR-negative HOS-143b failed to respond. FIG. 60C: Excluding KB cells, a semi-log correlation was established between specific lysis (%) at 16 hours of co-culture and functional FR levels on tumor cells. FIG. 60D: 3D diagrams depicting the relationships between the levels of CAR-T cell derived Th1 cytokines (IFNg, IL-2 and TNFa) after 44 hours of co-culture at 10 nM EC17 with varying E/T ratios. FIG. 60E: CAR-T cell derived Th1 cytokine levels plotted against FR levels of FR+ target cell in a Log 10 scale.

FIG. 62A: Schematic diagram of the experimental layout to show animal collection schedule in relation to CAR-T cell injection and weekly EC17 doses (500 nmol/kg) in MDA-MB-231 tumor-bearing mice. A total of 15 mice received ~4.8 million of EGFRt-sorted CAR-T cells on day 0 (3 mice had large tumors to begin with). FIG. 62B: Left panel showing measurements of tumor volume and change in body weight; Middle plot showing CAR-T cell expansion in the blood 7 days after a single dose of EC17; Right bar graph showing differentiation profiles of circulating CD4/CD8 CAR-T cell subsets in mice with small and larger tumors. FIG. 62C: Measurements of change in tumor volume and body weight. FIG. 62D: Top plot showing CAR-T cell kinetics in the blood (solid line) versus that of tumor (dotted line). Bottom bar graph showing changes in CAR-T cell phenotypes in the blood. FIG. 62E: Kinetic changes in the surface expression of activation markers (4-1BB, PD1) on tumor-infiltrating CAR-T cells.

FIG. 63A: Measurements of change in tumor volume and body weight of NSG mice xenografted with large MDA-MB-231 tumors and treated with CAR-T cells (~10 million "clinical facsimile") plus EC17 SIW at 500 nmol/kg while being maintained on FA-replete or FA-deficient diet throughout the study (n=5). FIG. 63B: Bar graph to show circulating CAR-T cells (human CD3ε+ EGFRt+) measured at the end of study on day 52 (FA-deficient) and day 59 (FA-replete), respectively. FIG. 63C: Representative flow cytometric dot plots to show an absence of circulating CAR-T cells in FA-deficient mice treated with CAR-T cells only (no EC17) and elevated numbers of circulating CAR-T cells in mice treated with CAR-T cells plus EC17 on FA-deficient diet compared to mice treated identically but on FA-replete diet. FIG. 63D: Loss of FR expression was detected in 2 out of 3 MDA-MB-231 tumors collected on day 59 from FA-replete animals and analyzed by flow cytometry (later confirmed by a quantitative radioligand binding assay, data not shown).

DEFINITIONS

Figure 1:
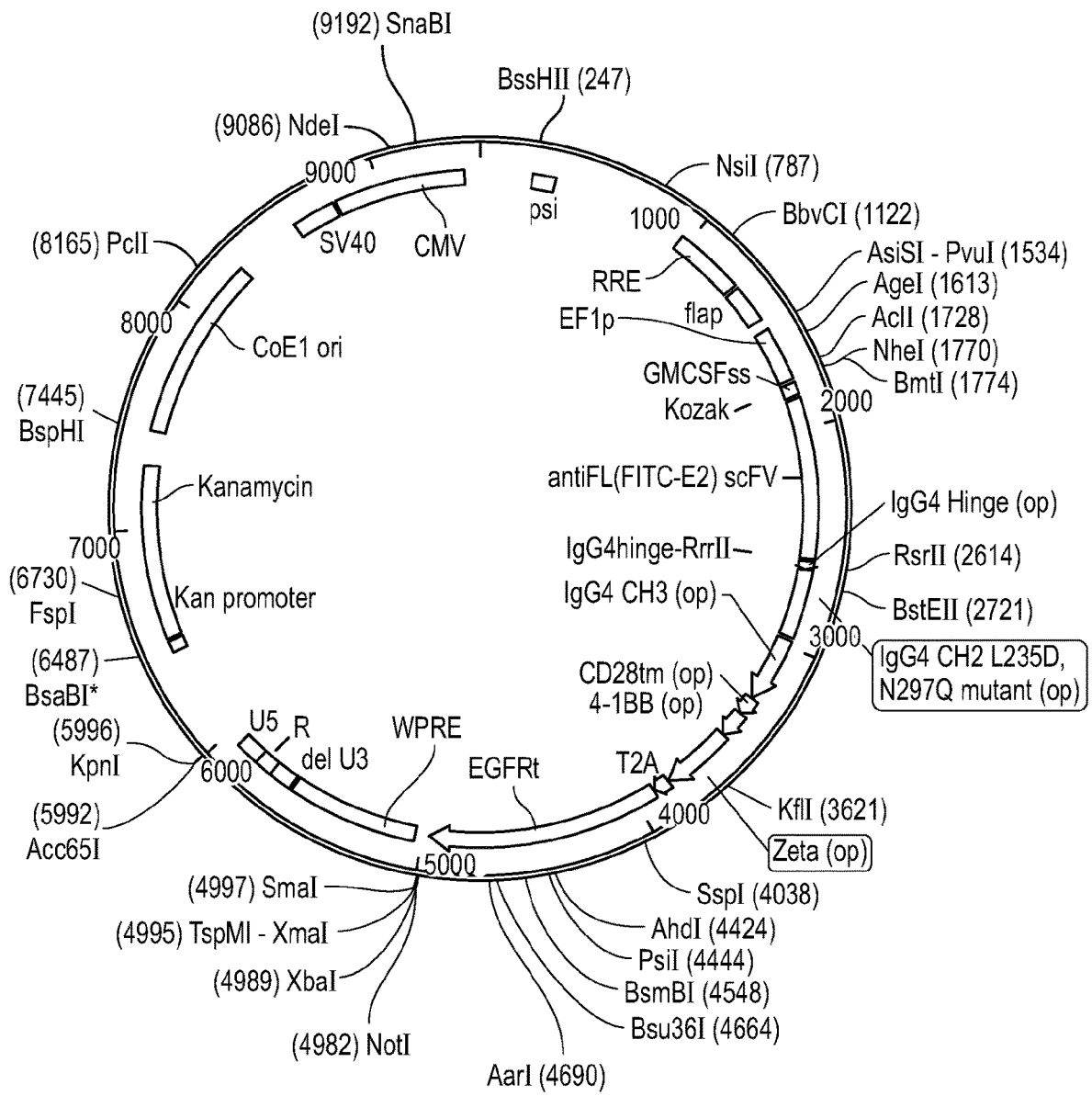
FIG. 1 shows the E2 construct vs. the 4M5.3 construct diagrammatically and shows a map of the E2 construct.

As used herein, "a" or "an" may mean one or more. As used herein, "about" in reference to a numeric value, including, for example, whole numbers, fractions, and percentages, generally refers to a range of numerical values (e.g., +/−5% to 10% of the recited value) that one of ordinary skill in the art would consider equivalent to the recited value (e.g., having the same function or result).

As used herein, the terms "treat," "treating," "treated," or "treatment" refer to both therapeutic treatment and prophylactic or preventative treatment.

As used herein, the terms "ameliorate," "ameliorating," "amelioration," or "ameliorated" in reference to cancer can mean reducing the symptoms of the cancer, reducing the size of a tumor, completely or partially removing the tumor (e.g., a complete or partial response), causing stable disease, preventing progression of the cancer (e.g., progression free survival), or any other effect on the cancer that would be considered by a physician to be a therapeutic, prophylactic, or preventative treatment of the cancer.

As used herein, the terms "administer," "administering," or "administered" mean all means of introducing the compound, or pharmaceutically acceptable salt thereof, or CAR T cell composition, wherein the CAR T cell composition comprises CAR T cells and wherein the CAR comprises an E2 anti-fluorescein antibody fragment, to the patient, including, but not limited to, oral, intravenous, intramuscular, subcutaneous, and transdermal.

As used herein, the term "off-target toxicity" means organ damage or a reduction in the patient's weight that is unacceptable to the physician treating the patient, or any other effect on the patient that is unacceptable to the physician treating the patient, for example, B cell aplasia, fever, a drop in blood pressure, or pulmonary edema.

As used herein, the terms "transduction" and "transfection" are used equivalently and the terms mean introducing a nucleic acid into a cell by any artificial method, including viral and non-viral methods.

DETAILED DESCRIPTION OF THE ILLUSTRATIVE EMBODIMENTS

In the various embodiments described herein, a small molecule ligand linked to a targeting moiety by a linker is used as a bridge between a cancer and CAR T cells (i.e, T cells expressing a chimeric antigen receptor), wherein the CAR T cells comprise a genetically engineered CAR directed to the targeting moiety, wherein the CAR comprises an E2 anti10 fluorescein antibody fragment. The bridge directs the CAR T cells to the cancer for amelioration of the cancer. In one embodiment, the "small molecule ligand" can be a folate, a CAIX ligand, DUPA, an NK-1R ligand, a ligand of gamma glutamyl transpeptidase, an NKG2D ligand, or a CCK2R ligand, each of which is a small molecule ligand that binds specifically to a cancer cell type (i.e., the receptor for each of these ligands is overexpressed on cancers compared to normal tissues).

The "targeting moiety" linked to the small molecule ligand binds to the recognition region of the genetically engineered CAR expressed by CAR T cells, wherein the CAR comprises an E2 anti-fluorescein antibody fragment. Accordingly, the recognition region of the CAR (e.g., a single chain fragment variable region (scFv) of an E2 anti-fluorescein antibody) is directed to the "targeting moiety." Thus, the small molecule ligand linked to a targeting moiety by a linker acts as a bridge between the cancer and the CAR T cells, wherein the CAR T cells comprise the genetically engineered CAR, directing the CAR T cells to the cancer for amelioration of the cancer.

The bridge is a small organic molecule so clearance from the bloodstream can be rapidly achieved (e.g., about 20 minutes or less). In one aspect, the CAR T cell response, wherein the CAR T cells comprise a genetically engineered CAR comprising an E2 antifluorescein antibody fragment, can be targeted to only those cancer cells expressing a receptor for the small molecule ligand portion of the 'bridge,' thereby reducing off-target toxicity to normal tissues. Additionally, this system can be 'universal' because one type of CAR T cell construct, wherein the CAR T cell comprises an E2 anti-fluorescein antibody fragment, can be 33 used to target a wide variety of cancers using different 'bridges'. Illustratively, the targeting moiety recognized by the CAR T cell, wherein the CAR T cell comprises a genetically engineered CAR comprising an E2 anti-fluorescein antibody fragment, may remain constant so that one type of CAR T cell, can be used, while the small molecule ligand that binds to the cancer can be altered to allow targeting of a wide variety of cancers.

In various embodiments described herein, the small molecule ligand linked to a targeting moiety by a linker is referred to as a "compound." In various embodiments, the clause "E2 anti-fluorescein antibody fragment" means a CAR comprising a fragment (e.g., an scFv fragment) of the E2 anti-fluorescein antibody. The E2 anti-fluorescein antibody is described, for example, in Vaughan, et al., *Nature Biotechnol.* Vol. 14(3), pp. 309-314, 1996, incorporated herein by reference. In various embodiments, the CAR can further comprise an IgG4 hinge domain, a CD3ζ activation domain, and/or a 4-1BB co-stimulation domain, or any other suitable domain such as the EGFRt domain. In still other embodiments, the CAR can be encoded by a polynucleotide having at least about 90%, 91%, 92%, 93%, 94%, 95%, 96%, 97%, 98%, 99%, or 99.5% identity to SEQ ID NO:1. In another illustrative embodiment, the CAR can be encoded by a polynucleotide that hybridizes under high stringency conditions to a polynucleotide having SEQ ID NO:1. In still another aspect, the CAR can be encoded by a polynucleotide having SEQ ID NO:1, or by a degenerate variant of SEQ ID NO:1. In other embodiments, the CAR protein sequence can have at least about 90%, 91%, 92%, 93%, 94%, 95%, 96%, 97%, 98%, or 99% identity to SEQ ID NO:2. In yet another embodiment, the CAR protein sequence can have up to about 50 conservative amino acid substitutions. In any of the embodiments described herein, the CAR binds fluorescein.

In one embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a first dose of a CAR T cell composition, wherein the CAR T cell composition comprises CAR T cells, wherein the CAR T cells comprise a CAR, and wherein the CAR comprises an E2 anti-fluorescein antibody fragment, and iii) administering to the patient a second dose of the CAR T cell composition wherein the CAR T cell composition comprises CAR T cells, wherein the CAR T cells comprise a CAR, and wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition comprising CAR T cells, wherein the CAR T cells comprise a CAR, wherein the CAR comprises an E2 antifluorescein antibody fragment, and wherein the CAR T cell composition comprises a mixture of the CAR T cells and non-transformed T cells.

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells wherein the CAR T cells comprise a CAR, wherein the CAR comprises an E2 anti-fluorescein antibody fragment, and iii) administering to the patient a folate, a conjugate comprising a folate wherein the conjugate comprising a folate does not comprise a targeting moiety, or a drug that inhibits activation of the CAR T cells.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is administered at a dose of about 10 nmoles/kg of body weight of the patient to about 2500 nmoles/kg of body weight of the patient, and ii) administering to the patient a CAR T cell composition comprising CAR T cells, wherein the CAR T cells comprise a CAR, wherein the CAR comprises an E2 anti-fluorescein antibody fragment, and wherein the CAR T cells are at a dose of about 1 million of the CART cells to about 15 million of the CART cells.

In still another embodiment, a method of treatment of a cancer is provided. The method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR, wherein the CAR comprises an E2 anti-fluorescein antibody fragment, and iii) ending the continuous administration of the compound, or the pharmaceutically acceptable salt thereof, to inhibit or prevent cytokine release syndrome in the patient.

In another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR, wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient, and ii) administering to the patient a CAR T cell composition comprising CAR T cells wherein the CAR T cells comprise a CAR, wherein the CAR comprises an E2 anti-fluorescein antibody fragment.

In yet another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii)

administering to the patient a dose of a CAR T cell composition comprising CAR T cells wherein the CAR T cells comprise a CAR and wherein the CAR comprises an E2 anti-fluorescein antibody fragment.

Several embodiments are described by the following enumerated clauses. Any of the following embodiments in combination with any applicable embodiments described in the Summary section of this patent application, in the Detailed Description of the Illustrative Embodiments section, the Examples section, or the claims of this patent application, are also contemplated.

1. A method of treatment of a cancer, the method comprising i) administering to a patient a compound, or a pharmaceutically acceptable salt thereof, wherein the compound comprises a small molecule ligand linked to a targeting moiety by a linker; ii) administering to the patient a first dose of a CAR T cell composition comprising CAR T cells wherein the CAR T cells comprise a CAR directed to the targeting moiety and wherein the CAR comprises an E2 anti-fluorescein antibody fragment; and iii) administering to the patient a second dose of a CAR T cell composition comprising CAR T cells wherein the CAR T cells comprise the CAR directed to the targeting moiety and wherein the CAR comprises an E2 anti-fluorescein antibody fragment.

2. A method of treatment of a cancer, the method comprising i) administering to a patient a compound, or a pharmaceutically acceptable salt thereof, wherein the compound comprises a small molecule ligand linked to a targeting moiety by a linker; and ii) administering to the patient a CAR T cell composition wherein the CAR T cell composition comprises CAR T cells, wherein the CAR T cells comprise a CAR directed to the targeting moiety wherein the CAR comprises an E2 anti-fluorescein antibody fragment, and wherein the CAR T cell composition comprises a mixture of the CAR T cells and non-transformed T cells.

3. A method of treatment of a cancer, the method comprising i) administering to a patient a compound, or a pharmaceutically acceptable salt thereof, wherein the compound comprises a small molecule ligand linked to a targeting moiety by a linker; ii) administering to the patient a CAR T cell composition wherein the CAR T cell composition comprises CAR T cells wherein the CAR T cells comprise a CAR directed to the targeting moiety and wherein the CAR comprises an E2 anti-fluorescein antibody fragment; and iii) administering to the patient a folate, a conjugate comprising a folate wherein the conjugate comprising a folate does not comprise a targeting moiety, or an agent that inhibits activation of the CAR T cells.

4. The method of clause 3 wherein step iii comprises administering a folate.

5. The method of any one of clauses 3 or 4 wherein step iii comprises administering folic acid or leucovorin.

6. The method of clause 3 wherein step iii comprises administering the conjugate comprising a folate.

7. The method of clause 6 wherein the conjugate comprising a folate comprises a folate linked to one or more amino acids.

8. The method of clause 7 wherein the conjugate comprising a folate has the formula

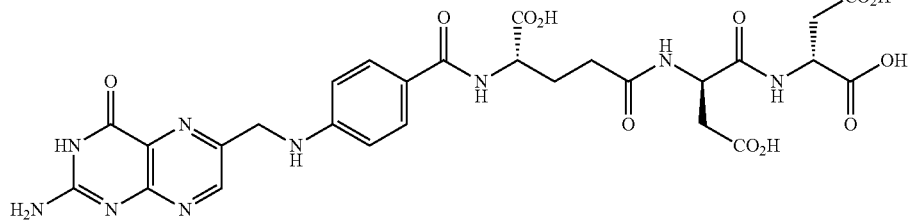

9. The method of any one of clauses 3 to 8 wherein the folate has the formula

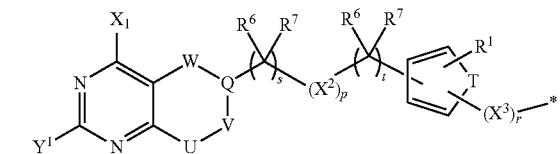

wherein X1 and Y1 are each-independently selected from the group consisting of halo, R2, OR2, SR3, and NR4R5; U, V, and W represent divalent moieties each independently selected from the group consisting of —(R6a)C═, —N═, —(R6a)C(R7a)—, and —N(R4a)-; Q is selected from the group consisting of C and CH; T is selected from the group consisting of S, O, N, and —C═C—; X2 and X3 are each independently selected from the group consisting of oxygen, sulfur, —C(Z)—, —C(Z)O—, —OC(Z)—, —N(R4b)-, —C(Z)N(R4b)-, —N(R4b)C(Z)—, —OC(Z)N(R4b)-, —N(R4b)C(Z)O—, —N(R4b)C(Z)N(R5b)—, —S(O)—, —S(O)2-, —N(R4a)S(O)2-, —C(R6b)(R7b)-, —N(C≡CH)—, —N(CH2C≡CH)—, C1-C12 alkylene, and C1-C12 alkyeneoxy, where Z is oxygen or sulfur; R1 is selected-from the group consisting of hydrogen, halo, C1-C12 alkyl, and C1-C12 alkoxy; R2, R3, R4, R4a, R4b, R5, R5b, R6b, and R7b are each independently selected from the group consisting of hydrogen, halo, C1-C12 alkyl, C1-C12 alkoxy, C1-C12 alkanoyl, C1-C12 alkenyl, C1-C12 alkynyl, (C1-C12 alkoxy)carbonyl, and (C1-C12 alkylamino)carbonyl; R6 and R7 are each independently selected from the group consisting of hydrogen, halo, C1-C12 alkyl, and C1-C12 alkoxy; or, R6 and R7 are taken together to form a carbonyl group; R6a and R7a are each independently selected from the group consisting of hydrogen, halo, C1-C12 alkyl, and C1-C12 alkoxy; or R6a and R7a are taken together to form a carbonyl group; p, r, s, and t are each independently either 0 or 1; and * represents a covalent bond to the rest of the conjugate.

10. The method of clause 3 wherein the agent that inhibits activation of the CART cells is administered and is selected from the group consisting of a lymphocyte-specific protein tyrosine kinase inhibitor, a PI3 kinase inhibitor, an inhibitor of an IL-2 inducible T cell kinase, a JAK inhibitor, a BTK inhibitor, EC2319, and an agent that blocks CART cell binding to the compound, or the pharmaceutically acceptable salt thereof, but does not bind to the cancer.

11. The method of clause 10 wherein the agent that inhibits activation of the CAR T cells is administered and the agent is a lymphocyte-specific protein tyrosine kinase inhibitor.

12. The method of clause 11 wherein the lymphocyte-specific protein tyrosine kinase inhibitor is Dasatinib.

13. The method of clause 10 wherein the agent that inhibits activation of the CAR T cells is administered and the agent is a PI3 kinase inhibitor.

14. The method of clause 13 wherein the PI3 kinase inhibitor is GDC0980.

15. The method of clause 10 wherein the agent that inhibits activation of the CAR T cells is administered and the agent is an IL-2 inducible T cell kinase inhibitor.

16. The method of clause 15 wherein the IL-2 inducible T cell kinase inhibitor is BMS-509744.

17. The method of clause 10 wherein the agent that inhibits activation of the CAR T cells is administered and is an agent that blocks CAR T cell binding to the compound, or the pharmaceutically acceptable salt thereof, but does not bind to the cancer.

18. The method of clause 17 wherein the agent is fluoresceinamine, FITC, or sodium fluorescein.

19. The method of clause 18 wherein the agent is FITC.

20. The method of clause 18 wherein the agent is sodium fluorescein.

21. The method of any one of clauses 17 to 20 wherein the agent that inhibits activation of the CART cells is administered at a dose of about 0.01 to about 300 umoles/kg of body weight of the patient.

22. The method of any one of clauses 17 to 20 wherein the agent that inhibits activation of the CART cells is administered at a dose of about 0.06 to about 100 umoles/kg of body weight of the patient.

23. The method of any one of clauses 17 to 20 wherein the agent that inhibits activation of the CART cells is administered at a dose of about 0.06 to about 90 umoles/kg of body weight of the patient.

24. The method of any one of clauses 17 to 20 wherein the agent that inhibits activation of the CART cells is administered at a dose of about 0.06 to about 80 umoles/kg of body weight of the patient.

25. The method of any one of clauses 17 to 20 wherein the agent that inhibits activation of the CART cells is administered at a dose of about 0.06 to about 70 umoles/kg of body weight of the patient.

26. The method of any one of clauses 17 to 20 wherein the agent that inhibits activation of the CART cells is administered at a dose of about 0.06 to about 60 umoles/kg of body weight of the patient.

27. The method of any one of clauses 17 to 20 wherein the agent that inhibits activation of the CART cells is administered at a dose of about 0.06 to about 50 umoles/kg of body weight of the patient.

28. The method of any one of clauses 17 to 20 wherein the agent that inhibits activation of the CART cells is administered at a dose of about 0.06 to about 40 umoles/kg of body weight of the patient.

29. The method of any one of clauses 17 to 20 wherein the agent that inhibits activation of the CART cells is administered at a dose of about 0.06 to about 30 umoles/kg of body weight of the patient.

30. The method of any one of clauses 17 to 20 wherein the agent that inhibits activation of the CART cells is administered at a dose of about 0.06 to about 20 umoles/kg of body weight of the patient.

31. The method of any one of clauses 17 to 20 wherein the agent that inhibits activation of the CART cells is administered at a dose of about 0.06 to about 10 umoles/kg of body weight of the patient.

32. The method of any one of clauses 17 to 20 wherein the agent that inhibits activation of the CAR T cells is administered at a dose of about 0.06 to about 8 umoles/kg of body weight of the patient.

33. The method of any one of clauses 17 to 20 wherein the agent that inhibits activation of the CAR T cells is administered at a dose of about 0.06 to about 6 umoles/kg of body weight of the patient.

34. The method of any one of clauses 3 to 33 wherein more than one dose is administered to the patient of the folate, the conjugate comprising a folate wherein the conjugate comprising a folate does not comprise a targeting moiety, or the agent that inhibits activation of the CAR T cells.

35. The method of any one of clauses 3 to 34 wherein the folate, the conjugate comprising a folate wherein the conjugate comprising a folate does not comprise a targeting moiety, or the agent that inhibits activation of the CAR T cells is administered to the patient before and/or after the compound, or the pharmaceutically acceptable salt thereof.

36. The method of any one of clauses 3 to 35 wherein administration of the folate, the conjugate comprising a folate wherein the conjugate comprising a folate does not comprise a targeting moiety, or the agent that inhibits activation of the CAR T cells causes reduction in cytokine levels in the patient.

37. The method of clause 36 wherein the reduction in cytokine levels occurs by about 3 hours after administration to the patient of the folate, the conjugate comprising a folate wherein the conjugate comprising a folate does not comprise a targeting moiety, or the agent that inhibits activation of the CAR T cells.

38. The method of clause 36 wherein the reduction in cytokine levels occurs by about 6 hours after administration to the patient of the folate, the conjugate comprising a folate wherein the conjugate comprising a folate does not comprise a targeting moiety, or the agent that inhibits activation of the CAR T cells.

39. The method of any one of clauses 36 to 38 wherein the reduction in cytokine levels is a reduction to about the cytokine levels in an untreated patient.

40. The method of any one of clauses 3 to 39 wherein the compound, or the pharmaceutically acceptable salt thereof, is administered before and subsequent to administration of the folate, the conjugate comprising a folate wherein the conjugate comprising a folate does not comprise a targeting moiety, or the agent that inhibits activation of the CAR T cells.

41. The method of any one of clauses 3 to 40 wherein CAR T cell number increases in the blood of the patient after administration of the folate, the conjugate comprising a folate wherein the conjugate comprising a folate does not comprise a targeting moiety, or the agent that inhibits activation of the CAR T cells, even though cytokine levels in the patient are reduced.

42. The method of any one of clauses 3 to 41 wherein CART cell activation is enhanced or maintained, relative to a patient not treated with a rescue agent, after administration of the folate, the conjugate comprising a folate wherein the conjugate comprising a folate does not comprise a targeting moiety, or the agent that inhibits activation of the CAR T cells, even though cytokine levels in the treated patient are reduced.

43. The method of any one of clauses 3 to 42 wherein the cancer comprises a tumor and tumor size in the patient is not increased when the folate, the conjugate comprising a folate wherein the conjugate comprising a folate does not comprise a targeting moiety, or the agent that inhibits activation of the CAR T cells is administered to the patient.

44. The method of clause 43 wherein a complete response for the tumor is obtained.

45. The method of any one of clauses 3 to 44 wherein the folate, the conjugate comprising a folate wherein the conjugate comprising a folate does not comprise a targeting moiety, or the agent that inhibits activation of the CAR T cells the agent that inhibits activation of the CAR T cells is administered to the patient when the CRS grade reaches 1, 2, 3, or 4.

46. The method of clause 45 wherein the agent that inhibits activation of the CAR T cells is administered to the patient when the CRS grade reaches 3 or 4.

47. The method of any one of clauses 3 to 46 wherein lung edema is reduced.

48. The method of any one of clauses 1 to 47 wherein the compound, or the pharmaceutically acceptable salt thereof, is administered at a dose of about 10 nmoles/kg of body weight of the patient to about 2500 nmoles/kg of body weight of the patient; and the CAR T cells are at a dose of about 1 million of the CAR T cells to about 15 million of the CAR T cells.

49. The method of clause 48 wherein the compound, or the pharmaceutically acceptable salt thereof, is administered at a dose of about 10 nmoles/kg to about 100 nmoles/kg of body weight of the patient.

50. The method of any one of clauses 48 to 49 wherein the compound, or the pharmaceutically acceptable salt thereof, is administered at a dose of about 10 nmoles/kg to about 50 nmoles/kg of body weight of the patient.

51. The method of any one of clauses 48 to 50 wherein the compound, or the pharmaceutically acceptable salt thereof, is administered at a dose of about 10 nmoles/kg to about 20 nmoles/kg of body weight of the patient.

52. The method of clause 48 wherein the compound, or the pharmaceutically acceptable salt thereof, is administered at a dose of about 10 nmoles/kg to about 600 nmoles/kg of body weight of the patient.

53. The method of clause 48 wherein the compound, or the pharmaceutically acceptable salt thereof, is administered at a dose of about 200 nmoles/kg to about 600 nmoles/kg of body weight of the patient.

54. The method of clause 48 wherein the compound, or the pharmaceutically acceptable salt thereof, is administered at a dose of about 400 nmoles/kg to about 600 nmoles/kg of body weight of the patient.

55. The method of any one of clauses 48 to 54 wherein the CAR T cells are at a dose of about 1 million of the CAR T cells to about 12.5 million of the CART cells.

56. The method of any one of clauses 48 to 55 wherein the CAR T cells are at a dose of about 1 million of the CAR T cells to about 7 million of the CAR T cells.

57. The method of any one of clauses 48 to 56 wherein the CAR T cells are at a dose of about 1 million of the CAR T cells to about 5 million of the CAR T cells.

58. The method of any one of clauses 48 to 57 wherein the CAR T cells are at a dose of about 2 million of the CAR T cells to about 5 million of the CAR T cells.

59. The method of any one of clauses 1 to 58 further comprising the step of ending continuous administration of the compound, or the pharmaceutically acceptable salt thereof, to inhibit or prevent cytokine release syndrome in the patient.

60. The method of any one of clauses 1 to 59 wherein the compound, or the pharmaceutically acceptable salt thereof, is administered continuously for at least one hour to the patient.

61. The method of any one of clauses 1 to 59 wherein the compound, or the pharmaceutically acceptable salt thereof, is administered continuously for at least four hours to the patient.

62. The method of any one of clauses 1 to 59 wherein the compound, or the pharmaceutically acceptable salt thereof, is administered continuously for at least six hours to the patient.

63. The method of any one of clauses 1 to 62 wherein the compound, or the pharmaceutically acceptable salt thereof, is administered to the patient every other day.

64. The method of any one of clauses 1 to 62 wherein the compound, or the pharmaceutically acceptable salt thereof, is administered to the patient three times weekly.

65. The method of any one of clauses 1 to 62 wherein the compound, or the pharmaceutically acceptable salt thereof, is administered to the patient two times weekly.

66. The method of any one of clauses 1 to 62 wherein the compound, or the pharmaceutically acceptable salt thereof, is administered to the patient once weekly.

67. The method of any one of clauses 1 to 62 wherein compound, or the pharmaceutically acceptable salt thereof, is administered to the patient until an unacceptable loss of body weight of the patient, a fever, a drop in blood pressure, or pulmonary edema occurs.

68. A method of treatment of a cancer, the method comprising i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof; and ii) administering to the patient a CAR T cell composition comprising CAR T cells wherein the CAR T cells comprise a CAR directed to the targeting moiety and wherein the CAR comprises an E2 anti-fluorescein antibody fragment.

69. The method of clause 68 wherein at least a first dose, a second dose, and a third dose of the compound, or the pharmaceutically acceptable salt thereof, are administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

70. The method of clause 68 wherein at least a first dose, a second dose, a third dose, and a fourth dose of the compound, or the pharmaceutically acceptable salt thereof, are administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

71. The method of clause 70 wherein the second dose of the compound, or the pharmaceutically acceptable salt thereof, is about 100-fold greater in amount than the first dose of the compound, or the pharmaceutically acceptable salt thereof, wherein the third dose of the compound, or the pharmaceutically acceptable salt thereof, is about 1000-fold greater in amount than the first dose of the compound, or the pharmaceutically acceptable salt thereof, and wherein the fourth dose of the compound, or the pharmaceutically acceptable salt thereof, is about 10000-fold greater in amount than the first dose of the compound, or the pharmaceutically acceptable salt thereof.

72. The method of clause 68 wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof.

73. A method of treatment of a cancer, the method comprising i) administering to a patient a first dose of a compound, or a pharmaceutically acceptable salt thereof, wherein the compound comprises a small molecule ligand linked to a targeting moiety by a linker; ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof and iii) administering to the patient a dose of a CAR T cell composition comprising CAR T cells wherein the CAR T cells comprise a CAR directed to the targeting moiety and wherein the CAR comprises an E2 anti-fluorescein antibody fragment.

74. The method of clause 74 wherein the second dose of the compound, or the pharmaceutically acceptable salt thereof, is at least about 60 percent lower in amount than the first dose of the compound, or the pharmaceutically acceptable salt thereof.

75. The method of clause 74 wherein the second dose of the compound, or the pharmaceutically acceptable salt thereof, is at least about 70 percent lower in amount than the first dose of the compound, or the pharmaceutically acceptable salt thereof.

76. The method of clause 74 wherein the second dose of the compound, or the pharmaceutically acceptable salt thereof, is at least about 80 percent lower in amount than the first dose of the compound, or the pharmaceutically acceptable salt thereof.

77. The method of clause 74 wherein the second dose of the compound, or the pharmaceutically acceptable salt thereof, is at least about 90 percent lower in amount than the first dose of the compound, or the pharmaceutically acceptable salt thereof.

78. The method of clause 74 wherein the second dose of the compound, or the pharmaceutically acceptable salt thereof, is at least about 95 percent lower in amount than the first dose of the compound, or the pharmaceutically acceptable salt thereof.

79. The method of clause 74 wherein the second dose of the compound, or the pharmaceutically acceptable salt thereof, is at least about 96 percent lower in amount than the first dose of the compound, or the pharmaceutically acceptable salt thereof.

80. The method of clause 74 wherein the second dose of the compound, or the pharmaceutically acceptable salt thereof, is at least about 97 percent lower in amount than the first dose of the compound, or the pharmaceutically acceptable salt thereof.

81. The method of clause 74 wherein the second dose of the compound, or the pharmaceutically acceptable salt thereof, is at least about 98 percent lower in amount than the first dose of the compound, or the pharmaceutically acceptable salt thereof.

82. The method of clause 74 wherein the second dose of the compound, or the pharmaceutically acceptable salt thereof, is at least about 99 percent lower in amount than the first dose of the compound, or the pharmaceutically acceptable salt thereof.

83. The method of clause 74 wherein the second dose of the compound, or the pharmaceutically acceptable salt thereof, is at least about 99.5 percent lower in amount than the first dose of the compound, or the pharmaceutically acceptable salt thereof.

84. The method of any one of clauses 73 to 83 wherein the first dose of the compound, or the pharmaceutically acceptable salt thereof, is about 100 nmoles/kg to about 1000 nmoles/kg of body weight of the patient.

85. The method of any one of clauses 73 to 83 wherein the first dose of the compound, or the pharmaceutically acceptable salt thereof, is about 100 nmoles/kg to about 900 nmoles/kg of body weight of the patient.

86. The method of any one of clauses 73 to 83 wherein the first dose of the compound, or the pharmaceutically acceptable salt thereof, is about 100 nmoles/kg to about 800 nmoles/kg of body weight of the patient.

87. The method of any one of clauses 73 to 83 wherein the first dose of the compound, or the pharmaceutically acceptable salt thereof, is about 100 nmoles/kg to about 700 nmoles/kg of body weight of the patient.

88. The method of any one of clauses 73 to 83 wherein the first dose of the compound, or the pharmaceutically acceptable salt thereof, is about 100 nmoles/kg to about 600 nmoles/kg of body weight of the patient.

89. The method of any one of clauses 73 to 83 wherein the first dose of the compound, or the pharmaceutically acceptable salt thereof, is about 200 nmoles/kg to about 600 nmoles/kg of body weight of the patient.

90. The method of any one of clauses 73 to 83 wherein the first dose of the compound, or the pharmaceutically acceptable salt thereof, is about 400 nmoles/kg to about 600 nmoles/kg of body weight of the patient.

91. The method of any one of clauses 73 to 83 wherein the first dose of the compound, or the pharmaceutically acceptable salt thereof, is about 500 nmoles/kg of body weight of the patient.

92. The method of clause 84 wherein the second dose of the compound, or the pharmaceutically acceptable salt thereof, is about 0.5 nmoles/kg to about 500 nmoles/kg of body weight of the patient.

93. The method of clause 85 wherein the second dose of the compound, or the pharmaceutically acceptable salt thereof, is about 0.5 nmoles/kg to about 450 nmoles/kg of body weight of the patient.

94. The method of clause 86 wherein the second dose of the compound, or the pharmaceutically acceptable salt thereof, is about 0.5 nmoles/kg to about 400 nmoles/kg of body weight of the patient.

95. The method of clause 87 wherein the second dose of the compound, or the pharmaceutically acceptable salt thereof, is about 0.5 nmoles/kg to about 350 nmoles/kg of body weight of the patient.

96. The method of clause 88 wherein the second dose of the compound, or the pharmaceutically acceptable salt thereof, is about 0.5 nmoles/kg to about 300 nmoles/kg of body weight of the patient.

97. The method of clause 89 wherein the second dose of the compound, or the pharmaceutically acceptable salt thereof, is about 1 nmole/kg to about 300 nmoles/kg of body weight of the patient.

98. The method of clause 90 wherein the second dose of the compound, or the pharmaceutically acceptable salt thereof, is about 2 nmoles/kg to about 300 nmoles/kg of body weight of the patient.

99. The method of clause 91 wherein the second dose of the compound, or the pharmaceutically acceptable salt thereof, is about 2 nmoles/kg to about 250 nmoles/kg of body weight of the patient.

100. The method of any one of clauses 92 to 99 wherein the second dose of the compound, or the pharmaceutically acceptable salt thereof, is about 5 nmoles/kg to about 40 nmoles/kg of body weight of the patient.

101. The method of any one of clauses 92 to 99 wherein the second dose of the compound, or the pharmaceutically acceptable salt thereof, is about 40 nmoles/kg to about 150 nmoles/kg of body weight of the patient.

102. The method of any one of clauses 73 to 101 further comprising administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof.

103. The method of clause 102 further comprising administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof.

104. The method of any one of clauses 73 to 103 wherein the dose(s) of the compound, or the pharmaceutically acceptable salt thereof, administered after the first dose of the compound, or the pharmaceutically acceptable salt thereof, maintain inhibition of growth of the cancer relative to the first dose of the compound, or the pharmaceutically acceptable salt thereof.

105. The method of any one of clauses 73 to 104 wherein the CART cells are administered at a dose of about 1 million of the CAR T cells to about 40 million of the CAR T cells.

106. The method of any one of clauses 73 to 105 wherein the dose(s) of the compound, or the pharmaceutically acceptable salt thereof, administered after the first dose of the compound, or the pharmaceutically acceptable salt thereof, are administered once weekly.

107. The method of any one of clauses 73 to 105 wherein the dose(s) of the compound, or the pharmaceutically acceptable salt thereof, are administered twice weekly.

108. The method of any one of clauses 1 to 107 wherein the CAR further comprises an IgG4 hinge domain, a CD3ζ activation domain, and a 4-1BB co-stimulation domain.

109. The method of any one of clauses 1 to 108 wherein the E2 anti-fluorescein antibody fragment is an scFv fragment.

110. The method of any one of clauses 1 to 109 wherein the CAR protein sequence has at least about 90% identity to SEQ ID NO:2.

111. The method of any one of clauses 1 to 10 9 wherein the CAR protein sequence has at least about 95% identity to SEQ ID NO:2.

112. The method of any one of clauses 1 to 109 wherein the CAR protein sequence has at least about 98% identity to SEQ ID NO:2.

113. The method of any one of clauses 1 to 112 wherein the CAR binds fluorescein.

114. The method of any one of clauses 1 to 109 wherein the CAR protein sequence has up to about 50 conservative amino acid substitutions and wherein the CAR binds fluorescein.

115. The method of any one of clauses 1 to 109 wherein the CAR is encoded by a polynucleotide having at least about 90% identity to SEQ ID NO:1.

116. The method of any one of clauses 1 to 109 wherein the CAR is encoded by a polynucleotide having at least about 95% identity to SEQ ID NO:1.

117. The method of any one of clauses 1 to 109 wherein the CAR is encoded by a polynucleotide having at least about 98% identity to SEQ ID NO:1.

118. The method of any one of clauses 115 to 117 wherein the CAR binds fluorescein.

119. The method of any one of clauses 1 to 118 wherein the CAR is encoded by a polynucleotide that hybridizes under high stringency conditions to a polynucleotide having SEQ ID NO:1 and wherein the CAR binds fluorescein.

120. The method of any one of clauses 1 to 119 wherein the CAR is encoded by a polynucleotide having SEQ ID NO:1, or by a degenerate variant of SEQ ID NO:1.

121. The method of any one of clauses 1 to 120 wherein the ligand is selected from the group consisting of a folate, DUPA, an NK-1R ligand, a CAIX ligand, a ligand of gamma glutamyl transpeptidase, an NKG2D ligand, and a CCK2R ligand.

122. The method of any one of clauses 1 to 121 wherein the targeting moiety is fluorescein, or a pharmaceutically acceptable salt thereof.

123. The method of any one of clauses 1 to 122 wherein the linker comprises polyethylene glycol (PEG), polyproline, a hydrophilic amino acid, a sugar, an unnatural peptidoglycan, a polyvinylpyrrolidone, pluronic F-127, or a combination thereof.

124. The method of any one of clauses 1 to 123 wherein the linker comprises PEG.

125. The method of any one of clauses 1 to 124 wherein the compound, or the pharmaceutically acceptable salt thereof, has the formula

B-L-T, wherein B represents the small molecule ligand, L represents the linker, and T represents the targeting moiety, and wherein L comprises a structure having the formula

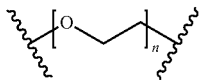

wherein n is an integer from 0 to 200.

126. The method of any one of clauses 1 to 125 wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, acute myelocytic leukemia, lymphocytic lymphoma, myeloid leukemia, myelomonocytic leukemia, hairy cell leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, and adenocarcinoma of the gastroesophageal junction.

127. The method of any one of clauses 1 to 126 wherein the cancer is a folate receptor expressing cancer.

128. The method of any one of clauses 1 to 127 wherein the cancer is an endometrial cancer.

129. The method of any one of clauses 1 to 127 wherein the cancer is a non-small cell lung cancer.

130. The method of any one of clauses 1 to 127 wherein the cancer is an ovarian cancer.

131. The method of any one of clauses 1 to 127 wherein the cancer is a triple negative breast cancer.

132. The method of any one of clauses 1 to 127 wherein the cancer is acute myelocytic leukemia.

133. The method of clause 132 wherein the cancer expresses the folate receptor-β.

134. The method of any one of clauses 1 to 133 wherein multiple doses of the CAR T cell composition are administered.

135. The method of any one of clauses 1 to 134 wherein at least two doses of the CAR T cell composition are administered.

136. The method of any one of clauses 1 to 135 wherein the patient is imaged prior to administration of the compound, or the pharmaceutically acceptable salt thereof, or prior to administration of the CAR T cell composition.

137. The method of any one of clauses 1 to 136 wherein the compound, or the pharmaceutically acceptable salt thereof, is not an antibody, and does not comprise a fragment of an antibody.

138. The method of any one of clauses 1 to 137 wherein the targeting moiety does not comprise a peptide epitope.

139. The method of any one of clauses 1 to 138 wherein cytokine release resulting in off-target toxicity in the patient does not occur and wherein CAR T cell toxicity to the cancer occurs.

140. The method of any one of clauses 1 to 138 wherein off-target tissue toxicity does not occur in the patient and wherein CAR T cell toxicity to the cancer occurs.

141. The method of any one of clauses 1 to 138 wherein the cancer comprises a tumor, wherein tumor size is reduced in the patient, and wherein off-target toxicity does not occur.

142. The method of any one of clauses 1 to 141 wherein CRS is reduced or prevented and the method results in a decrease in tumor volume in the patient.

143. The method of any one of clauses 1 to 142 wherein body weight loss due to CRS is reduced or prevented.

144. The method of any one of clauses 59 to 67 further comprising re-administering the compound, or the pharmaceutically acceptable salt thereof, to the patient.

145. The method of clause 144 wherein the subsequent administration of the compound, or the pharmaceutically acceptable salt thereof, causes CAR T cell activation and an increase in cytokine levels in the patient.

146. The method of any one of clauses 1 to 145 wherein the cancer comprises a tumor and wherein a complete response for the tumor is obtained.

147. The method of any one of clauses 1 to 146 wherein the CAR T cells have a central memory/effector memory phenotype.

148. The method of any one of clauses 1 to 147 wherein the CD8:CD4 ratio of the CART cells is about 1:1.

Thus, in one embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a first dose of a CAR T cell composition, wherein the CAR T cell composition comprises CAR T cells, wherein the CAR T cells comprise a CAR, and wherein the CAR comprises an E2 anti-fluorescein antibody fragment, and iii) administering to the patient a second dose of the CAR T cell composition wherein the CAR T cell composition comprises CAR T cells, wherein the CAR T cells comprise a CAR, and wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition comprising CAR T cells, wherein the CAR T cells comprise a CAR, wherein the CAR comprises an E2 anti-fluorescein antibody fragment, and wherein the CAR T cell composition comprises a mixture of the CAR T cells and non-transformed T cells.

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells wherein the CAR T cells comprise a CAR, wherein the CAR comprises an E2 anti-fluorescein antibody fragment, and iii) administering to the patient a folate, a conjugate comprising a folate wherein the conjugate comprising a folate does not comprise a targeting moiety, or a drug that inhibits activation of the CAR T cells.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and wherein the compound, or the pharmaceutically acceptable salt thereof, is administered at a dose of about 10 nmoles/kg of body weight of the patient to about 2500 nmoles/kg of body weight of the patient, and ii) administering to the patient a CAR T cell composition comprising CAR T cells, wherein the CAR T cells comprise a CAR, wherein the CAR comprises an E2 anti-fluorescein antibody fragment, and wherein the CAR T cells are at a dose of about 1 million of the CART cells to about 15 million of the CART cells.

In still another embodiment, a method of treatment of a cancer is provided. The method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR, wherein the CAR comprises an E2 anti-fluorescein antibody fragment, and iii) ending the continuous administration of the compound, or the pharmaceutically acceptable salt thereof, to inhibit or prevent cytokine release syndrome in the patient.

In another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR, wherein the CAR comprises an E2 anti-fluorescein antibody fragment.

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker and wherein the compound, or the pharmaceutically acceptable salt thereof, is administered once weekly to the patient, and ii) administering to the patient a CAR T cell composition comprising CAR T cells wherein the CAR T cells comprise a CAR, wherein the CAR comprises an E2 anti-fluorescein antibody fragment.

In yet another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii) administering to the patient a dose of a CAR T cell composition comprising CAR T cells wherein the CAR T cells comprise a CAR and wherein the CAR comprises an E2 anti-fluorescein antibody fragment.

Accordingly, various embodiments are provided in the preceding paragraphs and in the clause list above, and all applicable embodiments described in this "Detailed Description of Illustrative Embodiments," the Summary section, the Examples, and the claims apply to the these embodiments.

As described herein, a "patient" can be a human or, in the case of veterinary applications, the patient can be a laboratory, an agricultural, a domestic, or a wild animal. In various aspects, the patient can be a laboratory animal such as a rodent (e.g., mouse, rat, hamster, etc.), a rabbit, a monkey, a chimpanzee, a domestic animal such as a dog, a cat, or a rabbit, an agricultural animal such as a cow, a horse, a pig, a sheep, a goat, or a wild animal in captivity such as a bear, a panda, a lion, a tiger, a leopard, an elephant, a zebra, a giraffe, a gorilla, a dolphin, or a whale.

In various embodiments, the cancer to be treated can be selected from a carcinoma, a sarcoma, an osteosarcoma, a lymphoma, a melanoma, a mesothelioma, a nasopharyngeal carcinoma, a leukemia, an adenocarcinoma, or a myeloma. In other embodiments, the cancer may be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, osteosarcoma, cancer of the urethra, prostate cancer, chronic leukemia, acute leukemia, including acute myelocytic leukemia, a lymphocytic lymphoma, myeloid leukemia, myelomonocytic leukemia, hairy cell leukemia, pleural mesothelioma, cancer of the bladder, Burkitt's lymphoma, cancer of the ureter, cancer of the kidney, renal cell carcinoma, carcinoma of the renal pelvis, a neoplasm of the central nervous system (CNS), primary CNS lymphoma, a spinal axis tumor, a brain stem glioma, a pituitary adenoma, and an adenocarcinoma of the gastroesophageal junction.

In some aspects of these embodiments, the cancer is a folate receptor expressing cancer. In another embodiment, the cancer is a folate receptor α-expressing cancer. In yet another embodiment, the cancer is a folate receptor β-expressing cancer. In some aspects of these embodiments, the cancer is an endometrial cancer, a non-small cell lung cancer, an ovarian cancer, or a triple-negative breast cancer. In another embodiment, the cancer being treated is a tumor. In another embodiment, the cancer is malignant. In another embodiment, the cancer is acute myelocytic leukemia. In yet another embodiment, the cancer is acute myelocytic leukemia and the cancer expresses the folate receptor-β. In still another embodiment, the cancer is acute myelocytic leukemia and the CAR-T cells have a central memory/effector memory phenotype. In yet another embodiment, the CD8:CD4 ratio of the CAR T cells is about 1:1, about a 1.2 to 1 ratio, about a 1 to 1.2 ratio, about a 1.3 to 1 ratio, about a 1 to 1.3 ratio, about a 1.4 to 1 ratio, about a 1 to 1.4 ratio, about a 1.5 to 1 ratio, or about a 1 to 1.5 ratio. In another embodiment where the cancer is acute myelocytic leukemia or another cancer, the CAR T cells associated with the tumor can have increased CD25 expression relative to the CAR T cells not associated with the tumor.

In one embodiment, the "small molecule ligand" can be a folate, DUPA (a ligand bound by PSMA-positive human prostate cancer cells and other cancer cell types), an NK-1R ligand (receptors for NK-1R the ligand found, for example, on cancers of the colon and pancreas), a CAIX ligand (receptors for the CAIX ligand found, for example, on renal, ovarian, vulvar, and breast cancers), a ligand of gamma glutamyl transpeptidase (the transpeptidase overexpressed, for example, in ovarian cancer, colon cancer, liver cancer, astrocytic gliomas, melanomas, and leukemias), an NKG2D ligand (receptors for the NKG2D ligand found, for example, on cancers of the lung, colon, kidney, prostate, and on T and B cell lymphomas), or a CCK2R ligand (receptors for the CCK2R ligand found on cancers of the thyroid, lung, pancreas, ovary, brain, stomach, gastrointestinal stroma, and colon, among others), each of which is a small molecule ligand that binds specifically to a cancer cell type (i.e., the receptor for each of these ligands can be overexpressed on cancers compared to normal tissues).

In one embodiment, the small molecule ligand may have a mass of less than about 10,000 Daltons, less than about 9000 Daltons, less than about 8,000 Daltons, less than about 7000 Daltons, less than about 6000 Daltons, less than about 5000 Daltons, less than about 4500 Daltons, less than about 4000 Daltons, less than about 3500 Daltons, less than about 3000 Daltons, less than about 2500 Daltons, less than about 2000 Daltons, less than about 1500 Daltons, less than about 1000 Daltons, or less than about 500 Daltons. In another embodiment, the small molecule ligand may have a mass of about 1 to about 10,000 Daltons, about 1 to about 9000 Daltons, about 1 to about 8,000 Daltons, about 1 to about 7000 Daltons, about 1 to about 6000 Daltons, about 1 to about 5000 Daltons, about 1 to about 4500 Daltons, about 1 to about 4000 Daltons, about 1 to about 3500 Daltons, about 1 to about 3000 Daltons, about 1 to about 2500 Daltons, about 1 to about 2000 Daltons, about 1 to about 1500 Daltons, about 1 to about 1000 Daltons, or about 1 to about 500 Daltons.

In one embodiment, a DUPA derivative can be the ligand of the small molecule ligand linked to a targeting moiety, and DUPA derivatives are described in WO 2015/057852, incorporated herein by reference.

In one embodiment, the small molecule ligand in the context of the "small molecule ligand linked to a linker" is a folate. In various embodiments, the folate can be folic acid, a folic acid analog, or another folate receptor-binding molecule. In various embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors.

Other folate receptor-binding analogs include aminopterin, amethopterin (methotrexate), N10-methylfolate, 2-deaminohydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the small molecule ligand in the context of the "small molecule ligand linked to a linker" can have the formula

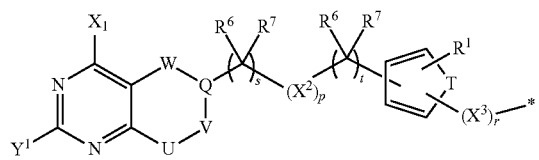

wherein $X^1$ and $Y^1$ are each-independently selected from the group consisting of halo, $R^2$, $OR^2$, $SR^3$, and $NR^4R^5$; U, V, and W represent divalent moieties each independently selected from the group consisting of $-(R^{6a})C=$, $-N=$, $-(R^{6a})C(R^{7a})-$, and $-N(R^{4a})-$; Q is selected from the group consisting of C and CH; T is selected from the group consisting of S, O, N, and $-C=C-$; $X^2$ and $X^3$ are each independently selected from the group consisting of oxygen, sulfur, $-C(Z)-$, $-C(Z)O-$, $-OC(Z)-$, $-N(R^{4b})-$, $-C(Z)N(R^{4b})-$, $-N(R^{4b})C(Z)-$, $-OC(Z)N(R^{4b})-$, $-N(R^{4b})C(Z)O-$, $-N(R^{4b})C(Z)N(R^{5b})-$, $-S(O)-$, $-S(O)_2-$, $-N(R^{4a})S(O)_2-$, $-C(R^{6b})(R^{7b})-$, $-N(C\equiv CH)-$, $-N(CH_2C\equiv CH)-$, $C_1-C_{12}$ alkylene, and $C_1-C_{12}$ alkyeneoxy, where Z is oxygen or sulfur; $R^1$ is selected-from the group consisting of hydrogen, halo, $C_1-C_{12}$ alkyl, and $C_1-C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1-C_{12}$ alkyl, $C_1-C_{12}$ alkoxy, $C_1-C_{12}$ alkanoyl, $C_1-C_{12}$ alkenyl, $C_1-C_{12}$ alkynyl, ($C_1-C_{12}$ alkoxy)carbonyl, and ($C_1-C_{12}$ alkylamino)carbonyl; $R^6$ and $R^7$ are each independently selected from the group consisting of hydrogen, halo, $C_1-C_{12}$ alkyl, and $C_1-C_{12}$ alkoxy; or, $R^6$ and $R^7$ are taken together to form a carbonyl group; $R^{ha}$ and $R^{7a}$ are each independently selected from the group consisting of hydrogen, halo, $C_1-C_{12}$ alkyl, and $C_1-C_{12}$ alkoxy; or $R^{6a}$ and $R^{7a}$ are taken together to form a carbonyl group; p, r, s, and t are each independently either 0 or 1; and * represents a covalent bond to the rest of the conjugate.

In one aspect, the "targeting moiety" that binds to the CAR comprising an E2 anti-fluorescein antibody fragment and expressed by CAR T cells can be selected, for example, from fluorescein, fluorescein isothiocyanate (FITC), and NHS-fluorescein. The identity of the targeting moiety is limited only in that it should be recognized and bound by the CAR comprising an E2 anti-fluorescein antibody fragment, preferably with specificity, and that it have a relatively low molecular weight. In various aspects, exemplary targeting moieties are haptens, including small molecular weight organic molecules.

In one illustrative embodiment, the targeting moiety can have the following illustrative structure:

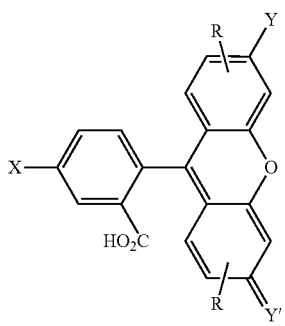

where X is oxygen, nitrogen, or sulfur, and where X is attached to linker L; Y is $OR^a$, $NR^a_2$, or $NR^a_3{}^+$; and Y' is O, NRa, or $NR^a_2{}^+$; where each R is independently selected in each instance from H, fluoro, sulfonic acid, sulfonate, and salts thereof, and the like; and $R^a$ is hydrogen or alkyl.

In one illustrative aspect, the linker can comprise polyethylene glycol (PEG), polyproline, a hydrophilic amino acid, a sugar, an unnatural peptidoglycan, a polyvinylpyrrolidone, pluronic F-127, or a combination thereof.

In another illustrative aspect, the linker in the compound, or pharmaceutically acceptable salt thereof, described herein can comprise a direct linkage (e.g., a reaction between the isothiocyanate group of FITC and a free amine group of a small molecule ligand) or the linkage can be through an intermediary linker. In one embodiment, if present, an intermediary linker can be any biocompatible linker known in the art, such as a divalent linker. In one illustrative embodiment, the divalent linker can comprise about 1 to about 30 carbon atoms. In another illustrative embodiment, the divalent linker can comprise about 2 to about 20 carbon atoms. In other embodiments, lower molecular weight divalent linkers (i.e., those having an approximate molecular weight of about 30 to about 300 Daltons) are employed. In another embodiment, linkers lengths that are suitable include, but are not limited to, linkers having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, or more atoms.

In various embodiments, the small molecule ligand linked to a targeting moiety can be of the formula

B-L-T, wherein B represents the small molecule ligand, L represents the linker, and T represents the targeting moiety, and wherein L comprises a structure having the formula

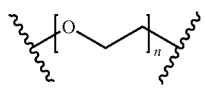

wherein n is an integer from 0 to 200. In another embodiment, n can be an integer from 0 to 150, 0 to 110, 0 to 100, 0 to 90, 0 to 80, 0 to 70, 0 to 60, 0 to 50, 0 to 40, 0 to 30, 0 to 20, 0 to 15, 0 to 14, 0 to 13, 0 to 12, 0 to 11, 0 to 10, 0 to 9, 0 to 8, 0 to 7, 0 to 6, 0 to 5, 0 to 4, 0 to 3, 0 to 2, 0 to 1, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 15 to 31, 15 to 32, 15 to 33, 15 to 34, 15 to 35, 15 to 36, 15 to 37, 15 to 38, 15 to 39, 15 to 40, 15 to 50, 15 to 60, 15 to 70, 15 to 80, 15 to 90, 15 to 100, 15 to 110, 15 to 120, 15 to 130, 15 to 140, 15 to 150, or n can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 108, 110, 120, 130, 140, or 150.

In another embodiment, the linker may be a divalent linker that may include one or more spacers. Illustrative spacers are shown in the following table. The following non-limiting, illustrative spacers are described where * indicates the point of attachment to the small molecule ligand or to the targeting moiety, or to other divalent linker portions.

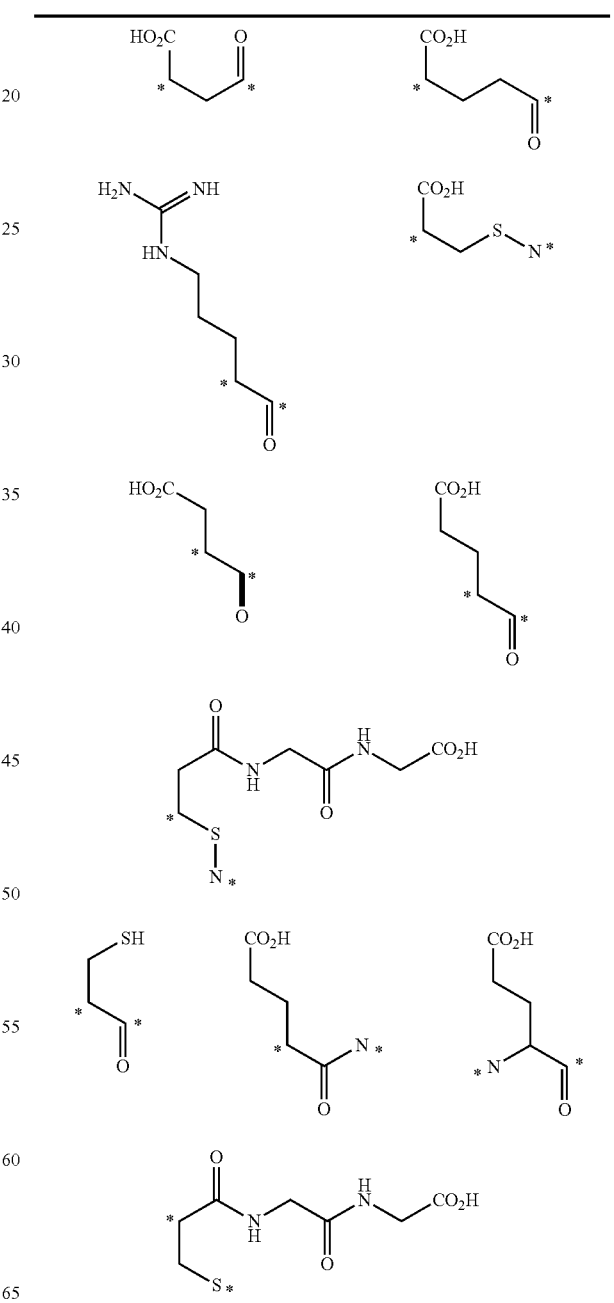

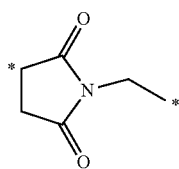 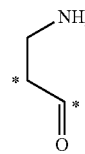
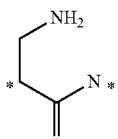 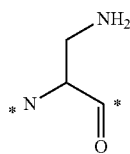
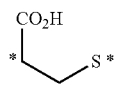 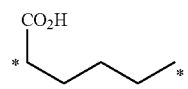
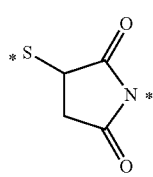 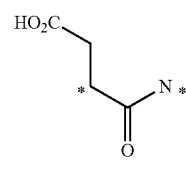
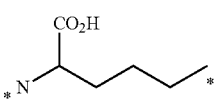 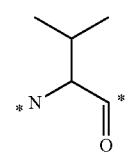
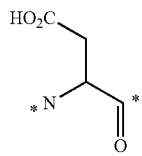
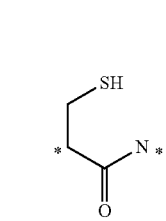 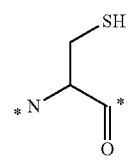
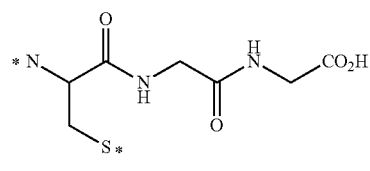 [SMILES: NC(CS)C(=O)NCC(=O)NCC(=O)O]
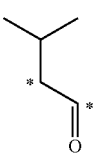 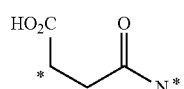 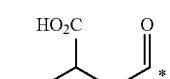
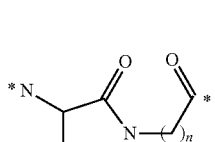 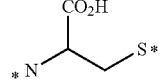
n = 1-3
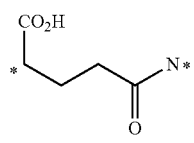 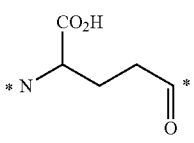
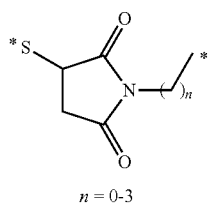 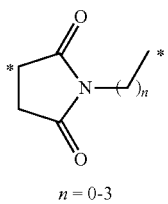
n = 0-3    n = 0-3
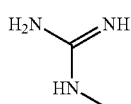 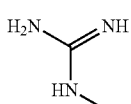
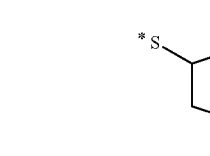
n = 1-3
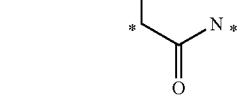 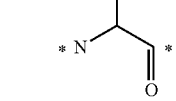
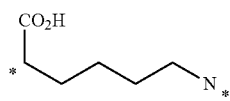 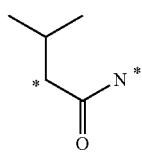
In other embodiments, the small molecule ligand linked to a targeting moiety (bridge) can have any of the following structures.

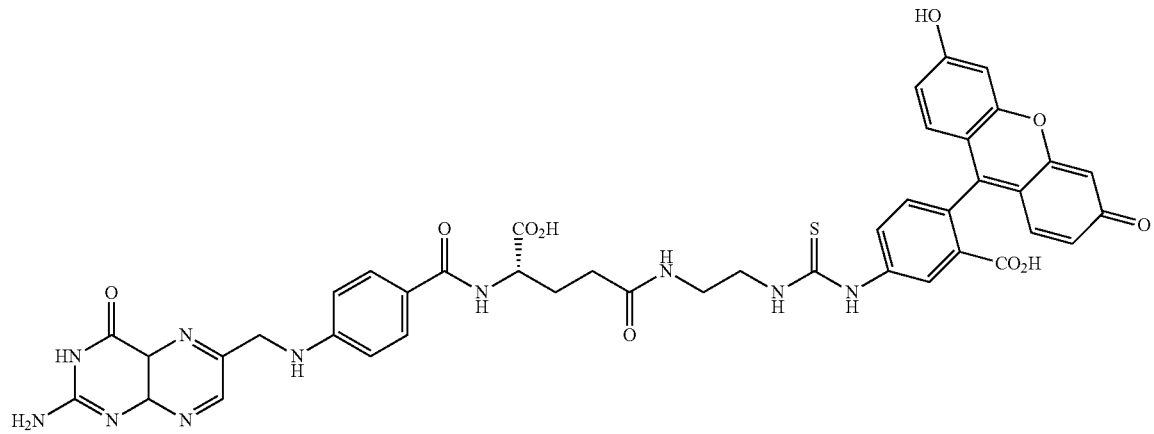
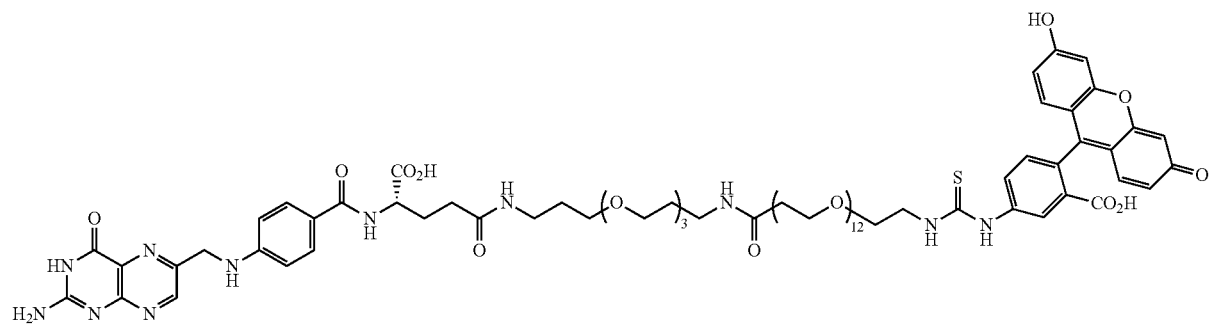
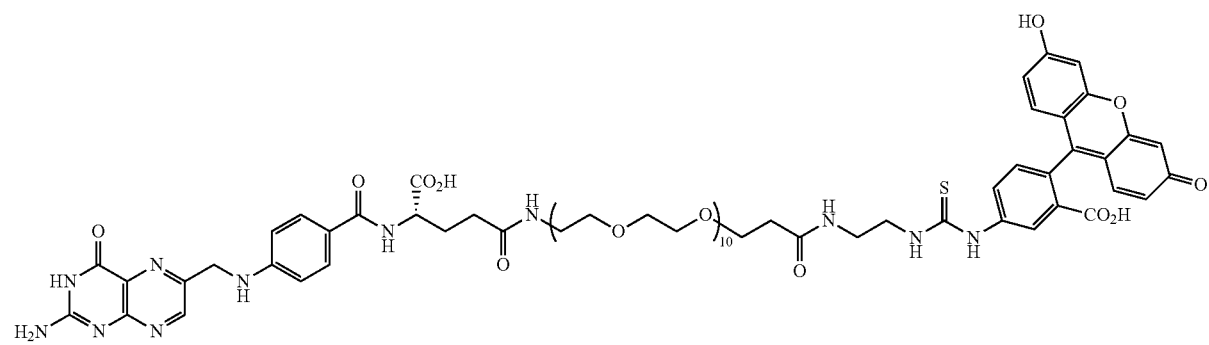
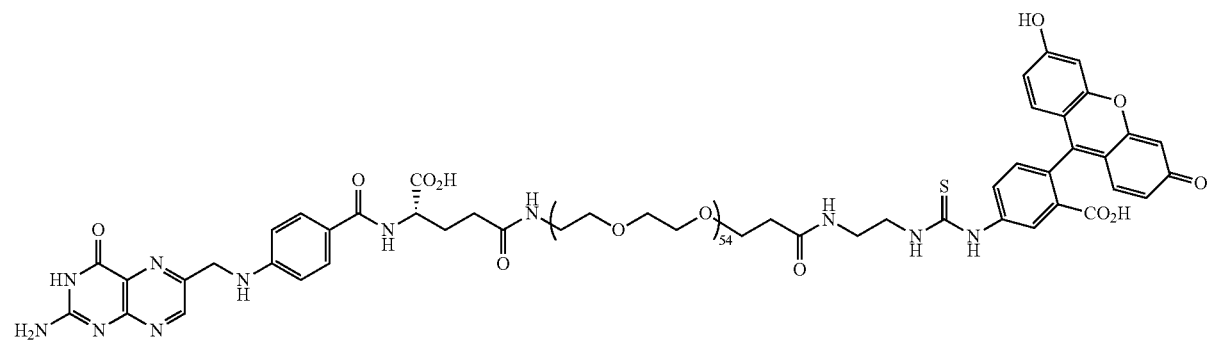

-continued
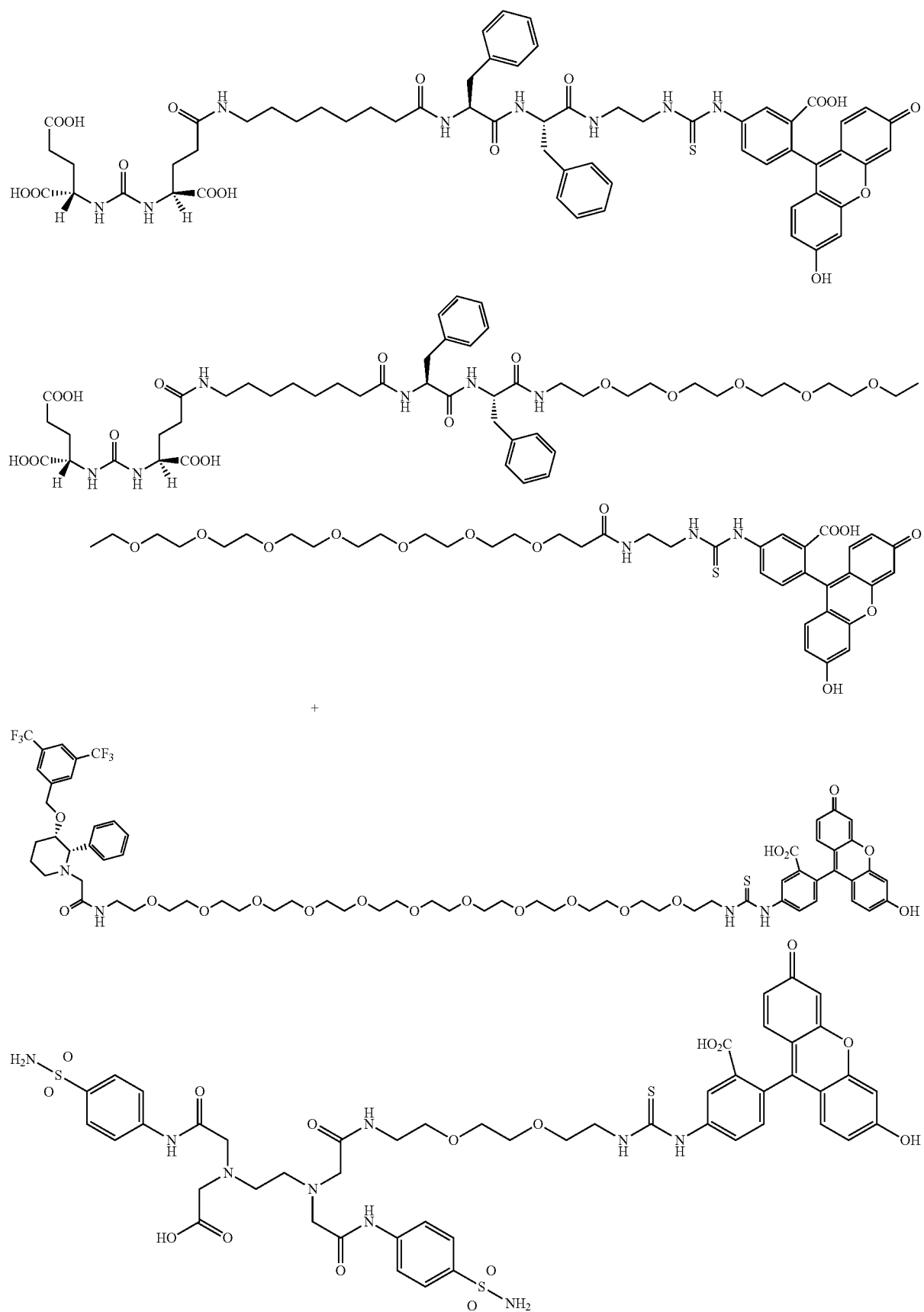

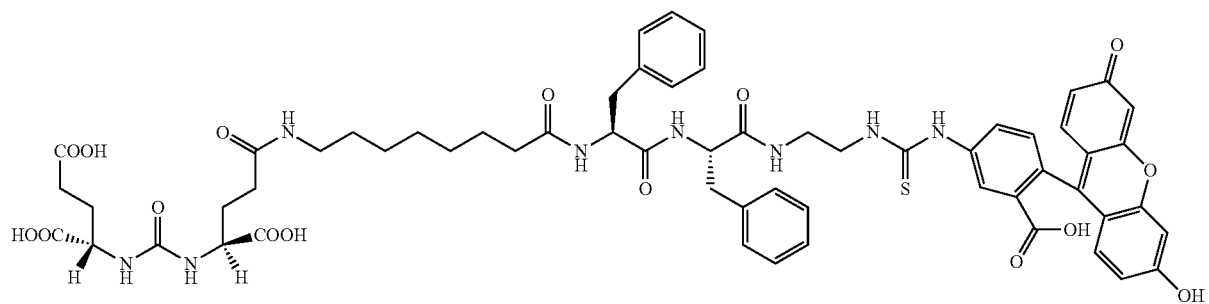
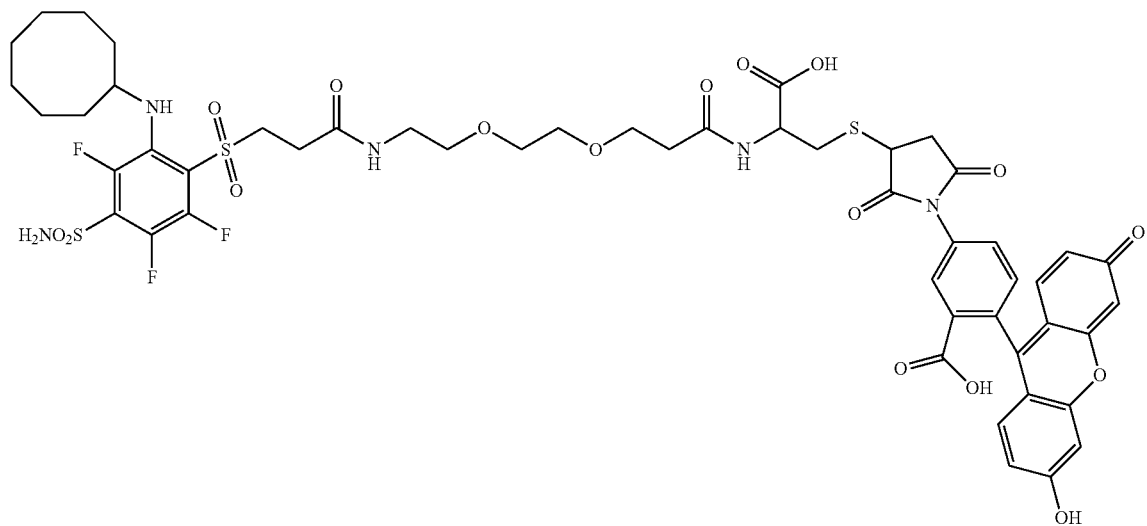
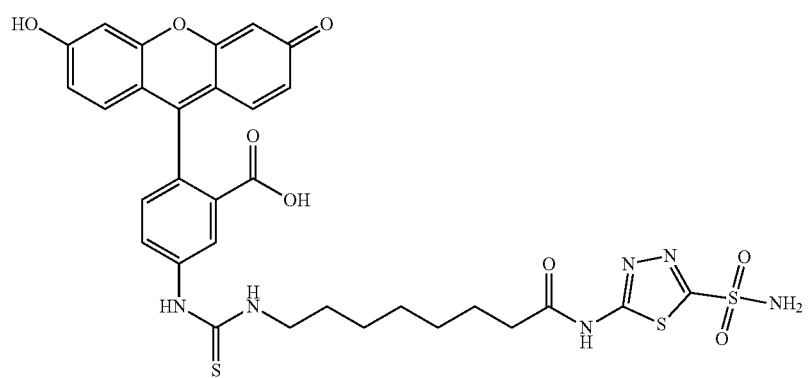

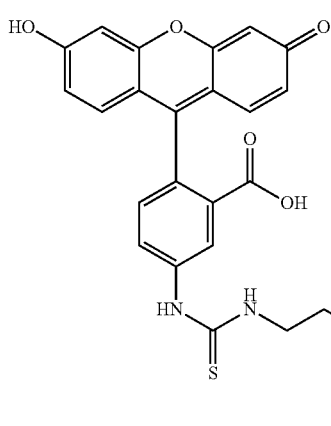
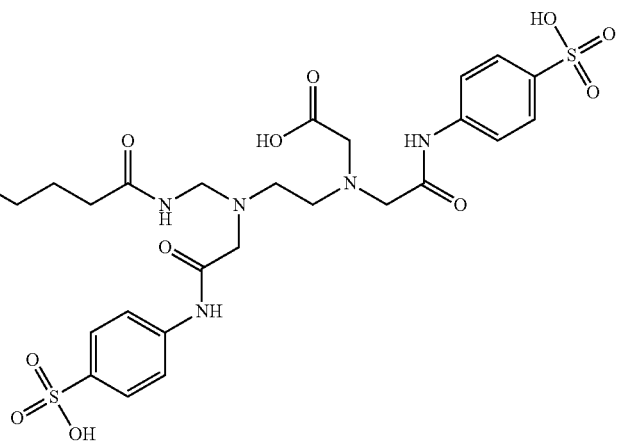

-continued

In other embodiments, the compound, or the pharmaceutically acceptable salt thereof, is not an antibody, and does not comprise a fragment of an antibody. In yet another embodiment, the targeting moiety does not comprise a peptide epitope.

In one illustrative embodiment, the small molecule ligand linked to a targeting moiety by a linker (the bridge) comprises fluorescein isothiocyanate (FITC) linked to the small molecule ligand. In one aspect, the cancer may overexpress a receptor for the small molecule ligand. In another aspect, for example, cytotoxic T cells, or another type of T cell, can be transformed to express a CAR that comprises an E2 antifluorescein antibody fragment. In this aspect, the CAR may target FITC, decorating the cancer with FITC molecules as a result of binding of the small molecule ligand to the cancer. Thus, toxicity to normal, non-target cells can be avoided. In this embodiment, when the E2 anti-fluroescein antibody fragment CAR-expressing T cells bind FITC, the CAR T cells are activated and the cancer is ameliorated.

A "pharmaceutically acceptable salt" of a small molecule ligand linked to a targeting moiety by a linker is contemplated. As used herein, the term "pharmaceutically acceptable salt" refers to those salts whose counter ions may be used in pharmaceuticals. In various embodiments, such salts include, but are not limited to 1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or 2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like. Pharmaceutically acceptable salts are well-known to those skilled in the art, and any such pharmaceutically acceptable salt is contemplated in connection with the embodiments described herein.

In various embodiments, suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

In various embodiments, suitable base salts are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one illustrative aspect, the compound, or a pharmaceutically salt thereof, described herein may contain one or more chiral centers, or may otherwise be capable of existing as multiple stereoisomers. Accordingly, various embodiments may include pure stereoisomers as well as mixtures of stereoisomers, such as enantiomers, diastereomers, and enantiomerically or diastereomerically enriched mixtures. In one aspect, the compound, or pharmaceutically acceptable salt thereof, described herein may be capable of existing as geometric isomers. Accordingly, various embodiments may include pure geometric isomers or mixtures of geometric isomers.

In some aspects, the compound, or pharmaceutically acceptable salt thereof, described herein may exist in unsolvated forms as well as solvated forms, including hydrated forms. In general, the solvated forms are equivalent to unsolvated forms and are encompassed within the scope of the present invention.

The methods described herein also utilize T lymphocytes (e.g., cytotoxic T lymphocytes) engineered to express a chimeric antigen receptor (CAR) comprising an E2 antifluorescein antibody fragment, that recognizes and binds to the targeting moiety (e.g., fluorescein, fluorescein isothiocyanate (FITC), and NHS-fluorescein) of the bridge. In one embodiment, the CARs described herein comprise three domains including 1) a recognition region (e.g., a single chain fragment variable (scFv) region of an E2 anti-fluorescein antibody, an Fab fragment, and the like) which recognizes and binds to the targeting moiety with specificity, 2) a co-stimulation domain which enhances the proliferation and survival of the T lymphocytes, and 3) an activation signaling domain which generates a T lymphocyte activation signal.

In various aspects, as non-limiting examples, scFv regions of antibodies that bind a fluorescein, fluorescein isothiocyanate (FITC), and NHS-fluorescein can be used. In illustrative non-limiting embodiments, the scFv regions can be prepared from (i) the E2 antibody known in the art that binds the targeting moiety, and (iii) sequence variants derived from the scFv regions of such antibodies, e.g., scFv regions having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the scFv region from which they are derived.

In one aspect, the co-stimulation domain serves to enhance the proliferation and survival of the cytotoxic T lymphocytes upon binding of the CAR to a targeting moiety. Suitable co-stimulation domains include, but are not limited to, CD28, CD137 (4-1BB), a member of the tumor necrosis factor (TNF) receptor family, CD134 (OX40), a member of the TNFR-superfamily of receptors, CD27, CD30, CD150, DAP10, NKG2D, and CD278 (ICOS), a CD28-superfamily co-stimulatory molecule expressed on activated T cells, or combinations thereof. In one illustrative embodiment, the co-stimulation domains of the engineered CAR comprise CD 28 and CD137. A skilled artisan will understand that sequence variants of these co-stimulation domains can be used without adversely impacting the invention, where the variants have the same or similar activity as the domain upon which they are modeled. In various embodiments, such variants can have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the domain from which they are derived.

In an illustrative embodiment, the activation signaling domain serves to activate T lymphocytes (e.g., cytotoxic T lymphocytes) upon binding of the CAR to a targeting moiety. In various embodiments, suitable activation signaling domains include the T cell CD3ζ chain, CD3 delta receptor protein, mb1 receptor protein, B29 receptor protein, and Fc receptor γ. The skilled artisan will understand that sequence variants of these activation signaling domains can be used where the variants have the same or similar activity as the domain upon which they are modeled. In various embodiments, the variants have at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity with the amino acid sequence of the domain from which they are derived.

In one aspect, constructs encoding the CARs comprising the E2 anti-fluorescein antibody fragment are prepared using genetic engineering techniques. Such techniques are described in detail in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

As examples, a plasmid or viral expression vector (e.g., a lentiviral vector, a retrovirus vector, sleeping beauty, and piggyback (transposon/transposase systems that include a non-viral mediated CAR gene delivery system)) can be prepared that encodes a fusion protein comprising a recognition region, one or more co-stimulation domains, and an activation signaling domain, in frame and linked in a 5' to 3' direction. In other embodiments, other arrangements are acceptable and include a recognition region, an activation signaling domain, and one or more co-stimulation domains. In one embodiment, the placement of the recognition region in the fusion protein will generally be such that display of the region on the exterior of the cell is achieved. In one embodiment, the CARs comprising the E2 anti-fluorescein antibody fragment may include additional elements, such as a signal peptide (e.g., CD8a signal peptide) to ensure proper export of the fusion protein to the cell surface, a transmembrane domain to ensure the fusion protein is maintained as an integral membrane protein (e.g., CD8a transmembrane domain, CD28 transmembrane domain, or CD3ζ transmembrane domain), and a hinge domain (e.g., CD8a hinge or IgG4 hinge) that imparts flexibility to the recognition region and allows strong binding to the targeting moiety, and any other suitable domain.

A diagram of an exemplary CAR construct wherein the expressed CAR comprises the E2 anti-fluorescein antibody fragment is shown in FIG. 1 where the fusion protein sequence is incorporated into an expression vector and where the CAR comprises an E2 anti-fluorescein antibody fragment, an IgG4 hinge domain, a CD28 transmembrane domain, and where the co-stimulation domain is CD137 (4-1BB), and the activation signaling domain is CD3ζ. The CAR can comprise additional suitable domains. An exemplary nucleic acid sequence of a CAR insert is provided as SEQ ID NO:1 and the exemplary encoded amino acid sequence is provided as SEQ ID NO:2. As used herein, "SEQ ID NO:1" means the sequence beginning at the underlined "agc" codon and ending with the underlined "ggc" codon. This portion of the longer sequence, encodes the CAR that is inserted into the T cell membrane. The other portions of the longer sequence include coding sequence for signal peptides, the EGFRt domain, etc. which are not part of the CAR that is inserted into the membrane and which functions as the chimeric antigen receptor. As used herein, "SEQ ID NO:2" means the sequence beginning at the underlined "S" and ending with the underlined "G". This portion of the longer sequence is the amino acid sequence for the CAR that is inserted into the T cell membrane. The other portions of the longer sequence include amino acid sequences for signal peptides, the EGFRt domain, etc. which are not part of the CAR inserted into the membrane and which functions as the chimeric antigen receptor. In yet another embodiment, SEQ ID NO:2 can comprise or consist of humanized, or human amino acid sequences. SEQ ID NOS:1 and 2 are as described above. The start and stop codons in the longer nucleic acid sequence are underlined and the longer sequence is an exemplary sequence that can be used for transduction of T cells for use in the methods as described herein.

(E2 anti-fluorescein antibody fragment CAR nucleic acid sequence (insert))
SEQ ID NO: 1 atgcttctcctggtgacaagcttctgctctgtgagttaccacacccagc attcctcctgatcccaagcgtgctgacacagcctagctccgtgtctgccg cccctggccagaaagtgaccatcagctgtagcggcagcaccagcaacatc ggcaacaactacgtgtcctggtatcagcagcaccccggcaaggcccccaa gctgatgatctacgacgtgtccaagcggcccagcggcgtgcccgatagat tttccggcagcaagagcggcaacagcgccagcctggatatcagcggcctg cagtctgaggacgaggccgactactattgcgccgcctgggacgatagcct gagcgagttcctgtttggcaccggcaccaagctgacagtgctgggcggag gcggaggatctggcggcggaggaagtggcggaggggggatctcaggtgcag ctggtggaaagcggcggcaacctggtgcagcctggcggatctctgagact gagctgtgccgccagcggcttcaccttcggcagcttcagcatgagctggg tgcgccaggctcctggggggaggactggaatgggtggcaggactgagcgcc agaagcagcctgacccactacgccgatagcgtgaaggccggttcaccat cagcccgggacaacgccaagaacagcgtgtacctgcagatgaacagcctgc gggtggaagatccgccgtgtactactgcgccagacggtcctacgacagc agcggctactggggccacttctacagctacatggacgtgtggggccaggg caccctcgtgacagtgtctgagagcaagtacggaccgccctgccccccctt gccctgccccgagttcgacggcggacccagcgtgttcctgttccccccc aagcccaaggacaccctgatgatcagccggaccccgaggtgacctgcgt ggtggtggacgtgagccaggaagatccgaggtccagttcaattggtacg tggacggcgtgaagtgcacaacgccaagaccaagcccagagaggaacag ttccagagcacctaccggggtggtgtctgtgctgaccgtgctgcaccagga ctggctgaacggcaaagaatacaagtgcaaggtgtccaacaagggcctgc ccagcagcatcgaaaagaccatcagcaaggccaagggccagcctcgcgag ccccaggtgtacaccctgcctccctcccaggaagagatgaccaagaacca ggtgtccctgacctgcctggtgaagggcttctaccccagcgacatcgccg tggagtgggagagcaacggccagcctgagaacaactacaagaccaccct cccgtgctggacagcgacggcagcttcttcctgtacagccggctgaccgt ggacaagagccggtggcaggaaggcaacgtcttagctgcagcgtgatgc acgaggcctgcacaaccactacacccagaagagcctgagcctgtccctg ggcaagatgttctgggtgctggtggtggtgggcgggtgctggcctgcta cagcctgctggtgacagtggccttcatcatcttttgggtgaaacggggca gaaagaaactcctgtatatattcaaacaaccatttatgagaccagtacaa actactcaagaggaagatggctgtagctgccgatttccagaagaagaaga aggaggatgtgaactgcgggtgaagttcagcagaagcgccgacgcccctg cctaccagcagggccagaatcagctgtacaacgagctgaacctgggcaga agggaagagtacgacgtcctggataagcggagaggccgggaccctgagat gggcggcaagcctcggcggaagaaccccaggaaggcctgtataacgaac tgcagaaagacaagatggccgaggcctacagcgagatcggcatgaaggc gagcggaggcggggcaagggccacgacggcctgtatcagggcctgtccac cgccaccaaggatacctacgacgccctgcacatgcaggcctgccccccaa ggctcgagggcggcggagagggcagaggaagtcttctaacatgcggtgac gtggaggagaatccgcccctaggatgcttctcctggtgacaagcttct gctctgtgagttaccacacccagcattcctcctgatcccacgcaaagtgt gtaacggaataggtattggtgaatttaaagactcactccataaatgct acgaatattaaacacttcaaaaactgcacctccatcagtggcgatctcca catcctgccggtggcatttagggggtgactccttcacacatactcctcctc tggatccacaggaactggatattctgaaaaccgtaaaggaaatcacaggg ttttttgctgattcaggcttggcctgaaaacaggacggacctccatgcctt tgagaacctagaaatcatacgcggcaggaccaagcaacatggtcagtttt ctcttgcagtcgtcagcctgaacataacatccttgggattacgctccctc aaggagataagtgatggagatgtgataatttcaggaaacaaaaatttgtg ctatgcaaatacaataaactggaaaaaactgtttgggacctccggtcaga aaaccaaaattataagcaacagaggtgaaaacagctgcaaggccacaggc caggtctgccatgccttgtgctcccccgagggctgctggggccggagcc cagggactgcgtctcttgccgaatgtcagccgaggcagggaatgcgtgg acaagtgcaaccttctggagggtgagccaagggagtttgtggagaactct gagtgcatacagtgccacccagagtgcctgcctcaggccatgaacatcac ctgcacaggacggggaccagacaactgtatccagtgtgcccactacattg acggcccccactgcgtcaagacctgcccggcaggagtcatgggagaaaac aacaccctggtctggaagtacgcagacgccggccatgtgtgccacctgtg ccatccaaactgcacctacggatgcactgggccaggtcttgaaggctgtc caacgaatgggcctaagatcccgtccatcgccactgggatggtggggcc ctcctcttgctgctggtggtggccctggggatcggcctcttcatgtga (E2 anti-fluorescein antibody fragment CAR amino acid sequence (insert))
SEQ ID NO: 2

MLLLVTSLLLCELPHPAFLLIPSVLTQPSSVSAAPGQKVTISCSGSTSNI

GNNYVSWYQQHPGKAPKLMIYDVSKRPSGVPDRFSGSKSGNSASLDISGL

QSEDEADYYCAAWDDSLSEFLFGTGTKLTVLGGGGSGGGGSGGGGSQVQ

LVESGGNLVQPGGSLRLSCAASGFTFGSFSMSWVRQAPGGGLEWVAGLSA

RSSLTHYADSVKGRFTISRDNAKNSVYLQMNSLRVEDTAVYYCARRSYDS

SGYWGHFYSYMDVWGQGTLVTVSESKYGPPCPPCPAPEFDGGPSVFLPPP

KPKDTLMISRTPEVTCVVVDVSQEDPEVQFNWYVDGVEVHNAKTKPREEQ

FQSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKMFWVLVVVGGVLACYSLLVTVAFIIFWVKRGRKKLLYIFKQPFMRPVQ

TTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPRLEGGGEGRGSLLTCGD

-continued

```
VEENPGPRMLLLVTSLLLCELPHPAFLLIPRKVCNGIGIGEFKDSLSINA

TNIKHFKNCTSISGDLHILPVAFRGDSFTHTPPLDPQELDILKTVKEITG

FLLIQAWPENRTDLHAFENLEIIRGRTKQHGQFSLAVVSLNITSLGLRSL

KEISDGDVIISGNKNLCYANTINWKKLFGTSGQKTKIISNRGENSCKATG

QVCHALCSPEGCWGPEPRDCVSCRNVSRGRECVDKCNLLEGEPREFVENS

ECIQCHPECLPQAMNITCTGRGPDNCIQCAHYIDGPHCVKTCPAGVMGEN

NTLVWKYADAGHVCHLCHPNCTYGCTGPGLEGCPTNGPKIPSIATGMVGA

LLLLLVVALGIGLFM
```

In one embodiment, the CAR, expressing the E2 anti-fluorescein antibody fragment, comprises a recognition region and the recognition region is a single chain fragment variable (scFv) region of the E2 anti-fluorescein antibody, a co-stimulation domain and the co25 stimulation domain is CD137 (4-1BB), and an activation signaling domain and the activation signaling domain is a T cell CD3ζ chain. In another embodiment, the CAR can further comprise any additional suitable domains. It is well-known to the skilled artisan that an anti-FITC scFv and an anti-fluorescein scFv are equivalent terms.

In various embodiments, the "E2 anti-fluorescein antibody fragment" can be a CAR comprising a fragment (e.g., an scFv fragment) of the E2 anti-fluorescein antibody. The E2 anti-fluorescein antibody is described, for example, in Vaughan, et al., *Nature Biotechnol*. Vol. 14(3), pp. 309-314, 1996, incorporated herein by reference. In one embodiment, the CAR expressing the E2 anti-fluorescein antibody fragment can have a binding affinity for fluorescein of about 0.7 nM to about 0.8 nM, about 0.72 nM to about 0.8 nM, about 0.73 nM to about 0.8 nM, about 0.72 nM to about 7.8 nM, about 0.73 to about 0.77 nM, or about 0.75 nM.

In various embodiments, the CAR can further comprise an IgG4 hinge domain, a CD3ζ activation domain, and/or a 4-1BB co-stimulation domain, and other suitable domains. In still other embodiments, the CAR can be encoded by a polynucleotide having at least about 90%, 91%, 92%, 93%, 94%, 95%, 96%, 97%, 98%, 99%, or 99.5% identity to SEQ ID NO:1. In another illustrative embodiment, the CAR can be encoded by a polynucleotide that hybridizes under high stringency conditions to a polynucleotide having SEQ ID NO:1. In still another aspect, the CAR can be encoded by a polynucleotide having SEQ ID NO:1, or by a degenerate variant of SEQ ID NO:1. In other embodiments, the CAR protein sequence can have at least about 90%, 91%, 92%, 93%, 94%, 95%, 96%, 97%, 98%, 99%, or 99.5% identity to SEQ ID NO:2. In yet another embodiment, the CAR protein sequence can have up to about 50 conservative amino acid substitutions. In any of the embodiments described herein, the CAR binds fluorescein.

In one embodiment, T lymphocytes (e.g., cytotoxic T lymphocytes) can be genetically engineered to express a CAR construct, wherein the CAR construct expresses an E2 anti-fluorescein antibody fragment, by transfecting a population of the T lymphocytes with an expression vector encoding the CAR construct expressing the E2 anti-fluorescein antibody fragment. Suitable methods for preparing a transduced population of T lymphocytes expressing the E2 anti-fluorescein antibody fragment are well-known to the skilled artisan, and are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference.

In one embodiment, CART cells comprising a nucleic acid of SEQ ID NO:1 can be used as described herein. In another embodiment, CAR T cells comprising a polypeptide of SEQ ID NO:2 can be used as described herein. In another illustrative aspect, a nucleic acid (e.g., an isolated nucleic acid) comprising SEQ ID NO:1 and encoding a chimeric antigen receptor can be used to prepare the CAR T cells for use as described herein. In yet another embodiment, a chimeric antigen receptor polypeptide comprising SEQ ID NO:2 can be used to prepare the CAR T cells for use as described herein. In another embodiment, a vector comprising SEQ ID NO:1 can be used to prepare the CAR T cells for use as described herein. In another aspect, a lentiviral vector is provided comprising SEQ ID NO:1 can be used to prepare the CAR T cells for use as described herein. In yet another embodiment, SEQ ID NO:2 can comprise or consist of humanized, or human amino acid sequences.

In each of these embodiments, variant nucleic acid sequences or amino acid sequences having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to SEQ ID NO:1 are contemplated. In another embodiment, the nucleic acid sequence can be a variant nucleic acid sequence having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to SEQ ID NO:1 as long as the variant sequence encodes a polypeptide of SEQ ID NO:2. In another embodiment, the nucleic acid sequence or the amino acid sequence can be a variant nucleic acid or amino acid sequence having at least about 80%, at least about 90%, at least about 91%, at least about 92%, at least about 93%, at least about 94%, at least about 95%, at least about 96%, at least about 97%, at least about 98%, at least about 99%, or at least about 99.5% sequence identity to SEQ ID NO:1 along a stretch of 200 nucleic acids or, for SEQ ID NO:2, along a stretch of 200 amino acids. In one embodiment, determination of percent identity or similarity between sequences can be done, for example, by using the GAP program (Genetics Computer Group, software; now available via Accelrys), and alignments can be done using, for example, the ClustalW algorithm (VNTI software, InforMax Inc.). A sequence database can be searched using the nucleic acid or amino acid sequence of interest. Algorithms for database searching are typically based on the BLAST software (Altschul et al., 1990). In some embodiments, the percent identity can be determined along the full-length of the nucleic acid or amino acid sequence.

Also within the scope of the invention, nucleic acids complementary to the nucleic acid represented by SEQ ID NO:1 can be used to prepare the CAR T cells for use as described herein, and those that hybridize to the nucleic acid represented by SEQ ID NO:1, or those that hybridize to its complement under highly stringent conditions can be used. In accordance with the invention "highly stringent conditions" means hybridization at 65° C. in 5×SSPE and 50% formamide, and washing at 65° C. in 0.5×SSPE. Conditions for high stringency, low stringency and moderately stringent hybridization are described in Sambrook et al., "Molecular Cloning: A Laboratory Manual", 3rd Edition, Cold Spring Harbor Laboratory Press, (2001), incorporated herein by reference, and Green and Sambrook, "Molecular Cloning: A Laboratory Manual", 4th Edition, Cold Spring Harbor Laboratory Press, (2012), incorporated herein by reference. In some illustrative aspects, hybridization occurs along the full-length of the nucleic acid.

In still other embodiments, the CAR for use in the methods described herein can be encoded by a polynucleotide having at least about 90%, 91%, 92%, 93%, 94%, 95%, 96%, 97%, 98%, 99%, or 99.5% identity to SEQ ID NO:1. In another illustrative embodiment, the CAR can be encoded by a polynucleotide that hybridizes under high stringency conditions to a polynucleotide having SEQ ID NO:1. In still another aspect, the CAR can be encoded by a polynucleotide having SEQ ID NO:1, or by a degenerate variant of SEQ ID NO:1. As used herein, a degenerate variant refers to the genetic code having more than one codon to specify any particular amino acid. The degenerate variant codons specifying each amino acid are wellknown in the art. In yet another aspect, a substitution can be made to optimize the level of production of the polypeptide in a particular prokaryotic or eukaryotic host cell (i.e., a codonusage variant).

In other embodiments, the CAR protein sequence can have at least about 90%, 91%, 92%, 93%, 94%, 95%, 96%, 97%, 98%, or 99% identity to SEQ ID NO:2. In yet another embodiment, the CAR protein sequence can have up to about 50 conservative amino acid substitutions. In one embodiment, the CAR protein sequence that expresses the E2 antifluorescein antibody fragment, can have up to about 5 conservative amino acid substitutions, up to about 10 conservative amino acid substitutions, up to about 15 conservative amino acid substitutions, up to about 20 conservative amino acid substitutions, up to about 25 conservative amino acid substitutions, up to about 30 conservative amino acid substitutions, up to about 35 conservative amino acid substitutions, up to about 40 conservative amino acid substitutions, up to about 45 conservative amino acid substitutions, up to about 50 conservative amino acid substitutions, up to about 55 conservative amino acid substitutions, up to about 60 conservative amino acid substitutions, up to about 65 conservative amino acid substitutions, up to about 70 conservative amino acid substitutions, or up to about 75 conservative amino acid substitutions. As is well known to those skilled in the art, altering any non-critical amino acid of a polypeptide by conservative amino acid substitution should not significantly alter the activity of that polypeptide because the side-chain of the replacement amino acid should be able to form similar bonds and contacts as the side chain of the amino acid which has been replaced. In any of the embodiments described herein, the CAR binds fluorescein.

In one illustrative aspect, non-conservative substitutions are possible provided that these do not excessively affect the fluorescein-binding activity of the E2 anti-fluorescein antibody fragment polypeptide. As is well-known in the art, a "conservative substitution" of an amino acid or a "conservative substitution variant" of a polypeptide refers to an amino acid substitution which maintains: 1) the secondary structure of the polypeptide; 2) the charge or hydrophobicity of the amino acid; and 3) the bulkiness of the side chain or any one or more of these characteristics. In one embodiment, the conservative amino acid substitution can be with an amino acid analog. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. An exemplary list of conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In one embodiment, the T lymphocytes (e.g., cytotoxic T lymphocytes used to prepare CAR T cells expressing the E2 anti-fluorescein antibody fragment, or non-transformed T cells), used in the methods described herein, can be autologous cells, although heterologous cells can also be used, such as when the patient being treated has received high-dose chemotherapy or radiation treatment to destroy the patient's immune system. In one embodiment, allogenic cells can be used.

In one aspect, the T lymphocytes can be obtained from a patient by means well-known in the art. For example, T cells (e.g., cytotoxic T cells or non-transformed T cells) can be obtained by collecting peripheral blood from the patient, subjecting the blood to Ficoll density gradient centrifugation, and then using a negative T cell isolation kit (such as EasySep™ T Cell Isolation Kit) to isolate a population of T cells from the peripheral blood. In one illustrative embodiment, the population of T lymphocytes (e.g., cytotoxic T cells or non-transformed T cells) need not be pure and may contain other cells such as other types of T cells (in the case of cytotoxic T cells, for example), monocytes, macrophages, natural killer cells, and B cells. In one aspect, the population being collected can comprise at least about 90% of the selected cell type, at least about 91%, 92%, 93%, 94%, 95%, 96%, 97%, 98%, 99%, or 100% of the selected cell type.

In one embodiment, after the T lymphocytes (e.g., cytotoxic T cells used to prepare CAR T cells expressing the E2 anti-fluorescein antibody fragment) are obtained, the cells are cultured under conditions that promote the activation of the cells. In this embodiment, the culture conditions may be such that the cells can be administered to a patient without concern for reactivity against components of the culture medium. For example, the culture conditions may not include bovine serum products, such as bovine serum albumin. In one illustrative aspect, the activation can be achieved by introducing known activators into the culture medium, such as anti-CD3 antibodies in the case of cytotoxic T cells. Other suitable activators include anti-CD28 antibodies. In one aspect, the population of lymphocytes can be cultured under conditions promoting activation for about 1 to about 4 days. In one embodiment, the appropriate level of activation can be determined by cell size, proliferation rate, or activation markers determined by flow cytometry.

In one illustrative embodiment, after the population of T lymphocytes (e.g., cytotoxic T lymphocytes used to prepare CAR T cells expressing the E2 anti-fluorescein antibody fragment) has been cultured under conditions promoting activation, the cells can be transfected with an expression vector encoding a CAR comprising the E2 anti-fluorescein antibody fragment. Suitable vectors and transfection methods for use in various embodiments are described above. In one aspect, after transfection, the cells can be immediately administered to the patient or the cells can be cultured for at least about 1, 2, 3, 4, 5, 6, 7, 8, 9, 10, 11, 12, 13, 14, 15, 16, 17, 18 or more days, or between about 5 and about 12 days, between about 6 and about 13 days, between about 7 and about 14 days, or between about 8 and about 15 days, for example, to allow time for the cells to recover from the transfection. In one aspect, suitable culture conditions can be similar to the conditions under which the cells were cultured for activation either with or without the agent that was used to promote activation.

Thus, as described above, in one illustrative aspect, the methods of treatment described herein can further comprise 1) obtaining a population of autologous or heterologous T lymphocytes (e.g., cytotoxic T lymphocytes used to prepare CAR T cells expressing the E2 anti-fluorescein antibody fragment), 2) culturing the T lymphocytes under conditions that promote the activation of the cells, and 3) transfecting the lymphocytes with an expression vector encoding a CAR comprising an E2 anti-fluorescein antibody fragment to form CAR T cells expressing the E2 anti-fluorescein antibody fragment.

In one illustrative embodiment, when the cells have been transfected and activated, a composition comprising the CAR T cells, wherein the CAR T cells comprise a CAR comprising an E2 anti-fluorescein antibody fragment can be prepared and administered to the patient, with or without non-transformed T cells. In one embodiment, culture media that lacks any animal products, such as bovine serum, can be used to culture the CAR T cells expressing the E2 anti-fluorescein antibody fragment and/or the non-transformed T cells. In another embodiment, tissue culture conditions typically used by the skilled artisan to avoid contamination with bacteria, fungi and mycoplasma can be used. In an exemplary embodiment, prior to being administered to a patient, the cells (e.g., CAR T cells expressing the E2 anti-fluorescein antibody fragment and/or non-transformed T cells) are pelleted, washed, and are resuspended in a pharmaceutically acceptable carrier or diluent. Exemplary compositions comprising CAR-expressing T lymphocytes expressing the E2 anti-fluorescein antibody fragment (e.g., cytotoxic T lymphocytes) or non-transformed T cells include compositions comprising the cells in sterile 290 mOsm saline, in infusible cryomedia (containing Plasma-Lyte A, dextrose, sodium chloride injection, human serum albumin and DMSO), in 0.9% NaCl with 2% human serum albumin, or in any other sterile 290 mOsm infusible materials. Alternatively, in another embodiment, depending on the identity of the culture medium, the CAR T cells expressing the E2 anti-fluorescein antibody fragment, or non-transformed T cells, can be administered in the culture media as the composition, or concentrated and resuspended in the culture medium before administration. In various embodiments, the CAR T cell composition wherein the CAR comprises the E2 anti-fluorescein antibody fragment, with or without non-transformed T cells, can be administered to the patient via any suitable means, such as parenteral administration, e.g., intradermally, subcutaneously, intramuscularly, intraperitoneally, intravenously, or intrathecally.

In one aspect, the total number of CAR T cells expressing the E2 anti-fluorescein antibody fragment and the concentration of the cells in the composition administered to the patient will vary depending on a number of factors including the type of T lymphocytes (e.g., cytotoxic T lymphocytes) being used, the binding specificity of the CAR that comprises the E2 anti-fluorescein antibody fragment, the identity of the targeting moiety and the small molecule ligand, the identity of the cancer, the location of the cancer in the patient, the means used to administer the compositions to the patient, and the health, age and weight of the patient being treated. In various embodiments, suitable compositions comprising transduced CAR T cells expressing the E2 anti-fluorescein antibody fragment include those having a volume of about 0.1 ml to about 200 ml and about 0.1 ml to about 125 ml.

In various embodiments, the transduced CAR T cells, wherein the CAR T cells comprise a CAR comprising an E2 anti-fluorescein antibody fragment, administered to the patient can comprise from about $1\times10^5$ to about $1\times10^{15}$ or $1\times10^6$ to about $1\times10^{15}$ transduced CAR T cells expressing the E2 anti-fluorescein antibody fragment. In various embodiments about $1\times10^5$ to about $1\times10^{10}$, about $1\times10^6$ to about $1\times10^{10}$, about $1\times10^6$ to about $1\times10^9$, about $1\times10^6$ to about $1\times10^8$, about $1\times10^6$ to about $2\times10^7$, about $1\times10^6$ to about $3\times10^7$, about $1\times10^6$ to about $1.5\times10^7$, about $1\times10^6$ to about $1\times10^7$, about $1\times10^6$ to about $9\times10^6$, about $1\times10^6$ to about $8\times10^6$, about $1\times10^6$ to about $7\times10^6$, about $1\times10^6$ to about $6\times10^6$, about $1\times10^6$ to about $5\times10^6$, about $1\times10^6$ to about $4\times10^6$, about $1\times10^6$ to about $3\times10^6$, about $1\times10^6$ to about $2\times10^6$, about $2\times10^6$ to about $6\times10^6$, about $2\times10^6$ to about $5\times10^6$, about $3\times10^6$ to about $6\times10^6$, about $4\times10^6$ to about $6\times10^6$, about $4\times10^6$ to about $1\times10^7$, about $1\times10^6$ to about $1\times10^7$, about $1\times10^6$ to about $1.5\times10^7$, about $1\times10^6$ to about $2\times10^7$, about $0.2\times10^6$ to about $1\times10^7$, about $0.2\times10^6$ to about $1.5\times10^7$, about $0.2\times10^6$ to about $2\times10^7$, or about $5\times10^6$ CART cells expressing the E2 anti-fluorescein antibody fragment can be administered to the patient. In one aspect, in any embodiment described herein, a single dose or multiple doses of the CAR T cells expressing the E2 anti-fluorescein antibody fragment can be administered to the patient. In any of the embodiments described in this paragraph or herein, the CAR T cell numbers can be in kg of patient body weight. In any embodiment described herein, the CAR T cells expressing the E2 anti-fluorescein antibody fragment can be administered before the compound, or the pharmaceutically acceptable salt thereof. As would be understood, the designations i), ii), and iii), etc. for steps of any method described herein do not indicate an order unless otherwise stated.

In the various embodiments described herein, non-transformed T cells can also be administered with the CAR T cells expressing the E2 anti-fluorescein antibody fragment and can be administered in amounts described herein for the CAR T cells expressing the E2 anti-fluorescein antibody fragment, and the non-transformed T cells. In one aspect, a mixture of CAR T cells, wherein the CAR T cells comprise a CAR comprising the E2 anti-fluorescein antibody fragment, and non-transformed T cells can be administered a single time or multiple times, or combinations of doses of pure CAR T cells expressing the E2 anti-fluorescein antibody fragment and mixtures of CAR T cells expressing the E2 anti-fluorescein antibody fragment, and non-transformed T cells, can be administered (e.g., a dose of CAR T cells expressing the E2 anti-fluorescein antibody fragment followed by one or more doses of a mixture of CAR T cells expressing the E2 anti-fluorescein antibody fragment and non-transformed T cells). As is clear to the skilled artisan from the disclosure herein, a "mixture" of CAR T cells expressing the E2 anti-fluorescein antibody fragment and non-transformed T cells as described herein, means that CAR T cells expressing the E2 anti-fluorescein antibody fragment are mixed with non-transformed T cells that have not been exposed to a construct used for expression of a CAR comprising an E2 anti-fluorescein antibody fragment.

In other embodiments, the dose of the CAR T cells expressing the E2 anti-fluorescein antibody fragment administered to the patient in the CAR T cell composition is selected from the group consisting of about 1 million, about 2 million, about 3 million, about 4 million, about 5 million, about 6 million, about 7 million, about 8 million, about 9 million, about 10 million, about 11 million, about 12 million, about 12.5 million, about 13 million, about 14 million, and about 15 million of the CAR T cells expressing the E2 anti-fluorescein antibody fragment.

In still other illustrative embodiments, the CAR T cell composition comprising CAR T cells expressing the E2 anti-fluorescein antibody fragment is administered by injection into the patient's bloodstream, and the CAR T cells expressing the E2 anti-fluorescein antibody fragment in the patient's bloodstream are at least 5 percent, at least 7 percent, at least 10 percent, at least 11 percent, at least 12 percent, at least 13 percent, at least 14 percent, or at least 15 percent of the patient's total T cells in the patient's bloodstream by about four weeks after injection of the CART cell composition, at least 20 percent, 25 percent, 30 percent, 35 percent, 40 percent, or 50 percent by about 3 weeks after injection of the CAR T cell composition, at least 60 percent, 65 percent, 70 percent, 75 percent, or 80 percent by about 2 weeks after injection of the CART cell composition, or at least 85 percent, 90 percent, or 95 by about 1 week after injection of the CAR T cell composition.

In embodiments described herein, the CAR T cell composition can comprise CAR T cells expressing the E2 anti-fluorescein antibody fragment, without any other cell type, or non-transformed T cells can be administered to the patient in combination with CAR T cells expressing the E2 anti-fluorescein antibody fragment. For embodiments where multiple doses of the CAR T cell composition are administered, any dose can comprise CAR T cells expressing the E2 anti-fluorescein antibody fragment or a mixture of CAR T cells expressing the E2 anti-fluorescein antibody fragment and non-transformed T cells. In various embodiments, the non-transformed T cells can be administered in amounts described herein for the CAR T cells expressing the E2 anti-fluorescein antibody fragment.

In another embodiment, any dose of the CAR T cell composition can comprise a mixture of the CAR T cells expressing the E2 anti-fluorescein antibody fragment, and non-transformed T cells in a ratio selected from about 1:5 of the CAR T cells expressing the E2 anti-fluorescein antibody fragment to the non-transformed T cells, about 1:4 of the CAR T cells expressing the E2 anti-fluorescein antibody fragment to the non-transformed T cells, about 1:3 of the CAR T cells expressing the E2 anti-fluorescein antibody fragment to the non-transformed T cells, about 1:2 of the CAR T cells expressing the E2 anti-fluorescein antibody fragment to the non-transformed T cells, and about 1:1 of the CAR T cells expressing the E2 anti-fluorescein antibody fragment to the non-transformed T cells.

In still other embodiments, any dose of the CAR T cell composition can comprise a mixture of the CAR T cells expressing the E2 anti-fluorescein antibody fragment, and non-transformed T cells in a ratio of from about 1:1 to about 1:5 of the CAR T cells expressing the E2 anti-fluorescein antibody fragment to the non-transformed T cells, or the CAR T cell composition can comprise a mixture of about 10 million of the CAR T cells expressing the E2 anti-fluorescein antibody fragment and about 40 million non-transformed T cells, about 15 million of the CAR T cells expressing the E2 anti-fluorescein antibody fragment and about 35 million of the non-transformed T cells, about 20 million of the CAR T cells expressing the E2 anti-fluorescein antibody fragment and about 30 million of the non-transformed T cells, or about 25 million of the CAR T cells expressing the E2 anti-fluorescein antibody fragment and about 25 million of the non-transformed T cells.

The compound, or pharmaceutically acceptable salt thereof, or CAR T cell composition, wherein the composition comprises CAR T cells comprising a CAR comprising an E2 anti-fluorescein antibody fragment, described herein can be administered to the patient using any suitable method known in the art. As described herein, the term "administering" or "administered" includes all means of introducing the compound, or pharmaceutically acceptable salt thereof, or CAR T cell composition comprising CAR T cells having a CAR comprising an E2 anti-fluorescein antibody fragment to the patient, including, but not limited to, oral, intravenous, intramuscular, subcutaneous, transdermal, and the like. In one aspect, the compound, or pharmaceutically acceptable salt thereof, described herein may be administered in unit dosage forms and/or formulations containing conventional nontoxic pharmaceutically-acceptable carriers, adjuvants, and vehicles.

In one aspect, the compound, or pharmaceutically acceptable salt thereof, or CAR T cell composition wherein the CAR T cell composition comprises CAR T cells expressing a CAR comprising an E2 anti-fluorescein antibody fragment, as described herein may be administered directly into the blood stream, into muscle, or into an internal organ. In various embodiments, suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. In other embodiments, any of the liquid formulations described herein may be adapted for parenteral administration as described herein. The preparation under sterile conditions, by lyophilization to produce a sterile lyophilized powder for a parenteral formulation, may readily be accomplished using standard pharmaceutical techniques well-known to those skilled in the art. In one embodiment, the solubility of the compound, or pharmaceutically acceptable salt thereof, used in the preparation of a parenteral formulation may be increased by the use of appropriate formulation techniques, such as the incorporation of solubility-enhancing agents.

The amount of the compound, or pharmaceutically acceptable salt thereof, to be administered to the patient can vary significantly depending on the cancer being treated, the route of administration of the compound, or pharmaceutically acceptable salt thereof, and the tissue distribution. The amount to be administered to a patient can be based on body surface area, mass, and physician assessment. In various embodiments, amounts to be administered can range, for example, from about 0.05 mg to about 30 mg, 0.05 mg to about 25.0 mg, about 0.05 mg to about 20.0 mg, about 0.05 mg to about 15.0 mg, about 0.05 mg to about 10.0 mg, about 0.05 mg to about 9.0 mg, about 0.05 mg to about 8.0 mg, about 0.05 mg to about 7.0 mg, about 0.05 mg to about 6.0 mg, about 0.05 mg to about 5.0 mg, about 0.05 mg to about 4.0 mg, about 0.05 mg to about 3.0 mg, about 0.05 mg to about 2.0 mg, about 0.05 mg to about 1.0 mg, about 0.05 mg to about 0.5 mg, about 0.05 mg to about 0.4 mg, about 0.05 mg to about 0.3 mg, about 0.05 mg to about 0.2 mg, about 0.05 mg to about 0.1 mg, about 0.01 mg to about 2 mg, about 0.3 mg to about 10 mg, about 0.1 mg to about 20 mg, or about 0.8 to about 3 mg. One of skill in the art will readily appreciate that the dose may vary within the various ranges provided above based on the factors noted above, and may be at the physician's discretion.

In other embodiments, the dose of the compound, or pharmaceutically acceptable salt thereof, can range, for example, from about 50 nmoles/kg to about 3000 nmoles/kg of patient body weight, about 50 nmoles/kg to about 2000 nmoles/kg, about 50 nmoles/kg to about 1000 nmoles/kg, about 50 nmoles/kg to about 900 nmoles/kg, about 50 nmoles/kg to about 800 nmoles/kg, about 50 nmoles/kg to about 700 nmoles/kg, about 50 nmoles/kg to about 600 nmoles/kg, about 50 nmoles/kg to about 500 nmoles/kg, about 50 nmoles/kg to about 400 nmoles/kg, about 50 nmoles/kg to about 300 nmoles/kg, about 50 nmoles/kg to about 200 nmoles/kg, about 50 nmoles/kg to about 100 nmoles/kg, about 100 nmoles/kg to about 300 nmoles/kg, about 100 nmoles/kg to about 500 nmoles/kg, about 100 nmoles/kg to about 1000 nmoles/kg, about 100 nmoles/kg to about 2000 nmoles/kg of patient body weight. In other embodiments, the dose may be about 1 nmoles/kg, about 5 nmoles/kg, about 10 nmoles/kg, about 20 nmoles kg, about 25 nmoles/kg, about 30 nmoles/kg, about 40 nmoles/kg, about 50 nmoles/kg, about 60 nmoles/kg, about 70 nmoles/kg, about 80 nmoles/kg, about 90 nmoles/kg, about 100 nmoles/kg, about 150 nmoles/kg, about 200 nmoles/kg, about 250 nmoles/kg, about 300 nmoles/kg, about 350 nmoles/kg, about 400 nmoles/kg, about 450 nmoles/kg, about 500 nmoles/kg, about 600 nmoles/kg, about 700 nmoles/kg, about 800 nmoles/kg, about 900 nmoles/kg, about 1000 nmoles/kg, about 2000 nmoles/kg, about 2500 nmoles/kg or about 3000 nmoles/kg of body weight of the patient.

In various other embodiments, the dose of the compound, or the pharmaceutically acceptable salt thereof, may range from, for example, about 10 nmoles/kg to about 10000 nmoles/kg, from about 10 nmoles/kg to about 5000 nmoles/kg, from about 10 nmoles/kg to about 3000 nmoles/kg, about 10 nmoles/kg to about 2500 nmoles/kg, about 10 nmoles/kg to about 2000 nmoles/kg, about 10 nmoles/kg to about 1000 nmoles/kg, about 10 nmoles/kg to about 900 nmoles/kg, about 10 nmoles/kg to about 800 nmoles/kg, about 10 nmoles/kg to about 700 nmoles/kg, about 10 nmoles/kg to about 600 nmoles/kg, about 10 nmoles/kg to about 500 nmoles/kg, about 10 nmoles/kg to about 400 nmoles/kg, about 10 nmoles/kg to about 300 nmoles/kg, about 10 nmoles/kg to about 200 nmoles/kg, about 10 nmoles/kg to about 150 nmoles/kg, about 10 nmoles/kg to about 100 nmoles/kg, about 10 nmoles/kg to about 90 nmoles/kg, about 10 nmoles/kg to about 80 nmoles/kg, about 10 nmoles/kg to about 70 nmoles/kg, about 10 nmoles/kg to about 60 nmoles/kg, about 10 nmoles/kg to about 50 nmoles/kg, about 10 nmoles/kg to about 40 nmoles/kg, about 10 nmoles/kg to about 30 nmoles/kg, about 10 nmoles/kg to about 20 nmoles/kg, about 200 nmoles/kg to about 900 nmoles/kg, about 200 nmoles/kg to about 800 nmoles/kg, about 200 nmoles/kg to about 700 nmoles/kg, about 200 nmoles/kg to about 600 nmoles/kg, about 200 nmoles/kg to about 500 nmoles/kg, about 250 nmoles/kg to about 600 nmoles/kg, about 300 nmoles/kg to about 600 nmoles/kg, about 300 nmoles/kg to about 500 nmoles/kg, or about 400 nmoles/kg to about 600 nmoles/kg, of body weight of the patient. In various other embodiments, the dose of the compound, or the pharmaceutically acceptable salt thereof, may range from, for example, about 1 nmoles/kg to about 10000 nmoles/kg, from about 1 nmoles/kg to about 5000 nmoles/kg, from about 1 nmoles/kg to about 3000 nmoles/kg, about 1 nmoles/kg to about 2500 nmoles/kg, about 1 nmoles/kg to about 2000 nmoles/kg, about 1 nmoles/kg to about 1000 nmoles/kg, about 1 nmoles/kg to about 900 nmoles/kg, about 1 nmoles/kg to about 800 nmoles/kg, about 1 nmoles/kg to about 700 nmoles/kg, about 1 nmoles/kg to about 600 nmoles/kg, about 1 nmoles/kg to about 500 nmoles/kg, about 1 nmoles/kg to about 400 nmoles/kg, about 1 nmoles/kg to about 300 nmoles/kg, about 1 nmoles/kg to about 200 nmoles/kg, about 1 nmoles/kg to about 150 nmoles/kg, about 1 nmoles/kg to about 100 nmoles/kg, about 1 nmoles/kg to about 90 nmoles/kg, about 1 nmoles/kg to about 80 nmoles/kg, about 1 nmoles/kg to about 70 nmoles/kg, about 1 nmoles/kg to about 60 nmoles/kg, about 1 nmoles/kg to about 50 nmoles/kg, about 1 nmoles/kg to about 40 nmoles/kg, about 1 nmoles/kg to about 30 nmoles/kg, or about 1 nmoles/kg to about 20 nmoles/kg. In yet other embodiments, the dose may be about 0.1 nmoles/kg, about 0.2 nmoles/kg, about 0.3 nmoles/kg, about 0.4 nmoles kg, or about 0.5 nmoles/kg, about 0.1 nmoles/kg to about 1000 nmoles/kg, about 0.1 nmoles/kg to about 900 nmoles/kg, about 0.1 nmoles/kg to about 850 nmoles/kg, about 0.1 nmoles/kg to about 800 nmoles/kg, about 0.1 nmoles/kg to about 700 nmoles/kg, about 0.1 nmoles/kg to about 600 nmoles/kg, about 0.1 nmoles/kg to about 500 nmoles/kg, about 0.1 nmoles/kg to about 400 nmoles/kg, about 0.1 nmoles/kg to about 300 nmoles/kg, about 0.1 nmoles/kg to about 200 nmoles/kg, about 0.1 nmoles/kg to about 100 nmoles/kg, about 0.1 nmoles/kg to about 50 nmoles/kg, about 0.1 nmoles/kg to about 10 nmoles/kg, or about 0.1 nmoles/kg to about 1 nmoles/kg of body weight of the patient. In other embodiments, the dose may be about 0.3 nmoles/kg to about 1000 nmoles/kg, about 0.3 nmoles/kg to about 900 nmoles/kg, about 0.3 nmoles/kg to about 850 nmoles/kg, about 0.3 nmoles/kg to about 800 nmoles/kg, about 0.3 nmoles/kg to about 700 nmoles/kg, about 0.3 nmoles/kg to about 600 nmoles/kg, about 0.3 nmoles/kg to about 500 nmoles/kg, about 0.3 nmoles/kg to about 400 nmoles/kg, about 0.3 nmoles/kg to about 300 nmoles/kg, about 0.3 nmoles/kg to about 200 nmoles/kg, about 0.3 nmoles/kg to about 100 nmoles/kg, about 0.3 nmoles/kg to about 50 nmoles/kg, about 0.3 nmoles/kg to about 10 nmoles/kg, or about 0.3 nmoles/kg to about 1 nmoles/kg of body weight of the patient. In these embodiments, "kg" is kilograms of body weight of the patient. In one aspect, a single dose or multiple doses of the compound, or pharmaceutically acceptable salt thereof, may be administered to the patient.

In another embodiment, between about 20 ug/kg of body weight of the patient and about 3 mg/kg of body weight of the patient of the compound, or the pharmaceutically acceptable salt thereof, can be administered to the patient. In another aspect, amounts can be from about 0.2 mg/kg of body weight of the patient and about 0.4 mg/kg of body weight of the patient, or can be about 50 ug/kg of body weight of the patient. In one aspect, a single dose or multiple doses of the compound, or the pharmaceutically acceptable salt thereof, may be administered to the patient.

In one embodiment, the small molecule ligand linked to the targeting moiety (the compound) can be administered to the patient before the CAR T cell composition comprising CAR T cells wherein the CAR T cells have a CAR comprising an E2 anti-fluorescein antibody fragment. In another embodiment, the small molecule ligand linked to the targeting moiety (bridge) can be administered to the patient at the same time as the CAR T cell composition comprising CAR T cells wherein the CAR T cells have a CAR comprising an E2 anti-fluorescein antibody fragment, but in different formulations, or in the same formulation. In yet another embodiment, the small molecule ligand linked to the targeting moiety can be administered to the patient after the CAR T cell composition comprising CAR T cells wherein the CAR T cells have a CAR comprising an E2 anti-fluorescein antibody fragment.

In one illustrative aspect, the timing between the administration of the CAR T cells having a CAR comprising an E2 anti-fluorescein antibody fragment, and the small molecule linked to the targeting moiety (bridge) may vary widely depending on factors that include the type of CAR T cells expressing the E2 anti-fluorescein antibody fragment being used, the binding specificity of the CAR having the E2 anti-fluorescein antibody fragment, the identity of the targeting moiety and the small molecule ligand, the identity of the cancer, the location in the patient of the cancer, the means used to administer to the patient the CAR T cells expressing the E2 anti-fluorescein antibody fragment and the small molecule ligand linked to the targeting moiety, and the health, age, and weight of the patient. In one aspect, the small molecule ligand linked to the targeting moiety can be administered before or after the CAR T cells, such as within about 3, 6, 9, 12, 15, 18, 21, 24, 27, 30, 33, 36, 39, 42, 45, 48, or 51 hours, or within about 0.5, 1, 1.5, 2, 2.5, 3, 4 5, 6, 7, 8, 9, 10 or more days.

In one embodiment, any applicable dosing schedule known in the art can be used for administration of the compound, or the pharmaceutically acceptable salt thereof, or for the CAR T cell composition wherein the CAR T cell composition comprises CAR T cells having a CAR, wherein the CAR comprises an E2 anti-fluorescein antibody fragment. For example, once per day dosing (a.k.a qd), twice per day dosing (a.k.a. bid), three times per day dosing (a.k.a. tid), twice per week dosing (a.k.a. BIW), three times per week dosing (a.k.a. TIW), once weekly dosing, and the like, can be used. In one aspect, the dosing schedule selected for the compound, or the pharmaceutically acceptable salt thereof, and the CAR T cell composition wherein the CAR T cell composition comprises CAR T cells having a CAR, wherein the CAR comprises an E2 anti-fluorescein antibody fragment, can take into consideration the concentration of the compound, or the pharmaceutically acceptable salt thereof, and the number of CAR T cells expressing the E2 anti-fluorescein antibody fragment administered, to regulate the cytotoxicity of the CAR T cell composition wherein the CAR T cell composition comprises CAR T cells having a CAR, wherein the CAR comprises an E2 anti-fluorescein antibody fragment, and to control CRS.

In one embodiment, to prevent or inhibit cytokine release syndrome (CRS) in the patient, a method of treatment of a cancer is provided. The method comprises i) administering to a patient a compound, or a pharmaceutically acceptable salt thereof, wherein the compound comprises a small molecule ligand linked to a targeting moiety by a linker, ii) administering to the patient a CAR T cell composition wherein the CAR T cell composition comprises CAR T cells wherein the CAR T cells comprise a CAR, wherein the CAR comprises an E2 anti-fluorescein antibody fragment, and iii) administering to the patient a folate, a conjugate comprising a folate wherein the conjugate comprising a folate does not comprise a targeting moiety, or a drug that inhibits activation of the CAR T cells.

In this method embodiment, the step of administering to the patient a folate, a conjugate comprising a folate wherein the conjugate comprising a folate does not comprise a targeting moiety, or a drug that inhibits activation of the CAR T cells expressing the E2 anti-fluorescein antibody fragment can be used to prevent or inhibit CRS in the patient. In this embodiment, any of a folate, a conjugate comprising a folate wherein the conjugate comprising a folate does not comprise a targeting moiety, or a drug that inhibits activation of the CAR T cells expressing the E2 anti-fluorescein antibody fragment can be referred to herein as "a rescue agent". In one embodiment, a folate, such as folic acid, can be administered to prevent or inhibit CRS in the patient. In this embodiment, the folate inhibits interaction of the bridge (i.e., the small molecule ligand linked to the targeting moiety by a linker) with the receptors for the bridge on the tumor inhibiting tumor lysis and preventing or inhibiting CRS in the patient.

In another embodiment, the rescue agent can reduce CRS in as quickly as about 30 minutes, about 1 hour, about 2 hours, about 3 hours, about 4 hours, about 5 hours, about 6 hours, about 7 hours, about 8 hours, about 9 hours, or about 10 hours after administration of the rescue agent. For example, the grade of CRS can be reduced (e.g., grade 3 to grade 2, grade 4 to grade 3, etc.).

An exemplary grading system is shown below with columns 1-6 which are grades 0, 1, 2, 3, 4, and 5:

| CRS Grading Scale | | | | | |
| --- | --- | --- | --- | --- | --- |
| 0 | 1 | 2 | 3 | 4 | 5 |
| Normal | ~pilo ~greasy still active | pilo greasy less active | pilo, greasy bunched, thin not active, unless stimulated | moribund bunched, pale lethargic | Death |

In one embodiment, the folate administered as an inhibitor of binding of the bridge to the tumor can be, for example, folic acid, a folic acid analog, or another folate receptor binding molecule. In various embodiments, analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), N10-methylfolate, 2-deamino-hydroxyfolate, deaza analogs such as 1-deazamethopterin or 3-deazamethopterin, and 3',5'-dichloro-4-amino-4-deoxy-N10-methylpteroylglutamic acid (dichloromethotrexate).

In another embodiment, the folate administered as an inhibitor of binding of the bridge to the tumor has the formula

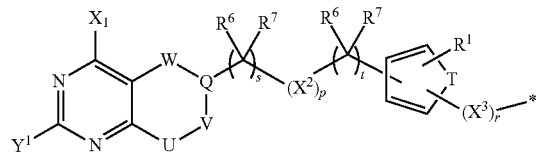

wherein $X^1$ and $Y^1$ are each-independently selected from the group consisting of halo, $R^2$, $OR^2$, $SR^3$, and $NR^4R^5$; U, V, and W represent divalent moieties each independently selected from the group consisting of —$(R^{6a})C$=, —N=, —$(R^{6a})C(R^{7a})$—, and —$N(R^{4a})$—; Q is selected from the group consisting of C and CH; T is selected from the group consisting of S, O, N, and —C≡C—; $X^2$ and $X^3$ are each independently selected from the group consisting of oxygen, sulfur, —C(Z)—, —C(Z)O—, —OC(Z)—, —$N(R^{4b})$—, —$C(Z)N(R^{4b})$—, —$N(R^{4b})C(Z)$—, —$OC(Z)N(R^{4b})$—, —$N(R^{4b})C(Z)O$—, —$N(R^{4b})C(Z)N(R^{5b})$—, —S(O)—, —$S(O)_2$—, —$N(R^{4a})S(O)_2$—, —$C(R^{6b})(R^{7b})$—, —N(C≡CH)—, —$N(CH_2C≡CH)$—, $C_1$-$C_{12}$ alkylene, and $C_1$-$C_{12}$ alkyeneoxy, where Z is oxygen or sulfur; $R^1$ is selected-from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, $(C_1$-$C_{12}$ alkoxy)carbonyl, and $(C_1$-$C_{12}$ alkylamino)carbonyl; $R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^ha$ and $R^{7a}$ are each independently selected from the group consisting of hydrogen, halo, $C_1$-$C_{12}$ alkyl, and $C_1$-$C_{12}$ alkoxy; or $R^ha$ and $R^{7a}$ are taken together to form a carbonyl group; p, r, s, and t are each independently either 0 or 1; and * represents a covalent bond to the rest of the conjugate.

In yet another embodiment, a conjugate comprising a folate can be administered to prevent or inhibit cytokine release syndrome (CRS) in the patient. CRS is a term well-known in the art and this syndrome can cause detrimental effects to the patient, including, but not limited to weight loss, high fever, pulmonary edema, and a dangerous drop in blood pressure.

In this embodiment, the conjugate comprising a folate does not comprise a targeting moiety, and, thus, the conjugate inhibits interaction of the bridge with the tumor to prevent tumor lysis and reduce CRS in the patient. In this embodiment, the folate moiety in the conjugate comprising a folate can comprise any of the folates described in the preceding paragraphs linked to a chemical moiety that does not comprise a targeting moiety. In one aspect, the conjugate comprising a folate can comprise a folate linked to one or more amino acids that do not comprise a targeting moiety. Illustratively, the conjugate comprising a folate can have the formula

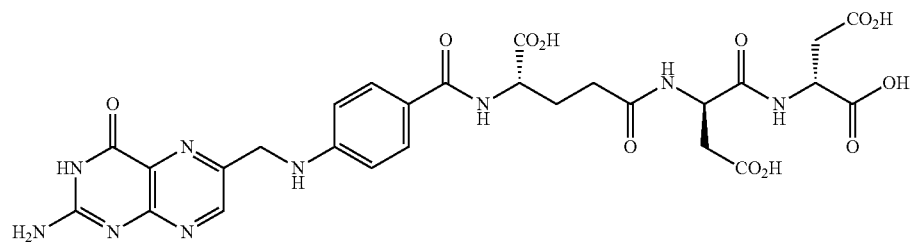 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

This compound can also be referred to as "EC923". In these embodiments, the folate or the conjugate comprising a folate can be administered to the patient in molar excess relative to the bridge (i.e., the small molecule ligand linked to a targeting moiety by a linker), such as a 10-fold excess, a 100-fold excess, a 200-fold excess a 300-fold excess a 400-fold excess a 500-fold excess a 600-fold excess a 700-fold excess a 800-fold excess a 900-fold excess, a 1000-fold excess, or a 10,000-fold excess of the folate or the conjugate comprising a folate relative to the small molecule ligand linked to a targeting moiety by a linker. The amount of the folate or the conjugate comprising a folate relative to the amount of the small molecule ligand linked to a targeting moiety by a linker needed to inhibit interaction of the bridge with the tumor can be determined by the skilled artisan.

In another embodiment, a rescue agent that inhibits activation of the CAR T cells expressing the E2 anti-fluorescein antibody fragment, can be administered to the patient to inhibit CAR T cell activation and to inhibit or prevent CRS in the patient. In one aspect the agent can be selected from the group consisting of a lymphocyte-specific protein tyrosine kinase inhibitor (e.g., Dasatinib), a PI3 kinase inhibitor (e.g., GDC0980), an inhibitor of an IL-2 inducible T cell kinase (e.g., BMS-509744)), JAK inhibitors, BTK inhibitors, Tociluzumab, SIP agonists (e.g., Siponimod and Ozanimod) and an agent that blocks CAR T cell binding to the bridge, but does not bind to the cancer (e.g., fluoresceinamine, FITC, or sodium fluorescein). It is understood by the skilled artisan that FITC (i.e., fluorescein) can be in the form of a salt (e.g., sodium fluorescein), or in its unsalted form, under physiological conditions or, for example, in a buffer at physiological pH. Accordingly, in one embodiment, when fluorescein is administered to a patient it may be in equilibrium between its salted form (e.g., sodium fluorescein) and its unsalted form. In another embodiment, a rescue agent that inhibits activation of CAR T cells can be a compound of the formula

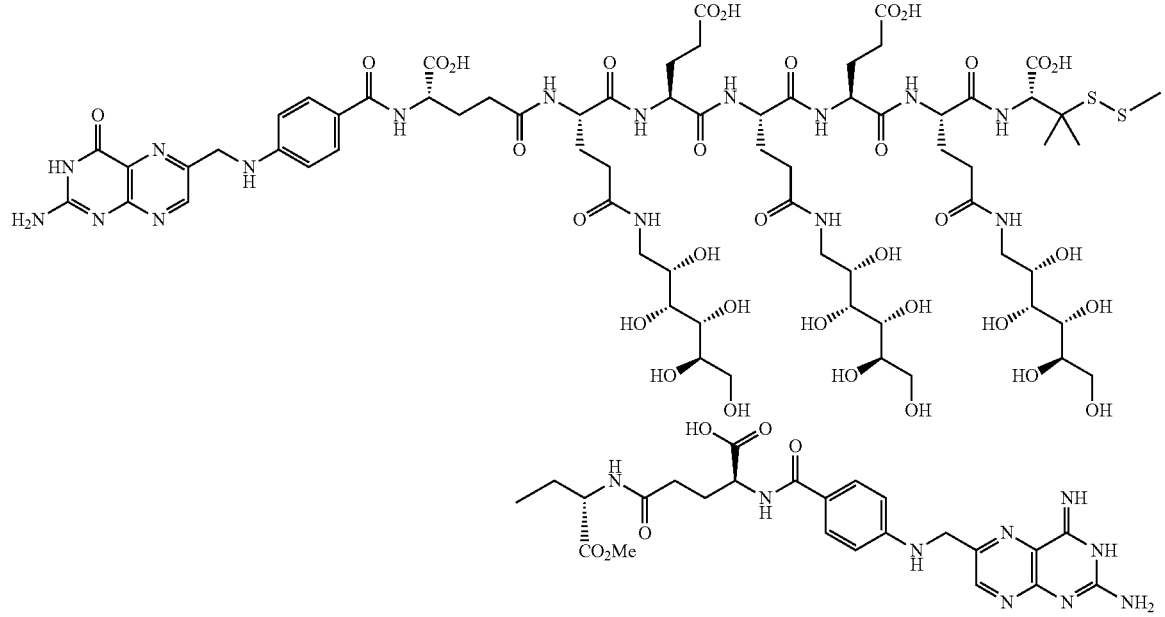

In various embodiments, the rescue agent can be administered at a concentration of from about 0.001 nM to about 100 mM, about 0.01 nM to about 100 mM, about 1 nM to about 100 mM, about 10 nM to about 100 mM, about 50 nM to about 100 mM, or from about 100 nM to about 100 mM in any appropriate volume, including, for example, 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 10 ml, 100 ml, or 1000 ml. In other embodiments, the rescue agent can be administered at a dose of about 0.01 to about 300 umoles/kg of body weight of the patient, about 0.06 to about 100 umoles/kg of body weight of the patient, about 0.06 to about 90 umoles/kg of body weight of the patient, about 0.06 to about 80 umoles/kg of body weight of the patient, about 0.06 to about 70 umoles/kg of body weight of the patient, about 0.06 to about 60 umoles/kg of body weight of the patient, about 0.06 to about 50 umoles/kg of body weight of the patient, about 0.06 to about 40 umoles/kg of body weight of the patient, about 0.06 to about 30 umoles/kg of body weight of the patient, about 0.06 to about 20 umoles/kg of body weight of the patient, about 0.06 to about 10 umoles/kg of body weight of the patient, about 0.06 to about 8 umoles/kg of body weight of the patient, or about 0.06 to about 6 umoles/kg of body weight of the patient.

In these embodiments, the rescue agent can be administered to the patient in molar excess relative to the compound, or its pharmaceutically acceptable salt (i.e., the small molecule ligand linked to a targeting moiety by a linker), such as about a 10-fold excess, about a 20-fold excess, about a 30-fold excess, about a 40-fold excess, about a 50-fold excess, about a 60-fold excess, about a 70-fold excess, about a 80-fold excess, about a 90-fold excess, about a 100-fold excess, about a 200-fold excess, about a 300-fold excess, about a 400-fold excess, about a 500-fold excess, about a 600-fold excess, about a 700-fold excess, about a 800-fold excess, about a 900-fold excess, about a 1000-fold excess, or about a 10,000-fold excess of the rescue agent relative to the small molecule ligand linked to a targeting moiety by a linker. The amount of the rescue agent relative to the amount of the small molecule ligand linked to a targeting moiety by a linker (bridge) needed to inhibit interaction of the compound, or its pharmaceutically acceptable salt, with the tumor and/or the CAR T cells expressing the E2 anti-fluorescein antibody fragment can be determined by the skilled artisan.

In another embodiment, more than one dose can be administered to the patient of the folate, the conjugate comprising a folate wherein the conjugate comprising a folate does not comprise a targeting moiety, or the agent that inhibits activation of the CAR T cells expressing the E2 anti-fluorescein antibody fragment.

In the 'rescue agent' embodiments described herein, the folate, the conjugate comprising a folate wherein the conjugate comprising a folate does not comprise a targeting moiety, or the agent that inhibits activation of the CAR T cells expressing the E2 anti-fluorescein antibody fragment, can be administered to the patient before and/or after the compound, or the pharmaceutically acceptable salt thereof. In another aspect, the compound, or the pharmaceutically acceptable salt thereof, can be administered before and subsequent to administration of the folate, the conjugate comprising a folate wherein the conjugate comprising a folate does not comprise a targeting moiety, or the agent that inhibits activation of the CAR T cells expressing the E2 anti-fluorescein antibody fragment. In this embodiment, the subsequent administration of the compound, or the pharmaceutically acceptable salt thereof, can cause activation of the CAR T cells expressing the E2 anti-fluorescein antibody fragment and an increase in cytokine levels in the patient.

In another embodiment, administration of the folate, the conjugate comprising a folate wherein the conjugate comprising a folate does not comprise a targeting moiety, or the agent that inhibits activation of the CAR T cells expressing the E2 anti-fluorescein antibody fragment, can cause reduction in cytokine levels in the patient. In yet another embodiment, the reduction in cytokine levels can occur by about 1 hour, by about 2 hours, by about 3 hours, by about 4 hours, by about 5 hours, by about 6 hours, by about 7 hours, or by about 8 hours after administration to the patient of the folate, the conjugate comprising a folate wherein the conjugate comprising a folate does not comprise a targeting moiety, or the agent that inhibits activation of the CAR T cells expressing the E2 anti-fluorescein antibody fragment. In another embodiment, the reduction in cytokine levels is a reduction to about the cytokine levels in an untreated patient.

In another illustrative embodiment, the number of the CAR T cells expressing the E2 anti-fluorescein antibody fragment can increase in the blood of the patient after administration of the folate, the conjugate comprising a folate wherein the conjugate comprising a folate does not comprise a targeting moiety, or the agent that inhibits activation of the CAR T cells expressing the E2 anti-fluorescein antibody fragment, even though cytokine levels in the patient are reduced. In another illustrative aspect, activation of the CAR T cells expressing the E2 anti-fluorescein antibody fragment can be enhanced or maintained, relative to a patient not treated with a rescue agent, after administration of the folate, the conjugate comprising a folate wherein the conjugate comprising a folate does not comprise a targeting moiety, or the rescue agent that inhibits activation of the CAR T cells wherein the CAR T cells comprise a CAR comprising the E2 anti-fluorescein antibody fragment, even though cytokine levels in the treated patient are reduced. In still another embodiment, the cancer comprises a tumor and tumor size in the patient is not increased when the folate, the conjugate comprising a folate wherein the conjugate comprising a folate does not comprise a targeting moiety, or the rescue agent that inhibits activation of the CAR T cells expressing the E2 anti-fluorescein antibody fragment is administered to the patient. In this embodiment, a complete response for the tumor can be obtained.

In other embodiments, the rescue agent that inhibits activation of the CAR T cells expressing the E2 anti-fluorescein antibody fragment is administered to the patient when the CRS grade reaches 1, 2, 3, or 4 or when the CRS grade reaches 3 or 4. In another aspect, lung edema is reduced in the patient when the rescue agent is administered.

In one embodiment described herein a method of treatment of a cancer is provided, and the method comprises i) administering continuously to a patient a compound, or a pharmaceutically acceptable salt thereof, wherein the compound comprises a small molecule ligand linked to a targeting moiety by a linker, ii) administering to the patient a CAR T cell composition comprising CAR T cells wherein the CAR T cells comprise a CAR comprising an E2 anti-fluorescein antibody fragment, and iii) ending the continuous administration of the compound, or the pharmaceutically acceptable salt thereof, to inhibit or prevent cytokine release syndrome in the patient.

In accordance with this embodiment, the term "continuously" can mean administering the compound, or the pharmaceutically acceptable salt thereof, to the patient, for example, at least one hour, at least four hours, at least six hours, at least eight hours, at least ten hours, at least twelve hours, or at least twenty-four hours, or can mean a regimen of daily or weekly administration, such as once a day, two times a day, three times a day, every day, every other day, one time weekly, two times weekly, three times weekly, or any other suitable regimen that would be considered continuous administration by a person skilled in the art. In another aspect, the term "continuously" can mean any combination of the embodiments described in this paragraph.

In this method embodiment, the step of "ending the continuous administration" of the compound, or the pharmaceutically acceptable salt thereof, to inhibit or prevent cytokine release syndrome in the patient, can mean, for example, discontinuing administration after administration for a continuous period of time, such as hours or days, or discontinuing a treatment regimen, such as the daily or weekly regimens described above. In another embodiment, the step of "ending the continuous administration" can mean, for example, administration until an unacceptable loss of body weight for the patient occurs, or until any other unacceptable side effect occurs such as a high fever, a drop in blood pressure, or pulmonary edema. In this embodiment, the step of "ending the continuous administration" of the compound, or the pharmaceutically acceptable salt thereof, does not mean a single treatment with the compound, or the pharmaceutically acceptable salt thereof, with no subsequent treatment with the compound, or the pharmaceutically acceptable salt thereof. In this method embodiment "to inhibit or prevent" cytokine release syndrome (CRS) means eliminating CRS or reducing or ameliorating the symptoms of CRS.

In one embodiment of the embodiment involving ending the continuous administration" of the compound, or the pharmaceutically acceptable salt thereof, the method can further comprise step iv) of re-administering the compound, or the pharmaceutically acceptable salt thereof, to the patient. In one embodiment, the compound, or the pharmaceutically acceptable salt thereof, can be administered, for example, once weekly and one dose can be omitted. In another embodiment, the compound, or the pharmaceutically acceptable salt thereof, can be administered on alternate days (i.e., every other day) and one or more (e.g., two, three, fours, etc.) doses can be omitted. In another embodiment, the compound, or the pharmaceutically acceptable salt thereof, can be administered twice weekly and one or more (e.g., two, three, fours, etc.) doses can be omitted. In another embodiment, the compound, or the pharmaceutically acceptable salt thereof, can be administered Monday, Tuesday, and the following Monday, and then dosing can be stopped for two weeks and the cycle repeated. In another embodiment, any of the regimen embodiments described above can be used and one or more (e.g., two, three, four, etc.) doses can be omitted. In these embodiments, the omitted doses can prevent or reduce CRS in the patient.

In yet another illustrative aspect, a method of treatment of a cancer is provided. The method comprises i) administering to a patient a compound, or a pharmaceutically acceptable salt thereof, wherein the compound comprises a small molecule ligand linked to a targeting moiety by a linker, wherein at least a first dose and a second dose of the compound, or the pharmaceutically acceptable salt thereof, are administered to the patient, wherein the first dose and the second dose are different, wherein the second dose of the compound, or the pharmaceutically acceptable salt thereof, is about 2-fold to about 15000-fold greater in amount than the first dose of the compound, or the pharmaceutically acceptable salt thereof, and ii) administering to the patient a CAR T cell composition comprising CAR T cells wherein the CAR T cells comprise a CAR comprising an E2 anti-fluorescein antibody fragment.

In this embodiment, the dose of the compound, or the pharmaceutically acceptable salt thereof, can be escalated gradually to inhibit or prevent cytokine release syndrome in the patient. For example, at least a first dose and a second dose of the compound, or the pharmaceutically acceptable salt thereof, can be administered to the patient, wherein the first dose and the second dose are different, wherein the second dose of the compound, or the pharmaceutically acceptable salt thereof, is about 20-fold to about 15000-fold greater, 2-fold to about 15000-fold greater in amount than the first dose of the compound, or the pharmaceutically acceptable salt thereof. In other embodiments, the second dose, or a subsequent dose, can be about 2-fold to about 5-fold, about 2-fold to about 10-fold, about 2-fold to about 20-fold, about 2-fold to about 30-fold, about 2-fold to about 40-fold, about 2-fold to about 50-fold, about 2-fold to about 60-fold, about 2-fold to about 70-fold, about 2-fold to about 80-fold, about 2-fold to about 90-fold, about 2-fold to about 100-fold, about 2-fold to about 15000-fold, about 2-fold to about 10000-fold, about 5-fold to about 9000-fold, about 5-fold to about 8000-fold, about 5-fold to about 7000-fold, about 5-fold to about 6000-fold, about 5-fold to about 5000-fold, about 5-fold to about 4000-fold, about 5-fold to about 3000-fold, about 5-fold to about 4000-fold, about 5-fold to about 3000-fold, about 5-fold to about 2000-fold, about 5-fold to about 1000-fold, about 5-fold to about 750-fold, about 2-fold to about 750-fold, about 5-fold to about 500-fold, about 5-fold to about 100-fold, about 800-fold to about 15000-fold, about 800-fold to about 10000-fold, about 800-fold to about 9000-fold, about 800-fold to about 8000-fold, about 800-fold to about 7000-fold, about 800-fold to about 6000-fold, about 800-fold to about 5000-fold, about 800-fold to about 4000-fold, about 800-fold to about 3000-fold, about 800-fold to about 2000-fold, about 800-fold to about 1000-fold, about 8000-fold to about 15000-fold, about 8000-fold to about 10000-fold, about 8000-fold to about 9000-fold, about 15000-fold, about 10000-fold, about 9000-fold, about 8000-fold, about 7000-fold, about 6000-fold, about 5000-fold, about 4000-fold, about 3000-fold, about 2000-fold, about 1000-fold, about 500-fold, about 400-fold, about 300-fold, about 200-fold, about 100-fold, about 90-fold, about 80-fold, about 70-fold, about 60-fold, about 50-fold, about 40-fold, about 30-fold, about 20-fold, about 10-fold, about 5-fold, or about 2-fold greater in amount than the first dose of the compound, or the pharmaceutically acceptable salt thereof.

In another illustrative embodiment of the dose escalation method, at least a first dose, a second dose, and a third dose of the compound, or the pharmaceutically acceptable salt thereof, can be administered to the patient, wherein the first dose, the second dose, and the third dose are different, wherein the second dose of the compound, or the pharmaceutically acceptable salt thereof, is about 2-fold to about 750-fold greater in amount than the first dose of the compound, or the pharmaceutically acceptable salt thereof, and wherein the third dose of the compound, or the pharmaceutically acceptable salt thereof, is about 800-fold to about 10000-fold greater in amount than the first dose of the compound, or the pharmaceutically acceptable salt thereof.

In another aspect of the dose escalation method, at least a first dose, a second dose, a third dose, and a fourth dose of the compound, or the pharmaceutically acceptable salt thereof, can be administered to the patient, wherein the first dose, the second dose, the third dose, and the fourth dose are different, wherein the second dose of the compound, or the pharmaceutically acceptable salt thereof, is about 2-fold to about 750-fold greater in amount than the first dose of the compound, or the pharmaceutically acceptable salt thereof, wherein the third dose of the compound, or the pharmaceutically acceptable salt thereof, is about 800-fold to about 7500-fold greater in amount than the first dose of the compound, or the pharmaceutically acceptable salt thereof, and wherein the fourth dose of the compound, or the pharmaceutically acceptable salt thereof, is about 8000 to about 15000-fold greater in amount than the first dose of the compound, or the pharmaceutically acceptable salt thereof.

In still another embodiment, the second dose of the compound, or the pharmaceutically acceptable salt thereof, can be about 100-fold greater in amount than the first dose of the compound, or the pharmaceutically acceptable salt thereof, the third dose of the compound, or the pharmaceutically acceptable salt thereof, can be about 1000-fold greater in amount than the first dose of the compound, or the pharmaceutically acceptable salt thereof, and the fourth dose of the compound, or the pharmaceutically acceptable salt thereof, can be about 10000-fold greater in amount than the first dose of the compound, or the pharmaceutically acceptable salt thereof. In an exemplary embodiment, the first dose of the compound, or the pharmaceutically acceptable salt thereof, is 0.05 nmoles/kg, the second dose is 5 nmoles/kg, the third dose is 50 nmoles/kg, and the fourth dose is 500 nmoles/kg. In the dose escalation embodiments described herein, the first, second, third, fourth, and any subsequent doses of the compound, or the pharmaceutically acceptable salt thereof, can be administered multiple times (e.g., the first dose at 0.05 nmoles/kg can be administered several times before the subsequent escalated doses are administered).

In another embodiment described herein, a method of treatment of a cancer is provided. The method comprises i) administering to a patient a first dose of a compound, or a pharmaceutically acceptable salt thereof, wherein the compound comprises a small molecule ligand linked to a targeting moiety by a linker, ii) administering to the patient at least a second dose of the compound, or a pharmaceutically acceptable salt thereof, wherein the second dose of the compound, or the pharmaceutically acceptable salt thereof, is at least about 50 percent lower in amount than the first dose of the compound, or the pharmaceutically acceptable salt thereof, and iii) administering to the patient a dose of a CAR T cell composition comprising CAR T cells wherein the CAR T cells comprise a CAR comprising an E2 anti-fluorescein antibody fragment.

In various embodiments of this dose de-escalation embodiment, the second dose of the compound, or the pharmaceutically acceptable salt thereof, can be at least about 60 percent lower in amount than the first dose of the compound, or the pharmaceutically acceptable salt thereof, at least about 70 percent lower in amount than the first dose of the compound, or the pharmaceutically acceptable salt thereof, at least about 80 percent lower in amount than the first dose of the compound, or the pharmaceutically acceptable salt thereof, at least about 90 percent lower in amount than the first dose of the compound, or the pharmaceutically acceptable salt thereof, at least about 95 percent lower in amount than the first dose of the compound, or the pharmaceutically acceptable salt thereof, at least about 96 percent lower in amount than the first dose of the compound, or the pharmaceutically acceptable salt thereof, at least about 97 percent lower in amount than the first dose of the compound, or the pharmaceutically acceptable salt thereof, at least about 98 percent lower in amount than the first dose of the compound, or the pharmaceutically acceptable salt thereof, at least about 99 percent lower in amount than the first dose of the compound, or the pharmaceutically acceptable salt thereof, or at least about 99.5 percent lower in amount than the first dose of the compound, or the pharmaceutically acceptable salt thereof.

In various embodiments of the dose de-escalation embodiment described herein, the first dose of the compound, or the pharmaceutically acceptable salt thereof, can be about 100 nmoles/kg to about 1000 nmoles/kg of body weight of the patient, about 100 nmoles/kg to about 900 nmoles/kg of body weight of the patient, about 100 nmoles/kg to about 800 nmoles/kg of body weight of the patient, about 100 nmoles/kg to about 700 nmoles/kg of body weight of the patient, about 100 nmoles/kg to about 600 nmoles/kg of body weight of the patient, about 200 nmoles/kg to about 600 nmoles/kg of body weight of the patient, about 400 nmoles/kg to about 600 nmoles/kg of body weight of the patient, or about 500 nmoles/kg of body weight of the patient.

In various embodiments of the dose de-escalation embodiment described herein, the second dose of the compound, or the pharmaceutically acceptable salt thereof, can be about 0.5 nmoles/kg to about 500 nmoles/kg of body weight of the patient, about 0.5 nmoles/kg to about 450 nmoles/kg of body weight of the patient, about 0.5 nmoles/kg to about 400 nmoles/kg of body weight of the patient, about 0.5 nmoles/kg to about 350 nmoles/kg of body weight of the patient, about 0.5 nmoles/kg to about 300 nmoles/kg of body weight of the patient, about 1 nmole/kg to about 300 nmoles/kg of body weight of the patient, about 2 nmoles/kg to about 300 nmoles/kg of body weight of the patient, about 2 nmoles/kg to about 250 nmoles/kg of body weight of the patient, about 5 nmoles/kg to about 40 nmoles/kg of body weight of the patient, or about 40 nmoles/kg to about 150 nmoles/kg of body weight of the patient.

In additional embodiments of the dose de-escalation embodiment described herein, the method can further comprise administering a third dose of the compound, or the pharmaceutically acceptable salt thereof, wherein the third dose of the compound, or the pharmaceutically acceptable salt thereof, is the same as the second dose of the compound, or the pharmaceutically acceptable salt thereof. In another embodiment, the method can further comprise administering a fourth dose of the compound, or the pharmaceutically acceptable salt thereof, wherein the fourth dose of the compound, or the pharmaceutically acceptable salt thereof, is the same as the second dose, or the pharmaceutically acceptable salt thereof, and the third dose of the compound, or the pharmaceutically acceptable salt thereof. In yet another embodiment, the dose(s) of the compound, or the pharmaceutically acceptable salt thereof, administered after the first dose of the compound, or the pharmaceutically acceptable salt thereof, can maintain inhibition of growth of the cancer relative to the first dose of the compound, or the pharmaceutically acceptable salt thereof.

In other embodiments of the dose de-escalation embodiment described herein, the CAR T cells expressing the E2 anti-fluorescein antibody fragment can be administered at a dose of about 1 million of the CART cells expressing the E2 anti-fluorescein antibody fragment to about 40 million of the CAR T cells expressing the E2 anti-fluorescein antibody fragment.

In still other embodiments, the dose(s) of the compound or the pharmaceutically acceptable salt thereof, administered after the first dose of the compound, or the pharmaceutically acceptable salt thereof, can be administered once or twice weekly. In still other embodiments of the dose de-escalation embodiment described herein, the method can further comprise the step of administering to the patient a folate, a conjugate comprising a folate wherein the conjugate comprising a folate does not comprise a targeting moiety, or an agent that inhibits activation of the CAR T cells expressing the E2 antifluorescein antibody fragment.

In another embodiment, the agent that inhibits activation of the CAR T cells expressing the E2 anti-fluorescein antibody fragment is administered to the patient and the agent is an agent that blocks binding of the CAR T cells expressing the E2 anti-fluorescein antibody fragment to the compound, or the pharmaceutically acceptable salt thereof, but does not bind to the cancer, and the agent is fluoresceinamine, sodium fluorescein, or fluorescein. In yet another embodiment, the agent is sodium fluorescein. In another embodiment, a method of treatment of a cancer is provided. The method comprises i) administering to a patient a first dose of a compound, or a pharmaceutically acceptable salt thereof, wherein the compound comprises a small molecule ligand linked to a targeting moiety by a linker and wherein the compound, or the pharmaceutically acceptable salt thereof, is administered to the patient at least about one hour prior to the administration of a CAR T cell composition comprising CAR T cells wherein the CAR T cells comprise a CAR comprising an E2 anti-fluorescein antibody fragment, ii) then administering to the patient a dose of the CAR T cell composition comprising CAR T cells wherein the CAR T cells comprise a CAR comprising an E2 anti-fluorescein antibody fragment, and iii) then administering to the patient a second dose of the compound, or the pharmaceutically acceptable salt thereof. In various embodiments of this pre-treatment embodiment, the first dose of the compound, or the pharmaceutically acceptable salt thereof, can be administered to the patient at least about two hours prior to the administration of the CAR T cell composition, at least about four hours prior to the administration of the CAR T cell composition, at least about eight hours prior to the administration of the CAR T cell composition, at least about twelve hours prior to the administration of the CAR T cell composition, at least about sixteen hours prior to the administration of the CAR T cell composition, at least about twenty hours prior to the administration of the CAR T cell composition, or at least about twenty-four hours prior to the administration of the CAR T cell composition, in each case wherein the CAR T cell composition comprises CAR T cells comprising a CAR comprising an E2 anti-fluorescein antibody fragment.

In various embodiments of this pre-treatment embodiment, the second dose of the compound, or the pharmaceutically acceptable salt thereof, can be administered to the patient by at least about twenty-four hours after the administration of the CAR T cell composition, by at least about twenty hours after the administration of the CAR T cell composition, by at least about eighteen hours after the administration of the CAR T cell composition, by at least about sixteen hours after the administration of the CAR T cell composition, by at least about fourteen hours after the administration of the CAR T cell composition, by at least about twelve hours after the administration of the CAR T cell composition, by at least about ten hours after the administration of the CAR T cell composition, by at least about eight hours after the administration of the CAR T cell composition, by at least about six hours after the administration of the CAR T cell composition, by at least about four hours after the administration of the CAR T cell composition, or by at least about two hours after the administration of the CAR T cell composition, in each case wherein the CAR T cell composition comprises CAR T cells comprising a CAR comprising an E2 anti-fluorescein antibody fragment.

In any of the embodiments described herein where a folate is the ligand linked to the targeting moiety by a linker, the patient can be put on a folate deficient diet prior to treatment with the methods described herein, or the patient can be administered a folate in the diet. In the embodiment where the patient is administered folate, the dose can range, for example, from about 50 nmol/kg to about 3000 nmol/kg of patient body weight, about 50 nmol/kg to about 2000 nmol/kg, about 50 nmol/kg to about 1000 nmol/kg, about 50 nmol/kg to about 900 nmol/kg, about 50 nmol/kg to about 800 nmol/kg, about 50 nmol/kg to about 700 nmol/kg, about 50 nmol/kg to about 600 nmol/kg, about 50 nmol/kg to about 500 nmol/kg, about 50 nmol/kg to about 400 nmol/kg, about 50 nmol/kg to about 300 nmol/kg, about 50 nmol/kg to about 200 nmol/kg, about 50 nmol/kg to about 100 nmol/kg, about 100 nmol/kg to about 300 nmol/kg, about 100 nmol/kg to about 500 nmol/kg, about 100 nmol/kg to about 1000 nmol/kg, about 100 nmol/kg to about 2000 nmol/kg of patient body weight. In other embodiments, the dose may be about 100 nmol/kg, about 150 nmol/kg, about 200 nmol/kg, about 250 nmol/kg, about 300 nmol/kg, about 350 nmol/kg, about 400 nmol/kg, about 450 nmol/kg, about 500 nmol/kg, about 600 nmol/kg, about 700 nmol/kg, about 800 nmol/kg, about 900 nmol/kg, about 1000 nmol/kg, about 2000 nmol/kg, or about 3000 nmol/kg of patient body weight. In these embodiments, "kg" is kilograms of patient body weight. In one aspect, the folate can be administered, for example, daily, weekly, biweekly, three times a week, or using any suitable regimen for administration of the folate.

In various embodiments described herein, the CAR T cells can persist in elevated numbers of circulating CART cells for as long as about 10 days, as long as about 15 days, as long as about 20 days, as long as about 25 days, as long as about 30 days, as long as about 35 days, as long as about 40 days, as long as about 45 days, as long as about 50 days, as long as about 55 days, as long as about 60 days, as long as about 65 days, as long as about 70 days, as long as about 75 days, or as long as about 80 days post CAR T cell administration.

In various embodiments described herein, half-maximal effective concentrations (EC50) for the compound, or the pharmaceutically acceptable salt thereof, can be about 1 pM to about 2 nM, about 1 pM to about 5 nM, about 1 pM to about 10 nM, about 1 pM to about 20 nM, about 1 pM to about 30 nM, about 1 pM to about 40 nM, about 1 pM to about 50 nM, about 1 pM to about 60 nM, about 1 pM to about 70 nM, about 1 pM to about 80 nM, about 1 pM to about 90 nM, about 1 pM to about 100 nM, about 1 pM to about 200 nM, about 1 pM to about 300 nM, about 1 pM to about 400 nM, about 1 pM to about 500 nM, about 1 pM to about 600 nM, about 1 pM to about 700 nM, about 1 pM to about 800 nM, about 1 pM to about 900 nM, about 1 nM, about 1 pM to about 900 pM, about 1 pM to about 800 pM, about 1 pM to about 700 pM, about 1 pM to about 600 pM, about 1 pM to about 500 pM, about 1 pM to about 400 pM, about 1 pM to about 300 pM, about 1 pM to about 200 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, or about 1 pM to about 5 pM.

In various embodiments described herein, the Kd for binding of the compound, or the pharmaceutically acceptable salt thereof, to the CAR T cells can be about 1 nM to about 100 nM, about 1 nM to about 200 nM, about 1 nM to about 300 nM, about 1 nM to about 400 nM, about 1 nM to about 500 nM, about 1 nM to about 600 nM, about 1 nM to about 700 nM, about 1 nM to about 800 nM, about 1 nM to about 900 nM, about 100 nM to about 500 nM, about 100 nM to about 400 nM, about 100 nM to about 300 nM, about 100 nM to about 200 nM, about 100 nM to about 150 nM, or about 130 nM.

In various illustrative embodiments described herein, the compound, or the pharmaceutically acceptable salt thereof, can be first administered to the patient about 1, about 2, about 3, about 4, about 5, about 6, about 7, about 8, about 9, or about 10 days before or after the CAR T cells, or on any appropriate day before or after the CAR T cells.

In the various embodiments described herein, EGFRt-sorted or unsorted CAR T cells can be used. In another embodiment, a "clinical facsimile" batch of CAR T cells can be used with a low differentiation profile. In another embodiment, a "research batch" of CAR T cells can be used. The "clinical facsimile" batch (~39% EGFRt+) can comprise CD4+ subsets at about 66% $T_{SCM}$ and about 32% $T_{CM}$ and CD8 subsets at about 95% $T_{SCM}$ and about 3% $T_{CM}$. The research batch (~23% EGFRt+) can comprise CD4 subsets at about 32% $T_{SCM}$, about 53% $T_{CM}$, about 11% $T_{EM}$ and about 3.7% $T_{EFF}$ and CD8 subsets at about 44% $T_{SCM}$, about 0.28% $T_{CM}$, about 3.4% $T_{EM}$ and about 52% $T_{EFF}$.

In various additional embodiments of this pre-treatment embodiment, cytokine release resulting in off-target toxicity in the patient does not occur, but toxicity of the CAR T cells, expressing the E2 anti-fluorescein antibody fragment, to the cancer occurs or off-target tissue toxicity does not occur in the patient, but toxicity of the CAR T cells expressing the E2 anti-fluorescein antibody fragment to the cancer occurs, or the cancer comprises a tumor, and tumor size is reduced in the patient, but off-target toxicity does not occur, or reduction in tumor size in the patient is greater than in a patient not pre-treated with the compound, or the pharmaceutically acceptable salt thereof, prior to administration of the CAR T cell composition comprising CAR T cells comprising a CAR comprising an E2 anti-fluorescein antibody fragment. As would be understood by a skilled artisan, the "target" can be the cancer (for example a tumor).

In another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR comprising an E2 anti-fluorescein antibody fragment, and wherein the small molecule ligand is a PSMA ligand and the targeting moiety is FITC. In this embodiment, the small molecule ligand linked to a targeting moiety by a linker can have the formula

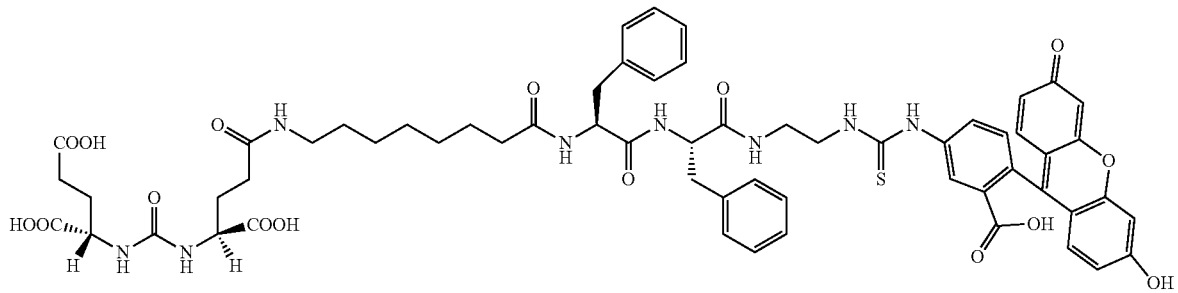 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

In yet another embodiment, a method of treatment of a cancer is provided. The method comprises i) administering to a patient a compound, or a pharmaceutically acceptable salt thereof, wherein the compound comprises a small molecule ligand linked to a targeting moiety by a linker, and ii) administering to the patient a CAR T cell composition wherein the CAR T cell composition comprises CAR T cells and wherein the CAR T cells comprise a CAR comprising an E2 anti-fluorescein antibody fragment, and wherein the small molecule ligand is a CAIX ligand and the targeting moiety is FITC. In this embodiment, the small molecule ligand linked to a targeting moiety by a linker can have the formula

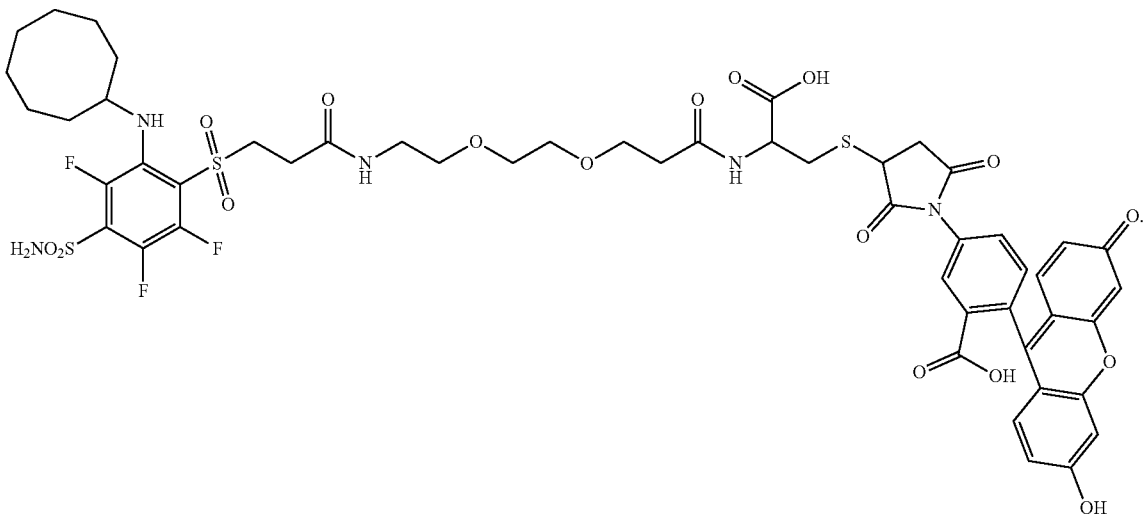 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

In still another embodiment, a method of treatment of a cancer is provided. The method comprises i) administering to a patient a first compound, or a pharmaceutically acceptable salt thereof, wherein the first compound, or the pharmaceutically acceptable salt thereof, comprises a PSMA ligand linked to FITC by a linker, ii) administering to the patient a second compound, or a pharmaceutically acceptable salt thereof, wherein the second compound, or the pharmaceutically acceptable salt thereof, comprises a CAIX ligand linked to FITC by a linker, and iii) administering to the patient a CAR T cell composition wherein the CAR T cell composition comprises CAR T cells and wherein the CAR T cells comprise a CAR comprising an E2 anti-fluorescein antibody fragment. In this embodiment, the first compound can have the formula

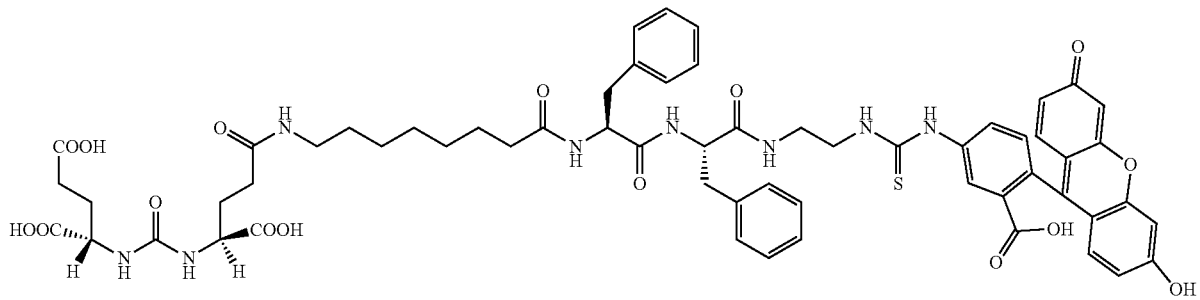 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

and the second compound can have the formula

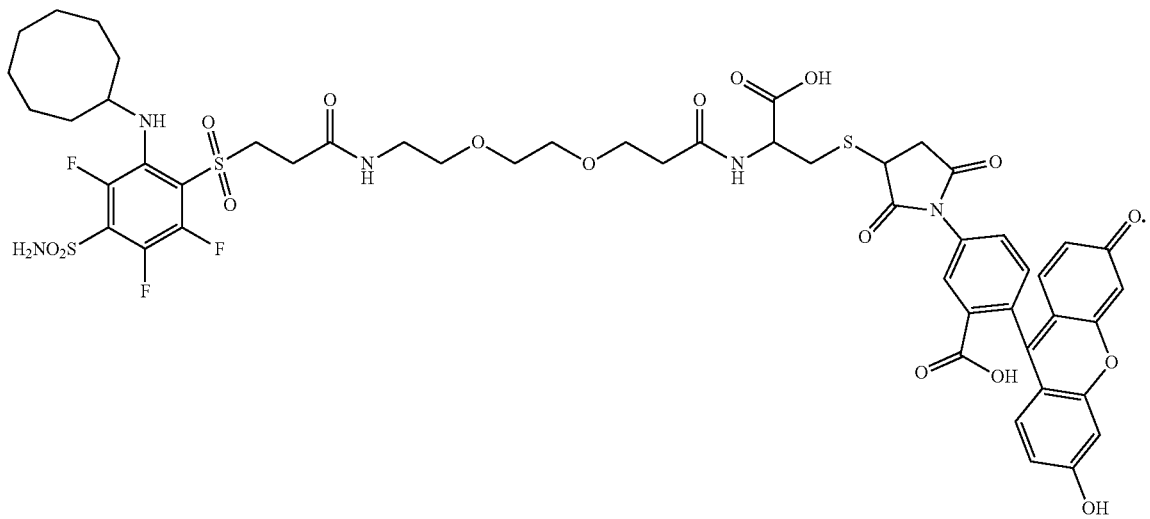 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

In one embodiment of the methods described herein, the cancer is imaged prior to administration to the patient of the compound, or the pharmaceutically acceptable salt thereof, or prior to administration of the CAR T cell composition to the patient, wherein the CAR T cell composition comprises CAR T cells comprising a CAR comprising an E2 anti-fluorescein antibody fragment. In one illustrative embodiment, imaging occurs by PET imaging. In other illustrative embodiments imaging occurs by Mill imaging or SPECT/CT imaging. The imaging method can be any suitable imaging method known in the art. In one embodiment, the imaging method can involve the use of the small molecule ligand described herein, but linked to an imaging agent suitable for the types of imaging described herein.

In any of the embodiments described herein, cytokine release resulting in off-target toxicity in the patient may not occur even though toxicity to the cancer of the CAR T cells expressing the E2 anti-fluorescein antibody fragment, occurs. In any embodiment described herein, off-target tissue toxicity may not occur in the patient even though toxicity to the cancer of the CAR T cells expressing the E2 anti-fluorescein antibody fragment, occurs. In any embodiment described herein, the cancer may comprise a tumor, and tumor size may be reduced in the patient, even though off-target toxicity does not occur. In any of the embodiments described herein, CRS can be reduced or prevented and the method can result in a decrease in tumor volume in the patient. In any embodiment described herein, body weight loss due to CRS can be reduced or prevented. In any embodiment described herein, the cancer can comprise a tumor and a complete response for the tumor can be obtained.

In another embodiment of the methods described herein, any of the methods described herein can be used alone, or any of the methods described herein can be used in combination with any other method or methods described herein.

EXAMPLES

Example 1

EC17 Dose De-Escalation can Reduce Therapy Related Toxicity

The effect of EC17 dose de-escalation was investigated on the anti-tumor activity and the toxicity (body weight changes) of CAR-T therapy. Two different anti-fluorescein scFv were used for the CAR constructions (FIG. 1). The first construct of CAR contains the following domains: antiFL (FITC-E2)scFv-IgG4 hinge (CH2 (L235D, N297Q)-CH3)-CD28 TM-4-1BB-CD3z-T2A-EGFRt. The second construct of CAR contains the following domains: antiFL(FITC-4M5.3)scFv-IgG4 hinge (CH2 (L235D, N297Q)-CH3)-CD28 TM-4-1BB-CD3z-T2A-EGFRt. The nucleic acid sequence and amino acid sequence of the CAR of each construct are shown as SEQ ID NOS:1 to 4. Human T cells were isolated, activated and transduced with a lentiviral vector carrying the appropriate CAR gene. CD4+ T cells with the CAR-modification and CD8+ T cells with the CAR-modification were isolated and cultured separately in vitro for about 7 days. CD4+ CAR-T cells and CD8+ CAR-T cells were mixed at a 1:1 ratio before i.v. administration for animal studies.

Figure 2A:
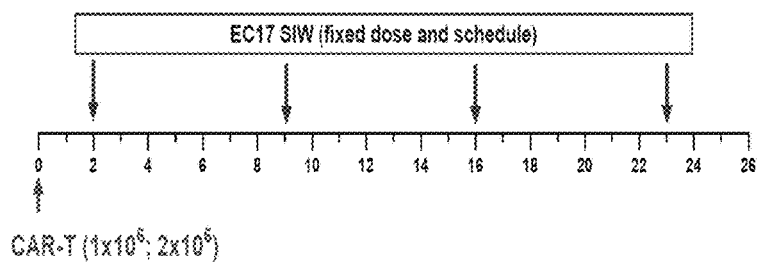
FIG. 2A shows an EC17 fixed dose scheme.
Figure 5A:
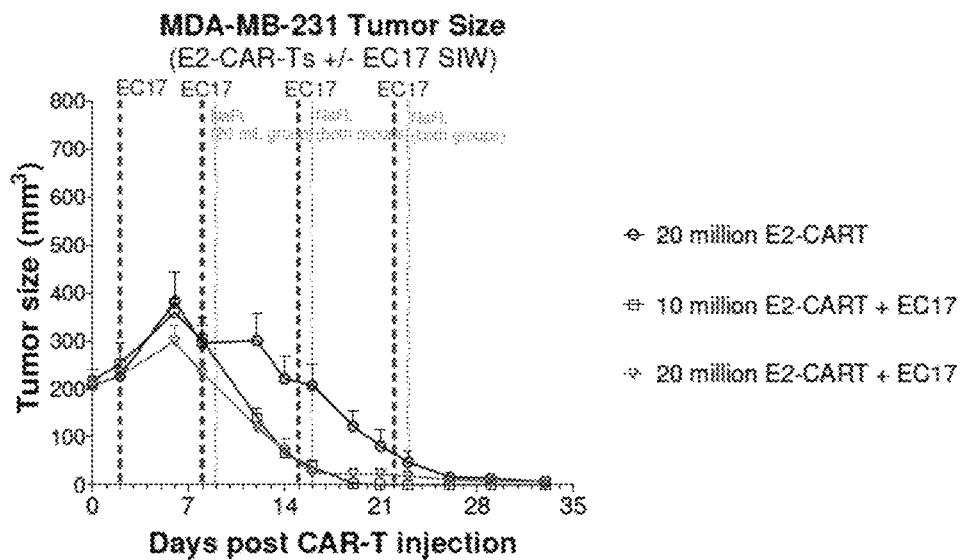
FIG. 5A and FIG. 5B show E2-CAR-T anti-tumor activity (10 and 20 million cells) and body weight changes at a fixed EC17 dosing regimen (500 nmol/kg, SIW). As shown, antitumor activity was maintained after NaFL rescue.
Figure 5B:
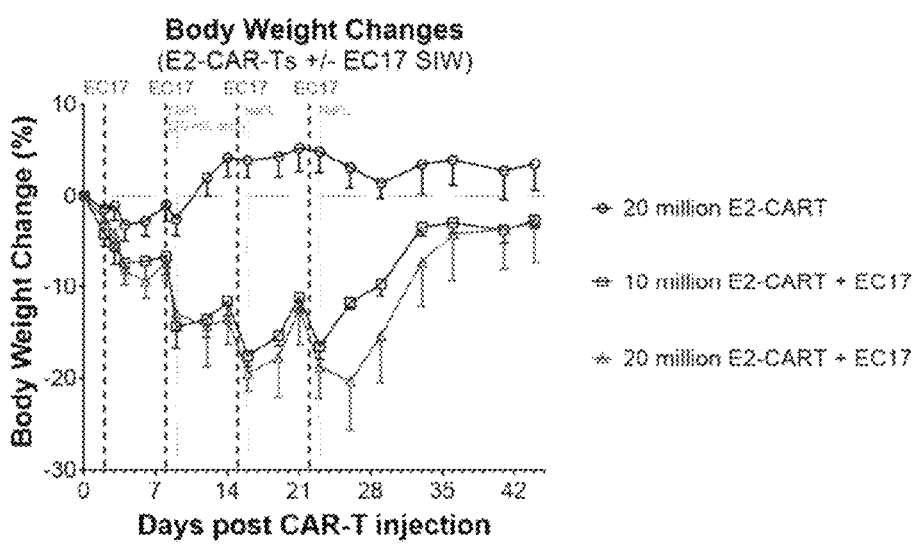

Mice bearing MDA-MB-231 tumors (150-250 mm$^3$) were used for in vivo studies to evaluate E2-CAR-T cells. In the first part of the study, 10 or 20 million E2-CAR-T cells were administered, and 500 nmol/kg EC17 was i.v. dosed weekly at days 2, 9, 16, 23, etc. post CAR-T administration (as shown in FIG. 2A). Mice administered with 20 million E2-CAR-T cells showed severe CRS after the second EC17 dose and had to be rescued with 6 umol/kg sodium fluorescein (NaFL). Both 10 million and 20 million CAR-T groups showed severe CRS after the third and the fourth EC17 doses and had to be rescued with NaFL (as indicated in FIGS. 5A and 5B). Both of these two groups showed severe body weight loss (~20%) during E2-CAR-T therapy, indicating that 10 or 20 million E2 CAR-T/EC17 500 nmol/kg SIW therapy had severe toxicity. (Although 20 million E2-CAR-T cells alone also showed anti-tumor activity (FIG. 5A, open circle), this was probably caused by allogeneic HLA-mismatched TCRs commonly found in "young" T cells cultured in-vitro for a shorter time.)

Figure 2B:
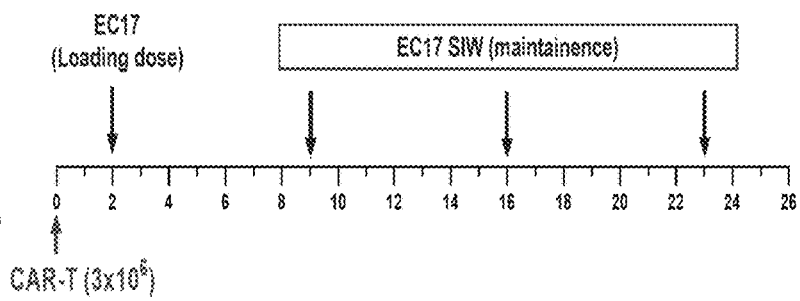
FIG. 2B shows a dose de-escalation scheme.
Figure 3A:
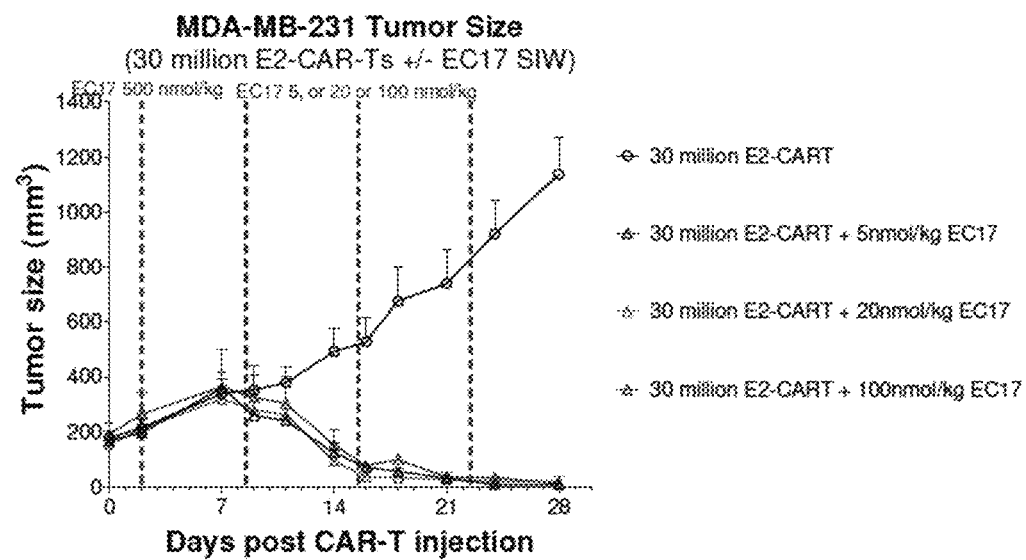
FIG. 3A and FIG. 3B show E2-CAR-T anti-tumor activity (30 million cells) with EC17 dose de-escalation and body weight changes. As shown, antitumor activity is maintained after NaFL rescue.
Figure 3B:
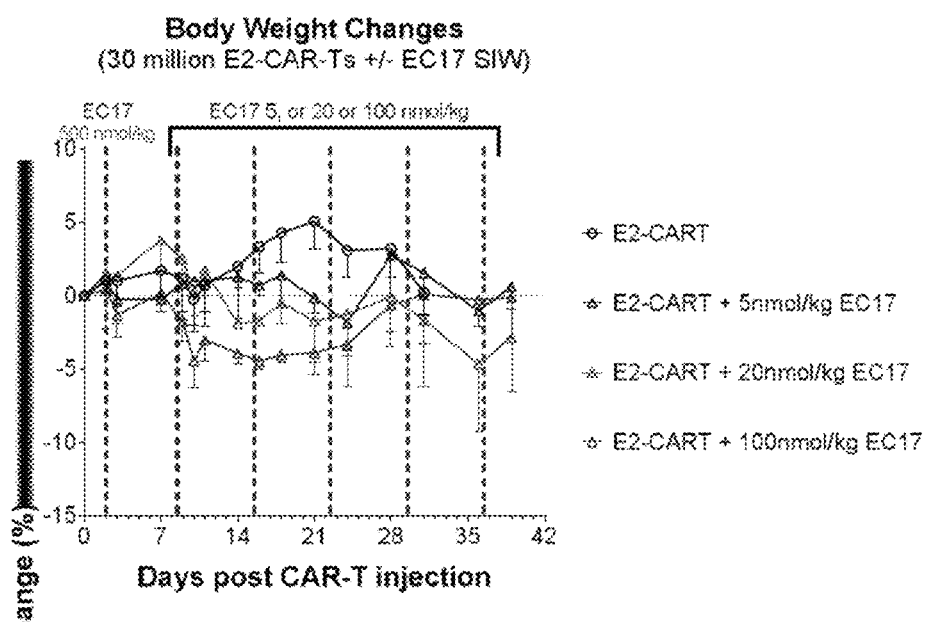

In the second part of the study, E2-CAR-T cells used were cultured in vitro for about 2 weeks. 30 million E2-CAR-T cells were administered and EC17 dosing was modified to de-escalation. As shown in FIG. 2B, 500 nmol/kg EC17 was dosed 2 days post CAR-T administration, then a lower dose of EC17 (5, or 20 or 100 nmol/kg) was administered weekly (at days 9, 16, 23, etc. post CAR-T administration). As shown in FIG. 3A, all three EC17 deescalation groups reached a complete response, indicating that bridge de-escalation does not affect the anti-tumor activity of CAR-T. More importantly, none of these three EC17 de20 escalation groups showed any severe CRS. As shown in FIG. 3B, all de-escalation groups showed very mild body weight loss although more CAR-T cells (30 million) were administered compared to the first part of study (10 or 20 million CAR-T cells). These data indicate that bridge de-escalation (one high-level loading dose followed with a reduced-level of maintenance doses) can reduce the toxicity while maintaining good anti-tumor activity of CAR-T cells.

Figure 6A:
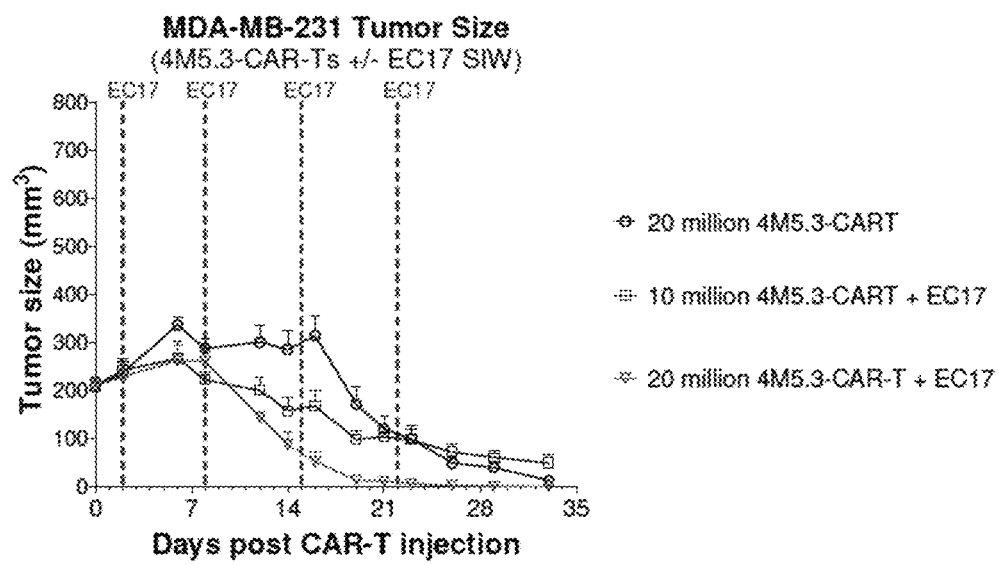
FIG. 6A and FIG. 6B show 4M5.3-CAR-T anti-tumor activity (10 and 20 million cells) and body weight changes at a fixed EC17 dosing regimen (500 nmol/kg, SIW). As shown, 4M5.3-CAR-T was less active than E2-CAR-T.
Figure 6B:
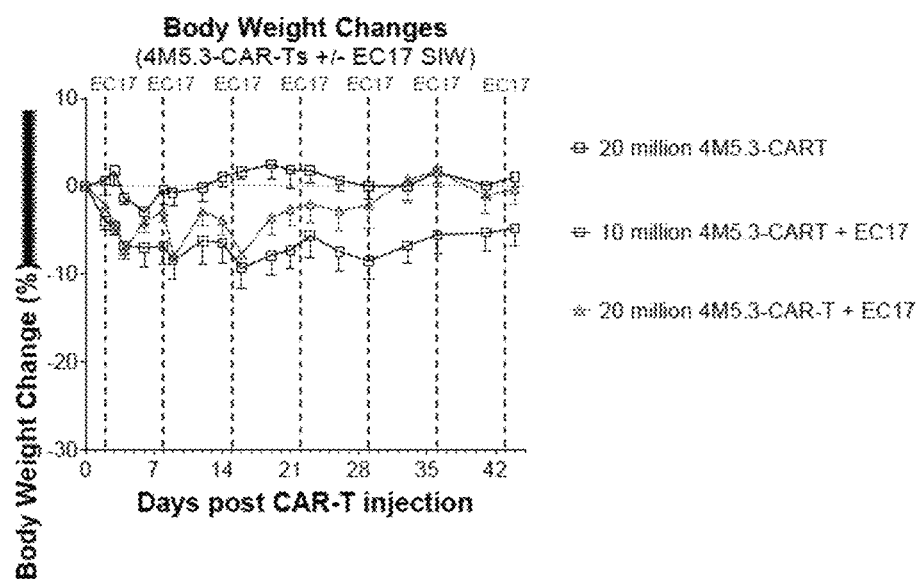

The second construct 4M5.3-CAR (antiFL(FITC-4M5.3) scFv-IgG4 hinge (CH2 (L235D, N297Q)-CH3)-CD28 TM-4-1BB-CD3z-T2A-EGFRt) was also evaluated. Mice bearing MDA-MB-231 tumors (150-250 mm$^3$) were used for in vivo studies to evaluate 4M5.3-CAR-T cells. In the first part of the study, 10 or 20 million 4M5.3-CAR-T cells were administered, and 500 nmol/kg EC17 was i.v. dosed weekly at days 2, 9, 16, 23, etc. post CAR-T administration (as shown in FIG. 2A). Mice administered with either 10 or 20 million 4M5.3-CAR-T cells did not show severe CRS or body weight loss after administering an EC17 dose (FIG. 6B), but their tumors were all reduced and eventually disappeared (FIG. 6A). 20 million CAR-T cells (upper line) showed better anti-tumor activity than 10 million CAR-T cells (middle line).

Figure 4A:
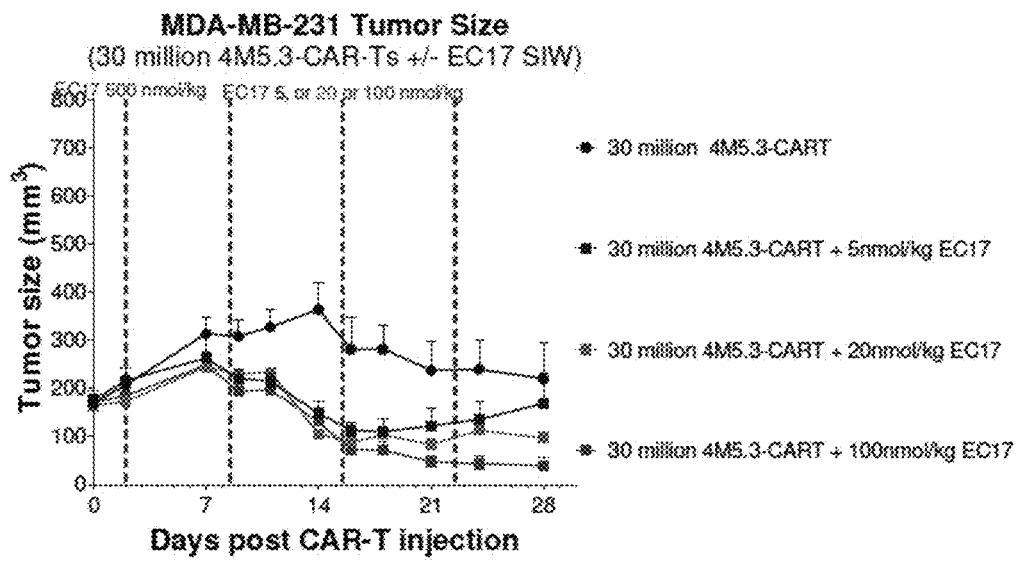
FIG. 4A and FIG. 4B show 4M5.3-CAR-T anti-tumor activity (30 million cells) with EC17 dose de-escalation and body weight changes. As shown, 4M5.3-CAR-T was less active than E2-CAR-T. In addition, EC17 dose dependent anti-tumor activity and body weight loss were observed.
Figure 4B:
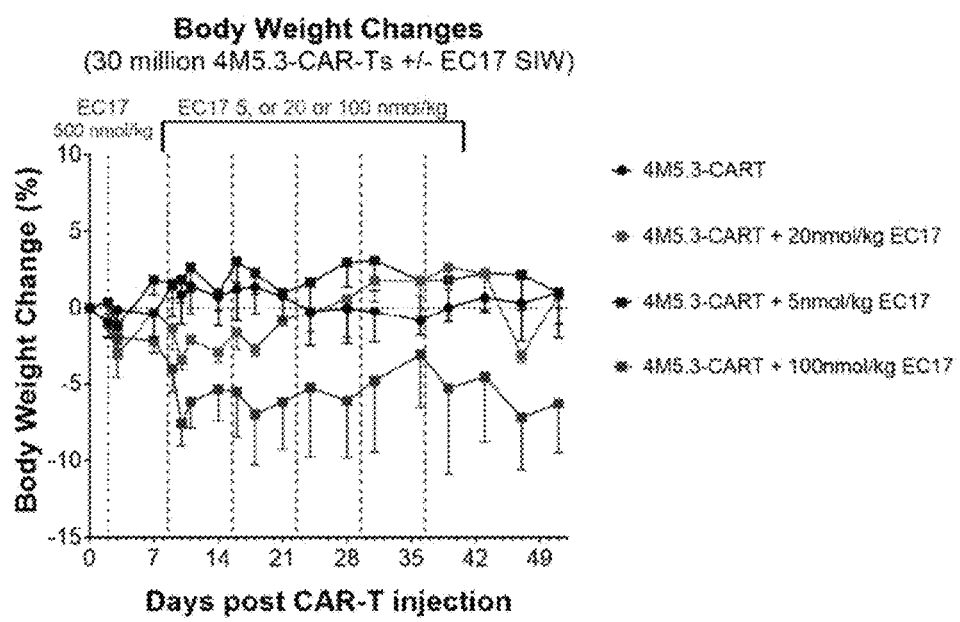

In the second part of the study, 4M5.3-CAR-T cells used were cultured in vitro for about 2 weeks. 30 million 4M5.3-CAR-T cells were administered and EC17 dosing was modified to de-escalation. As shown in FIG. 2B, 500 nmol/kg EC17 was dosed 2 days post CAR-T administration, then a lower dose of EC17 (5, or 20 or 100 nmol/kg) was administered weekly (at days 9, 16, 23, etc. post CAR-T administration). As shown in FIG. 4A, 100 nmol/kg EC17 de-escalation group showed the best anti-tumor activity and all tumors were cured (bottom line), whereas neither 5 nmole/kg EC17 group (second line from the top) nor 20 nmol/kg EC17 group (third line from the top) showed a complete response to the CAR-T therapy. The data indicate that CAR-T activity is controlled by the EC-17 dose used for de-escalation. Furthermore, as shown in FIG. 4B, body weight loss of mice in the three de-escalation groups was also dependent on EC17 dose. The 100 nmol/kg EC17 dose de-escalation group showed more body weight loss than the other two groups with either 5 or 20 nmol/lg EC17. These data indicate that bridge de-escalation (one high-level loading dose followed with reduced-level of maintenance doses) can control both anti-tumor activity and the toxicity of CAR-T therapy.

The only difference between E2-CAR and 4M5.3-CAR is the scFv sequences used. By comparing these two CARs with the same conditions, 10 million E2-CAR-T cells were found to have better anti-tumor activity than 10 million 4M5.3-CAR-T cells; 30 million E2-CAR-T cells also showed better anti-tumor activity than 30 million 4M5.3-CAR-T cells when EC17 dose de-escalation (5, or 20, or 100 nmol/kg) was tested.

As used herein, "SEQ ID NO:4" means the sequence beginning at the underlined "gac" codon and ending with the underlined "ggc" codon. This portion of the longer sequence, encodes the exemplary 4M5.3 CAR. The CAR is inserted into the T cell membrane. The other portions of the longer sequence include coding sequence for signal peptides, the EGFRt domain, etc. which are not part of the CAR that is inserted into the membrane and which functions as the chimeric antigen receptor. As used herein, "SEQ ID NO:3" means the sequence beginning at the underlined "D" and ending with the underlined "G". This portion of the longer sequence is the amino acid sequence for the CAR that is inserted into the T cell membrane. The other portions of the longer sequence include amino acid sequences for signal peptides, the EGFRt domain, etc. which are not part of the CAR inserted into the membrane and which functions as the chimeric antigen receptor. In yet another embodiment, SEQ ID NO:3 can comprise or consist of humanized, or human amino acid sequences. SEQ ID NOS:3 and 4 are as described above. The start and stop codons in the longer nucleic acid sequence are underlined and the longer sequence is an exemplary sequence that can be used for transduction of T cells to prepare the 4M5.3 CAR.

[4M5.3-CAR amino acid sequence (insert)]

SEQ ID NO: 3

MLLLVTSLLLCELPHPAFLLIPDVVMTQTPLSLPVSLGDQASISCRSSQS

LVHSNGNTYLRWYLQKPGQSPKVLIYKVSNRVSGVPDRFSGSGSGTDFTL

KINRVEAEDLGVYFCSQSTHVPWTFGGGTKLEIKSSADDAKKDAAKKDDA

KKDDAKKDGGVKLDETGGGLVQPGGAMKLSCVTSGFTFGHYWMNWVRQSP

EKGLEWVAQFRNKPYNYETYYSDSVKGRFTISRDDSKSSVYLQMNNLRVE

DTGIYYCTGASYGMEYLGQGTSVTVSESKYGPPCPPCPAPEFDGGPSVFL

FPPKPKDTLMISRTPEVTCVVVDVSQEDPEVQFNWYVDGVEVHNAKTKPR

EEQFQSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLS

LSLGKMFWVLVVVGGVLACYSLLVTVAFIIFWVKRGRKKLLYIFKQPFMR
PVQTTQEEDGCSCRFPEEEEGGCELRVKFSRSADAPAYQQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPRLEGGGEGRGSLLT
CGDVEENPGPRMLLLVTSLLLCELPHPAFLLIPRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFM

[4M5.3-CAR nucleotide acid sequence (insert)]
SEQ ID NO: 4
ATG(START)cttctcctggtgacaagccttctgctctgtgagttaccac
acccagcattcctcctgatcccagacgttgtaatgacccagacccctctg
tctctccccgtaagcttgggcgaccaggcgagcatctcttgtcggtcttc
ccagtccctggtccattcaaacggcaatacttacttgcggtggtacttgc
agaagcccggtcaatccccaaaagtgctgatatacaaggttagcaatcgg
gtcagtggagtgcccgaccgcttcagcggaagcggatccgggactgactt
cactctgaagatcaaccgggtagaagctgaagacctgggggtgtacttct
gctctcagtcaacacacgtgccatggccttggaggtggcaccaagctg
gaaatcaaatcatcagcggacgatgccaaaaaagacgcggccaagaagga
cgatgccaagaaggatgatgctaaaaaggatggcggagtcaaattggacg
agacaggcggggactggtgcagcccggcggtgccatgaaactgtcttgt
gtgaccagcggctttaccttcgggcattattggatgaactgggtgcgaca
gtctccagagaaagggctcgagtgggtggcccagtttcgaaataaaccgt
acaattatgagacctactattcagattctgtgaaagggcgcttcactatt
tcacgcgacgacagcaaaagttccgtctaccttcagatgaacaaccttag
agtggaggataccggaatatactactgcacgggtgccagttatggcatgg
agtacttggggcaggggacatctgtgaccgtttctgagagcaagtacgga
ccgccctgccccccttgccctgccccgagttcgacggcggacccagcgt
gttcctgttcccccccaagcccaaggacaccctgatgatcagccggaccc
ccgaggtgacctgcgtggtggtggacgtgagccaggaagatcccgaggtc
cagttcaattggtacgtggacggcgtggaagtgcacaacgccaagaccaa
gcccagagaggaacagttccagagcacctaccgggtggtgtctgtgctga
ccgtgctgcaccaggactggctgaacggcaaagaatacaagtgcaaggtg
tccaacaagggcctgcccagcagcatcgaaaagaccatcagcaaggccaa
gggccagcctcgcgagcccaggtgtacaccctgcctccctcccaggaag
agatgaccaagaaccaggtgtccctgacctgcctggtgaagggcttctac
cccagcgacatcgccgtggagtgggagagcaacggccagcctgagaacaa ctacaagaccacccctcccgtgctggacagcgacggcagcttcttcctgt
acagccggctgaccgtggacaagagccggtggcaggaaggcaacgtcttt
agctgcagcgtgatgcacgaggccctgcacaaccactacacccagaagag
cctgagcctgtccctgggcaagatgttctgggtgctggtggtggtgggcg
gggtgctggcctgctacagcctgctggtgacagtggccttcatcatcttt
tgggtgaaacggggcagaaagaaactcctgtatatattcaaacaaccatt
tatgagaccagtacaaactactcaagaggaagatggctgtagctgccgat
ttccagaagaagaagaaggaggatgtgaactgcgggtgaagttcagcaga
agcgccgacgcccctgcctaccagcagggccagaatcagctgtacaacga
gctgaacctgggcagaagggaagagtacgacgtcctggataagcggagag
gccgggaccctgagatgggcggcaagcctcggcggaagaaccccaggaa
ggcctgtataacgaactgcagaaagacaagatggccgaggcctacagcga
gatcggcatgaagggcgagcggaggcggggcaagggccacgacggcctgt
atcagggcctgtccaccgccaccaaggatacctacgacgccctgcacatg
caggccctgccccaaggctcgagggcggcgagagggcagaggaagtct
ctaacatgcggtgacgtggaggagaatcccggccctaggatgcttctcc
tggtgacaagccttctgctctgtgagttaccacacccagcattcctcctg
atcccacgcaaagtgtgtaacggaataggtattggtgaatttaaagactc
actctccataaatgctacgaatattaaacacttcaaaaactgcacctcca
tcagtggcgatctccacatcctgccggtggcatttaggggtgactccttc
acacatactcctcctctggatccacaggaactggatattctgaaaaccgt
aaaggaaatcacagggttttgctgattcaggcttggcctgaaaacagga
cggacctccatgcctttgagaacctagaaatcatacgcggcaggaccaag
caacatggtcagttttctcttgcagtcgtcagcctgaacataacatcctt
gggattacgctccctcaaggagataagtgatggagatgtgataatttcag
gaaacaaaatttgtgctatgcaaatacaataaactggaaaaaactgttt
gggacctccggtcagaaaaccaaaattataagcaacagaggtgaaaacag
ctgcaaggccacaggccaggtctgccatgccttgtgctcccccgagggct
gctggggcccggagcccagggactgcgtctcttgccggaatgtcagccga
ggcaggaatgcgtggacaagtgcaaccttctggagggtgagccaagga
gtttgtggagaactctgagtgcatacagtgccacccagagtgcctgcctc
aggccatgaacatcacctgcacaggacggggaccagacaactgtatccag
tgtgcccactacattgacggccccactgcgtcaagacctgcccggcagg
agtcatgggagaaaacaacaccctggtctggaagtacgcagacgccggcc
atgtgtgccacctgtgccatccaaactgcacctacggatgcactgggcca
ggtcttgaaggctgtccaacgaatgggcctaagatcccgtccatcgccac
tgggatggtggggccctcctcttgctgctggtggtggccctggggatcg
gcctcttcatgTGA (STOP CODON)

Example 2

Figure 7A:
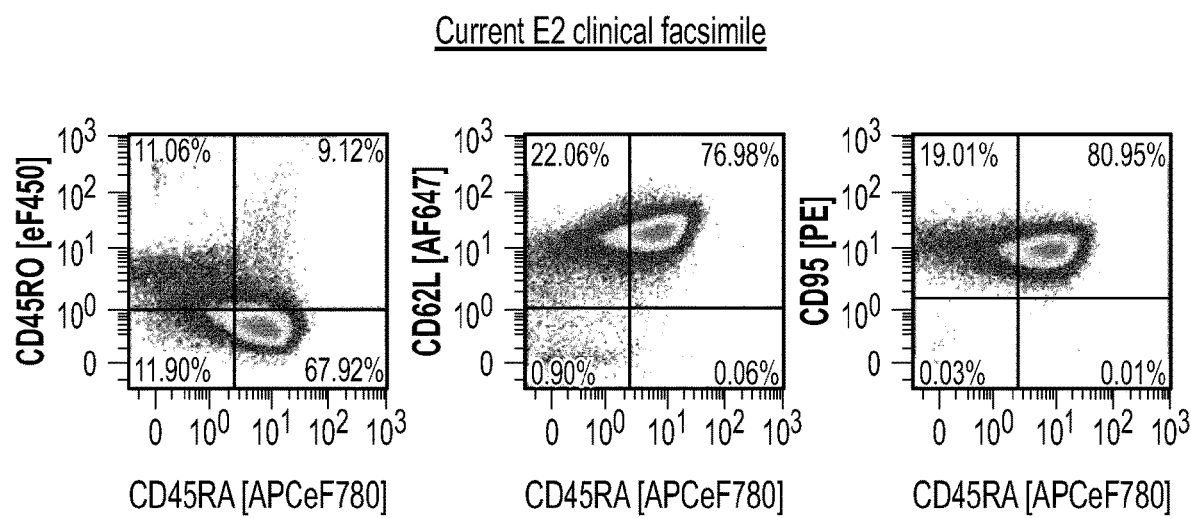
FIG. 7A and FIG. 7B show the phenotypic characterization of E2 CAR T cells prior to infusion into NSG mice.
Figure 7B:
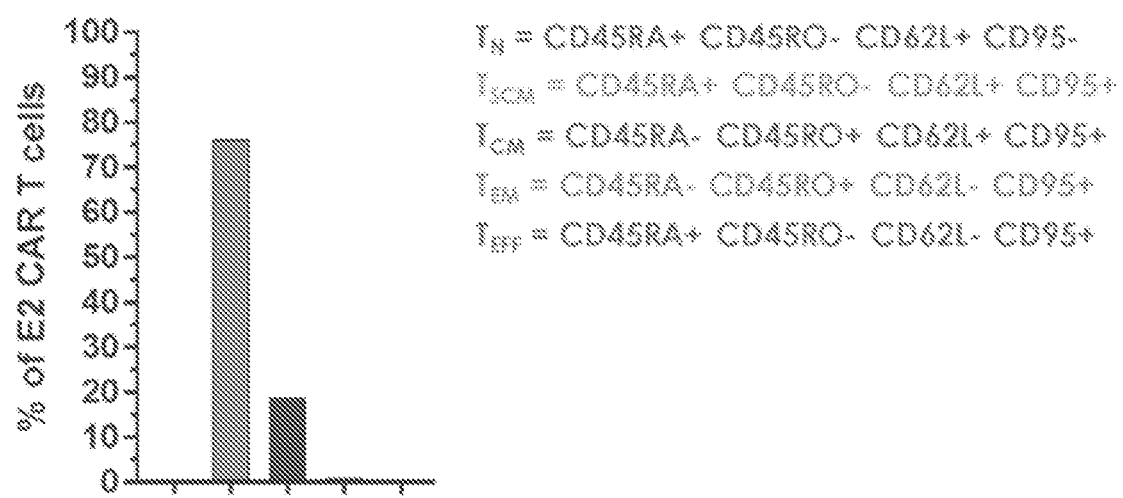
Figure 8A:
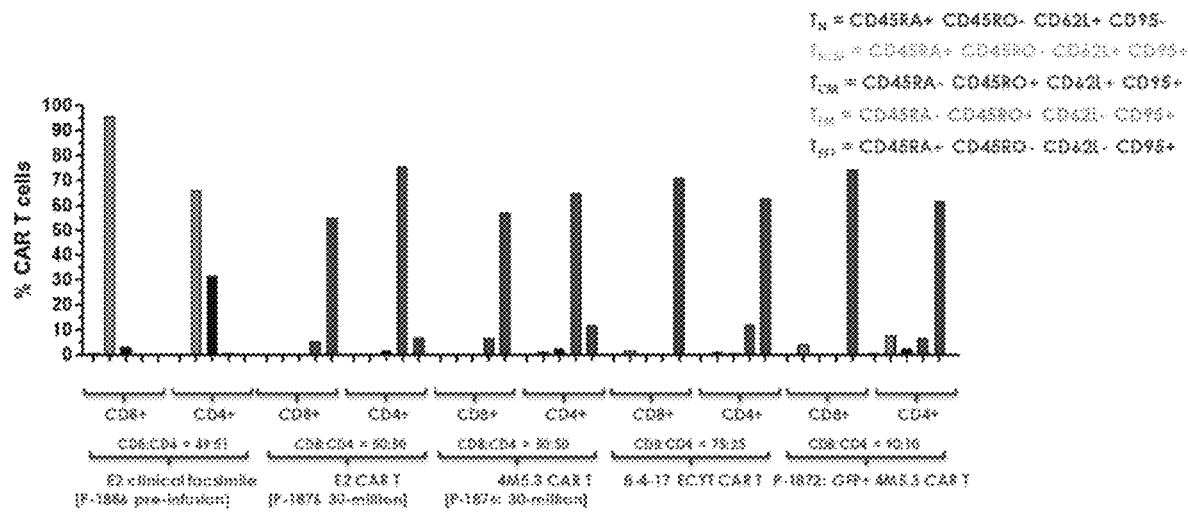
FIG. 8A and FIG. 8B show the comparison of CAR-T differentiation phenotypes in different preparations including E2-CAR-T cells and 4M5.3-CAR-T cells, and GFP+ 4M5.3 CAR-T cells.
Figure 8B:
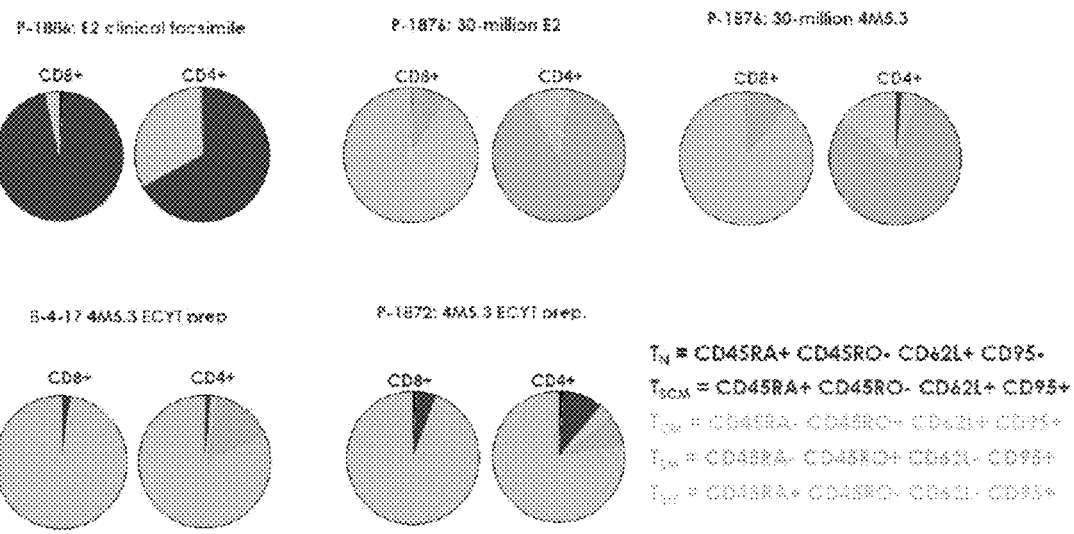

Characterization of CAR T Cell Differentiation Phenotypes Prior to Infusion into NSG Mice Multi-color flow cytometry was used to determine the phenotypes of CAR T cell products to be infused into tumor-bearing mice. The differentiation status of CD4+ and CD8+ subsets was analyzed using specific combinations of surface markers as shown in FIG. 7A. The unsorted E2 clinical facsimile CAR T cell product was made predominantly of the self-renewing Tscm/Tcm phenotype (FIG. 7B). In FIG. 7B, the highest bar is "Tscm" and the lower bar is "Tcm". In addition to differences in CD8:CD4 ratios shown in FIG. 8A, the current E2 clinical facsimile CAR T cells were different from the previously sorted E2/4M5.3 CAR-T cells and early GFP+4M5.3 CAR T in vivo study preparations (summarized as pie charts in FIG. 8B). In FIG. 8A, in the 10 groups from left to right, the bars represent the following—1 (high bar Tscm, lower bar Tcm), 2—(high bar Tscm, lower bar Tcm), 3—(high bar Teff, lower bar Tem), 4—(high bar Tem, lower bar Teff, lowest bar Tcm), 5—(high bar Teff, lower bar Tem), 6—(high bar Tem, lower bar Teff, lowest bar Tcm), 7—(high bar Teff, lower bar Tscm), 8—(high bar Teff, lower bar Tem), 9—(high bar Teff, lower bar Tscm), 10—(high bar Teff, lower bar Tsm, next lower bar Tem, lowest bar Tcm). Accordingly, CAR T cells of predominately Tscm/Tcm phenotype were expected to possess a superior anti-tumor phenotype when compared to past CAR T preparations which possess a more differentiated Tem/Teff phenotype. For the same reason, sCRS arises later for the current CAR-T preparation than the previous CAR-T preparations given the same EC17 dosing regimens.

Recovery of CAR T Cells after Cryopreservation

Cryopreserved CAR T cells were rapidly thawed in a 37° C. water bath then immediately placed into T cell recovery media (TexMACS™ Media containing glutamine (Miltenyi Biotec #130-097-196) supplemented with 2% human AB serum) and 50 U/mL recombinant human IL2 and cultured in vitro for approximately 3 to 5 days for T cell recovery.

Flow Cytometry Analysis

CAR T cells were harvested from in vitro recovery media and pelleted by centrifugation at 400 g for 5 minutes. The T cells were then resuspended in flow cytometry staining solution [1% bovine serum albumin, 50 mg/mL human IgG (Equitech Bio, cat #SLH56-0001), 0.9% sodium azide in a phosphate buffered saline, pH=7.4] supplemented with both antimouse FcγIII/II receptor (CD16/CD32) block [clone 2.4G2; BD Bioscience, catalog #553142 at 1:100 (v/v) dilution] and anti-human Fc Block [BD Biosciences, catalog #564220 at 1:50 (v/v) dilution]. Surface marker staining was performed with the addition of the following fluorochrome conjugated monoclonal antibodies added to each sample for 20 minutes on ice in the dark: anti-human CD45RA-APCeF780 [clone HI100, ThermoFisher #47-0458-42 at 1:20 (v/v) dilution], anti-human CD45RO-eF450 [clone UCHL1, Thermofisher #48-0457-42 at 1:20 (v/v) dilution], anti-human CD8α-PECγ7 [clone RPA-T8, BD Bioscience, catalog #557746 at 1:20 (v/v) dilution], anti-human CD4-Percpe710 [clone SK3, eBioscience catalog #46-0047-42 at 1:20 (v/v) dilution], biotinylated anti-human EGFR (Cetuximab; R&D Systems #FAB9577B-100 at 1:10 (v/v) followed by PE conjugated anti-biotin (BioLegend #53-9895-82 at 1:400 (v/v). After surface marker staining, T cells were washed with PBS and resuspended in cold PBS containing 3 μM propidium iodide and transferred to flow cytometry collection tubes. Flow cytometry data was collected on the Gallios flow cytometer (Beckman Coulter, Brea, Calif.), where a minimum of 20,000 events were collected and data was analyzed using Kaluza v1.5 software.

Example 3

E2 Anti-FITC Antibody Doesn't Bind with any Human Normal Tissues

Figure 9A:
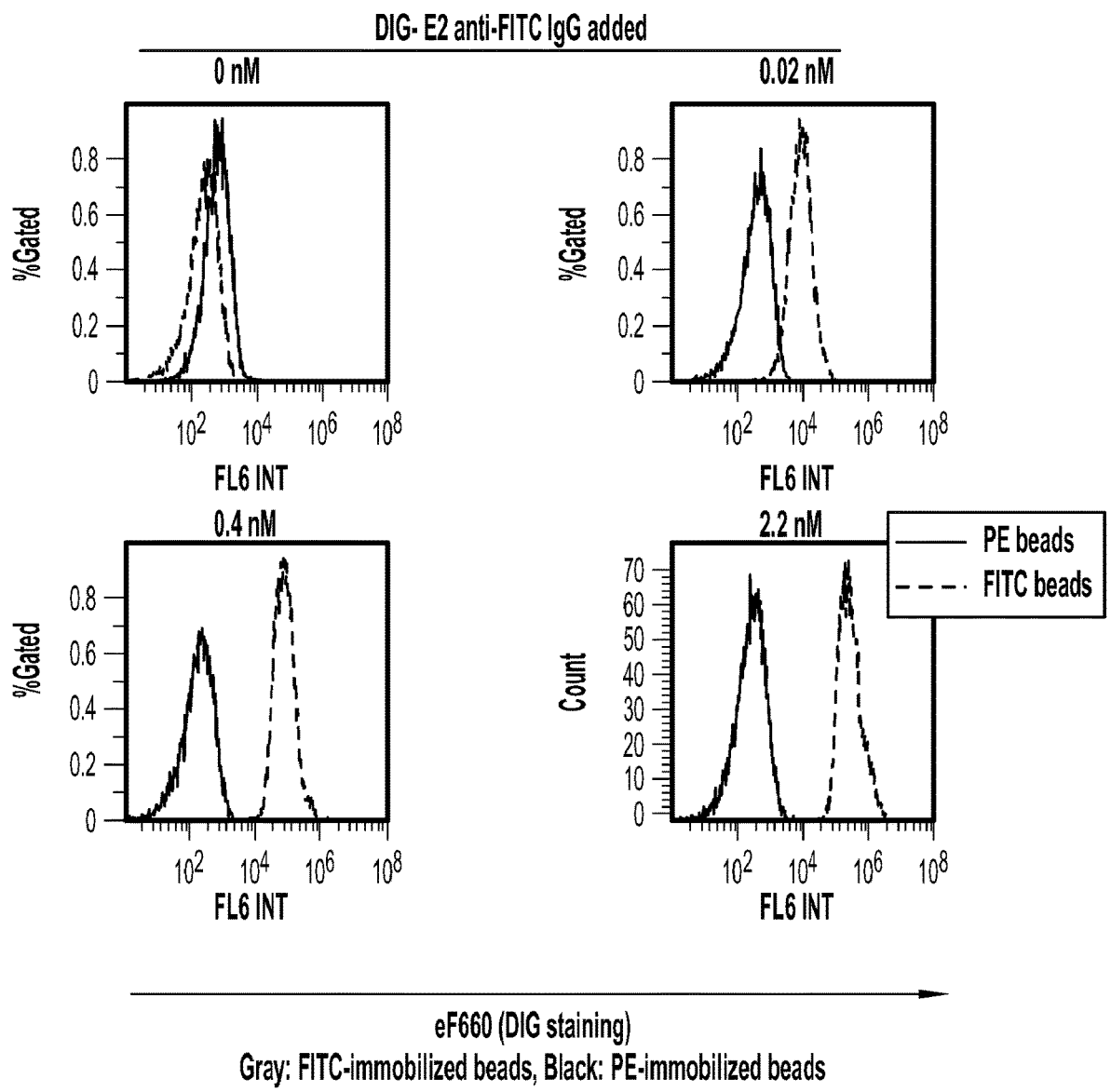
FIG. 9A and FIG. 9B show binding of DIG-labeled E2-IgG to FITC.
Figure 9B:
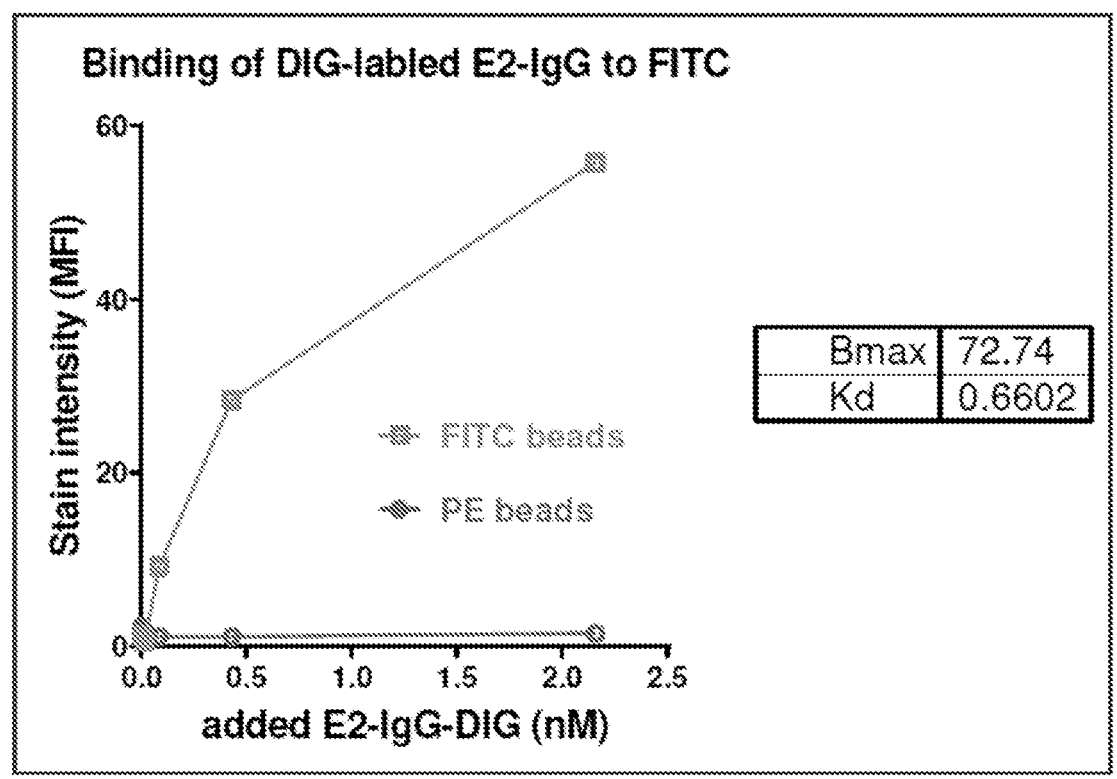

An E2 anti-FITC IgG antibody with the same variable fragment sequences as those in E2 anti-FITC CAR construct was used to test if E2 antibody has any binding with human normal tissues. A recombinant human E2 anti-FITC IgG1 Lambda 1 was expressed in HEK293 cells and purified by using a protein A affinity column. The purity of the antibody was over 98% by using SEC-HPLC analysis. The antibody was labeled with digoxigenin (DIG) using Mix-N-Stain DIG antibody labeling kit (Biotium). The binding affinity of DIG-labeled E2 antibody for FITC-immobilized beads was measured by FACS. Various concentrations of DIGE2 IgG were incubated with FITC-immobilized beads for 30 min at room temperature. After washing, a monoclonal anti-DIG Ab was added and incubated with beads for 30 min. An eF660 conjugated anti-mouse secondary antibody was added and incubated with the washed beads. The washed beads were analyzed for the eF660 signal by FACS. The PE-immobilized beads were used as the negative control beads. The fluorescence intensity of eF660 was plotted against the concentrations of added DIG-labeled E2-IgG and shown in FIG. 9. The binding affinity of DIG30 labeled E2 antibody for FITC was calculated by using PRISM software. As indicated in FIG. 9B insert, the Kd was about 0.66 nM, indicating that DIG-labeled E2 anti-FITC antibody has high binding affinity for FITC and can be used to evaluate E2 binding with human normal tissues.

Figure 10A:
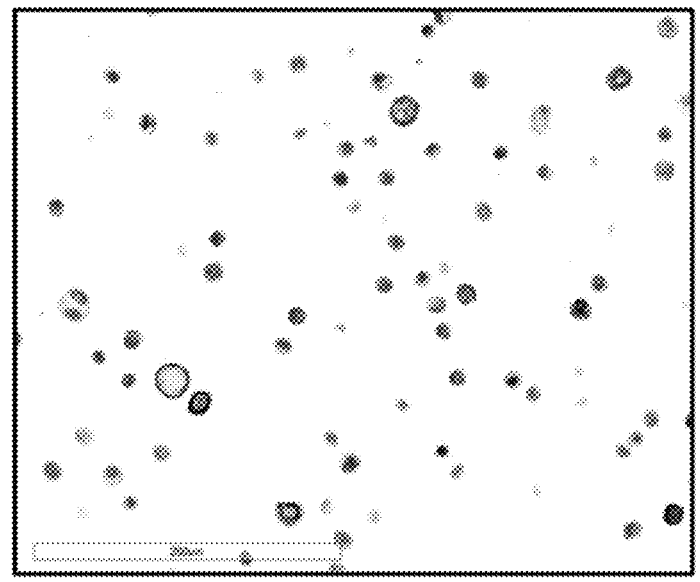
FIG. 10A and FIG. 10B show IHC staining of DIG-labeled E2 antibody on FITClabeled KB cells.
Figure 10B:
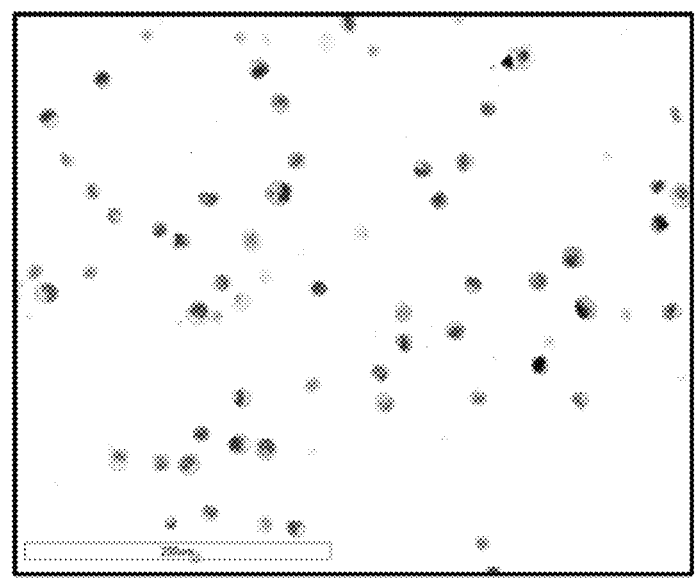

An IHC assay was developed to test the binding of E2 antibody to human tissues. Formalin-fixed, paraffin-embedded (FFEP) tissue section of the agar block with FITC-labeled KB cells was used as the positive control, while FFPE tissue section of unlabeled KB cells was used as the negative control. The tissue sections were deparaffinizaed and rehydrated, then antigen retrieval was done by incubating tissue sections with an antigen retrieval buffer (pH6.0) at 91° C. for 24 minutes, then DIG-E2 antibody was incubated with rehydrated tissue sections, and finally an anti-DIG IHC staining was performed. In brief, a monoclonal anti-DIG antibody was added and incubated, followed by a peoxidase-labeled anti-mouse secondary antibody. As shown in FIG. 10A, FITC-labeled KB cells showed positive staining, indicating that the E2 antibody binds with FITC on these labeled KB cells. The unlabeled KB cells did not show any staining (FIG. 10B).

Figure 11A:
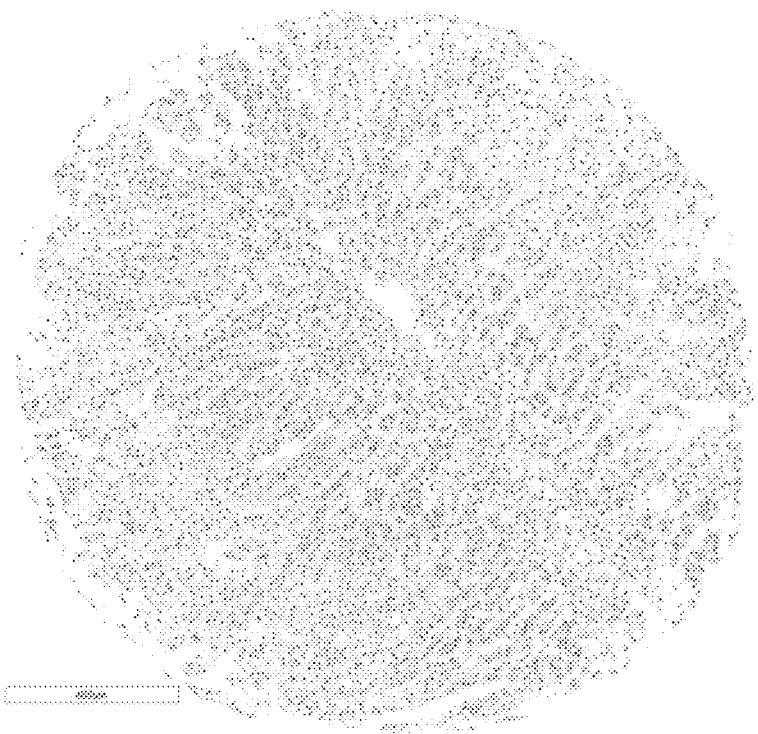
FIG. 11A and FIG. 11B show IHC staining of the bound DIG-E2 antibody in normal human organ tissues: Adrenal gland.
Figure 11B:
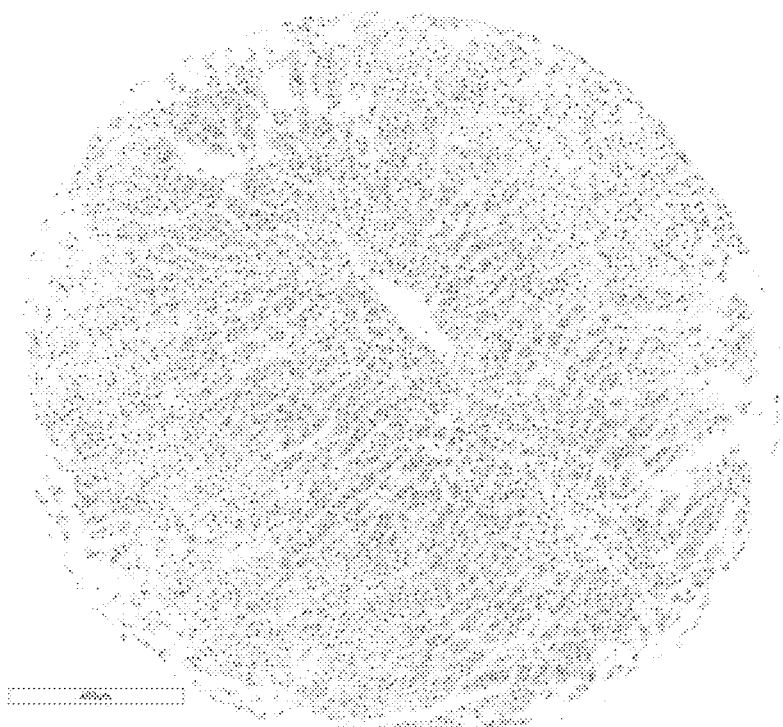
Figure 12A:
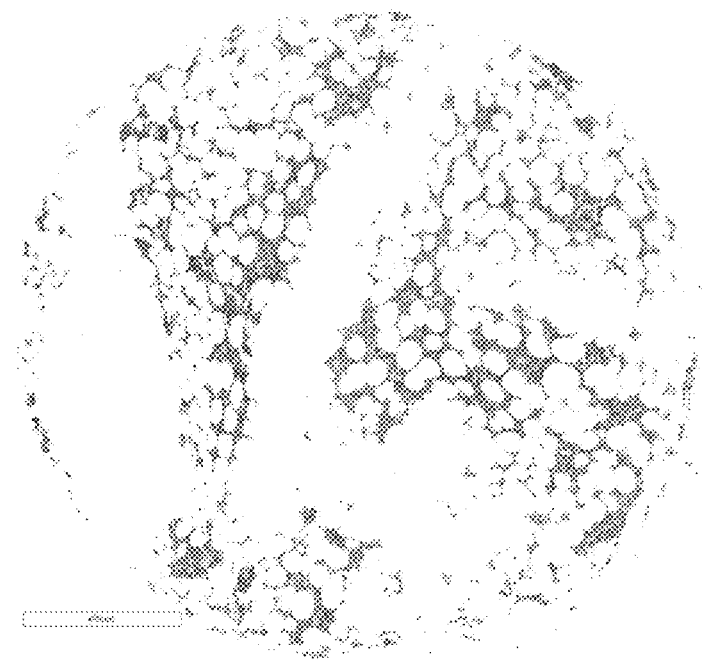
FIG. 12A and FIG. 12B show IHC staining of the bound DIG-E2 antibody in normal human organ tissues: Bone marrow.
Figure 12B:
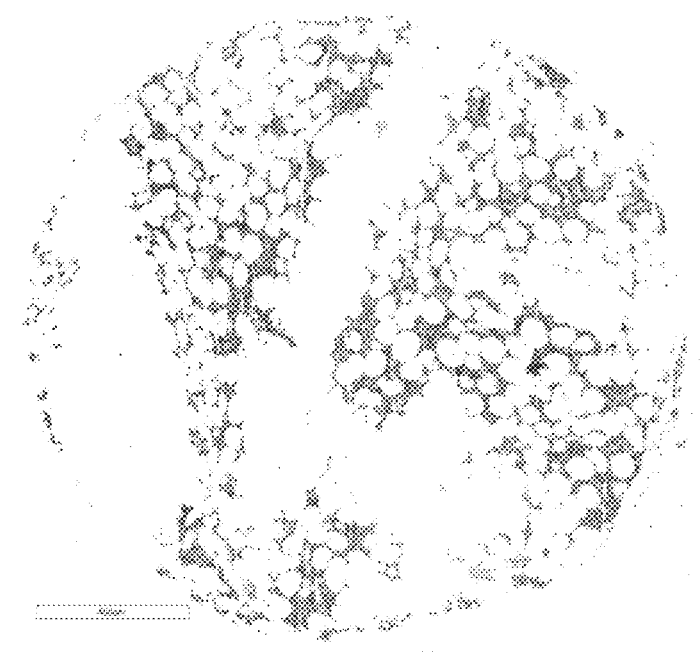
Figure 13A:
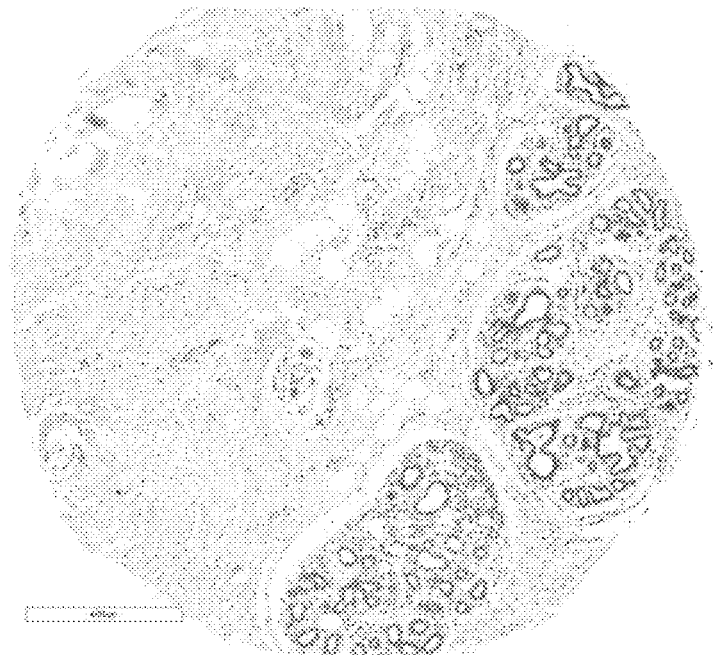
FIG. 13A and FIG. 13B show IHC staining of the bound DIG-E2 antibody in normal human organ tissues: Breast.
Figure 13B:
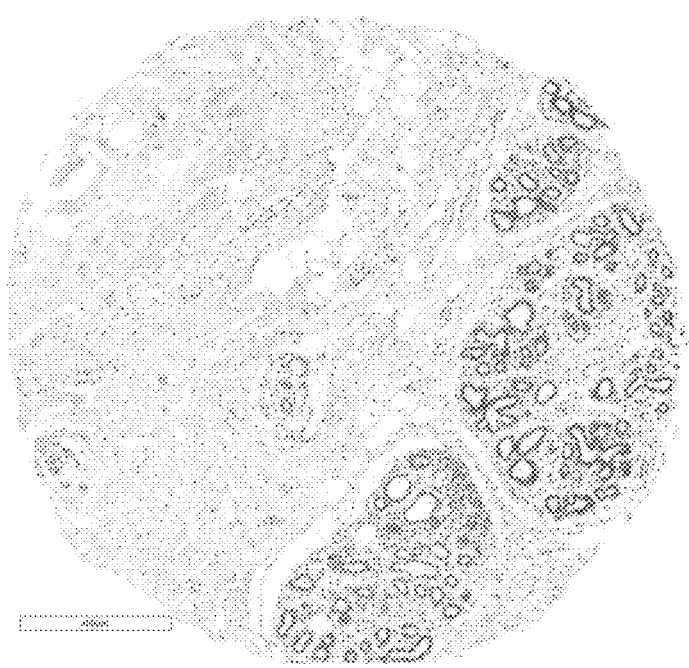
Figure 14A:
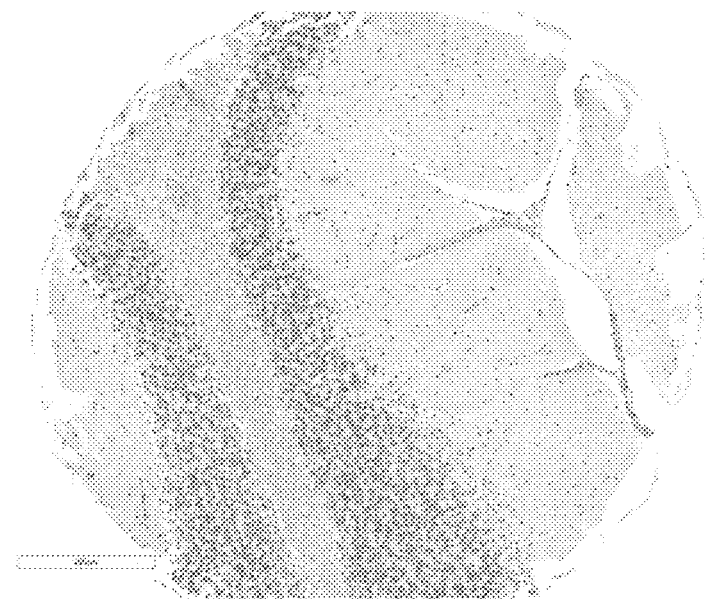
FIG. 14A and FIG. 14B show IHC staining of the bound DIG-E2 antibody in normal human organ tissues: Cerebellum tissue.
Figure 14B:
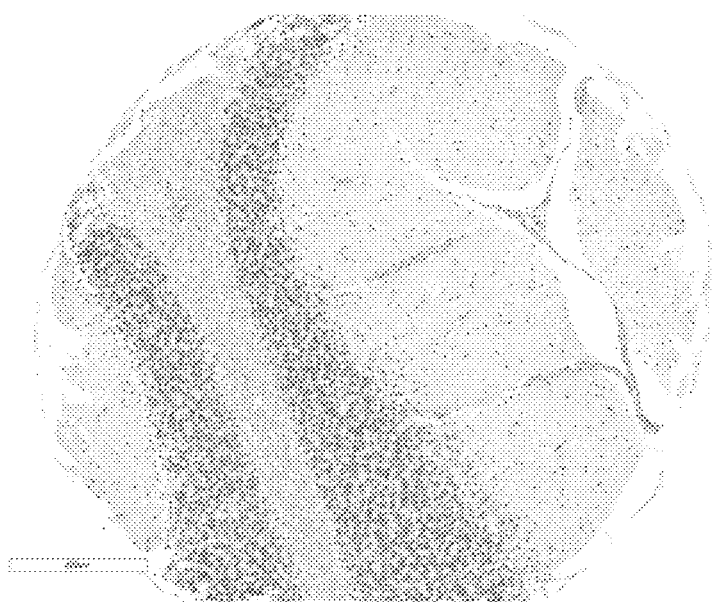
Figure 15A:
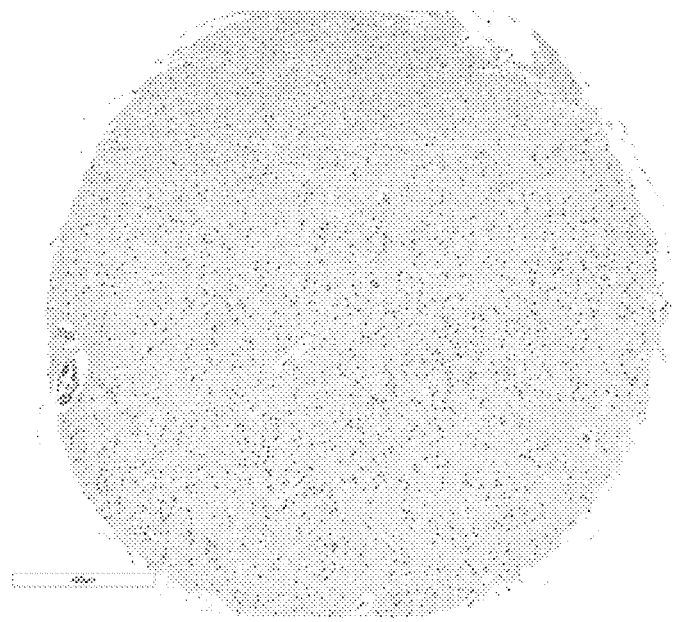
FIG. 15A and FIG. 15B show IHC staining of the bound DIG-E2 antibody in normal human organ tissues: Cervix.
Figure 15B:
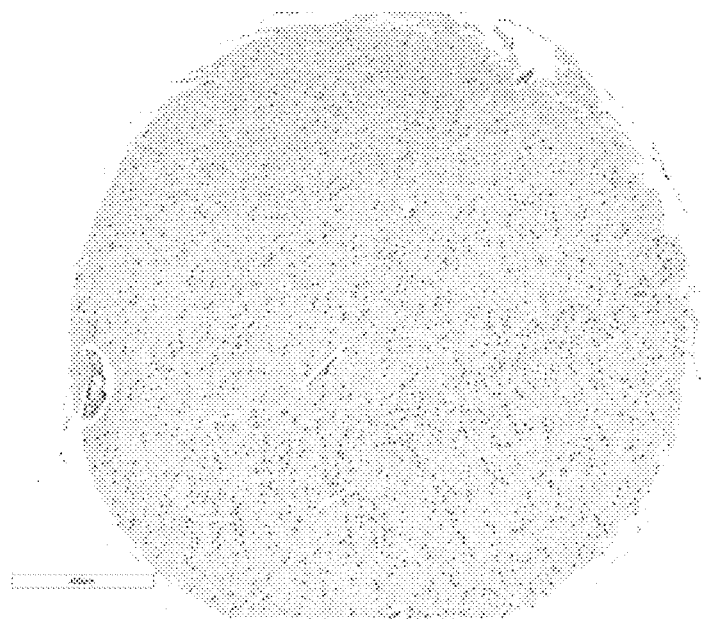
Figure 16A:
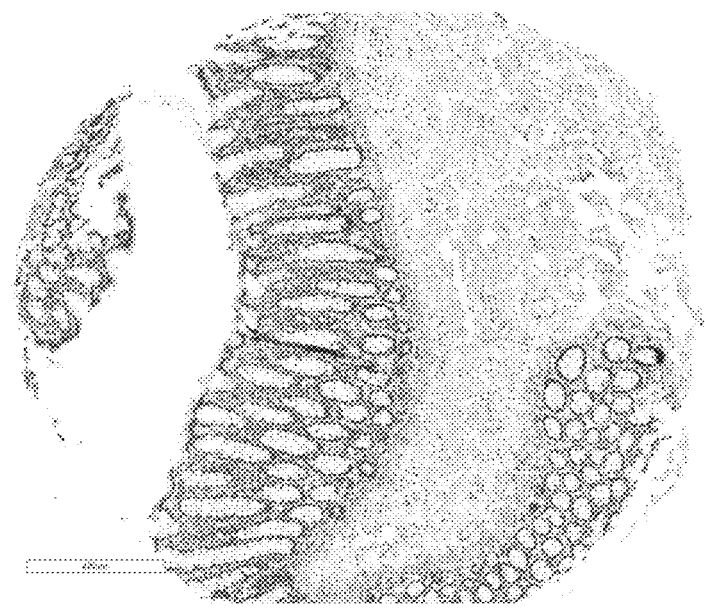
FIG. 16A and FIG. 16B show IHC staining of the bound DIG-E2 antibody in normal human organ tissues: Colon.
Figure 16B:
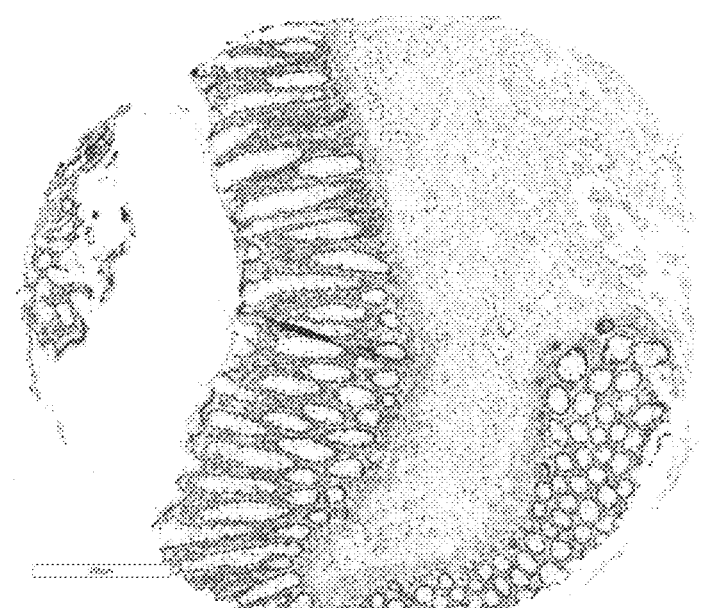
Figure 17A:
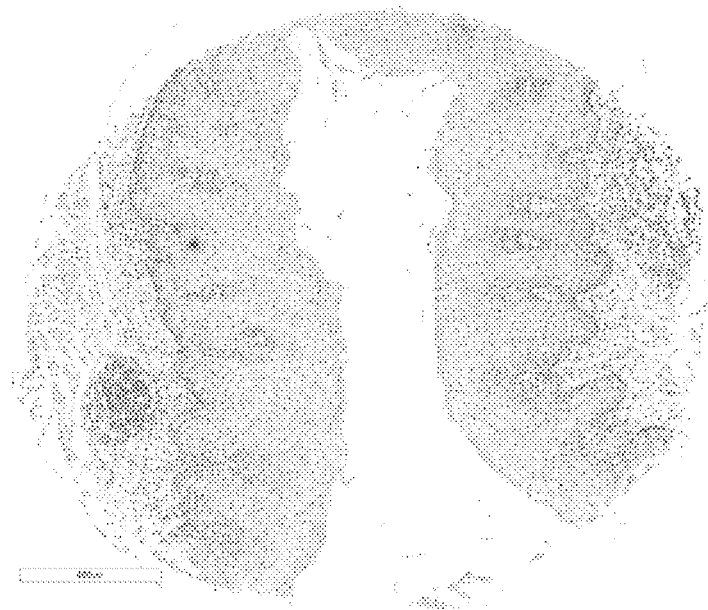
FIG. 17A and FIG. 17B show IHC staining of the bound DIG-E2 antibody in normal human organ tissues: Esophagus.
Figure 17B:
Figure 18A:
FIG. 18A and FIG. 18B show IHC staining of the bound DIG-E2 antibody in normal human organ tissues: Eye. Panel A: testing tissue section pre-incubated with DIG-E2 antibody; Panel B: control tissue section without pre-incubation with DIG-E2 antibody.
Figure 18B:
Figure 19A:
FIG. 19A and FIG. 19B show IHC staining of the bound DIG-E2 antibody in normal human organ tissues: Heart.
Figure 19B:
Figure 20A:
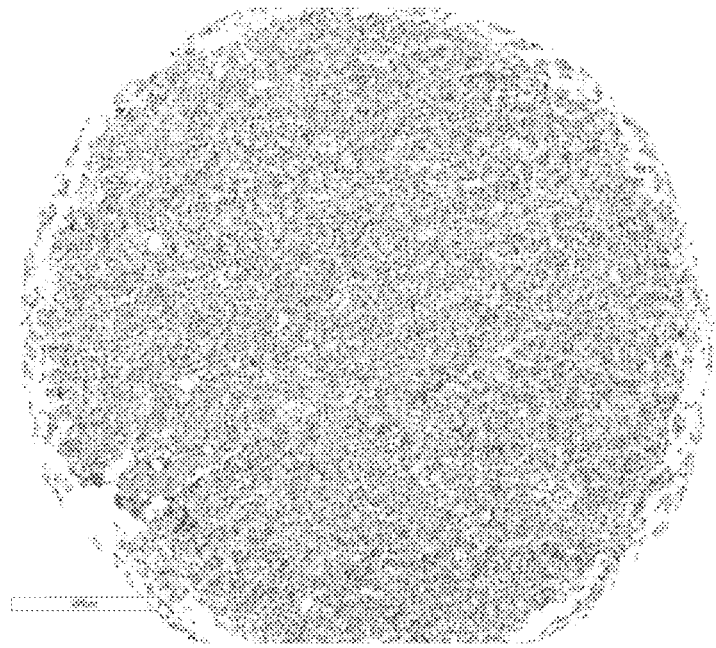
FIG. 20A and FIG. 20B show IHC staining of the bound DIG-E2 antibody in normal human organ tissues: Hypophysis.
Figure 20B:
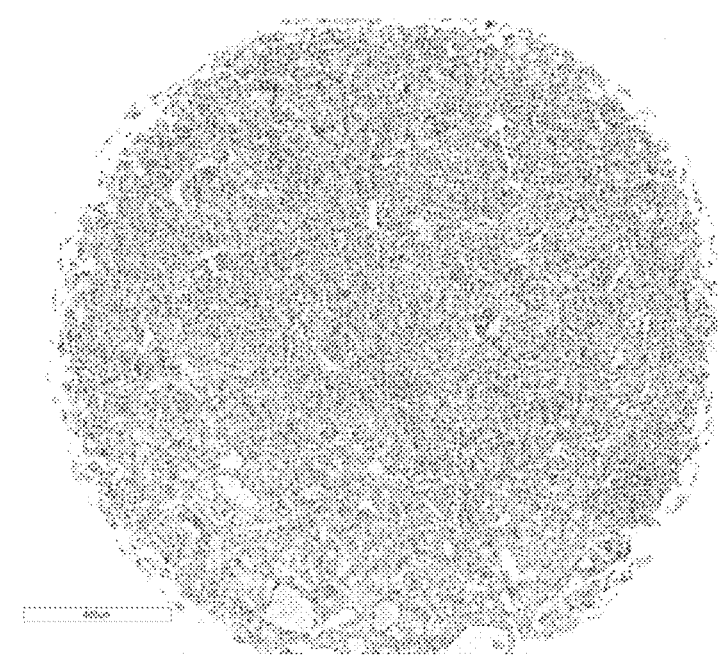
Figure 21A:
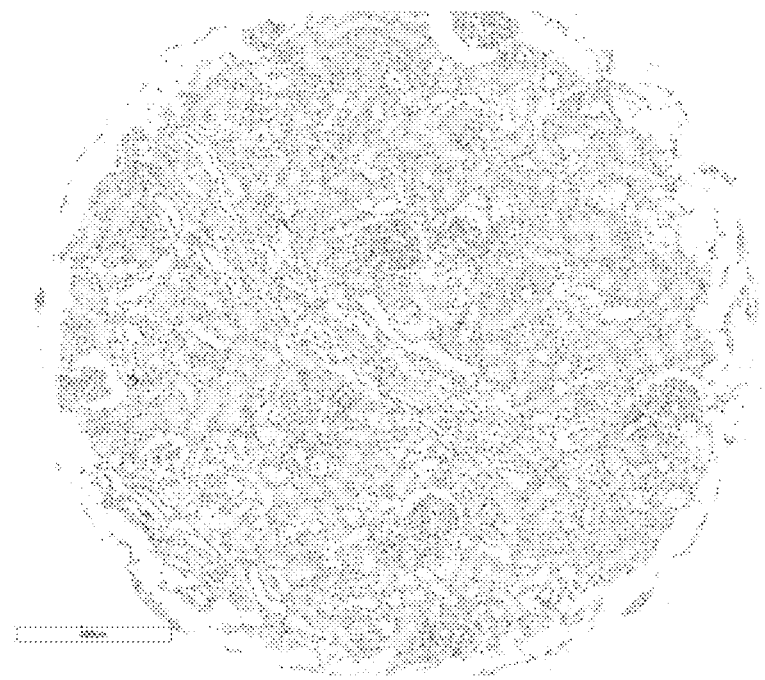
FIG. 21A and FIG. 21B show IHC staining of the bound DIG-E2 antibody in normal human organ tissues: Kidney.
Figure 21B:
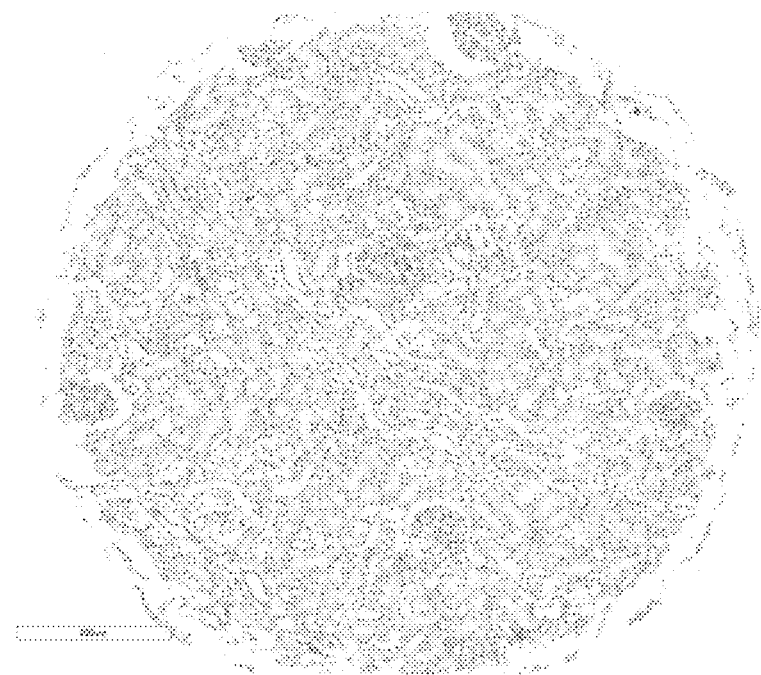
Figure 22A:
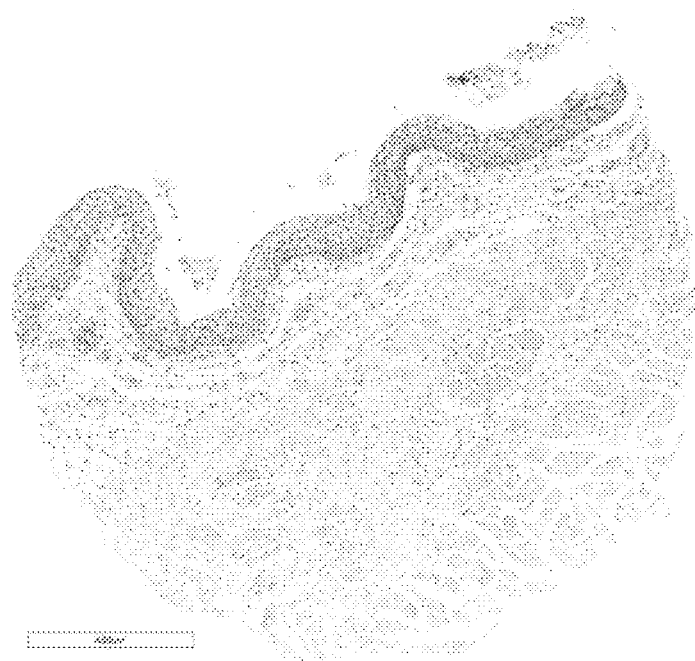
FIG. 22A and FIG. 22B show IHC staining of the bound DIG-E2 antibody in normal human organ tissues: Larynx.
Figure 22B:
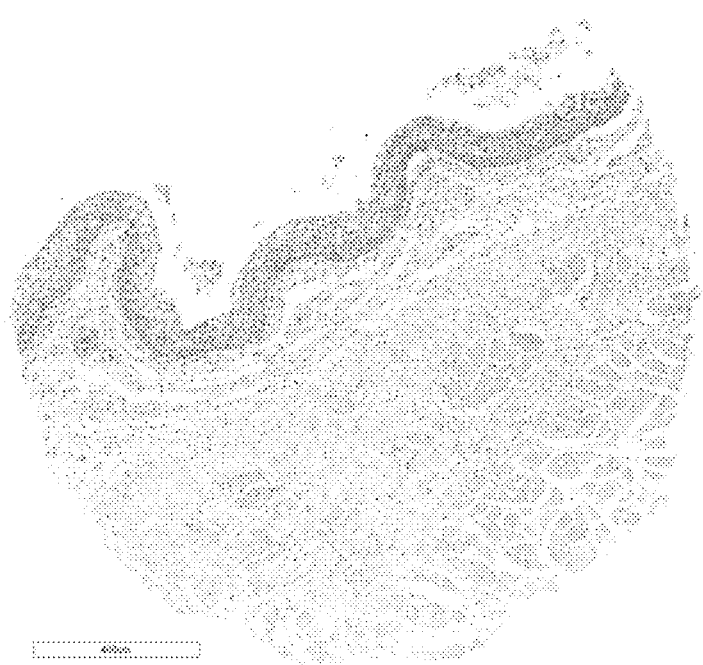
Figure 23A:
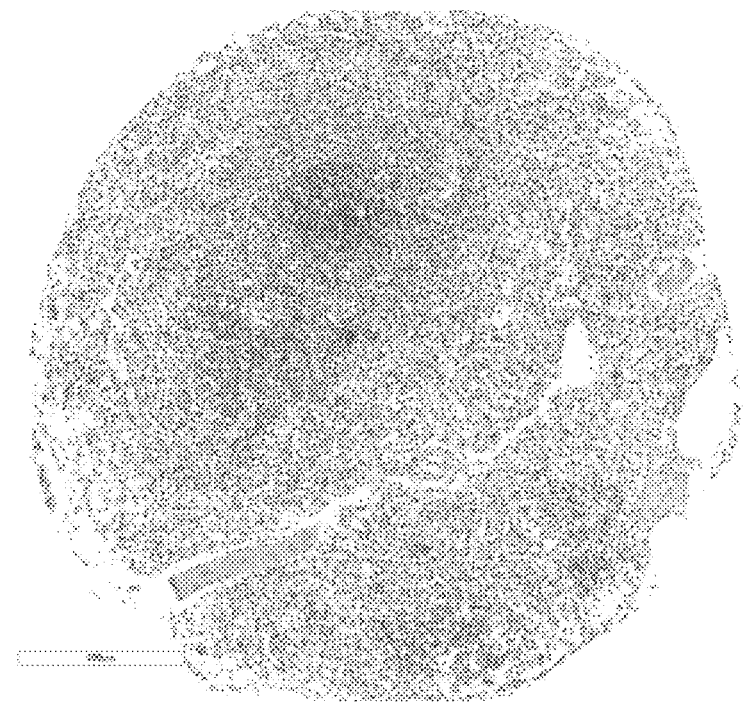
FIG. 23A and FIG. 23B show IHC staining of the bound DIG-E2 antibody in normal human organ tissues: Spleen.
Figure 23B:
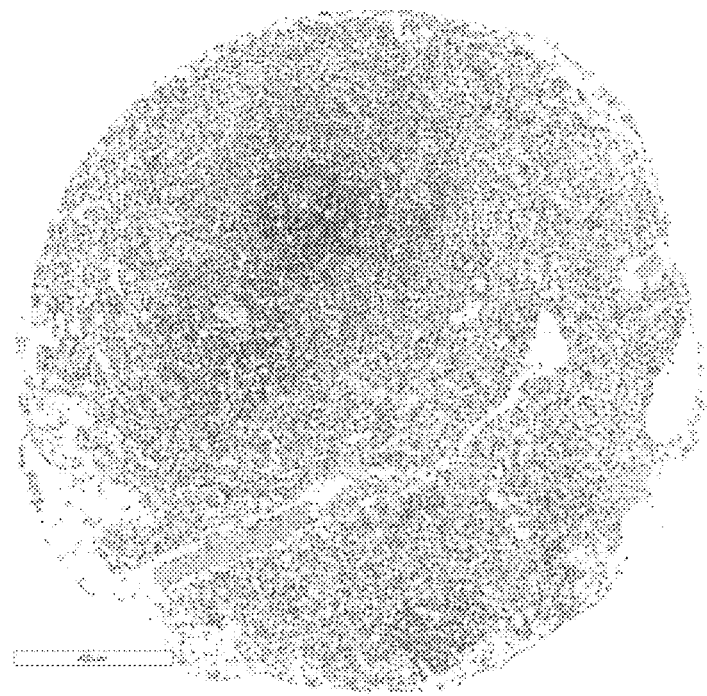
Figure 24A:
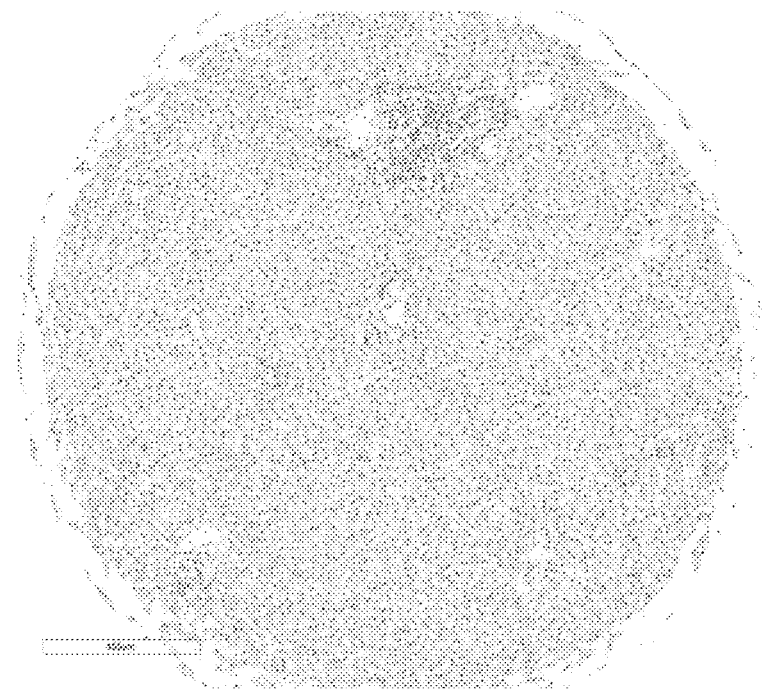
FIG. 24A and FIG. 24B show IHC staining of the bound DIG-E2 antibody in normal human organ tissues: Liver.
Figure 24B:
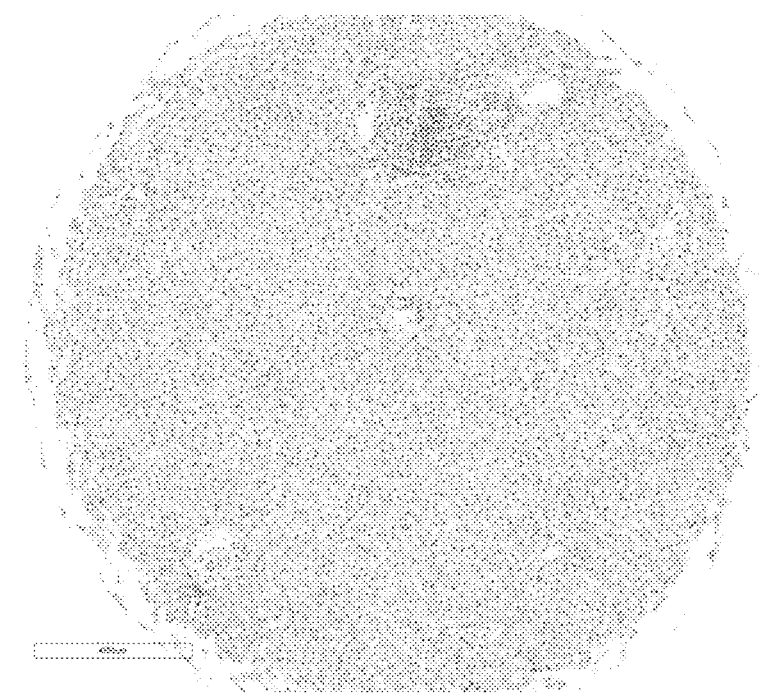
Figure 25A:
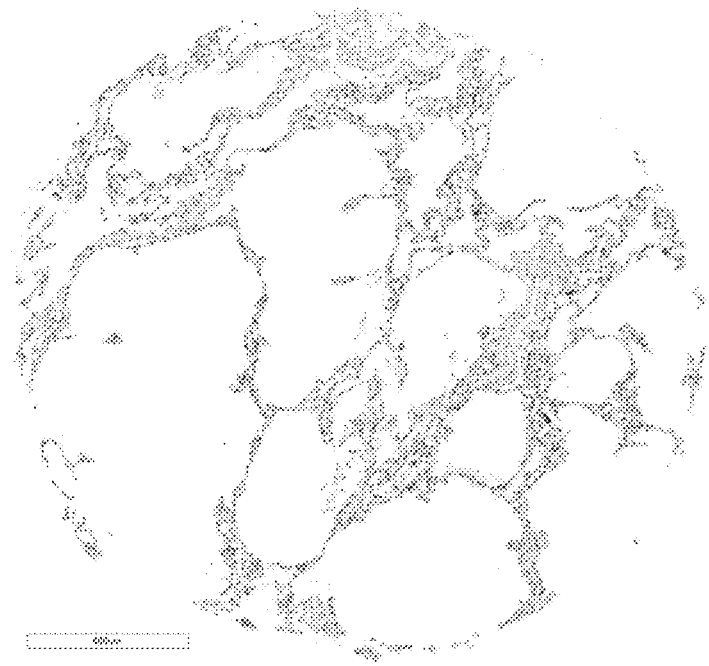
FIG. 25A and FIG. 25B show IHC staining of the bound DIG-E2 antibody in normal human organ tissues: Lung.
Figure 25B:
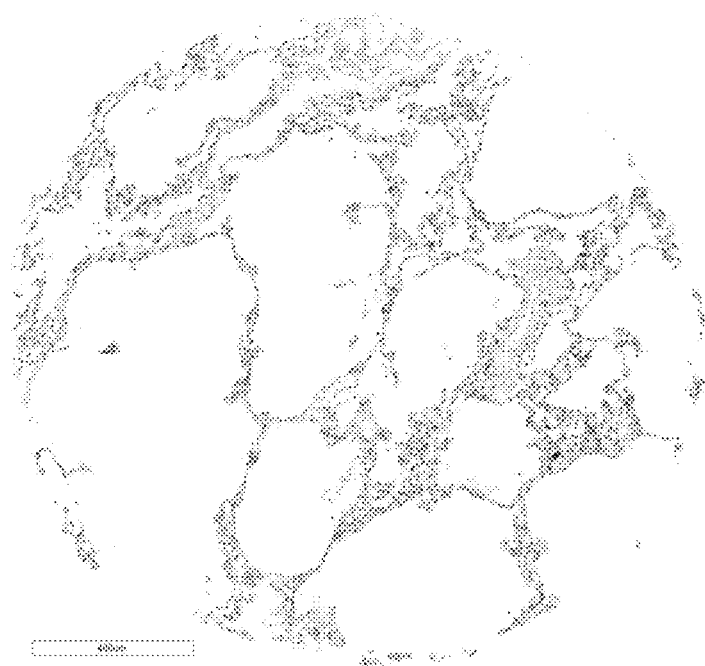
Figure 26A:
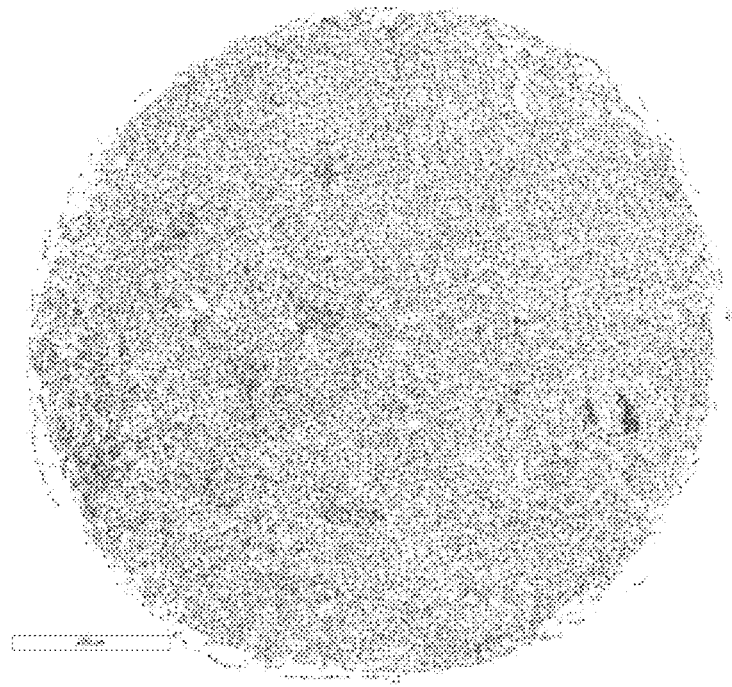
FIG. 26A and FIG. 26B show IHC staining of the bound DIG-E2 antibody in normal human organ tissues: Lymph node.
Figure 26B:
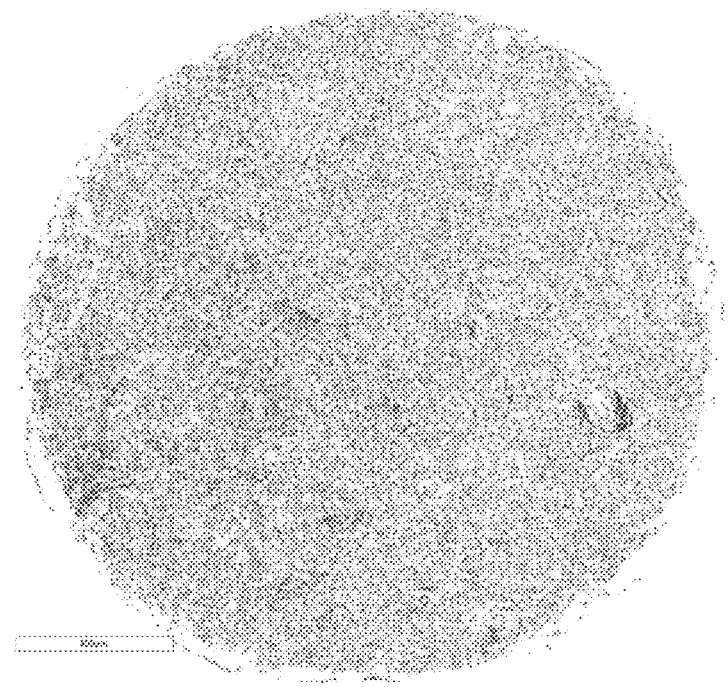
Figure 27A:
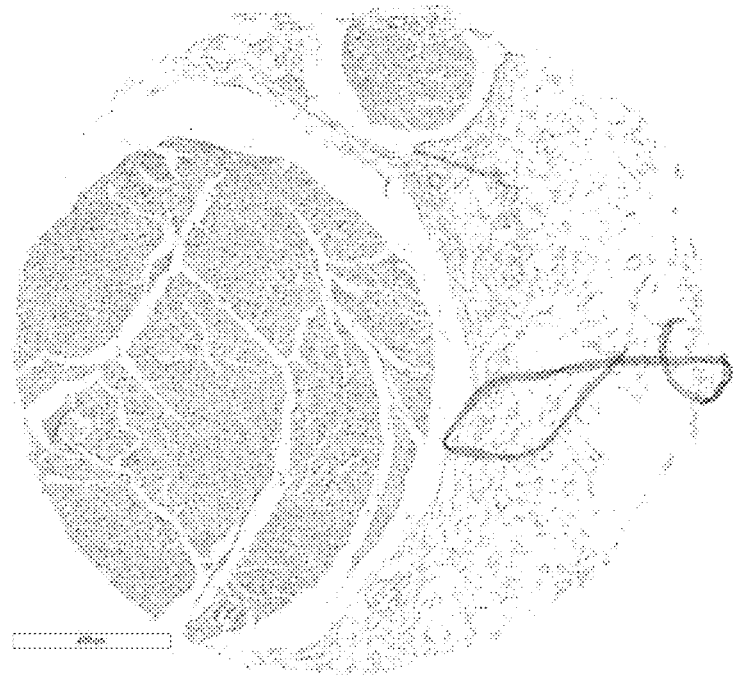
FIG. 27A and FIG. 27B show IHC staining of the bound DIG-E2 antibody in normal human organ tissues: Nerve.
Figure 27B:
Figure 28A:
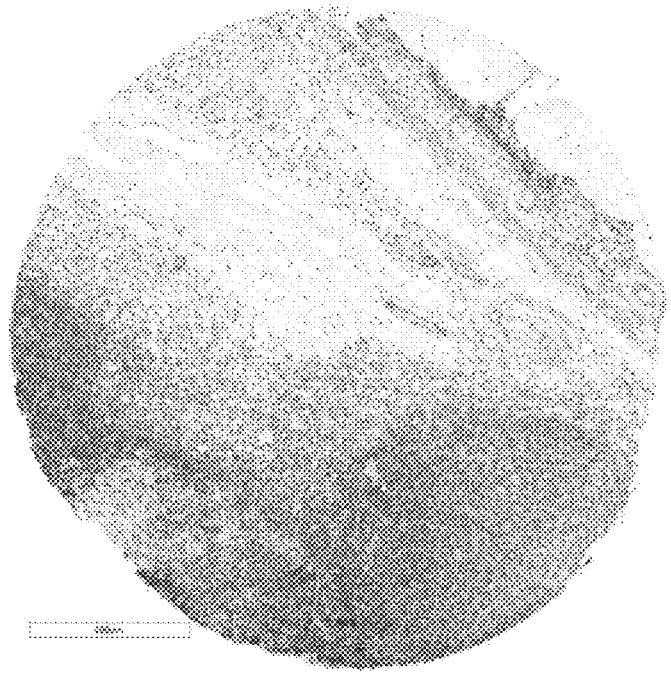
FIG. 28A and FIG. 28B show IHC staining of the bound DIG-E2 antibody in normal human organ tissues: Ovary.
Figure 28B:
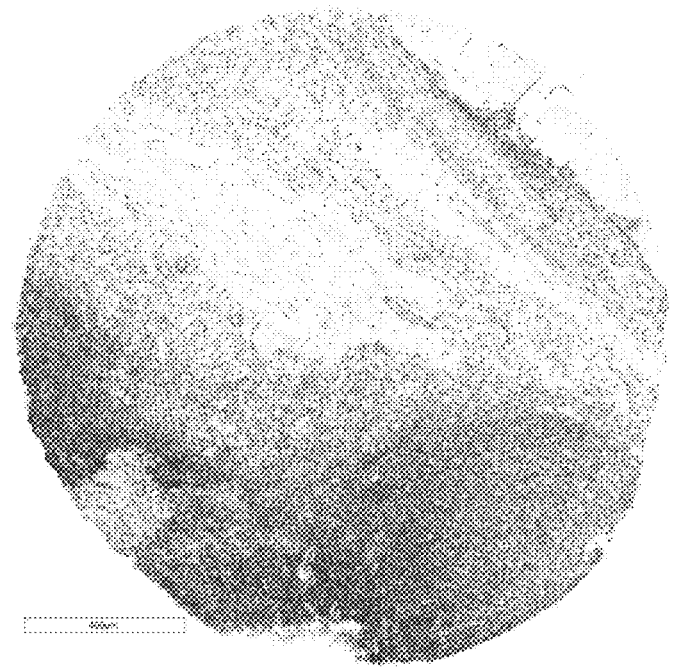
Figure 29A:
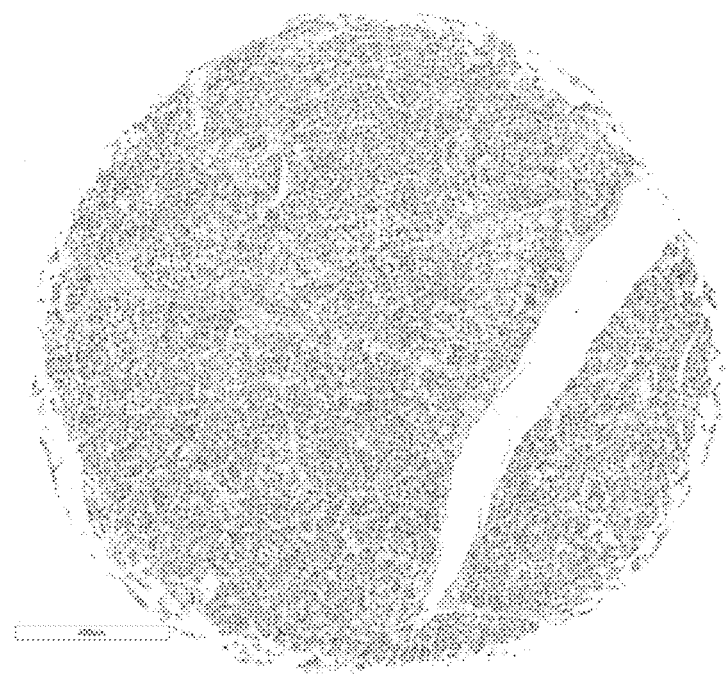
FIG. 29A and FIG. 29B show IHC staining of the bound DIG-E2 antibody in normal human organ tissues: Pancreas.
Figure 29B:
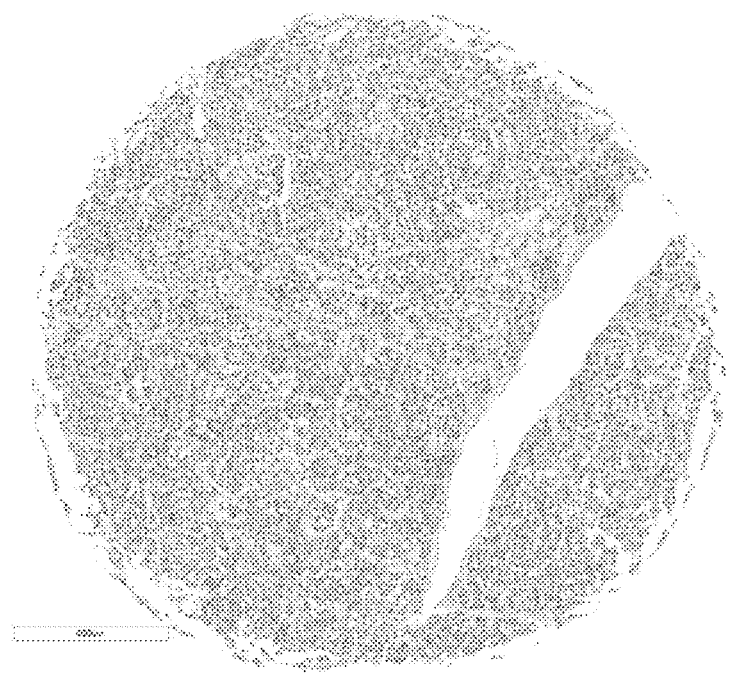
Figure 30A:
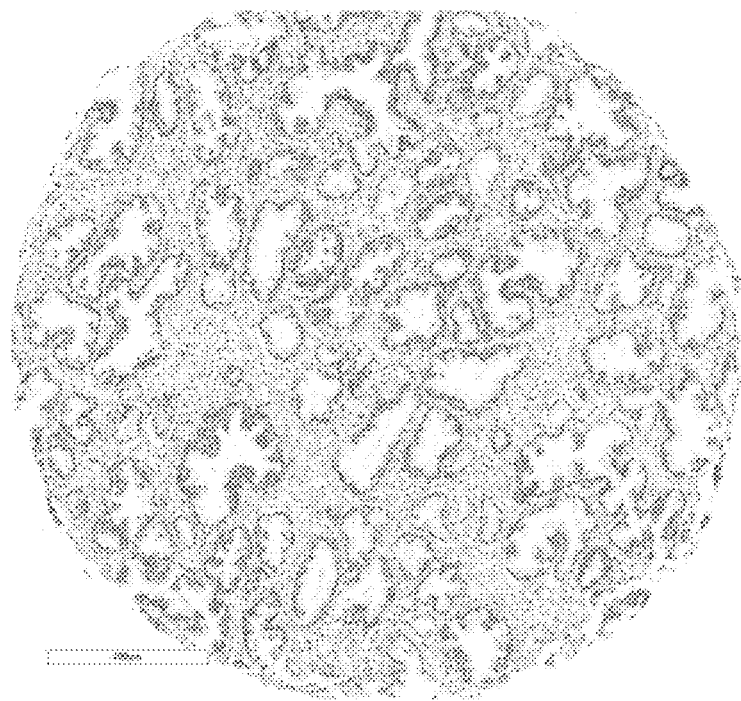
FIG. 30A and FIG. 30B show IHC staining of the bound DIG-E2 antibody in normal human organ tissues: Prostate.
Figure 30B:
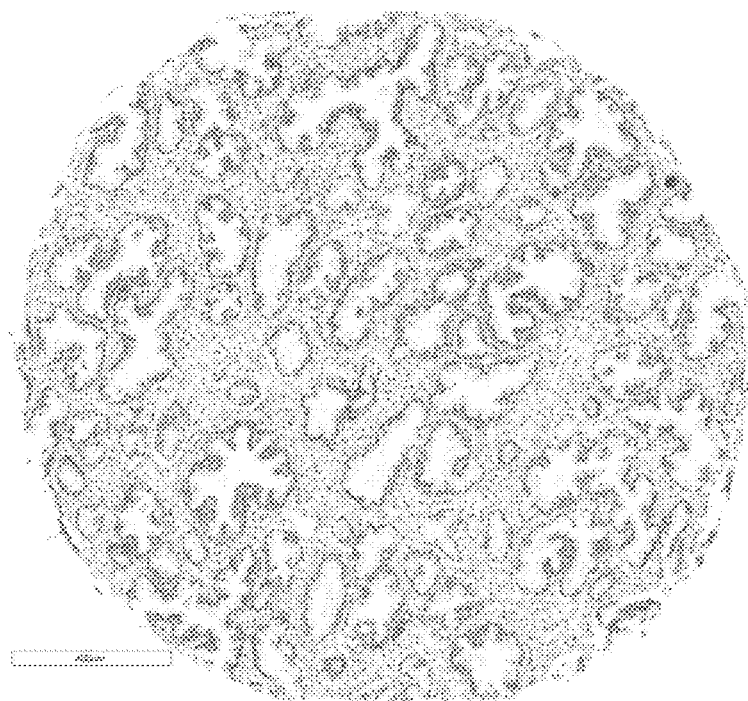
Figure 31A:
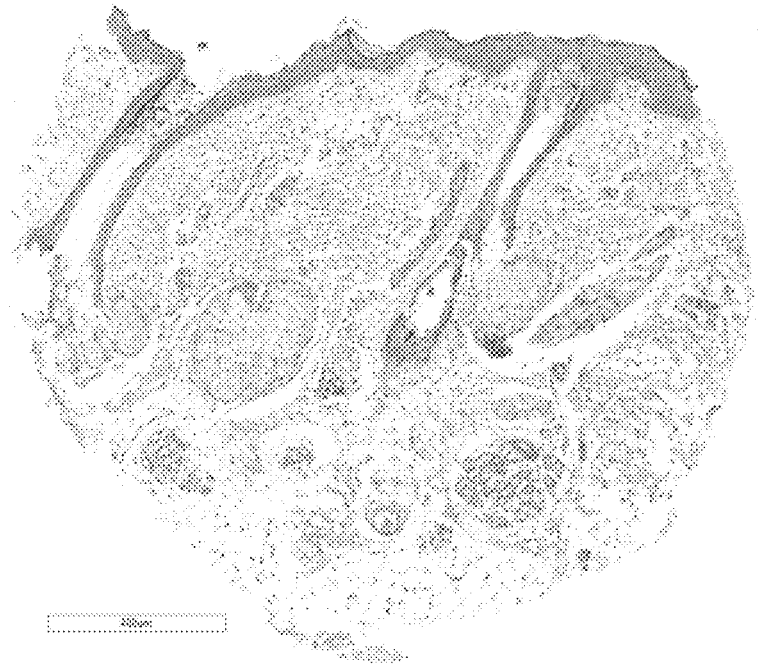
FIG. 31A and FIG. 31B shows IHC staining of the bound DIG-E2 antibody in normal human organ tissues: Skin.
Figure 31B:
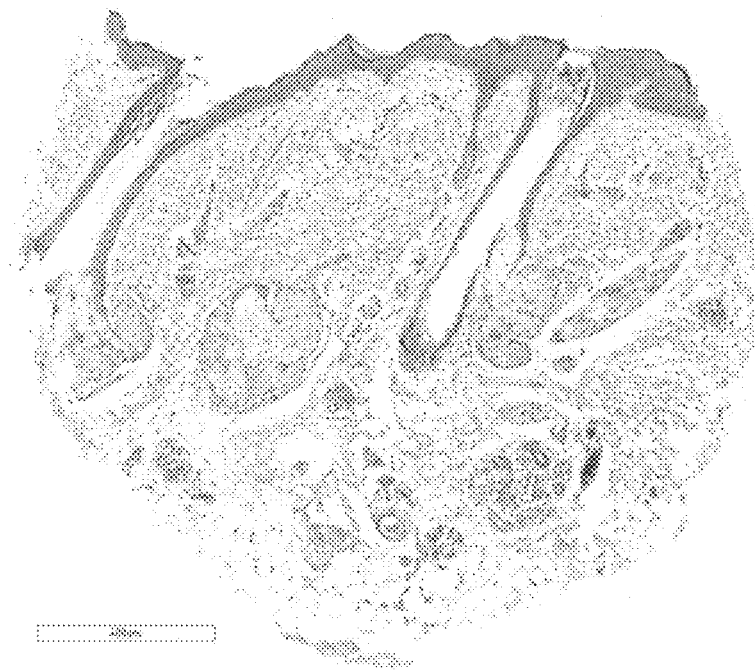
Figure 32A:
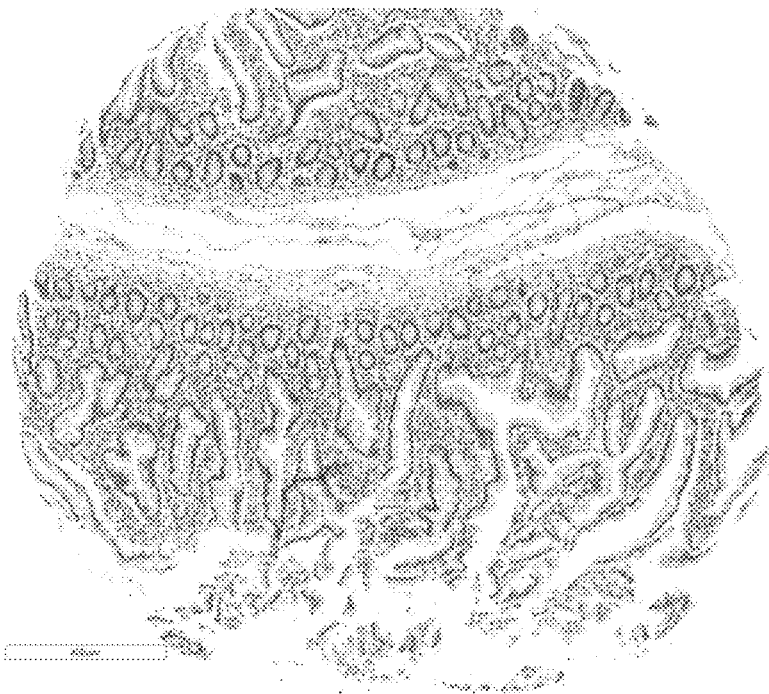
FIG. 32A and FIG. 32B show IHC staining of the bound DIG-E2 antibody in normal human organ tissues: Small intestine.
Figure 32B:
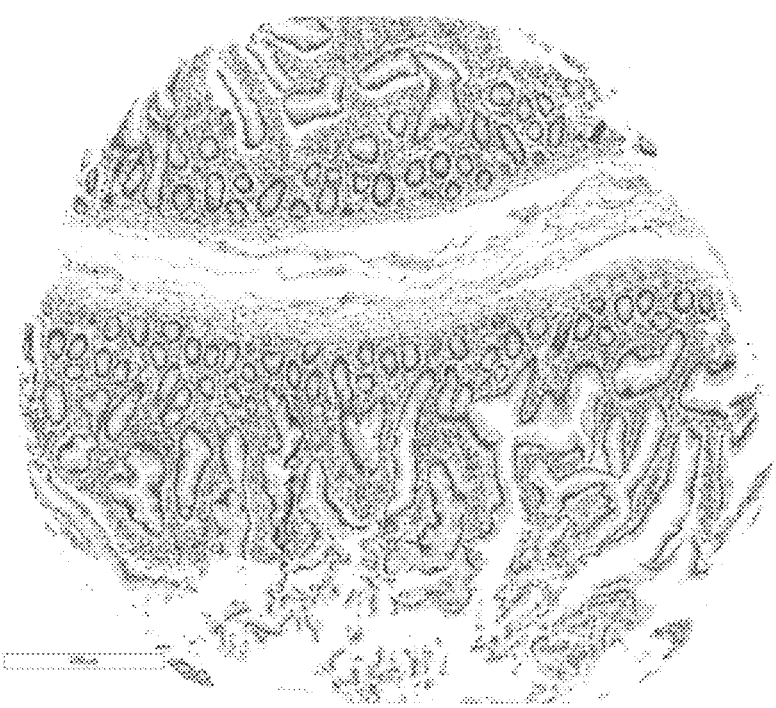
Figure 33A:
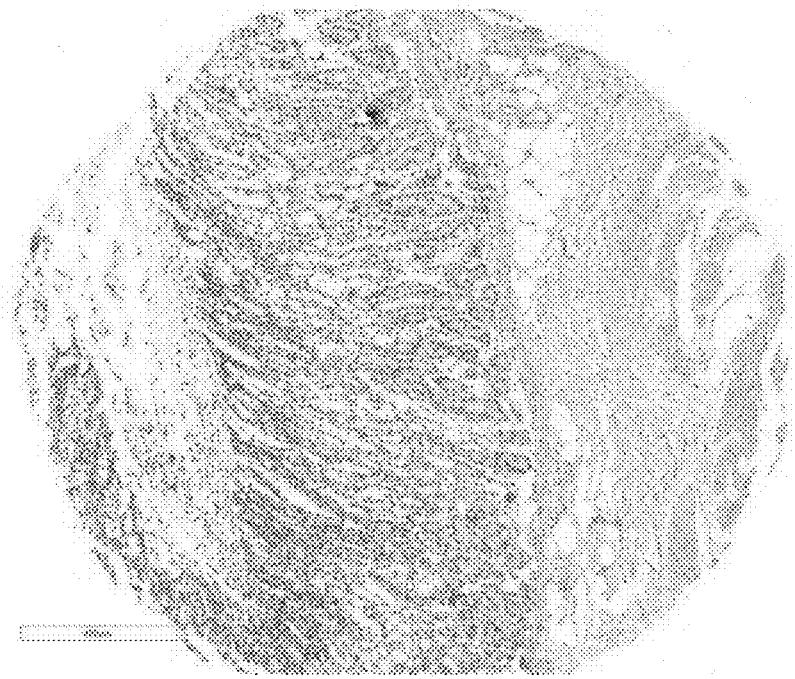
FIG. 33A and FIG. 33B show IHC staining of the bound DIG-E2 antibody in normal human organ tissues: Stomach.
Figure 33B:
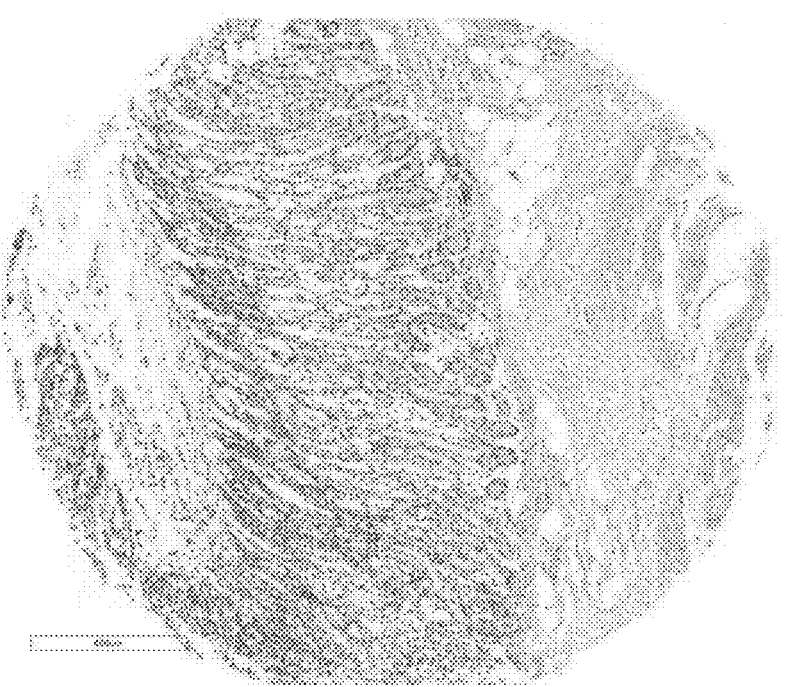
Figure 34A:
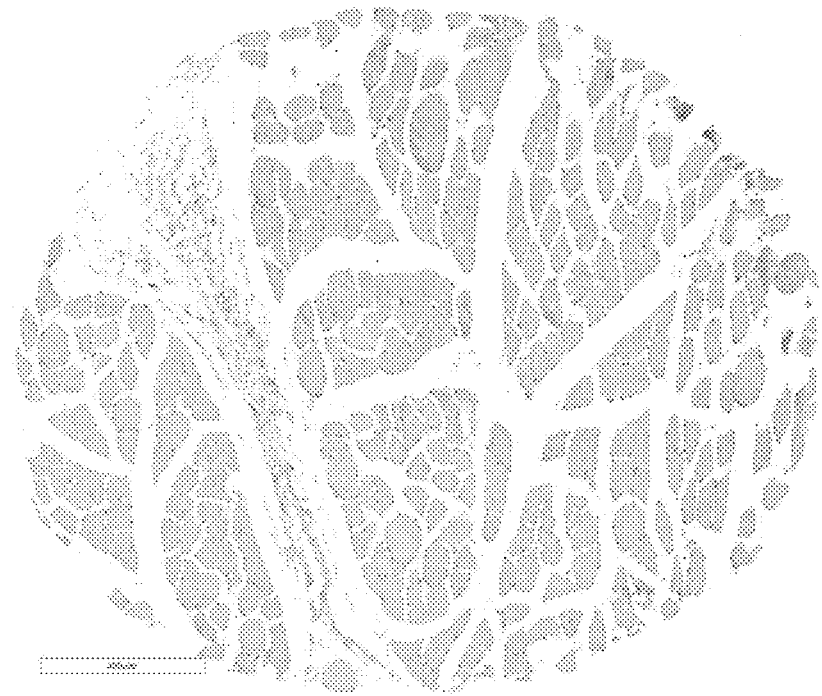
FIG. 34A and FIG. 34B show IHC staining of the bound DIG-E2 antibody in normal human organ tissues: Striated muscle.
Figure 34B:
Figure 35A:
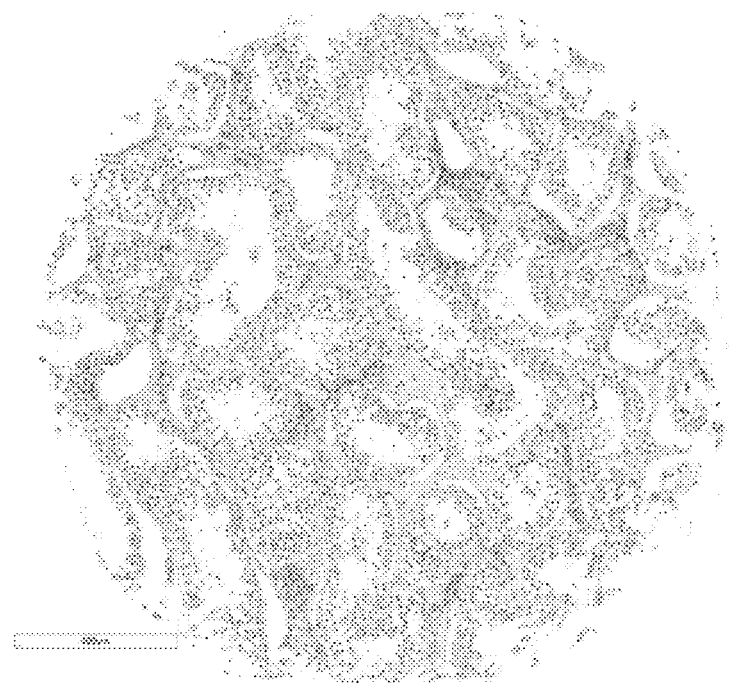
FIG. 35A and FIG. 35B show IHC staining of the bound DIG-E2 antibody in normal human organ tissues: Testis.
Figure 35B:
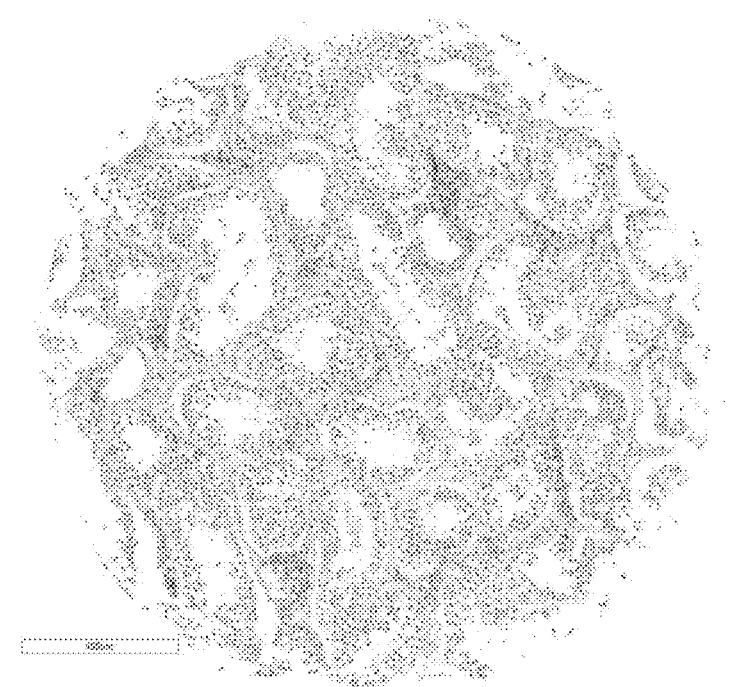
Figure 36A:
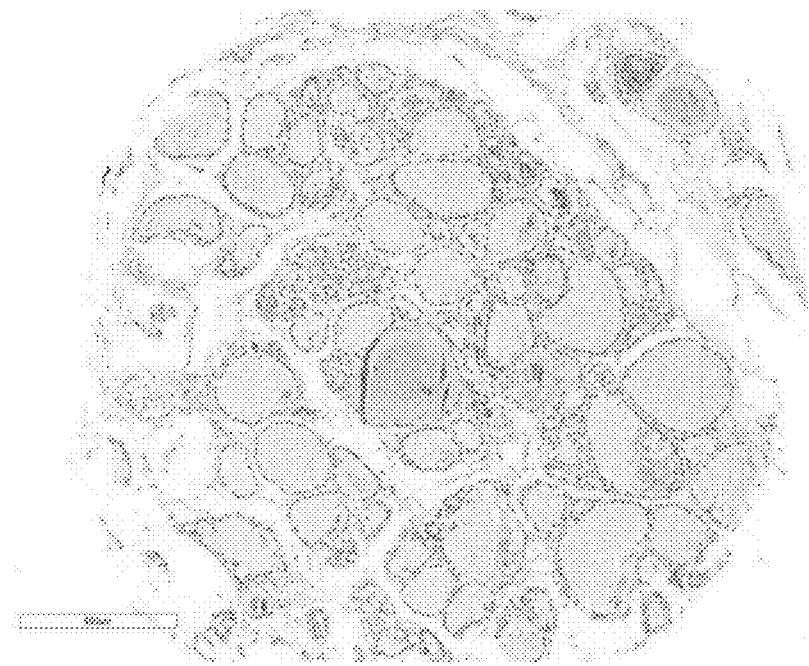
FIG. 36A and FIG. 36B show IHC staining of the bound DIG-E2 antibody in normal human organ tissues: Thymus gland.
Figure 36B:
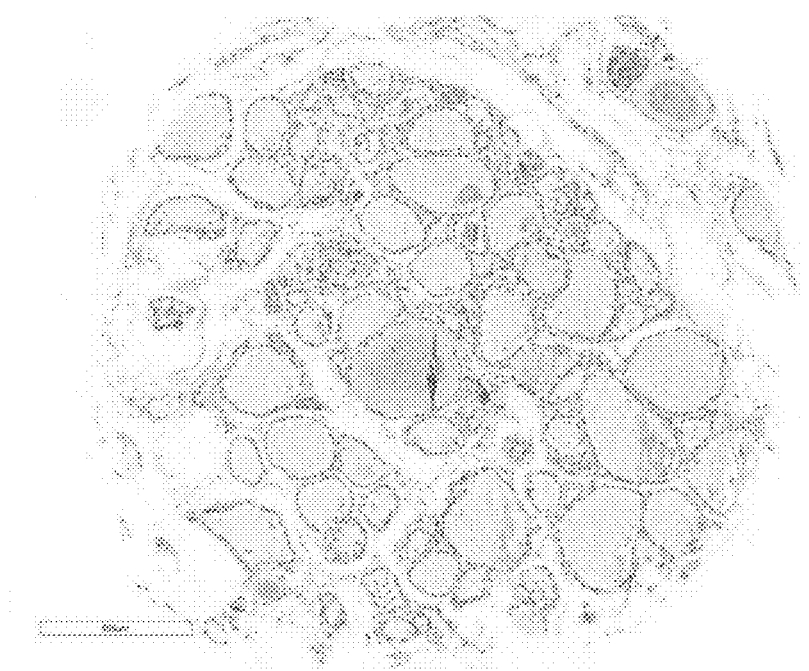
Figure 37A:
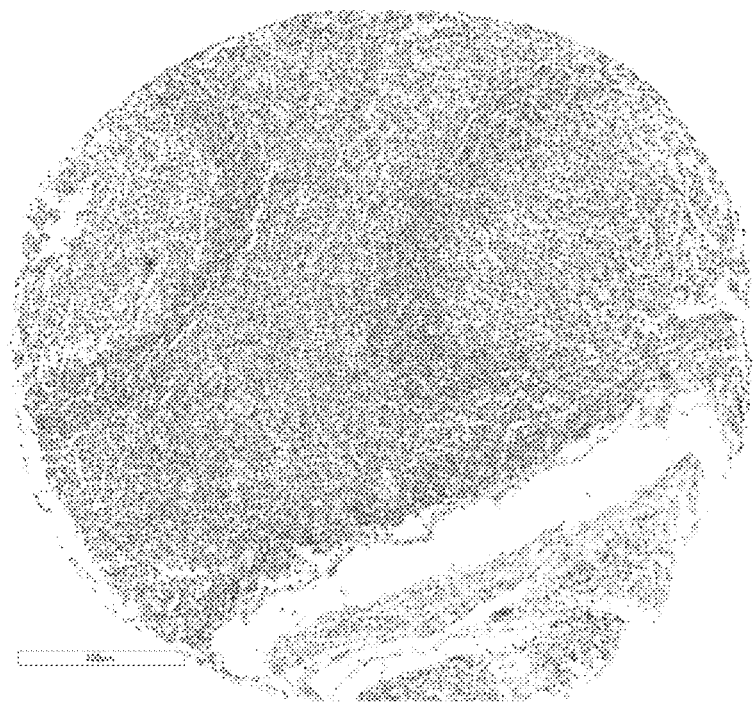
FIG. 37A and FIG. 37B show IHC staining of the bound DIG-E2 antibody in normal human organ tissues: Tongue.
Figure 37B:
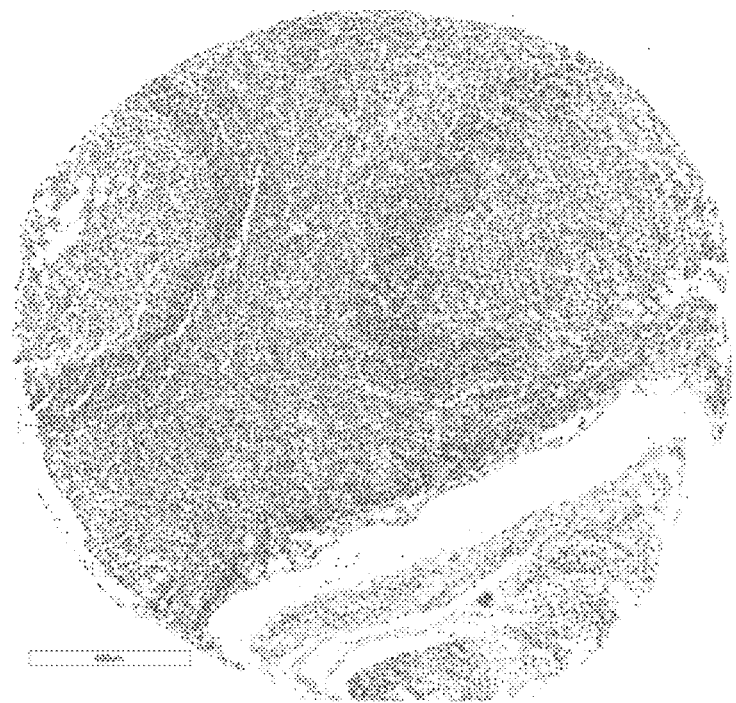
Figure 38A:
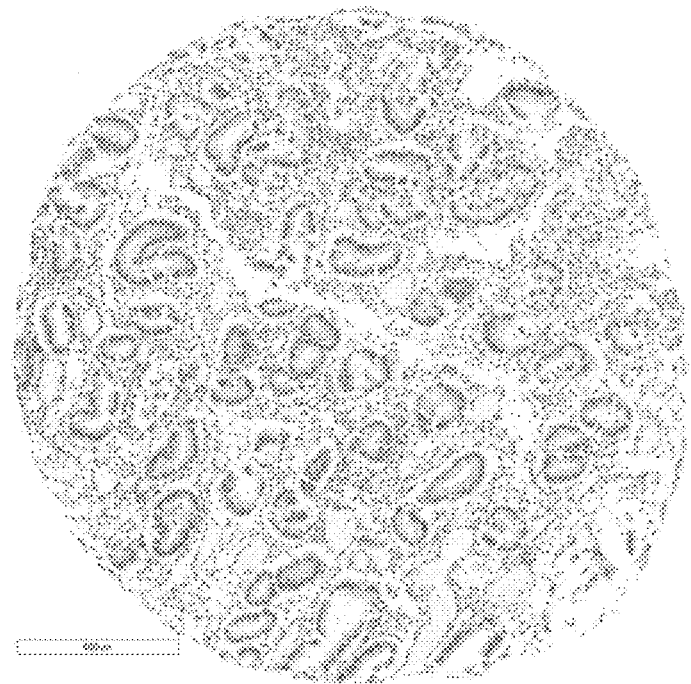
FIG. 38A and FIG. 38B show IHC staining of the bound DIG-E2 antibody in normal human organ tissues: Uterus.
Figure 38B:
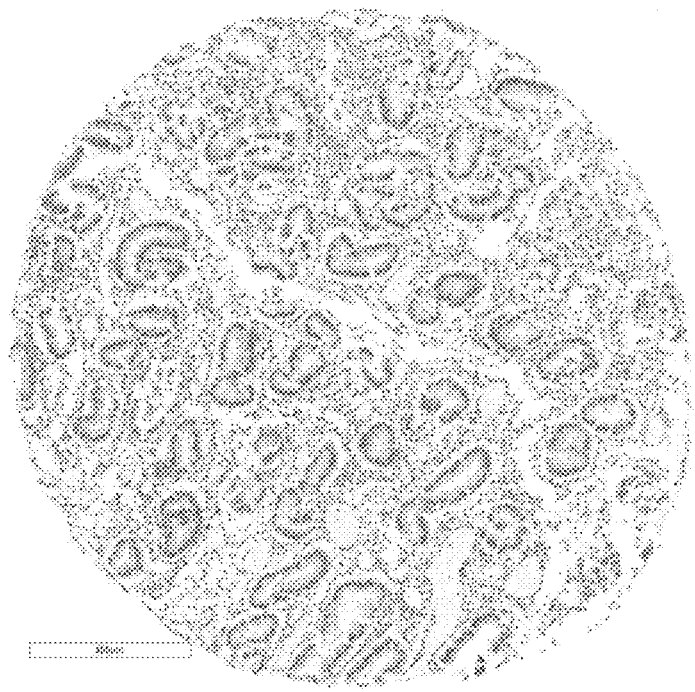

DIG-labeled E2 antibody was incubated with a human multiple organ normal tissue microarray (FDA999, US Biomax, Inc) and the binding of E2 antibody to human normal tissues was evaluated using the same IHC procedure with the same conditions described above. This multiple organ normal tissue microarray has 99 cores with 28 types of normal human organs, including adrenal gland (FIG. 11A, FIG. 11B), bone marrow (FIG. 12A, FIG. 12B), breast (FIG. 13A, FIG. 13B), cerebellum tissue (FIG. 14A, FIG. 14B), cervix (FIG. 15A, FIG. 15B), colon (FIG. 16A, FIG. 16B), esophagus (FIG. 17A, FIG. 17B), eye (FIG. 18A, FIG. 18B), heart (FIG. 19A, FIG. 19B), hypophysis (FIG. 20A, FIG. 20B), kidney (FIG. 21A, FIG. 21B), larynx (FIG. 22A, FIG. 22B), liver (FIG. 24A, FIG. 24B), lung (FIG. 25A, FIG. 25B), lymph node (FIG. 26A, FIG. 26B), nerve (FIG. 27A, FIG. 27B), ovary (FIG. 28A, FIG. 28B), pancreas (FIG. 29A, FIG. 29B), prostate (FIG. 30A, FIG. 30B), skin (FIG. 31A, FIG. 31B), small intestine (FIG. 32A FIG. 32B), spleen (FIG. 23A, FIG. 23B), stomach FIG. 33A, FIG. 33B), striated muscle (FIG. 34A, FIG. 34B), testis (FIG. 35A, FIG. 35B), thymus gland (FIG. 36A, FIG. 36B), tongue (FIG. 37A, FIG. 37B), and uterus (FIG. 38A, FIG. 38B). Organs taken from at least 3 normal human individuals were included in the microarray panel. As shown in FIGS. 11-38, no positive IHC staining was found in any of these 28 types of normal human organs tested, indicating that E2 anti-FITC antibody does not have any binding with normal human organ tissues. Some plasma cells showed certain levels of staining intensity in both the testing sections pre-incubated with DIG-E2 antibody and the negative control sections without pre-incubation with DIG-E2 antibody, indicating that this weak staining was nonspecific.

In conclusion, E2 anti-FITC antibody does not bind with any tested human normal organ tissues, indicating E2 anti-FITC CAR-T cell itself should not bind to and attack any human normal tissues in vivo.

Example 4

Synthesis of FITC-Folate

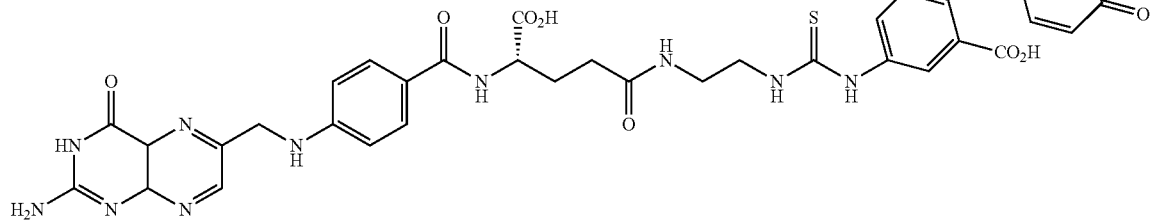

Folate-γ-ethylenediamine was coupled to fluorescein isothiocyanate (FITC) isomer I (Sigma-Aldrich) in anhydrous dimethylsulfoxide (DMF) in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, pH 7.4) and 1% acetonitrile (mobile phase B) and reaching 90% A and 10% B in 10 min at a flow rate of 20 mL/min. Under these conditions, the FITCfolate main peak typically eluted at 27-50 min. The quality of the FITC-folate fraction was monitored by analytical reverse-phase HPLC with a UV detector. Fractions with greater than 98.0% purity (LCMS) were lyophilized to obtain the final FITC-folate product. As known in the art, the compound with this structure is also referred to as EC17.

Example 5

Synthesis of FITC-PEG12-Folate

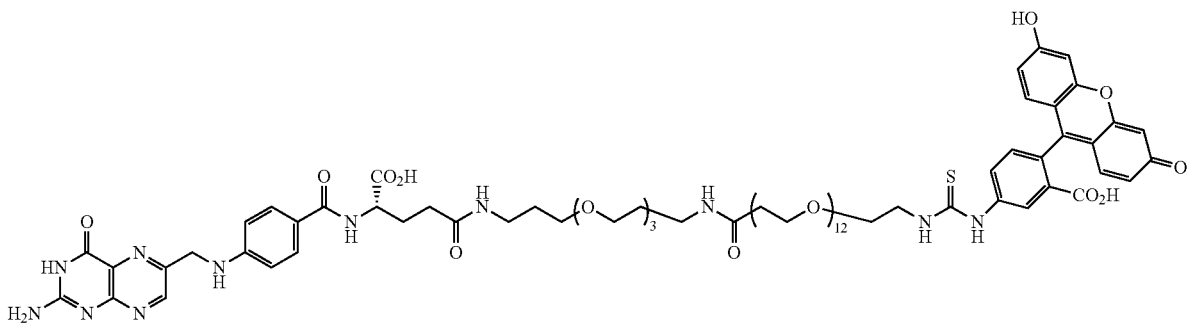

Universal polyethylene glycol (PEG) Nova Tag™ resin (0.2 g) was loaded into a peptide synthesis vessel and washed with isopropyl alcohol (i-PrOH) (3×10 mL) and dimethylformamide (DMF, 3×10 mL). 9-fluorenylmethoxycarbonyl (Fmoc) deprotection was carried out using 20% piperidine in DMF (3×10 mL). Kaiser tests were performed to assess reaction progress. To the vessel was then introduced a solution of Fmoc-L-glutamic acid 5-tertbutyl ester (Fmoc-Glu-(O-t-Bu)—OH) (23.5 mg) in DMF, N,N-diisopropylethylamine (i-Pr$_2$NEt) (4 equiv), and benzotriazol-1-yl-oxytripyrrolidinophosphonium hexafluorophosphate (PyBOP) (2 equiv). Fmoc deprotection was carried out using 20% piperidine in DMF (3×10 mL). To the vessel was then introduced a solution of N$^{10}$-TFA-Pte-OH (22.5 mg), DMF, i-Pr$_2$NEt (4 equiv), and PyBOP (2 equiv). Argon was bubbled for 2 h, and the resin was washed with DMF (3×3 mL) and i-PrOH (3×3 mL). After swelling the resin in dichloromethane (DCM), a solution of 1M hydroxybenzotriazole (HOBT) in DCM/trifluoroethane (TFE) (1:1) (2×3 mL) was added. Argon was bubbled for 1 h, the solvent was removed, and the resin was washed with DMF (3×3 mL) and i-PrOH (3×3 mL). After swelling the resin in DMF, a solution of Fmoc-NH-(PEG)12-COOH (46.3 mg) in DMF, i-Pr$_2$NEt (4 equiv), and PyBOP (2 equiv) was added. Argon was bubbled for 2 h, and the resin was washed with DMF (3×3 mL) and i-PrOH (3×3 mL). Fmoc deprotection was carried out using 20% piperidine in DMF (3×10 mL). Kaiser tests were performed to assess reaction progress. To the vessel was then introduced a solution of FITC (Life Technologies 21.4 mg) in DMF and i-Pr$_2$NEt (4 equiv), then Argon was bubbled for 2 h, and the resin was washed with DMF (3×3 mL) and i-PrOH (3×3 mL). Then to the vessel was added 2% NH$_2$NH$_2$ in DMF (2×2 mL). The final compound was cleaved from the resin using a TFA:H$_2$O: triisopropylsilane (TIS) (95:2.5:2.5) (Cleavage Solution) and concentrated under vacuum. The concentrated product was precipitated in Et2O and dried under vacuum. The crude product was purified using preparative RP-HPLC (mobile phase: A=10 mM ammonium acetate pH=7, B=ACN; method: 0% B to 30% B in 30 min at 13 mL/min). The pure fractions were pooled and freeze-dried, providing the FITC-PEG12-Folate.

Example 6

Synthesis of FITC-PEG20-Folate

Ethylenediamine, polymer-bound (200-400 mesh)-resin (50 mg) was loaded into a peptide synthesis vessel and swollen with DCM (3 mL) followed by DMF (3 mL). To the vessel was then introduced the Fmoc-PEG20-COOH solution (131 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete the reaction with Fmoc-Glu-OtBu (72 mg, 2.0 equiv) and Tfa.Pteroic-acid (41 mg, 1.2 equiv) coupling steps. The resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. The folate-peptide was cleaved from the resin using the Cleavage Solution. 10 mL of the cleavage mixture was introduced and argon was bubbled for 1.5 h. The cleavage mixture was drained into a clean flask. The resin was washed 3 times with more cleavage mixture. The combined mixture was concentrated under reduced pressure to a smaller volume (~5 mL) and precipitated in ethyl ether.

The precipitate was collected by centrifugation, washed with ethyl ether (3 times) and dried under high vacuum. The dried Folate-PEG$_{20}$-EDA (1.0 equiv) was treated with FITC (50 mg, 1.5 equiv) in DMSO and DIPEA at room temperature. Progress of the reaction monitored by LCMS. After 8 h the starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG20-Folate in 60% yield.

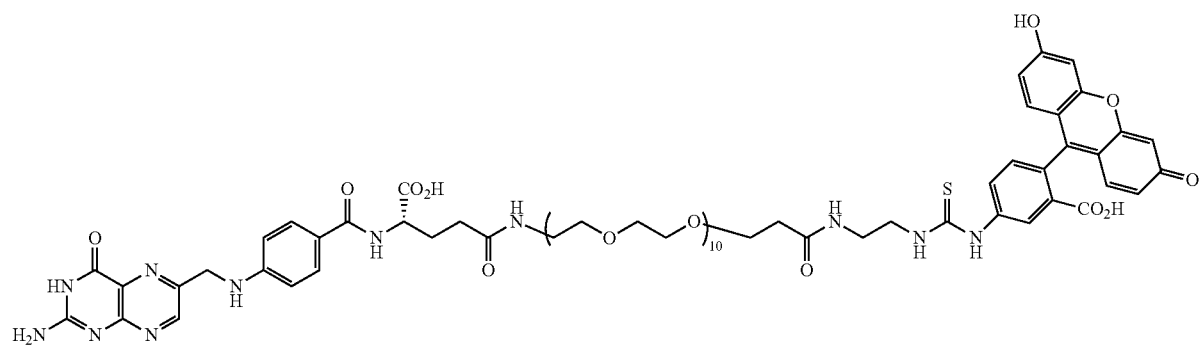

Example 7

Synthesis of FITC-PEG108-Folate

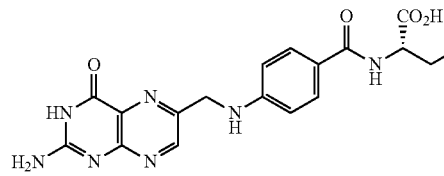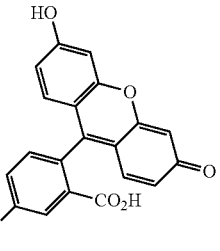

Ethylenediamine, polymer-bound (200-400 mesh)-resin (50 mg) was loaded in a peptide synthesis vessel and swollen with DCM (3 mL) followed by DMF (3 mL). To the vessel was then introduced the Fmoc-PEG36-COOH solution (161 mg, 1.0 equiv) in DMF, i-Pr$_2$NEt (6.0 equiv), and PyBOP (4.0 equiv). Argon was bubbled for 6 h, the coupling solution was drained, and the resin was washed with DMF (3×10 mL) and i-PrOH (3×10 mL). Kaiser tests were performed to assess reaction progress. Fmoc deprotection was carried out using 20% piperidine in DMF (3×10 mL), before each amino acid coupling. The above sequence was repeated to complete reaction with 2× Fmoc-PEG36-COOH (161 mg, 1.0 equiv), Fmoc-Glu-OtBu (72 mg, 2.0 equiv) and Tfa.Pteroic-acid (41.0 mg, 1.2 equiv) coupling steps. At the end the resin was washed with 2% hydrazine in DMF 3×10 mL (5 min) to cleave the trifluoro-acetyl protecting group on pteroic acid and washed with i-PrOH (3×10 mL) followed by DMF (3×10 mL). The resin was dried under argon for 30 min. Folate-peptide was cleaved from the resin using the Cleavage Solution. 10 mL of the cleavage mixture was introduced and argon was bubbled for 1.5 h. The cleavage mixture was drained into a clean flask. The resin was washed 3× with more Cleavage Solution. The combined mixture was concentrated under reduced pressure to a smaller volume (~5 mL) and precipitated in ethyl ether.

The precipitate was collected by centrifugation, washed with ethyl ether (3×) and dried under high vacuum. The dried Folate-PEG$_{108}$-EDA (1.0 equiv) was treated with FITC (50 mg, 1.5 equiv) in DMSO and DIPEA at room temperature. Reaction progress was monitored by LCMS.

After 10 h starting material was consumed to give the product. The crude reaction mixture was purified by preparative HPLC, (mobile phase A=10 mM Ammonium Acetate, pH=7; Organic phase B=Acetonitrile; Method: 0% B to 30% B in 35 minutes at 13 mL/min) and provided FITC-PEG108-Folate in 64% yield.

Example 8

Synthesis of FITC-DUPA

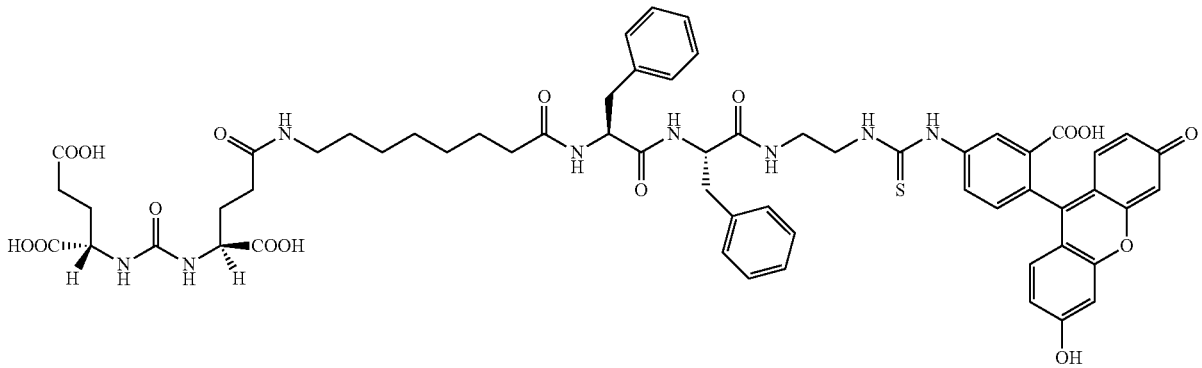 [SMILES: O=C(O)CC[C@H](NC(=O)N[C@@H](CCC(=O)NCCCCCCCC(=O)N[C@@H](Cc1ccccc1)C(=O)N[C@@H](Cc1ccccc1)C(=O)NCCNC(=S)Nc1ccc(-c2c3ccc(=O)cc-3oc3cc(O)ccc23)c(C(=O)O)c1)C(=O)O)C(=O)O]

DUPA-FITC was synthesized by solid phase methodology as follows. Universal Nova Tag™ resin (50 mg, 0.53 mM) was swollen with DCM (3 mL) followed by DMF 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)—OH (1.5 equiv), HATU (2.5 equiv), and i-Pr$_2$NEt (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/TFE (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and the resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. The final compound was cleaved from the resin using the Cleavage Solution and concentrated under vacuum. The concentrated product was precipitated in diethyl ether and dried under vacuum. The crude product was purified using preparative RP-HPLC [λ=488 nm; solvent gradient: 1% B to 80% B in 25 min, 80% B wash 30 min run; A=10 mM NH$_4$OAc, pH=7; B=acetonitrile (ACN)]. ACN was removed under vacuum, and purified fractions were freeze-dried to yield FITC-DUPA as a brownish-orange solid. RP-HPLC: tR=8.0 min (A=10 mM NH$_4$OAc, pH=7.0; B=ACN, solvent gradient: 1% B to 50% B in 10 min, 80% B wash 15 min run). 1H NMR (DMSO-d6/D$_2$O): δ 0.98-1.27 (ms, 9H); 1.45 (b, 3H); 1.68-1.85 (ms, 11H); $^1$H NMR (DMSO-d6/D$_2$O): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H), 6.61 (dd, J=5.3, 3.5 Hz, 2H); 6.64 (s, 2H); 7.05 (d, J=8.2 Hz, 2H), 7.19 (m, 5H); 7.76 (d, J=8.0 Hz, 1H); 8.38 (s, 1H). HRMS (ESI) (m/z): (M+H)+ calcd for $C_{51}H_{59}N_7O_{15}S$, 1040.3712, found, 1040.3702. UV/vis: λ max=491 nm.

Example 9

Synthesis of FITC-PEG12-DUPA introduced a solution of Fmoc-NH-(PEG)12-COOH (42.8 mg) in DMF, i-Pr$_2$NEt (2.5 equiv), and PyBOP (2.5 equiv). The resulting solution was bubbled with Ar for 1 h, the coupling solution was drained, and the resin washed with DMF (3×10 mL) and i-PrOH (3×10 mL). Kaiser tests were performed to assess reaction progress. Fmoc deprotection was carried out using 20% piperidine in DMF (3×10 mL). This procedure was repeated to complete the all coupling steps (2×1.5 equiv of Fmoc-Phe-OH and 1.5 equiv of 8-aminooctanoic acid and 1.2 equiv of DUPA were used on each of their respective coupling steps). After the DUPA coupling, the resin was washed with DMF (3×10 mL) and i-PrOH (3×10 mL) and dried under reduced pressure. The peptide was cleaved from the resin in the peptide synthesis vessel using the Cleavage Solution. 15 mL of the Cleavage Solution was added to the peptide synthesis vessel, and the reaction was bubbled under Ar for 15 min. The resin was treated with two additional 10 mL quantities of the Cleavage Solution for 5 min each. The cleavage mixture was concentrated to about 5 mL and precipitated with ethyl ether. The precipitate was collected by centrifugation, washed with ethyl ether (3×), and dried under high vacuum, resulting in the recovery of crude material. To a stirred solution of the crude DUPA-(PEG)12-EDA (10 mg) and FITC (5.6 mg) in dimethylsulfoxide (DMSO, 1 mL) was added i-Pr$_2$NEt (5 equiv) at room temperature and stirred for 6 h under argon. The reaction was monitored by LCMS and purified by preparative HPLC (mobile phase: A=10 mM ammonium

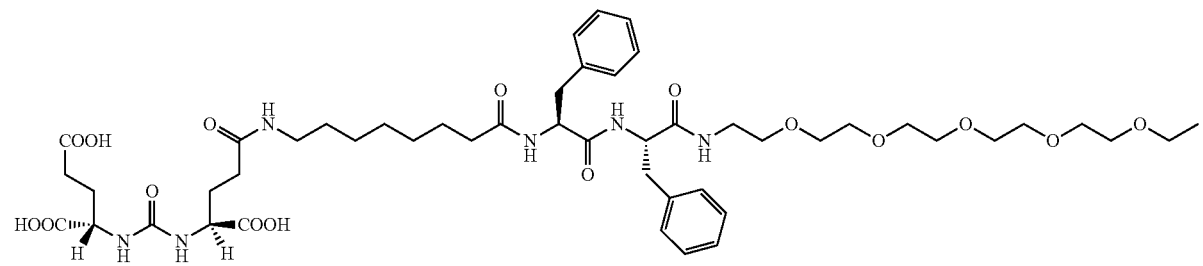

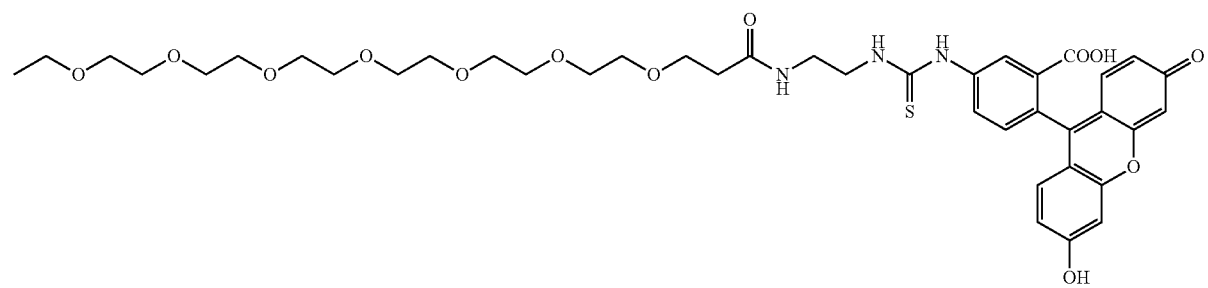

1,2-Diaminoethane trityl-resin (0.025 g) was loaded into a peptide synthesis vessel and washed with i-PrOH (3×10 mL), followed by DMF (3×10 mL). To the vessel was then acetate pH=7, B=ACN; method: 0% B to 50% B in 30 min at 13 mL/min). The purified fractions were pooled and freeze-dried, providing the FITCPEG12-DUPA.

Example 10

Synthesis of FITC-PEG11-NK1

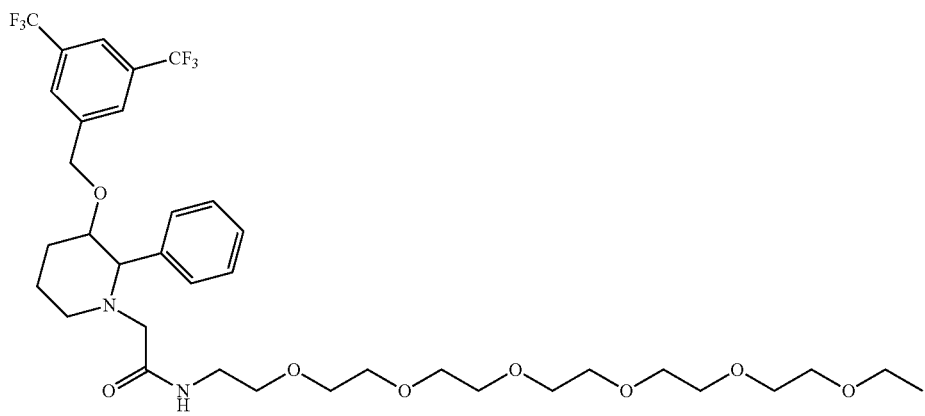

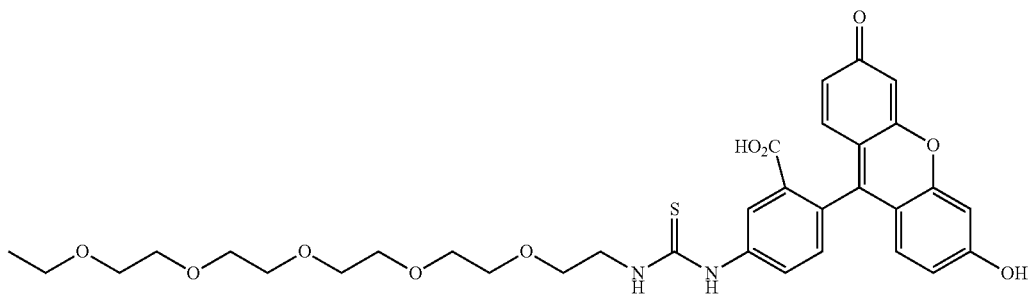

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG$_{11}$-NH$_2$) (Sigma, 0.0336 g, 0.0521 mmol, 1.2 eq.), Benzotriazol-1-yl-oxytripyrrolidinophosphonium hexafluorophosphate (PyBOP) (0.027 g, 0.0521 mmol, 1.2 eq.) in dry CHCl$_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, =220 nm, 254 nm). The pure fractions were collected, all organic solvents were evaporated and the sample was lyophilized for 48 h to provide the NK1-PEG$_{11}$-NHBoc. Yield: 40.13 mg (97%). To the NK1-PEG$_{11}$-NHBoc (0.0165 g, 0.015 mmol) in dry DCM was added trifluoroacetic acid (TFA, 20 eq.) and the reaction mixture was stirred for 4 h at r.t. The excess TFA was removed, and the remaining solution was diluted with water and extracted using CH$_2$Cl$_2$ (3×5 mL). The combined organic layers were washed with brine, dried (Na$_2$SO$_4$) and concentrated. The residue obtained was dried under vacuum and used for the next-step without further purification. A stirred solution of NK1-PEG$_{11}$-NH$_2$ (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added to diisopropylethyl amine (0.0028 mL, 0.0162 mmol, 2.0 eq.) at room temperature under argon. The reaction progress was monitored by LCMS and the product was purified by preparative RPHPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, =280 nm). The pure fractions were collected, all organic solvents were evaporated and the sample was lyophilized for 48 h to provide the FITC-PEG11-NK1 in a yield of 8.54 mg (77%).

*Note: The NK-1 compound was synthesized by a two-step procedure starting from the base ligand, which was prepared by using a procedure in the literature. (Ref: DESIGN AND DEVELOPMENT OF NEUROKININ-1 RECEPTOR-BINDING AGENT DELIVERY CONJUGATES, Application Number: PCT/US2015/44229; incorporated herein by reference.

Example 11

Synthesis of FITC-PEG2-CA9

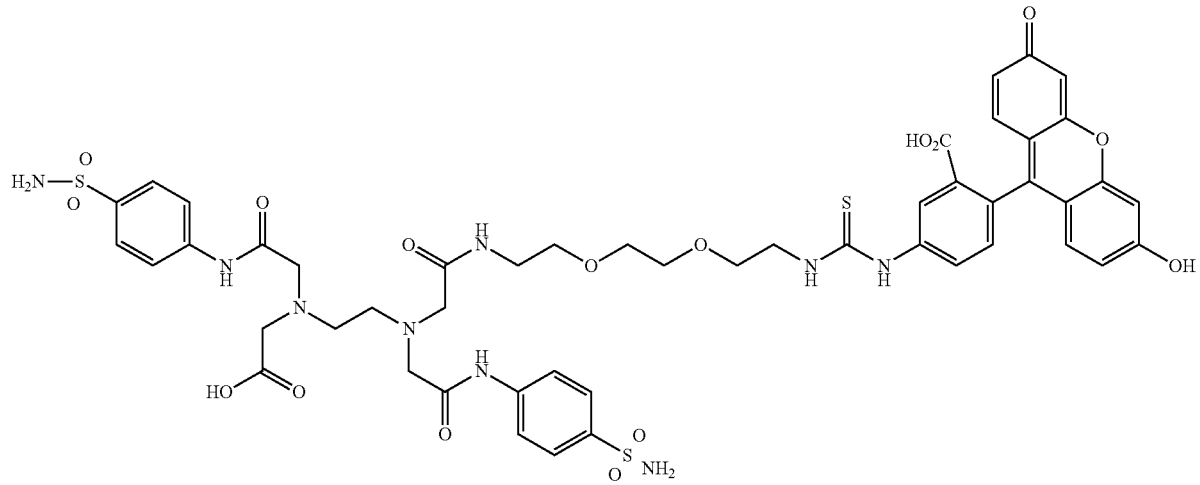

CA9 ligand (53.6 mg) was dissolved in DMF (2-3 mL) in a 50 mL round bottom flask using a Teflon magnetic stir bar. Ambient air was removed using a vacuum and replaced with nitrogen gas, this was done in three cycles. The round bottom flask was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 μL of Boc-PEG2-NH$_2$ (Sigma Aldrich). 5.4 μL of triethylamine (TEA) was added and the reaction was stirred overnight. The reaction mixture was purified using HPLC and confirmed with UHPLC-MS (target m/z of 831). Acetonitrile was removed using high vacuum rotary evaporation and the product lyopholized. The compound was mixed with 1:1 TFA:DCM for 30 minutes. The TFA/DCM was removed using high vacuum rotary evaporation followed by 30 minutes on high vacuum. The compound was then dissolved in DMF and combined with 5 molar equivalents of i-Pr$_2$NEt, 16 mg of fluorescein isothiocyanate (Life Technologies) and stirred for 1 h. The reaction mixture was purified by HPLC and the target compound was confirmed with UHPLC-MS (target m/z of 1120). The samples were lyophilized and stored at −20° C.

Example 12

FITC-DUPA

DUPA-FITC was synthesized by solid phase methodology as follows. Universal NovaTag resin (50 mg, 0.53 mM) was swollen with dichloromethane (DCM) (3 mL) followed by dimethylformamide (DMF, 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). After swelling the resin in DMF, a solution of DUPA-(OtBu)—OH (1.5 equiv), HATU (2.5 equiv) and DIPEA (4.0 equiv) in DMF was added. Argon was bubbled for 2 h, and resin was washed with DMF (3×3 mL) and i-PrOH (3×3 mL). After swelling the resin in DCM, a solution of 1 M HOBt in DCM/trifluoroethane (TFE) (1:1) (2×3 mL) was added. Argon was bubbled for 1 h, the solvent was removed and resin was washed with DMF (3×3 mL) and i-PrOH (3×3 mL). After swelling the resin in DMF, a solution of Fmoc-Phe-OH (2.5 equiv), HATU (2.5 equiv) and DIPEA (4.0 equiv) in DMF was added. Argon was bubbled for 2 h, and resin was washed with DMF (3×3 mL) and i-PrOH (3×3 mL). The above sequence was repeated for 2 more coupling steps for addition of 8-aminooctanoic acid and fluorescein isothiocyanate or rhodamine B isothiocyanate. Final compound was cleaved from the resin using a trifluoroacetic acid (TFA):H2O: triisopropylsilane: cocktail (95:2.5:2.5) and concentrated under vacuum. The concentrated product was precipitated in diethyl ether and dried under vacuum. The crude product was purified using preparative RP-HPLC [λ, =488 nm; solvent gradient: 1% B to 80% B in 25 min, 80% B wash 30 min run; A=10 mM NH$_4$OAc, pH=7; B=acetonitrile (ACN)]. ACN was removed under vacuum, and pure fractions were freeze-dried to yield DUPA-FITC as a brownish-orange solid. RP-HPLC: tR=8.0 min (A=10 mM NH$_4$OAc, pH=7.0; B=ACN, solvent gradient: 1% B to 50% B in 10 min, 80% B wash 15 min run). 1H NMR (DMSO-d6/D2O): δ 0.98-1.27 (ms, 9H); 1.45 (b, 3H); 1.68-1.85 (ms, 11H); 2.03 (m, 8H); 2.6-3.44 (ms, 12H); 3.82 (b, 2H); 4.35 (m, 1H); 6.53 (d, J=8.1 Hz, 2H); 6.61 (dd, J=5.3, 3.5 Hz, 2H); 6.64 (s, 2H); 7.05 (d, J=8.2 Hz, 2H); 7.19 (m, 5H); 7.76 (d, J=8.0 Hz, 1H); 8.38 (s, 1H). HRMS (ESI) (m/z): (M+H)+ calcd for C51H59N7O15S, 1040.3712, found, 1040.3702. UV/vis: λ max=491 nm.

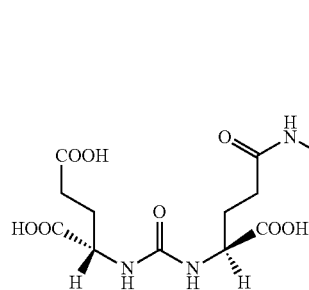
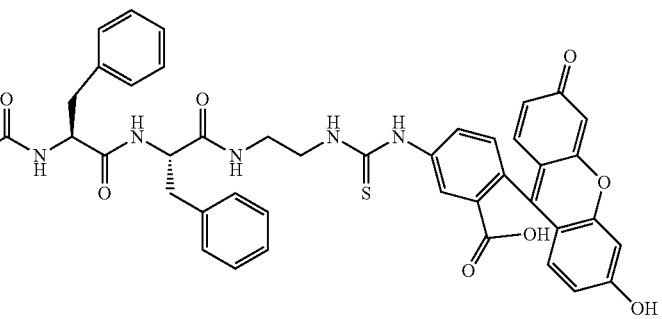

Example 13

FITC-CA9

In a 50 mL round bottom flask CA9 ligand (53.6 mg, synthesized in lab) was dissolved in a desired amount of N,N-Dimethylformamide (DMF) (2-3 mL) using a Teflon magnetic stir bar. Ambient air was removed using vacuum and replaced with nitrogen gas, this was done in three cycles. Then the round bottom was kept under constant nitrogen gas. To the flask, 28.9 mg of N-(3-Dimethylaminopropyl)-N'-ethylcarbodiimide hydrochloride (EDC) was added followed by 21.6 mg 1-Hydroxybenzotriazole hydrate (HOBt) and 18.9 µL of Boc-PEG2-NH2 (purchased from Sigma Aldrich). 5.4 µL of triethylamine (TEA) was added last and the reaction was allowed to stir overnight. The reaction mixture was purified using HPLC and confirm with UHPLC-MS (target m/z of 831). Acetonitrile was removed using high vacuum rotary evaporation and place on lyophilizer for 48 hours. Deprotection of Boc was done with with 1:1 TFA:DCM for 30 minutes. TFA/DCM was removed using high vacuum rotary evaporation followed by 30 minutes on high vacuum. The compound was then dissolved in DMF and combined with 5 molar equivalents of N,N-Diisopropylethylamine (DIPEA). 16 mg of fluorescein isothiocyanate (purchased from Life Technologies) was added to the solution and OH stirred for 1 hour. Reaction mixture was purified by HPLC and target compound was confirmed with UHPLC-MS (target m/z of 1120). The samples was placed on lyophilizer for 48 hours and store compound at −20° C.

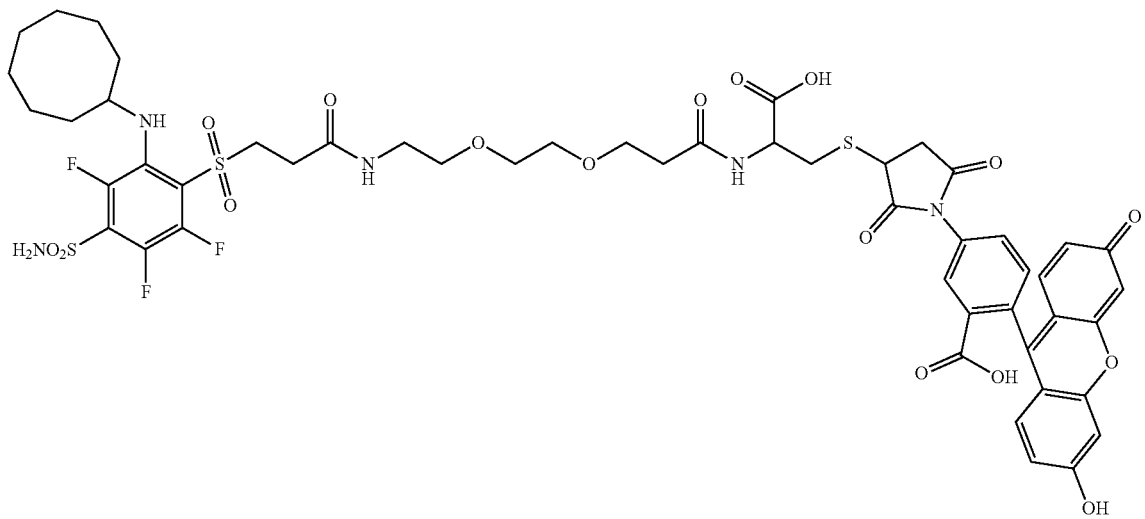 [SMILES: NS(=O)(=O)c1c(F)c(F)c(S(=O)(=O)CCC(=O)NCCOCCOCCC(=O)NC(CSC2CC(=O)N(c3ccc(-c4c5ccc(=O)cc-5oc5cc(O)ccc45)c(C(=O)O)c3)C2=O)C(=O)O)c(NC2CCCCCCC2)c1F]

Example 14

FITC-NK1R

To a stirred solution of NK-1 (0.02 g, 0.0433 mmol, 1.0 eq.), O-(2-Aminoethyl)-O'-[2-(Boc-amino)ethyl]decaethylene glycol (BocNH-PEG11-NH2) (Sigma, 0.0336 g, 0.0521 mmol, 1.2 eq.), Benzotriazol-1-yl-oxytripyrrolidinophosphonium hexafluorophosphate (PYBOP) (0.027 g, 0.0521 mmol, 1.2 eq.) in dry CH$_2$Cl$_2$ was added N,N-Diisopropylethylamine (DIPEA) (0.076 mL, 0.4338 mmol, 10 eq.) under argon at room temperature. The reaction progress was monitored by LCMS and purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, =220 nm, 254 nm). The pure fractions were collected, evaporated all organic solvents and lyophilized the sample for 48 h to furnish the NK1-PEG11-NHBoc. Yield: 40.13 mg (97%). To the NK1-PEG11-NHBoc (0.0165 g, 0.015 mmol) in dry $CH_2Cl_2$ was added trifluoroacetic acid (TFA, 20 eq.) and reaction mixture was stirred for 4 h at r.t. The excess of TFA was removed, diluted with water and extracted using $CH_2Cl_2$ (3×5 mL). The combined organic layers were washed with brine, dried (Na2SO4) and concentrated. The residue obtained was dried under vacuum and used for next-step without OH further purification. A stirred solution of NK1-PEG11-NH2 (0.008 g, 0.0081 mmol, 1.0 eq.), Fluorescein isothiocyanate (FITC) (Sigma, 0.0037 g, 0.0097 mmol, 1.2 eq.) in dry dimethylsulfoxide (DMSO, 0.3 mL) was added diisopropylethyl amine (0.0028 mL, 0.0162 mmol, 2.0 eq.) at room temperature under argon. The reaction progress was monitored by LCMS and purified by preparative RP-HPLC (Waters, XBridge™ Prep C18, 5 µm; 19×100 mm column, mobile phase A=20 mM ammonium acetate buffer, pH 7, B=acetonitrile, gradient 10-100% B in 30 min, 13 mL/min, =280 nm). The pure fractions were collected, evaporated all organic solvents and lyophilized the sample for 48 h to furnish the NK1-PEG11-FITC (5). Yield: 8.54 mg (77%).

The NK-1 compound was synthesized by a two-step procedure starting from base ligand, which was prepared by using a literature procedure. (Ref: DESIGN AND DEVELOPMENT OF NEUROKININ-1 RECEPTOR-BINDING AGENT DELIVERY CONJUGATES, Application Number: PCT/US2015/44229, incorporated herein by reference in its entirety).

Example 15

In Vitro Co-Culture E2 CAR T Activation and Target Cell Kill Assay

E2 CAR T cells were thawed and recovered from cryopreservation at a cell density between 0.5 million to 2 million T cells per milliliter of T cell growth media (TexMACS media+2% human AB serum+50 U/mL recombinant human IL2) for 4 days. Target cells which express different levels of surface folate receptor were also thawed and recovered from cryopreservation in growth media (folate deficient RPMI1640+10% FCS+ pen/strep for 4 days).

On day −1, 100,000 target cells were plated in 2 ml of growth media per well of a 12-well tissue culture plate to allow target cells to adhere and recover. On day 0, wells which received EC17 bridge molecule were treated with EC17 at 100 nM for 30 min in the tissue culture incubator. Afterwards, all media was washed off and replaced with fresh growth media free of folate and EC17. During the EC17 incubation, T cells were harvested, counted and after EC17 treatment was completed, 100,000 E2 CAR T cells were directly added onto each well of target cells in a total of 3 ml of growth media at a ratio of 1:1 (E:T) and incubated for both 1 and 2 days under standard tissue culture humidified conditions of 37° C. at 5% CO2. One day co-culture conditions were used to assay E2 CAR T cell activation by target cells and two-day incubation was used to assay target cell death.

To determine the E2 CAR T cell activity level after one day coculture with target cells possessing different levels of surface folate receptor, floating cells were harvested and pooled with the remaining adherent cells which were removed using a 5-minute 0.25% trypsin digest from the tissue culture plate. Pooled floating and adherent cells were pelleted with a 400×gravity centrifugation step for 5 minutes then resuspended in flow cytometry staining solution. Surface marker staining for E2 T cell identification via flow cytometry included anti-human EGFR and anti-human CD3 while detection of CAR T cell activation via flow cytometry utilized an anti-human CD137 stain. E2 CART cells were identified as EGFR+CD3+ while activated CAR T cells also co-expressed CD137 (see flow cytometry methods).

To determine the efficiency of E2 CAR T cell killing of target cells with different levels of surface folate receptor expression after a two day coculture, pooled and adherent cells were pelleted in the same manner as the one day coculture assay above then stained for E2 CAR T markers EGFR and CD3 then washed and stained for the apoptosis marker, Annexin V, by resuspending the flow antibody stained samples with Alexa Fluor 647 conjugated recombinant Annexin V (Invitrogen cat #A23204 at 1:50 dilution in 1× Annexin staining buffer provided) with 3 µM propidium iodide.

E2 CAR T Cell Activation is Dependent on EC17 Staining of Target Cells

Figure 39:
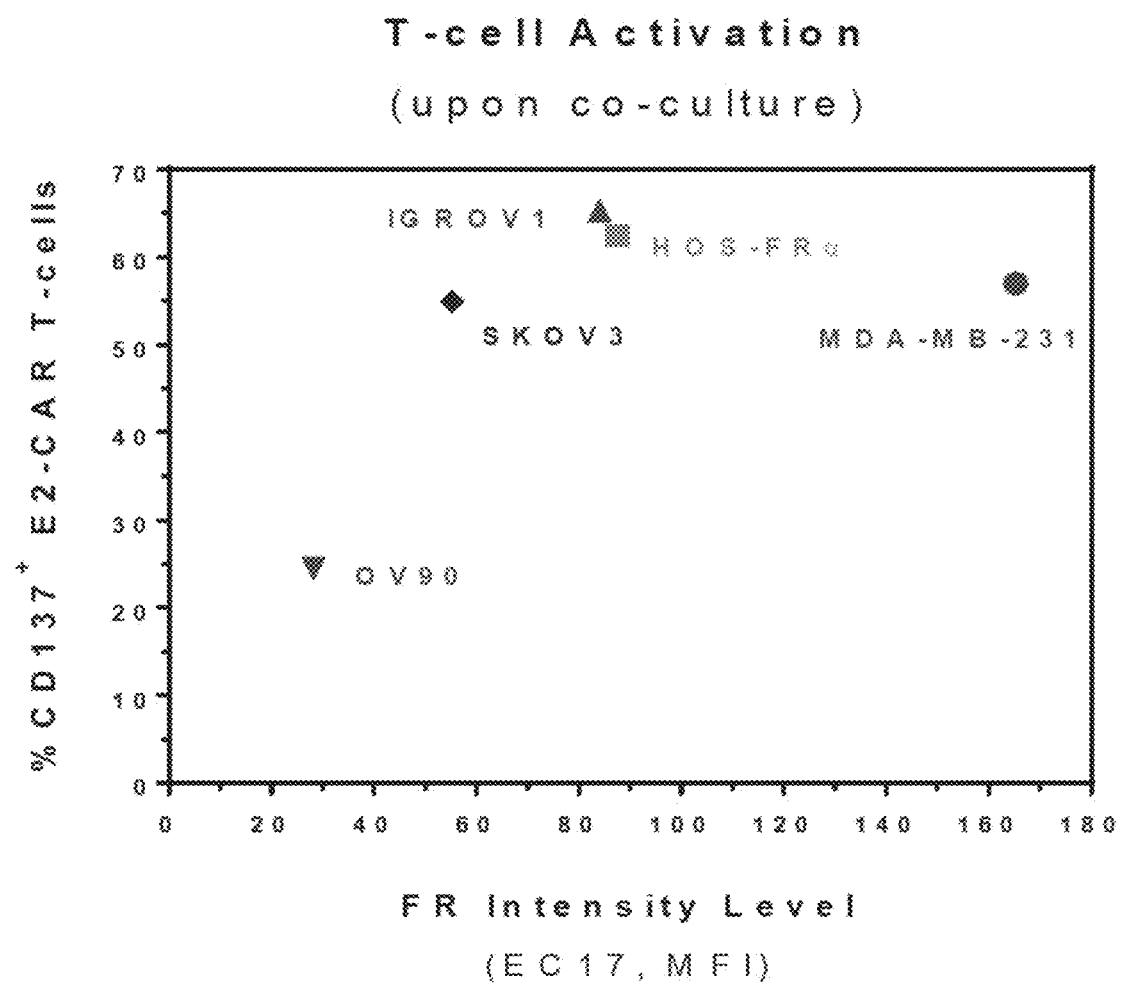
FIG. 39 is a chart showing T-cell activation in one day cocultures with various target cells. The percentage of E2 CAR T cells which are activated after the one-day coculture (y-axis) is graphed against FR expression level of the target cells at the time of the assay (x-axis). (▼) OV90 cells; (♦) SKOV3 cells; (▲) IGROV1 cells; (■) HOS-Frαcells; (●) MDA-MB-231 cells.

In an effort to understand the levels of folate receptor necessary to activate E2 CAR T cells, one day cocultures with target cells expressing surface folate receptor (FR) at varying levels was performed (FIG. 39). The percentage of E2 CAR T cells which are activated after the one-day coculture is graphed on the y-axis, while the FR expression level of the target cells at the time of the assay is graphed on the x-axis. Importantly the FR expression level data was acquired on the same day the assay was performed using the same target cells which were treated with EC17 but cultured without CAR T cells to avoid any artifacts of FR high expressing cells being culled by the CAR T cells. Four out of five target cell lines which express a wide range of folate receptor activated the CAR T cells to similar levels. Interestingly the low FR expressing cell line, OV90 (down triangle), expresses about 50% of the FR as the SKOV3 cells (diamond) and activates about 50% of the CAR T cells as the SKOV3 cells do. These data show that a wide range of EC17 will activate the E2 CAR T cells to similar levels suggesting there is a certain threshold of EC17 bound to the target cell is required to get the full activation of the E2 CAR T cells. Additionally, it is also suggested that there is a threshold of FR expression that will give a suboptimal E2 CAR T response.

E2 CAR T Cell Target Cell Killing

Figure 40:
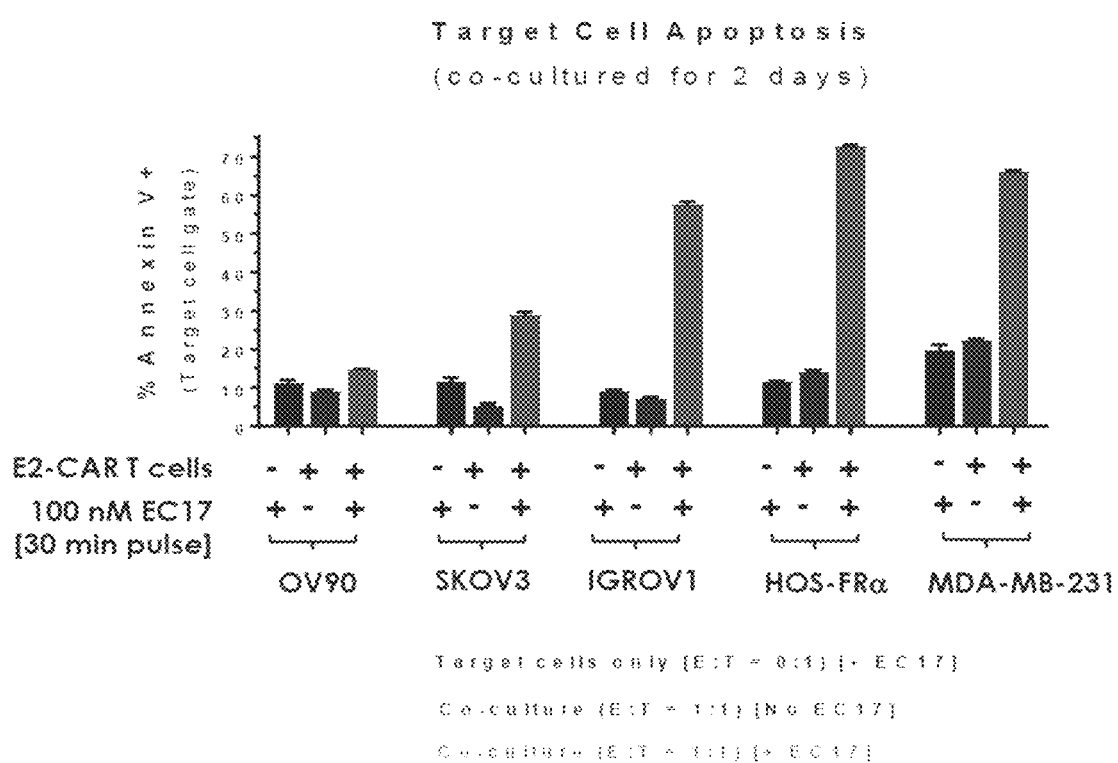
FIG. 40 is a graph showing target cell apoptosis in 2 day coculture with the 5 different cell types (OV90 cells; SKOV3 cells; IGROV1 cells; HOS-Frαcells; MDA-MB-231 cells) under three different conditions. For each cell type the conditions are as follows: Left bar target cells alone +EC17; Middle bar CART plus target cell cocultures without EC17 pretreatment; Right bar CAR T plus treated target cells with EC17 pre-treatment.

To confirm that E2 CAR T cell activation also translates to successful killing of the target cells we performed a two-day co-culture assay then looked at target cell (EGFR-CD3-) events via flow cytometry and determined the percentage of target cell staining with the apoptotic surface marker, Annexin V stain. In FIG. 40, the same five target cells as shown (as labeled on x-axis), each cultured for two days under three different conditions, shown as three different bars. The first bar in each group represents the basal level of target cell apoptosis as these were target cells treated with EC17 but cultured in the absence of E2 CAR T cells. The second bar in each group represents CAR T plus target cell cocultures without any previous EC17 treatment of target cells while the third bar in each group represents the CAR T plus EC17 pre-treated target cells. The y-axis shows the percentage of target cells which are apoptotic (Annexin V+). From these data it was discovered that CAR T cell activation translates well into target cell killing for the three highest folate receptor expressers (MDAMB231, HOS-FRα and IGROV1). However, for the SKOV3 cells which had the fourth lowest FR expression (FIG. 39, x-axis), similar E2 CAR T activation did not translate to similar target cell kill (FIG. 40). It is possible that this disconnect between CAR T cell activation and target cell apoptosis in SKOV 3 cells may not be a function of the low folate receptor expression. As previously stated each cancer cell may have evolved its own anti-apoptotic mechanism and it is possible that FR expression levels like that of SKOV3 cells but in a different cancer cell line, may be enough for a higher level of target cell apoptosis.

Taken together, the data from FIG. 39 and FIG. 40 demonstrate that EC17 binding to cancer cells is required for cell kill. These data further suggest that below a certain threshold of target cell bound EC17 a linear relationship between surface bound EC17 and E2 CAR T activation and killing exists.

Example 16

3H-Folic Acid Binding Assay

All tumor cell lines were seeded overnight in folate-free RPMI medium containing 10% heat-inactivated fetal calf serum. On the following day, the cells were incubated for 15 min on ice with 100 nM $^3$H-folic acid with and without 10 µM cold folic acid. After rising 3 times with cold 1×PBS, whole cells were lysed and total cell-associated radioactivity was counted in a scintillation counter. FR-specific binding of 3H-folic acid were determined by subtracting the counts of folic acid competed samples and calculated as number of molecules per cell using the specific activity of $^3$H-folic acid.

Figure 41:
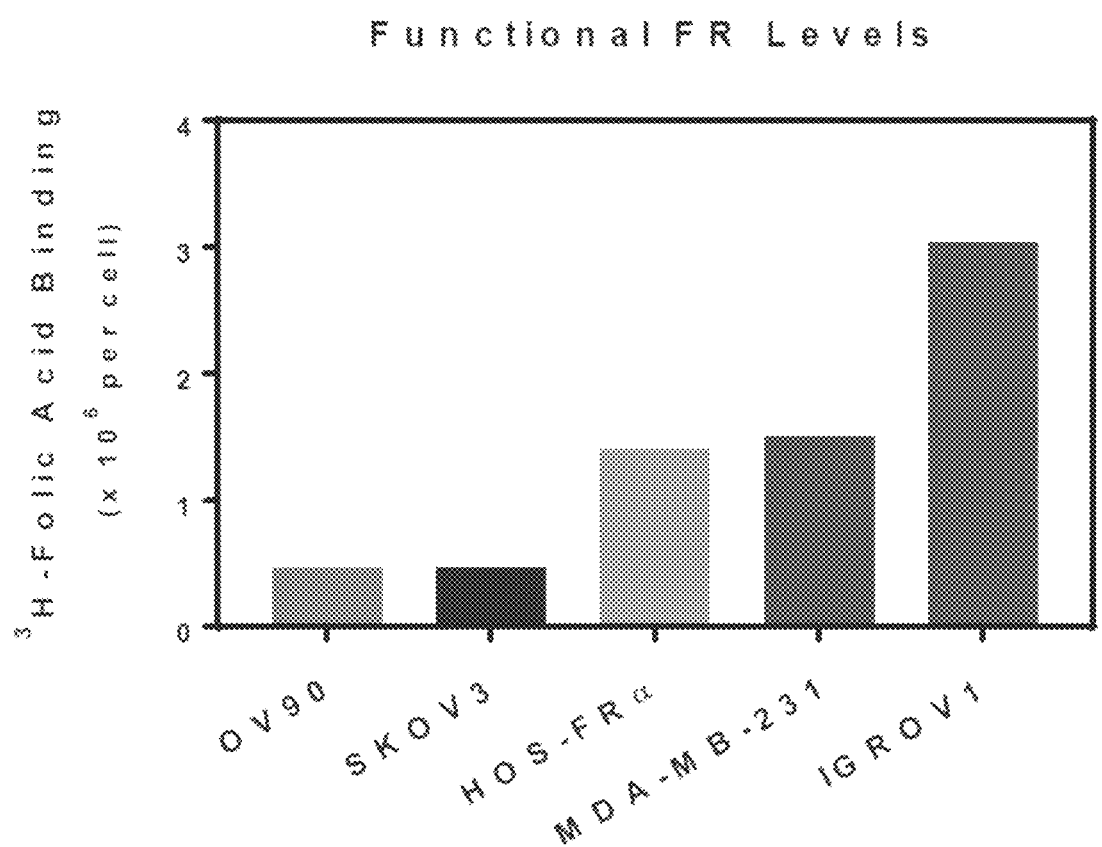
FIG. 41 is a chart showing functional folate receptor expression levels in 5 different cell types (OV90 cells; SKOV3 cells; IGROV1 cells; HOS-Frαcells; MDA-MB-231 cells).

FIG. 41 demonstrates various levels of FR expression in these cell lines. The order of FR levels are: IGROV1>MDA-MB-231, HOS-FRα>OV90, SKOV3.

Example 17

EC17/E2-CAR T-Cell Therapy in NSG Mice with and without Subcutaneously Implanted MDAMB-231-Tumors Tumor Implantation MDA-MB-231 tumor cells were grown in folate-deficient RPMI 1640 with 5-10% FBS at 37° C. in a 5% CO2 humidified atmosphere. MDA-MB-231 tumor cells were inoculated subcutaneously at 2.5×106 cells per animal. Only 42 out of the 66 mice were inoculated and the remaining 22 mice were kept tumor-free.

CAR-T Cell Administration

EGFRt-sorted anti-FITC E2 scFv-CAR T cells were frozen in a T-cell freezing medium. Vials of frozen CAR-T cells were immediately stored at −80° C. The CAR-T cells were quickly thawed at 37° C., washed twice with PBS, and used for animal injection at 10 million viable EGFRt+E2 CAR-T cells (CD4/CD8 at ~1:1) per animal. A small aliquot was taken on the day infusion for flow cytometric analysis of E2-CAR T-cell phenotypes.

Human/Mouse Cytokine Analyses

Mouse blood samples were processed for plasma and stored at −20° C. until use. A human TH1 cytokine panel (Biolegend, Cat. No. 740009) and a human hematopoietic stem cell cytokine panel (Biolegend, Cat. No. 740610) was used to detect human cytokines in the mouse blood. A mouse 13-plex inflammatory cytokine panel (Biolengend, No. 740150) was used to detect mouse cytokines. All analyses were performed per the manufacturer's instructions.

Flow Cytometry Analysis

Whole blood cell analysis: Plasma was removed from predetermined volumes of whole EDTA treated blood and RBCs were lysed with RBC lysis solution. The leukocyte pellets were then resuspended in flow cytometry staining solution (1% bovine serum albumin, 50 mg/mL human IgG (Equitech Bio, cat #SLH56-0001), 0.9% sodium azide in a phosphate buffered saline, pH=7.4) and leukocyte surface marker staining was performed using the following antibodies: anti-human CD45 [clone HI30, eBioscience #47-0459-42 at 1:20 (v/v) dilution], anti-human CD137 [clone 4B4-1, BD Bioscience #564092 at 1:20 (v/v) dilution], anti-human CD8a [clone RPA-T8, BD Bioscience, catalog #557746 at 1:20 (v/v) dilution], anti-human CD4 [clone SK3, eBioscience catalog #46-0047-42 at 1:20 (v/v) dilution], anti-human EGFR [R&D systems, clone Hu1, catalog #FAB9577B @ 1:10 (v/v)], anti-human PD1 [BD Biosciences, clone EH12.1, catalog #562511 @1:20 (v/v)], anti-human LAG3 [BD Biosciences, clone T47-530, catalog #565616 @1:20 (v/v)], anti-human TIM3 [BD Biosciences, clone 7D3, catalog #565558 @1:20 (v/v)], anti-human CD3ε [BD Biosciences, clone SK7, catalog #557832 @1:20 (v/v)]. After leukocyte staining, cells were washed with PBS and resuspended in cold PBS containing 53,000 CountBright™ beads (Invitrogen catalog #C36950) and transferred to flow cytometry collection tubes. Flow cytometry data was collected on the Gallios flow cytometer (Beckman Coulter, Brea, Calif.). Determination of the concentration of CAR T cells in each blood sample was calculated according to Invitrogen's instructions. CAR T cells were identified as human CD3ε+ EGFRt+ events and easily distinguished and counted using the Kaluza™ flow cytometry software. The number of CAR T cells in the circulation of each infused mouse was then represented on the graphs as the total number of CAR T cells per 100 µL of whole blood analyzed. Statistical significance was determined by utilizing an unpaired, two-tailed, students t30 test with significance set at p<0.05.

Tumor and tissue analysis: Solid tumors (100-1000 mm3) were harvested, weighed, and minced into small pieces then transferred into 50 mL tubes containing 20 mL of a tumor digestion cocktail. The enzymatic tumor digestion cocktail consisted of 0.5 mg/mL Collagenase IV (Sigma-Aldrich, Catalog #C5138), 0.5 mg/mL Hyaluronidase (Sigma-Aldrich, Catalog #H3506) and 0.1 mg/mL DNase I (Sigma-Aldrich, Catalog #DN25) in serum-free and folatedeficient RPMI1640 medium supplemented with antibiotics. The tumor fragments were digested for one hour at 37° C. at 300 rpm on a horizontal shaker. Afterwards, the tumor digest was centrifuged at 400×g for 5 minutes and tumor cell pellet underwent a red blood cell lysis step, was then washed with cold phosphate-buffered saline (PBS, pH 7.4) and finally filtered through a 40 µm nylon cell strainer.

E2-CAR-T Phenotypes and Proliferation In-Vivo

Expansion and persistence of CART cells in the blood has been reported to correlate with response to CD19 specific CAR T therapy in clinical studies. It is not unreasonable to presume that a larger pool of circulating blood borne E2 CAR T will allow for a greater response to EC17 directed attack on FR+ tumors in our in vivo models. As a measure of response of E2 CAR T cell therapy to EC17, we quantified the number of circulating E2 CART cells per 100 uL of whole blood and observed cohorts which received EC17 stimulation (cohorts 2, 3, 4 and 5) had at least more than 10-fold increase in circulation when compared to cohorts which did not receive EC17 (cohorts 1 and 6). Importantly this expansion of circulating CAR T cells within the blood is consistent with CAR T cell expansion in an antigen dependent manner. Additionally, we also observed persistence of the elevated numbers of circulating CAR T cells to be as long as 54 days post CAR T cell infusion and again CAR T persistence was dependent on EC17 (cohorts 2, 3, 4 and 5) when compared to cohorts 1 and 6 which did not receive EC17.

Tumor Vs Tumor-Free Mice

Figure 42:
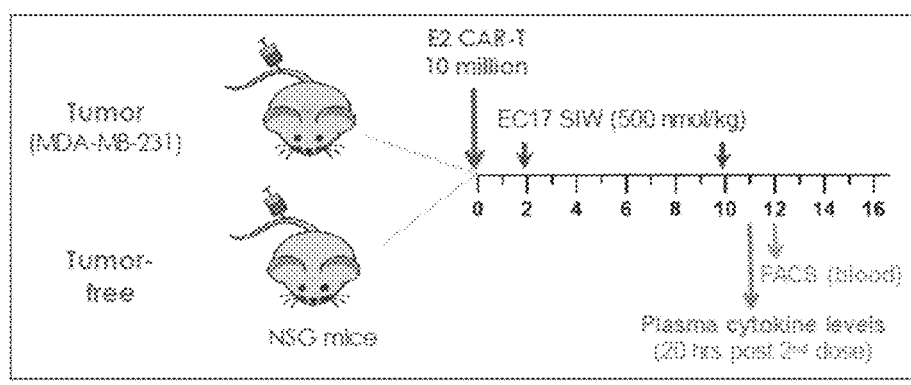
FIG. 42 is a cartoon showing the experimental timeline for tumor bearing and naïve mice.

As shown in FIG. 42, 10 million E2 CAR-T cells were i.v. injected into naïve NSG mice without tumor or NSG mice bearing MDA-MB-231 tumors. 500 nmol/kg EC17 was i.v. dosed on days 2 and 10 post CAR-T injection, and mice were euthanized 20 hours after second EC17 dose (day 11) for organ evaluation and blood analysis. The plasma samples were isolated from blood immediately and stored at −20° C. until cytokine analysis. On Day 12 post CAR-T injection, a separate set of animals were harvested for FACS analysis as described above.

Figure 43:
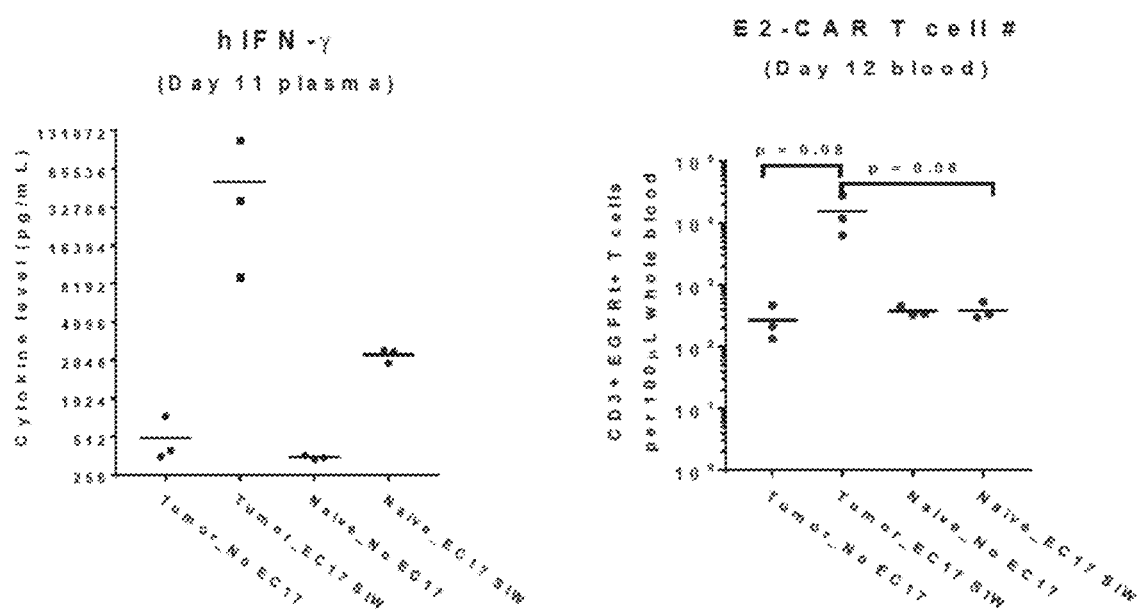
FIG. 43 (left panel) is a chart showing levels of cytokine IFN-γ was EC-17 dependent in both naïve and tumor bearing mice, and that the increase in IFN-γ was much lower in naïve mice compared to mice bearing MDA-MB-231 tumors (23-fold lower).

As shown in FIG. 43, cytokine production in tumor-bearing mice was EC17-dependent. The levels of cytokine including IL2, IFN-γ, IL-10 were all increased in tumor-bearing mice with EC17 relative to those without an EC17 dose. In naïve mice without a tumor, the upregulation of cytokine production was also observed in those mice dosed with EC17, but the increase in tumor-free mice was much lower comparing to those mice with MDA-MB-231 tumors (e.g. 23-fold lower for IFN-g).

Tumor-bearing mice had ~23-fold higher IFN-g production than tumor-free mice. While tumor-free mice (on FD-diet for ~2 months) showed some cytokine production post EC17 SIW500×2 doses, there was no detectable CAR-T cell expansion by FACS.

Example 18

Target-Specific Activity Demonstrated In-Vitro Using Humanized Anti-FITC scFv E2-CAR Construct and CAR-Modified T Cells Cell lines: All cell lines were maintained in RPMI 1640 (Irvine Scientific) supplemented with 2 mM L-glutamine (Cellgro), 25 mM HEPES (Irvine Scientific) and 10% heat-inactivated FBS (Hyclone) unless otherwise noted. Dr. Stanley Riddell (FHCRC) kindly provided the K562 target cell lines. The K562 OKT3 cell line was generated by transduction with an OKT3 transgene containing lentivirus. The OKT3 is a membrane tethered scFv that targets CD3epsilon. The MDA-MB-231 were provided by Endocyte and cultured in folate free DMEM. All cell lines were authenticated by STR Profiling matched to the DSMZ Database by the University of Arizona Genetics Core.

Cytotoxicity and cytokine secretion: Four-hour chromium release assays were performed. Briefly, target cells were labeled with $^{51}Cr$ (PerkinElmer) overnight, washed three times in PBS, and incubated in RPMI in triplicate at 5×103 cells/well with T-cells at various effector to target (E:T) ratios in a 96-well plate. Supernatants were harvested for γ-counting and specific lysis was calculated. For cytokine secretion, 5×10$^5$ T-cells were plated in triplicate with target cells at an E:T ratio of 2:1 in a 96-well plate for 24-hours and supernatants were analyzed by cytometric bead array using a Bio-Plex Human Cytokine Panel (Bio-Rad) according to the manufacturer's instructions. For EC17 labeled targets, the cells were incubated in the dark at room temperature for 1 hr with 100 nM EC17 in PBS prior to plating. When EC17 was used, cells were incubated with folate free RPMI during the assay.

Figure 44:
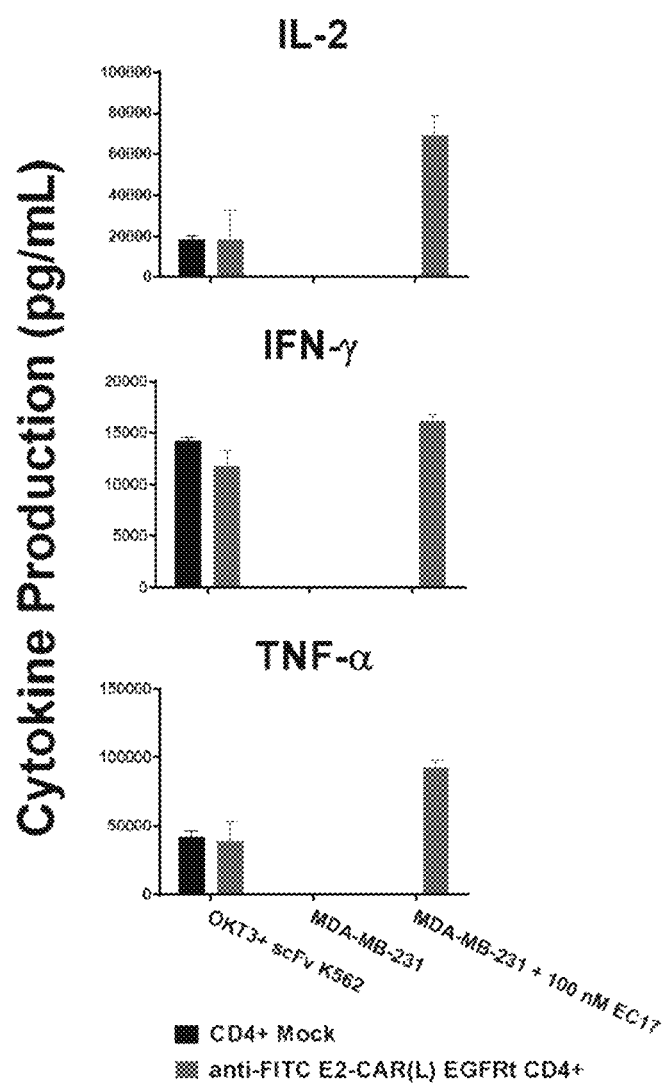
FIG. 44 (top panel) is a chart showing cytokine (IL-2) production from Mock TCells and anti-FLCAR T-cells at quantitatively similar levels in co-culture with the positive control cell line K562-OKT3 (left pair of bars, where Mock is the left bar and anti-FLCAR T20 cells is the right bar); no cytokine was produced by either Mock or anti-FLCAR T-cells upon coculture with K562 (middle); and anti-FLCAR T-cells were the only cells able to elicit secretion of the cytokine IL-2, but only with pretreatment of EC-17 (right, where only anti-FLCAR T-cells show a result).

Cytokine Release Assay:

CD4+ T cells were co-cultured at a 2:1 ratio T-cell to target for 24 hrs and then the supernatant was analyzed for the presence of effector cytokines IL-2, IFN-γ, and TNF-α. Assays were run in triplicate and data shown as mean±SE. As shown in FIG. 44, we observed that Mock and anti-FLCAR T-cells produced quantitatively similar levels of cytokine production in response to co-culture with the positive control cell line K562-OKT3. No cytokine was produced by either Mock or anti-FLCAR T-cells upon co-culture with K562. Cytokine release was dependent upon prior incubation of EC17 with the MDA-MB-231 cell line and the anti-FLCAR T-cells were the only cells able to elicit secretion of the cytokines IL-2, IFN-γ, and TNF-α against EC17 labeled MDA-MB-231.

Figure 45:
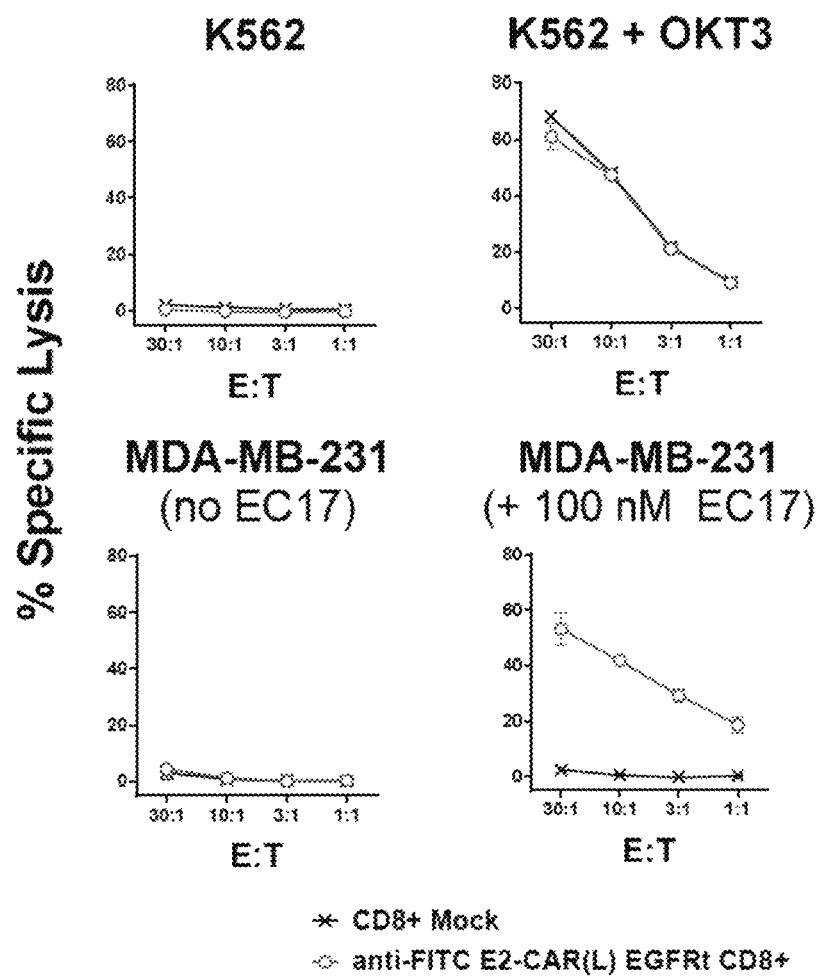
FIG. 45 (upper left) is a chart showing percentage lysis when CD8+ Mock T cells and anti-FLCAR T-cells are co-cultured with negative control K562 cells at a ratio of 30:1, 10:1, 3:1, or 1:1.
Figure 46:
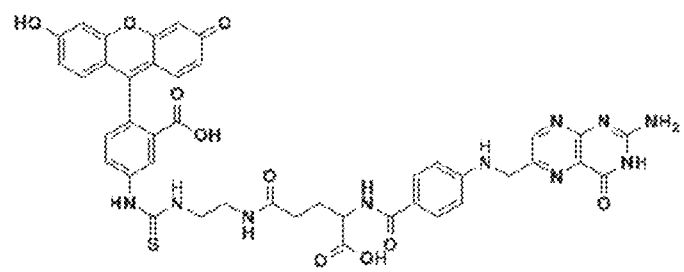
FIG. 46 (bottom) is a chart showing the dose response curve for FITC-folate.
Figure 46:
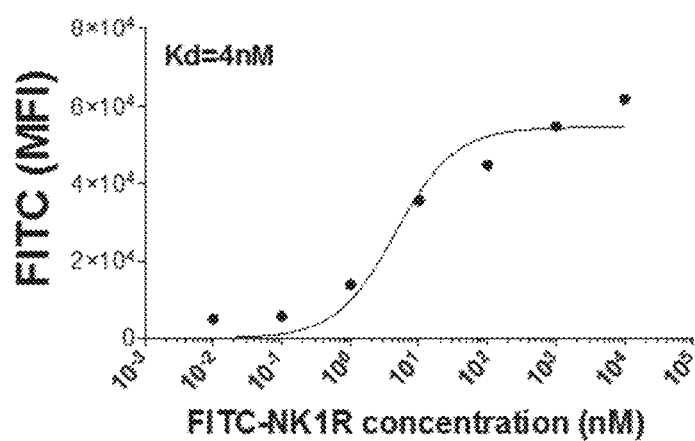
Figure 47:
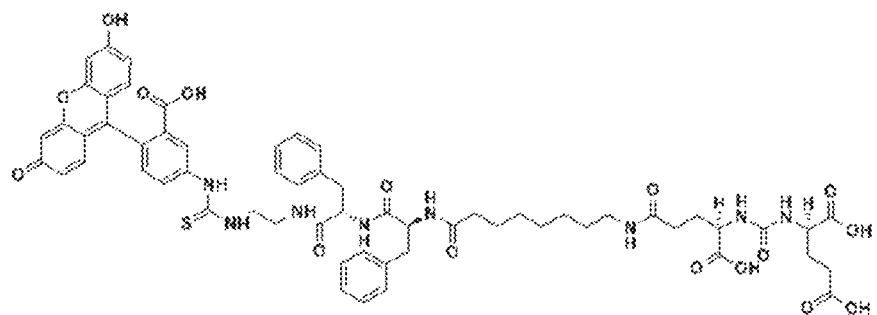
FIG. 47 (bottom) is a chart showing the dose response curve for FITC-DUPA.
Figure 47:
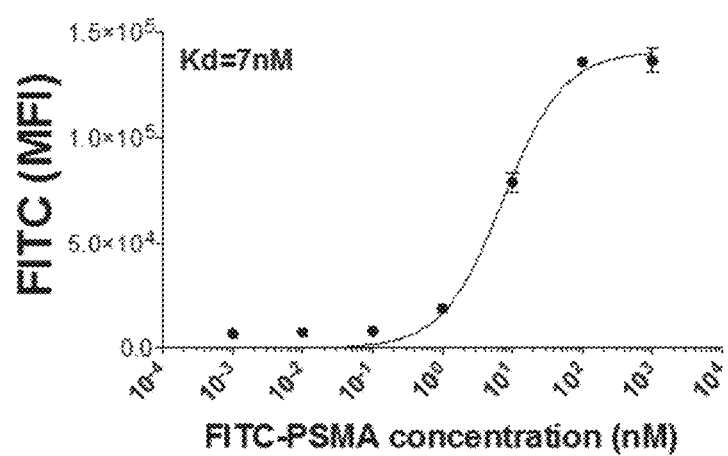
Figure 48:
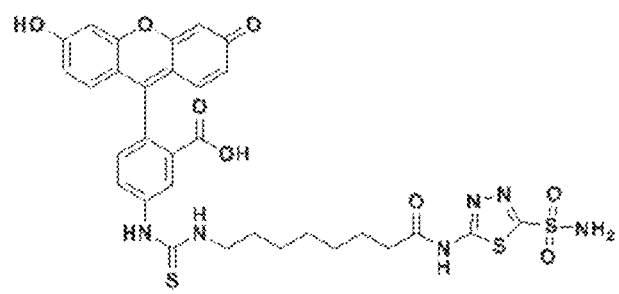
FIG. 48 (bottom) is a chart showing the dose response curve for FITC-CA9.
Figure 48:
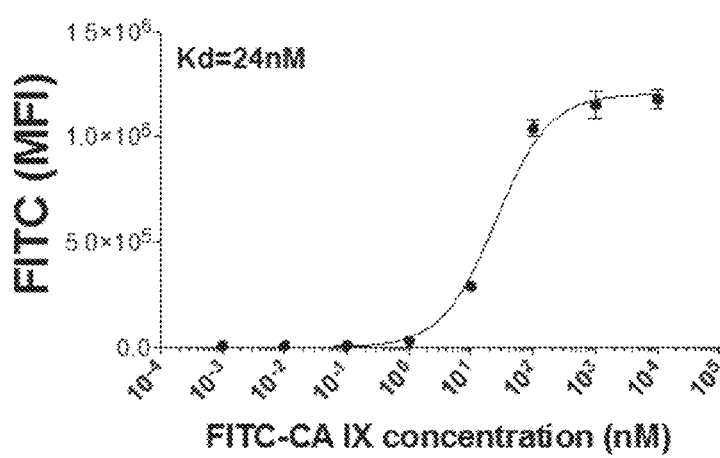
Figure 49:
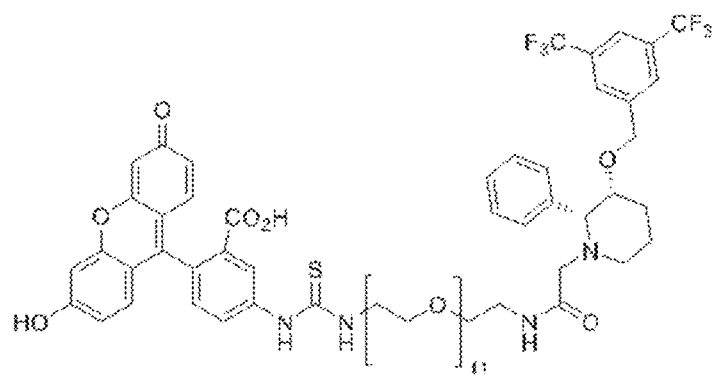
FIG. 49 (bottom) is a chart showing the dose response curve for FITC-NK1R.
Figure 49:
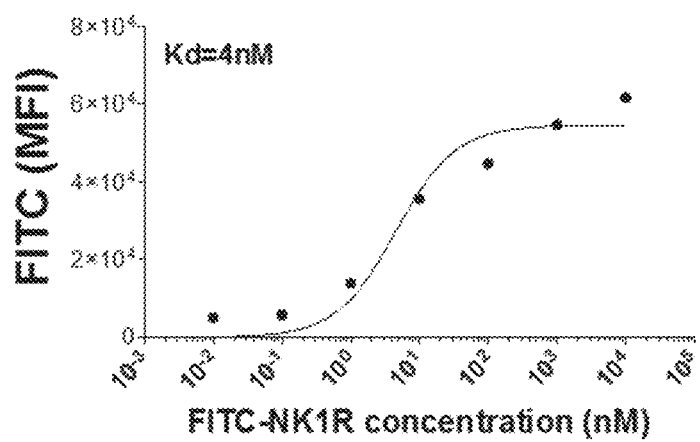

Chromium Release Assay:

CD8+ T cells were co-cultured with target cells at a 30:1, 10:1, 3:1, or 1:1 ratio. Percentage lysis (mean±SE) of triplicate wells is depicted. As shown in FIG. 45, the anti-FLCAR T-cells did not exhibit cytotoxicity against the negative control (K562) or unlabeled MDA-MB-231 cell lines. However, both the mock transduced and anti-FLCAR T-cells were able to induce similar levels of specific lysis against the positive control K562-OKT3 cell line. Furthermore, EC17 labeled MDA-MB-231 cells were efficiently recognized and lysed by anti-FLCAR T-cells whereas the mock T-cells were unable to confer lysis.

Example 19

Structure of Adapters for CAR-T Cells

Figure 50:
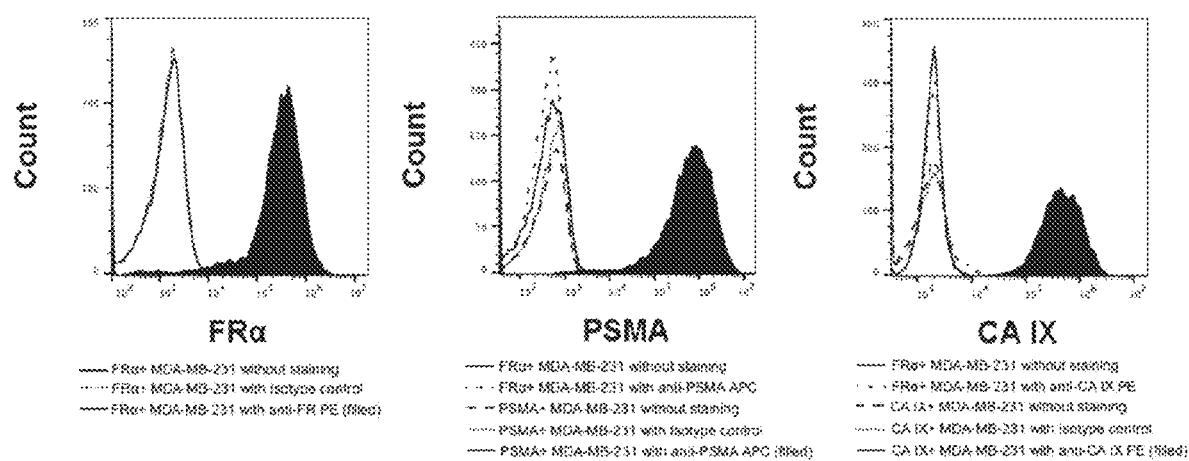
FIG. 50 shows binding (by FACS analysis) of bridges to tumor cells used in an in vivo model and expressing the receptor corresponding to the small molecule ligand of the bridge.
Figure 51:
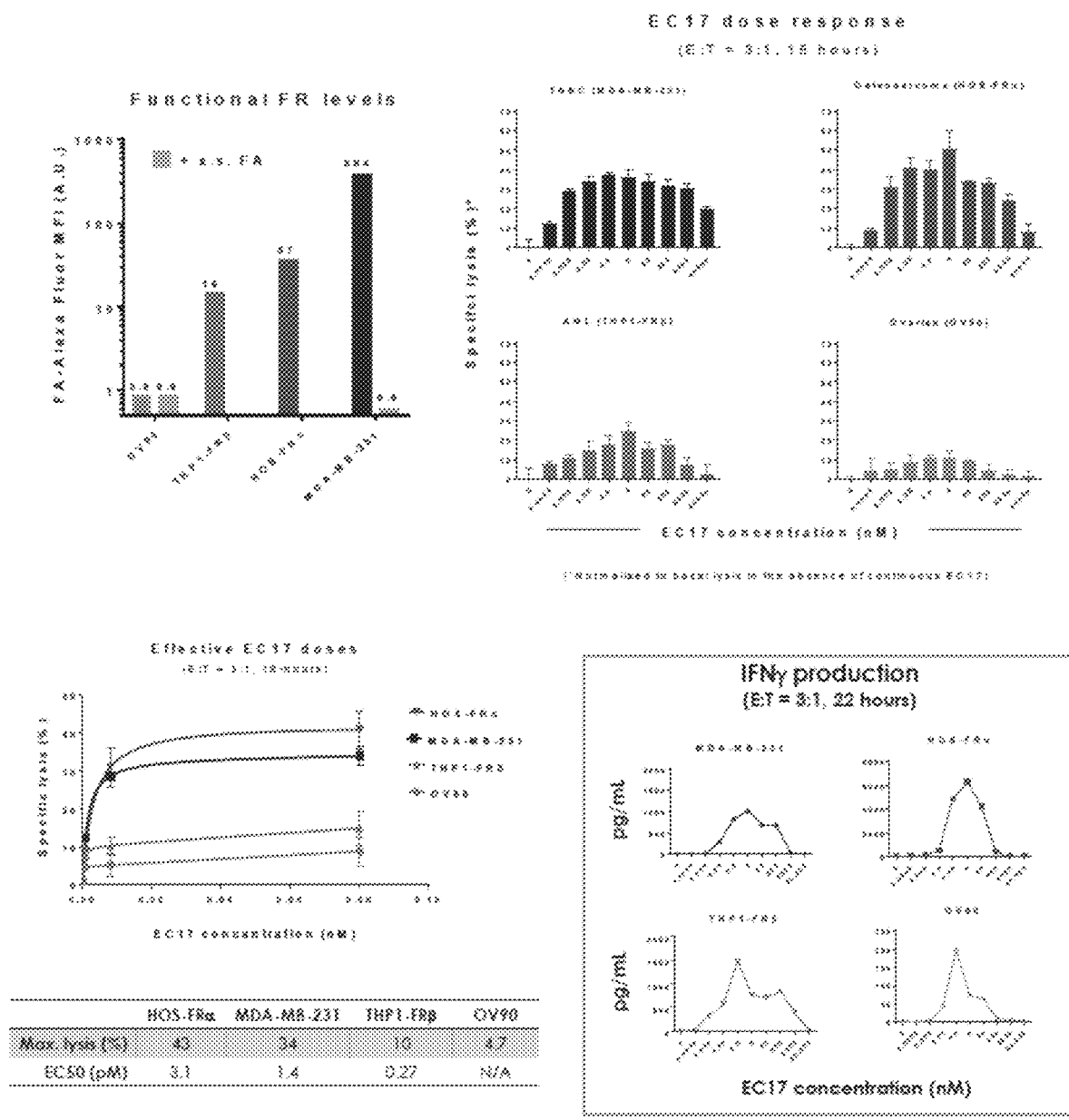
FIG. 51 shows EC17 induction of a potent FR-dependent tumor cell killing by CAR T cells.
Figure 52:
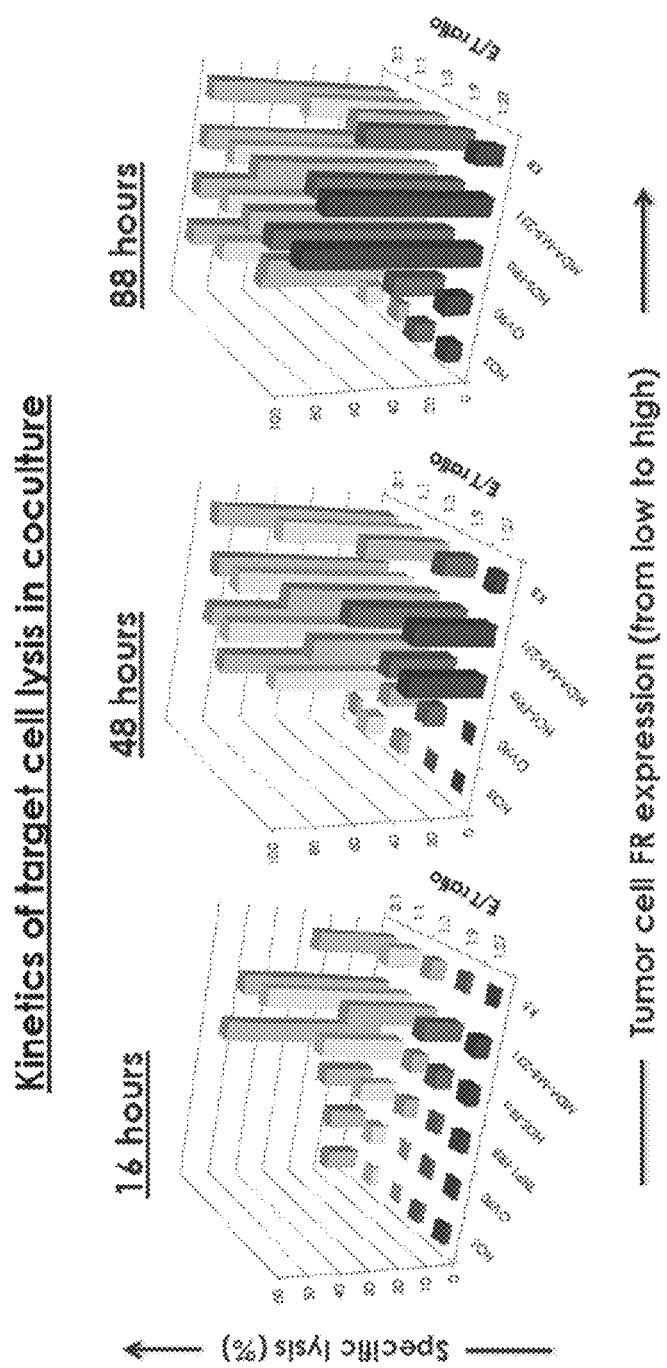
FIG. 52 shows the correlation of cytolytic activity of CAR T cells with functional FR levels on tumor cells.

FIGS. 46-49 shown the structures of bridges used in CAR-T cell experiments and their affinities, determined in vitro, for the types of cells the bridges are directed against (e.g., folate-FITC for folate receptor expressing cancer cells). FIG. 50 shows binding (by FACS analysis) of bridges to tumor cells used in an in vivo model and expressing the receptor corresponding to the small molecule ligand of the bridge.

For Examples 20 to 30—See FIGS. 55 to 63

Example 20

Cell Lines and Reagents

Unless otherwise noted, all FR+ and FR-negative cancer cell lines were maintained in RPMI-1640 medium (Gibco BRL) supplemented with 10% heat-inactivated fetal calf serum without (FFRPMI) or with (RPMI) 2.4 mM folic acid (FA). KB (FRa-expressing human cervical carcinoma with HeLa markers) and CHO-b (Chinese hamster ovary cells transfected with human FRb) were used as the sources of FRa and FRb for radioligand binding assays, respectively. MDA-MB-231 represents a FRa subclone of human triple negative breast cancer (TNBC) cell line. For AML studies, a green fluorescent protein (GFP)-expressing isogenic pairs of FRb– positive (THP1-FRb) and FR-negative (THP1-FG12) cell lines were provided. Both were established from THP-1 (ATCC, TIB-202), a commonly used cell model for researching pediatric AML which was originally derived from a 1-year-old male infant with acute monocytic leukemia. For osteosarcoma studies, HOS-FRa was established by lentiviral transduction of FRnegative HOS-143b (ATCC, CRL8303) with FOLR1 gene encoding the human FRa. HOS-143b is originally established from a primary tumor of a 13-year-old Caucasian female and highly tumorigenic in NSG mice. The GFP-expressing bioluminescent pairs of FR+ HOS-FRα$^{fluc}$ and FR-negative HOS-143b$^{fLuc}$ were transduced with lentiviral firefly luciferase.

LEGENDplex™ human cytokine panels were purchased from BioLegend (San Diego, Calif.). The lactate dehydrogenase (LDH) based CytoTox 96® non-radioactive cytotoxicity assay kit was purchased from Promega (Madison, Wis.). Commercially available anti-human antibodies used for multicolor flow cytometry were: CD45RA (clone HI100), CD45RO (clone UCHL1), CD4 (clone SK3), and CD69 (clone FN50) from Thermo Fisher Scientific (Waltham, Mass.); CD3ε (clone SK7), CD8α (clone RPA-T8), CD137/4-1BB (clone 4B4-1), CD25 (clone MA251), PD1 (clone EH12.1), LAG3 (clone T47-530), and TIM3 (clone 7D3) from BD Bioscience (San Jose, Calif.); biotinylated anti-human EGFR (Cetuximab, clone Hu1) from R&D systems (Minneapolis, Minn.); and FRα (clone LK26) from BioLegend (San Diego, Calif.). A fluorophore-conjugated anti-biotin was also purchased from BioLegend. APC-conjugated anti-FITC mouse IgG2a/kappa antibody (clone NAWESLEE), CountBright™ beads (Invitrogen), Annexin V staining buffer, and AlexaFluor-647-conjugated Annexin V were purchased from Thermo Fisher Scientific. For enzymatic digestion of tumor tissues, collagenase IV, hyaluronidase and DNase I were all purchased from Sigma-Aldrich (St. Louis, Mo.).

EC17 or folate-FITC [FA-(g)-ethylenediamine-FITC] was synthesized at Endocyte. 3HEC17 was either purchased from Moravek biochemicals (Brea, Calif.) at a specific activity of ~0.952 Ci/mmol or prepared at Endocyte by conjugating FITC with 3H-FA-(g)-ethylenediamine made by ViTrax (Placentia, Calif.) at a specific activity of ~1.2 Ci/mmol. 3H-FA was also purchased from ViTrax at a specific activity of 59 Ci/mmol. For CRS rescue, sodium fluorescein dosing solution was diluted from AK-FLUOR® 25% (fluorescein injection, USP) which was purchased from Purdue Pharmacy (NDC 17478-250-25).

Example 21

Humanized CAR Construct and CAR-Modified T Cells

Figure 55:
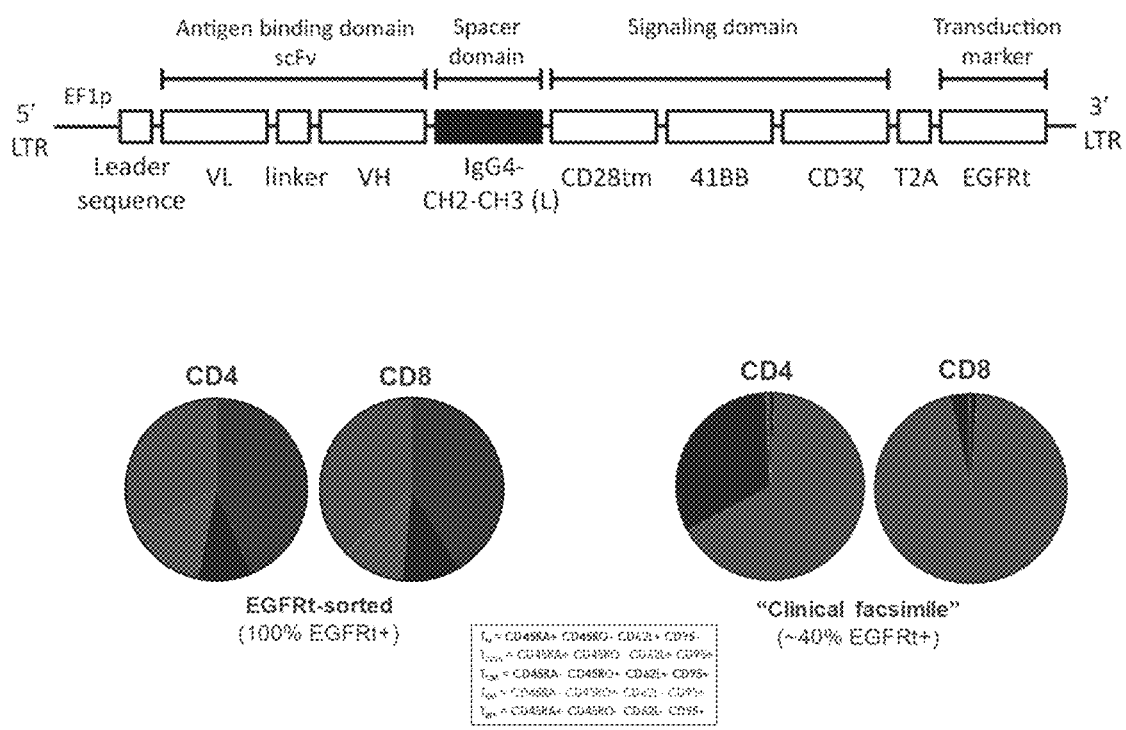
FIG. 55 shows a fully human CAR construct comprised of anti-FITC scFv (clone E2), a full-length IgG4 spacer (Fc derived hinge-CH2(L235D, N297Q)-CH3), CD28tm transmembrane domain, 4-1BB/CD3ζ cytoplasmic activation domains, and a non-functional truncated cell surface polypeptide of epidermal growth factor receptor (EGFRt). Bottom: Examples of CD4/CD8 T cell phenotyping performed by flow cytometry on an EGFRt-sorted (left pie charts) CAR-T cell preparation and an unsorted "clinical facsimile" (right pie charts). The color keys are as shown.

Previous studies used a GFP+ second-generation anti-FITC scFv (clone 4M5.3) CAR containing the hinge and transmembrane sequences of CD8α and 4-1BB/CD3ζ signaling domains (i.e., FITC-4M5.3-scFv-CD8ahinge-CD8atm-4-1BB/CD3z). For translation into firstin-human testing, the second-generation fully human FITC-specific (clone E2) CAR construct (herein referred to as E2) was developed (FIG. 55, top diagram). CAR-modified T cells are shown in FIG. 55, bottom pie charts.

The construct described herein is a FITC-specific CAR construct comprised of (1) a fully human anti-FITC scFv (clone E2, Kd=0.75 nM), (2) an IgG4 hinge-CH2(L235D, N297Q)-CH3 spacer fused to a CD28-transmembrane domain, (3) a second-generation 4-1BB/CD3-endodomain, and (4) a cell-surface human EGFRt tag (FIG. 55, top diagram) (SEQ ID NOS:1 and 2 are the nucleic acid and amino acid sequences, respectively). To generate CAR-modified T cells, lentivirus was produced in 293T cells co-transfected with CAR-encoding epHIV7 lentiviral vector. Donor CD4+ and CD8+ T cells were purified by immunomagnetic selection and transduced separately or at about a 50:50 ratio. In general, only one round of CD3/CD28 bead activation followed by one or two rounds of rapid in vitro expansion were carried out. For preclinical evaluations, several batches of EGFRt-sorted CD4, CD8 and unsorted CD4/CD8 CAR-T cells were used. All CAR-T cell preparations were analyzed prior to cryopreservation and after thawing to determine EGFRt expression and CD4/CD8 ratios by flow cytometry. Using combinations of surface markers, differentiation status of CD4+ and CD8+ CAR-T cell subsets on the day of infusion was analyzed and defined as TN, CD45RA+CD45RO−CD62L+CD95-naïve T cells; Tscm, CD45RA+CD45RO− CD62L+CD95+ stem cell memory T cells; Tcm, CD45RA− CD45RO+CD62L+ CD95+ central memory T cells; $T_{EM}$, CD45RA− CD45RO+ CD62L− CD95+ effector memory cells; and $T_{EFF}$, CD45RA+CD45RO− CD62L− CD95+ effector T cells. For preclinical testing described below, studies included two batches of EGFRt-sorted pure CD4 and CD8 subsets (after mixing at about 1:1 ratios) and several batches of unsorted ~1:1 EGFRt+CD4/CD8 admixture including a "clinical facsimile" preparation with low differentiation profiles.

Amid a series of different CAR constructs synthesized and evaluated, the fully human anti-FITC scFv (FITC-E2) CAR was chosen for preclinical development (FIG. 55). This second-generation fully human CAR consisted of anti-FITC scFv (clone E2), an IgG4-Fc spacer/hinge with double mutations in the CH2 region (L235D and N297Q) to reduce binding to FcγR, a CD28 transmembrane domain, and 4-1BB/CD3z signaling domains appended to a cell surface EGFRt tag by a T2A ribosomal skip sequence (i.e., FITC-E2-scFv-IgG4hinge-CD28tm-4-1BB/CD3z-T2A-EGFRt).

Figure 56A:
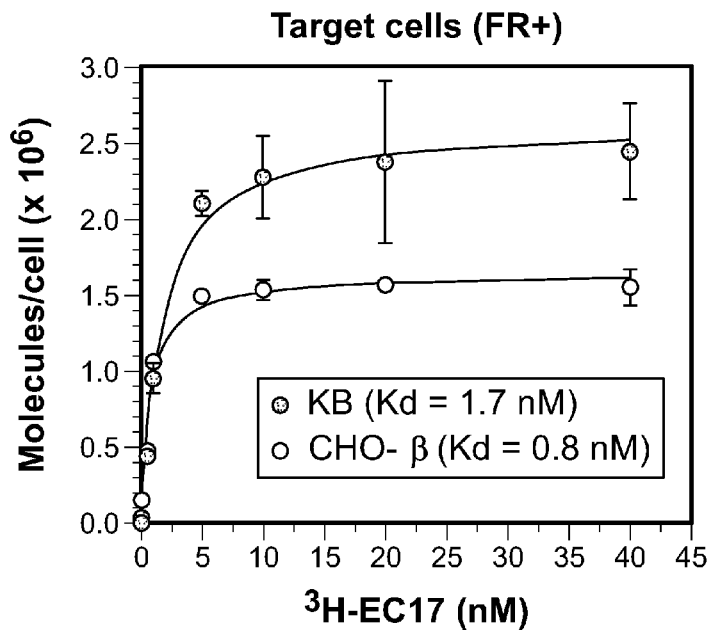
FIG. 56 A: Kd values of 3H-EC17 uptake by FR+ target cells after a 2 hour incubation at 37° C. (calculated from the numbers of molecules bound per cell).
FIG. 56B: Kd value of 3H-EC17 uptake by E2-CAR-T cells (~24% EGFRt+, ~95:5 CD8/CD4 ratio) after a 2 hour incubation at room temperate (calculated from total cell-associated radioactivity, DPM).
Figure 56B:
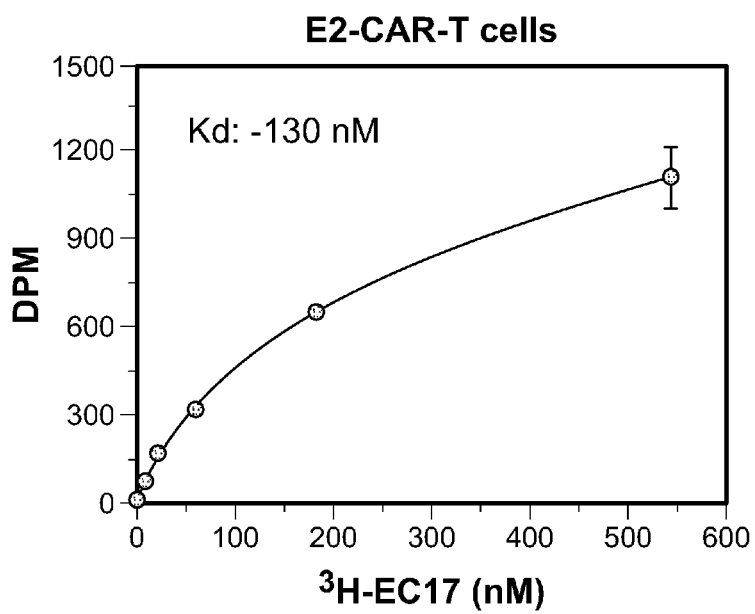
Figure 57B:
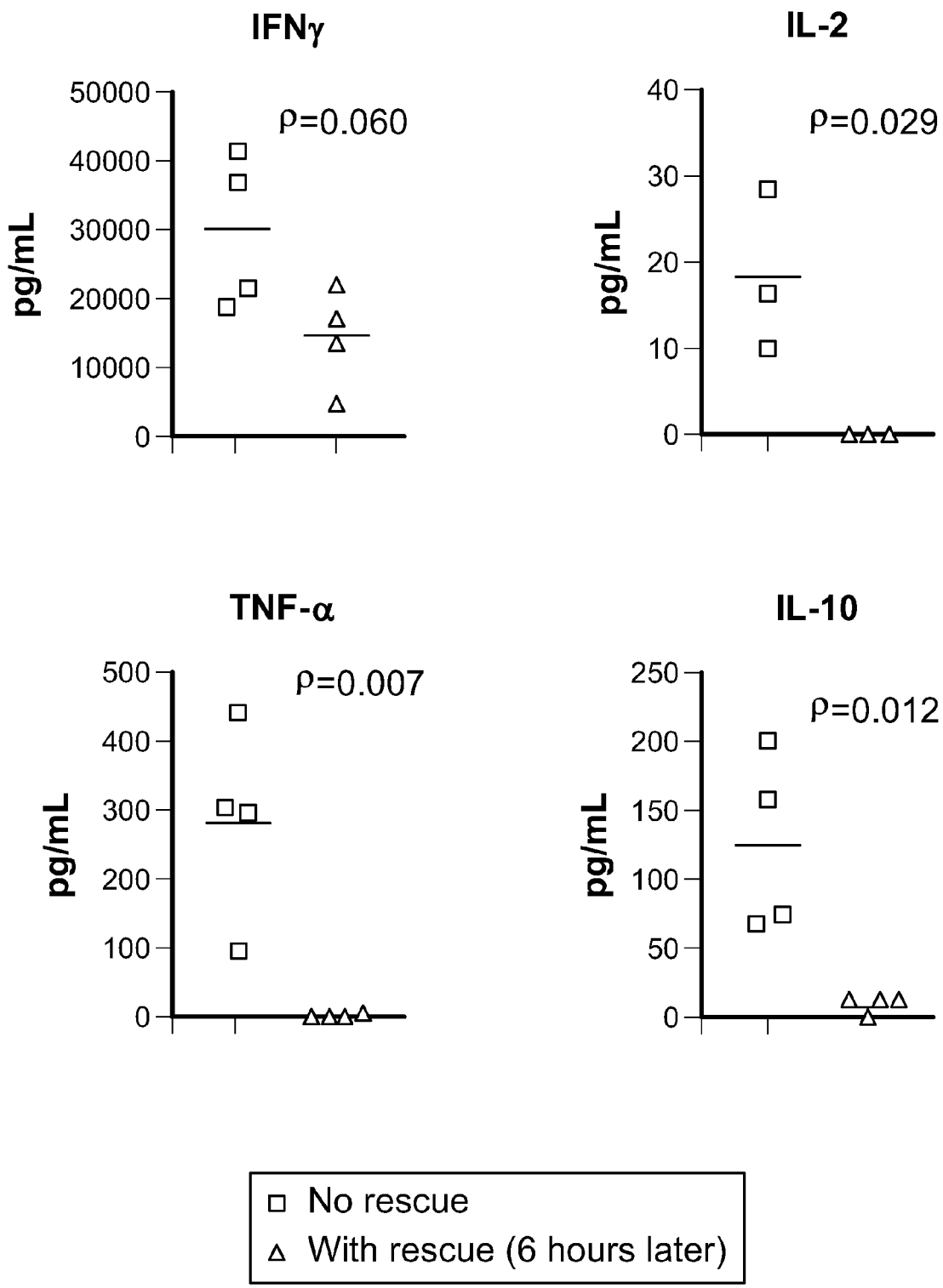

For preclinical studies, both EGFRt-sorted and unsorted E2 CAR-T cells were prepared at ~1:1 CD4/CD8 ratios, and T cell subtype phenotyping was routinely performed by flow cytometry at the time of CAR T cell infusion (day 0) for each in vivo experiment. A typical expression pattern of EGFRt-sorted CAR-T cells was comprised of both CD4 and CD8 subsets at approximately 42% $T_{SCM}$, 10% $T_{CM}$, 12% $T_{EM}$ and 34% $T_{EFF}$ (FIG. 55, pie charts on the left). Only EGFRt-sorted CAR-T cells were used for co-culture (FIGS. 53, 54, 56, 58, 59, and 61) and pharmacokinetic studies (FIG. 62A, FIG. 62B, FIG. 62C, FIG. 62D, FIG. 62E). For tumor therapy, a "clinical facsimile" batch with a low differentiation profile (FIG. 55, pie charts on the right) was used and this "clinical batch" was also used for MDA-MB-231 studies (FIG. 63A, FIG. 63B, FIG. 63C, FIG. 63D), and a research batch was used for THP1-FRb and HOS-FRα studies (FIG. 57A, FIG. 57B). The "clinical facsimile" batch (~39% EGFRt+) was comprised of CD4+ subsets at ~66% $T_{SCM}$ and ~32% $T_{CM}$ and CD8 subsets at ~95% $T_{SCM}$ and 3% $T_{CM}$. The research batch (~23% EGFRt+) was more differentiated and comprised of CD4 subsets at 32% $T_{SCM}$, 53% $T_{CM}$, 11% $T_{EM}$ and 3.7% $T_{EFF}$ and CD8 subsets at 44% Tscm, 0.28% Tcm, 3.4% $T_{EM}$ and 52% $T_{EFF}$.

Example 22

EC17 CAM'S Bispecific Affinity

The bispecific affinities of EC17 CAM were assessed using ³H-EC17 in cell-based radioligand binding assays. For binding to FR+ targets, KB and CHO-β cells were pre-seeded overnight in 24-well tissue culture plates and incubated with 0.1, 0.5, 1, 5, 10, 20, and 40 nM of ³H-EC17 in FFRPMI for 2 h at 37° C. Afterwards, the cells were rinsed with phosphate-buffered saline (PBS, pH 7.4) and lysed with 1% sodium dodecylsulfate. The whole cell lysates were quantitated for the level of radioactivity and cellular protein content by standard Pierce BCA protein assay. The number of ³H-EC17 molecules bound per cell was calculated to determine the dissociation constants (Kd) for FRα (KB) and FRβ (CHO-b) respectively (FIG. 56A, FIG. 56B).

Principle Components of CAM Controlled CAR T Cell Therapy. The basic components of the CAR-T cell therapy involve FITC as the pseudo tumor antigen, the high affinity EC17 CAM (a CAM is equivalent to a bridge or the "compound" in this application), and a rationally designed anti-FITC CAR and CAR-modified T cells. The EC17 has already been tested in the clinic for immunotherapy and optical imaging purposes. To directly quantify its bispecific binding affinities, $^3$H-EC17 was synthesized and radioligand binding assays were carried out on KB and CHO-β cell lines representing FRα+ and FRβ+ target cells, respectively, and on unsorted EGFRt CAR-T cells representing the effector cells. When binding to its targets, EC17 demonstrated similar affinities towards both FRα and FRβ with low Kd values of 1.7 nM and 0.8 nM, respectively (FIG. 56A). Upon binding to unsorted E2-CAR-T cells (~24% EGFRt+, ~95:5 CD8/CD4 ratio), the Kd value was estimated at ~130 nM (FIG. 56B).

Example 23

Tumor Models

All animal care and use were performed according to NIH guidelines and in compliance with protocols approved by the Purdue University Animal Use and Care Committee. Female 4 to 5-week-old NOD/SCID gamma (NSG™) mice (stock number: 005557) were purchased from The Jackson Laboratory (Bar Harbor, Me.). Unless specifically indicated, all animals were maintained on a FA-deficient diet (TestDiet, St. Louis, Mo.) upon arrival and throughout the study. To establish subcutaneous xenografts, MDA-MB-231 and HOS-FRα were implanted in the right flank region at $2.5 \times 10^6$ and $1 \times 10^6$ cells per animal, respectively. For intravenous xenografts, THP1-FRb cells were inoculated at $5 \times 10^6$ cells per animal. Subcutaneous tumors were measured 2-3 times per week with a caliper and calculated using the ellipsoidal formula (length×width)/2. Euthanasia was performed per study design or when (i) the animals had lost ³20% of body weight or approached moribund conditions, (ii) subcutaneous tumors reached ≥1500 mm³ in size, or (iii) animals displayed signs of swollen belly and severe distress (i.e., THP1-FRβ). All animal doses (CAR-T cells, EC17, sodium fluorescein) were given intravenously.

Example 24

Tumor Therapies

In a therapeutic setting, EC17 CAM can theoretically be given before or after CAR-T cell injection. As described herein, the first dose of EC17 was administered 2-3.5 days after CAR-T cells to allow for an observation period of human T cells in tumor-bearing mice. Two batches of unsorted E2 CAR-T cells (23% or 39% EGFRt+, 1:1 CD4/CD8) were used for in vivo studies. On the day of infusion for each experiment (day 0), frozen CAR-T cells were quickly thawed at 37° C., washed 2× with Dulbecco's 1×PBS (pH 7.4) and injected into the tail vein at desired EGFRt+E2-CAR-T cell doses. In addition, a small aliquot of CAR-T cells was analyzed by flow cytometry for CD4 to CD8 ratio and differentiation status of CAR-T cells. On the first day of EC17 dose, tumor-bearing animals were randomly assigned into groups according to their tumor sizes or the same number of days post intravenous implantation (i.e., THP1-FR(3)).

Example 25

Toxicity and CRS Rescue

Depending on the CAR-T cell dose and how EC17 is administered, tumor-bearing mice receiving FITC-specific CAR-T cells can experience severe CRS and varying degrees of body weight loss. Therefore, a CRS grading system (0-5 scale) was developed to empirically assess CRS toxicity from animals' gross morphology and social behavior to allow for better timing of CRS rescue. While grades 0 and 5 indicated normal (no CRS) or death (due to severe CRS), respectively, grades 1, 2, and 3-4 were considered mild, light-to-moderate, and severe CRS (FIG. 57A, table descriptions). In addition, all EC17 doses were intentionally given towards the end of any given day to allow potential CRS symptoms to develop overnight. On the days immediately following each EC17 dose, animals were scored and rescue agents such as sodium fluorescein, folic acid and leucovorin were used to mitigate CRS toxicity. In this particular instance, a batch of E2 CAR-T cells with a high EGFRt+CD4/CD8 ratio (~93:7) was given to HOS-FRα tumor-bearing mice at a mixture of ~2.5 million CD8 and ~33 million CD4 on day 0 (FIG. 57B, diagram). When EC17 was dosed respectively at 500, 100, and 500 nmol/kg on days 3, 10 and 12, low CRS (grades 1-2) was noted on days 4 and 11 but high CRS (grade 3) was noted on day 13. To mitigate the severe CRS toxicity, sodium fluorescein was intravenously administered at ~96 mg/kg in the morning of day 13 and mouse plasma samples were collected 6 hours later for analysis of CRS-associated cytokines.

To scrutinize the CRS rescue capabilities with sodium fluorescein, a CRS scoring system was developed that was able to capture the onset of severe CRS (grades 3/4) following EC17 administration (FIG. 57A). As shown by a challenging case of rapid CRS onset in HOS-FRα tumor-bearing mice due to a very high dose of 35 million total CAR-T cells (93:7 CD4/CD8), intravenous sodium fluorescein at a human equivalent dose (~95 mg/kg in mice) acted very quickly to reduce CAR-T cell derived human cytokines (FIG. 57B).

Example 26

Statistics

Statistical analyses were performed using the computer program GraphPad Prism (GraphPad Software Inc., San Diego, Calif.). Data were analyzed using Student's t-test or one-way ANOVA. If applicable, data were further analyzed across treatment groups using appropriate multiple comparison post-test. *=p<0.05 was considered statistically significant in all tests.

Example 27

Co-Culture Experiments

Figure 58:
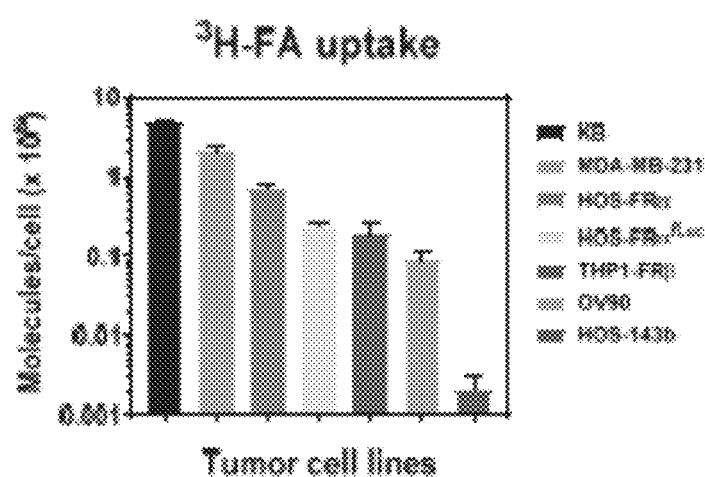
FIG. 58 shows functional FR levels on tumor cell measured by a 3H-FA (folic acid)-based binding assay (100 nM, 1 hour at 37° C.).

To investigate EC17 CAM action in vitro, pure EGFRt-sorted CD4 and CD8 CAR-T cells were admixed in a 1:1 ratio and matching mock-transduced T cells were included per experimental design. Other than FR+/− isogenic pairs of AML and osteosarcoma cell lines, KB, MDA-MB-231 and OV90 were added to represent different histological tumor types and FR expression levels. All FR+ target cell lines were subjected to a direct 3H-FA binding assay to quantitate the number of FR molecules bound/cell (FIG. 58). Prior to co-culture experiments, cryopreserved CAR-T cells were allowed to recover for 2-3 days in T cell culture medium. All effector and target cells were pre-washed with FFRPMI to remove any exogenous FA that could compete against EC17. Short-term coculture studies of ≤3 days were carried out in FFRPMI without adding any exogenous cytokines.

For an EC17 dose response study (FIG. 59A, FIG. 59B), FR+ cell lines (KB, MDA-MB-231, HOS-FRα, THP1-FRβ, OV90) were co-cultured with EGFRt-sorted E2-CAR-T cells at an effector-to-target (E/T) ratio of 1:1 in the presence of EC17 ranging from 0.1 pM to 100 μM in 10-fold increments. After 24 hours of co-culture, supernatants were harvested to determine tumor cell killing. To study the kinetics of T cell activation and FR correlation in vitro (FIG. 60A, FIG. 60B, FIG. 60C, FIG. 60D, FIG. 60E), co-cultures were carried out in FR+/− cell lines at varying E/T ratios (1:27, 1:9, 1:3, 1:1, 3:1) in the continuous presence of 10 nM EC17. The kinetics of tumor cell killing were quantified after 16 and 48 hours of co-culture. Meanwhile, a portion of the supernatants was taken after 44 hours of co-culture for measurement of IFNg, IL-2 and TNFα. Using Promega's CytoTox 96® LDH assay kit, target cell killing was quantified and expressed as specific lysis (%) which was normalized to basal levels in the absence of EC17 at defined E/T ratios. The LEGENDplex™ human Th1 cytokine panel (BioLegend, San Diego, Calif.) was used to determine CAR-T cell derived cytokines.

Figure 61A:
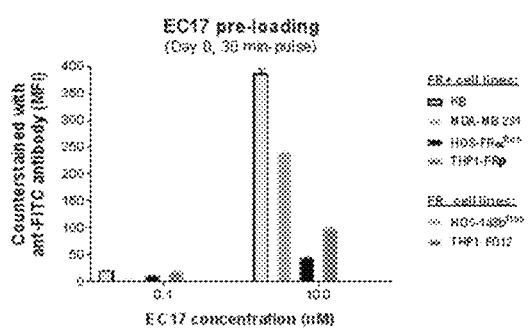
FIG. 61A shows bar graph to show EC17 loading status of target cells confirmed by flow cytometry and expressed as MFI (EC17 was undetectable on FR-negative cell lines).
Figure 61B:
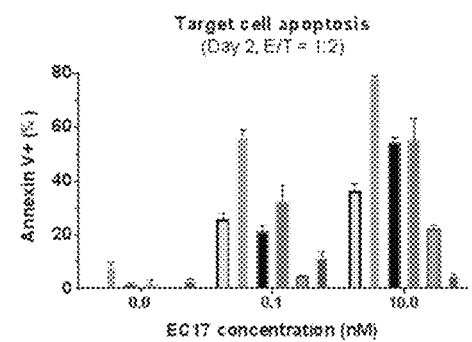
FIG. 61B shows target cell apoptosis (%) detected by Annexin V staining after 2 days of coculture as described in FIG. 54.

To study CAR-T cell activation in the presence of FR+ tumor cell targets (FIG. 53), co-culture experiments were initially carried out with MDA-MB-231, THP1-FRβ and HOS-FRα. After a 30-min exposure to media containing 100 nM EC17, all target cells were washed and then incubated at 1:1 E/T ratio with EGFRt-sorted E2-CAR-T cells (1:1 CD4/CD8) or mock transduced control T cells. After 24 hours of co-culture, the surface expression of T cell activation markers CD69, CD137 (4-1BB), and PD1 were analyzed by flow cytometry. For T cell exhaustion studies (FIG. 54), FR+(KB, MDA-MB-231, HOS-FRα$^{fLuc}$, THP1-FRβ) and FR-negative (HOS-143b$^{fLuc}$, THP1-FG12) tumor cell lines were used as targets. Here, target cells were incubated on day 0 without or with 0.1 and 10 nM of EC17 for 30 min at 37° C. and the status of EC17 "pre-loading" was assessed by counterstaining cell-surface EC17 with an anti-FITC antibody (FIG. 61A). Three days later, the surface expression of PD1, LAG3, and TIM3 inhibitor receptors on co-cultured CAR-T cells were analyzed and higher frequencies of double- and triple-positive cells were considered approaching an exhausted phenotype. As tumor cells used in this study showed variability of doubling times, target cell apoptosis (%) was measured as Annexin V+ after 2 days of co-culture and normalized against background levels of apoptosis of target cells cultured under the same conditions in the absence of T cells (FIG. 61B).

Functional FR Assessments

These functional FR assessments are applicable to several examples described herein. Besides pediatric cancer cell lines transfected with FRα (HOS-FRα) and FRβ (THP1-FRβ), cancer cell lines of different histology and FR expression levels (FIG. 58) were included. As estimated by a radioligand binding assay (100 nM $^3$H-FA, 1 h at 37° C.), the ranking order of total available FRs on these cell lines was: 9×10$^4$ (OV90, a low-FR expressing ovarian cancer cell line), 1.9×10$^5$ (THP1-FRβ), 2.4×10$^5$ (HOS-FRα$^{fLuc}$), 7×10$^5$ (HOS-FRα), 2.1×10$^6$ (MDAMB-231) and 4.8×10$^6$ (KB) FA molecules/cell. Also included as FR-negative controls were HOS-1431b$^{(fLuc)}$ and THP1-FG12 parent cell lines. Thus, the general ranking of functional FR expression on co-cultured FR+ cancer cell lines was: KB>MDA-MB-231>HOS-FRα>HOSFRα$^{fLuc}$>THP1-FRβ (AML)>OV90.

Correlation of FR Levels with Target Cell Lysis and Cytokine Production

To analyze FR dependency, 5 FR+(MDA-MB-231, KB, HOS-FRα, THP1-FRβ, OV90) and 1 FR-negative (HOS-143b) cell lines were co-cultured in the continuous presence of 10 nM EC17 with E2-CAR-T cells at varying E/T ratios (1:27, 1:9, 1:3, 1:1, and 3:1). Specific lysis (%) was quantified after 16 and 48 hours of co-culture, and Th1 cytokines (IFNg, TNFa) in culture media were measured after 44 hours of co-culture. While the onset of specific lysis (~16 hours) varied among different tumors, an increase in specific cytolysis was observed at 48 hours for all FR+ cancer cell lines (FIG. 60A). It generally took a longer time (48 hours) and a higher E/T ratio (≥1:1) to see significant activity in the lowest FR-expressing OV90 cells (FIG. 60A). The high FR-expressing KB cells responded very slowly and also required a higher E/T ratio (≥1:3) and longer exposure time to cause significant cell death (FIG. 60B, left plot). When enough effector cells were present (≥1:1 E/T ratios), all FR+ cancer cells responded after 48 hours of co-culture. Notably, only the FR-negative HOS-143b cells were essentially unharmed (FIG. 60B, right plot).

To establish a correlation of CAR-T cell activity with FR expression in vitro, the values of 16-h specific lysis were plotted at an E/T ratio of 1:1 against the functional FR levels found on tumor cells (FIG. 58). Excluding KB cells that showed an unusual resistance at the beginning, there was a strong semi-log correlation between FR expression and the onset of cytolysis with an R-value of 0.98 (FIG. 60C). Similarly, all but the FR-negative HOS-143b tumor cells triggered high levels of IFNγ, IL-2 and TNFα production after 44 hours of co-culture at an E/T ratio of 1:1 with E2-CAR-T cells (FIG. 60D). For Th1 cytokine production, a semi-log correlation was also observed with all cell lines included at R-values of 0.88 (IFNγ), 0.89 (IL-2) and 0.89 (TNFα) respectively (FIG. 60E). In short-term co-cultures, MDA-MB-231 was found most sensitive to killing by CAR-T cells, but HOS-FRα osteosarcoma and THP1-FRα AML also responded quickly in a FR level-dependent manner (FIG. 60, panel C).

High Potency of EC17 CAM in Effector/Target Cell Engagement In Vitro

Figures 59A, 59B:
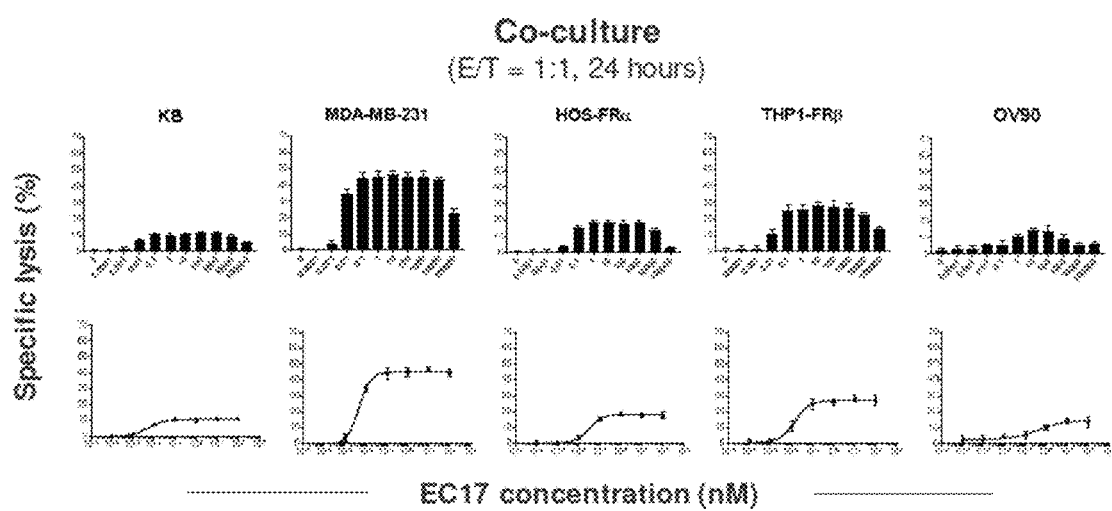
FIG. 59A shows full-range EC17 dose response in specific lysis (%) of 5 FR (folate receptor)+ tumor cell lines co-cultured with EGFRt-sorted CAR-T cells for 24 hours at 1:1 E/T (Effector/Target) ratio.
FIG. 59B shows maximum lysis (%) and EC50 values were obtained from the dose-response curves fitted up to 100 nM.

Monovalent EC17 in its free form (i.e. one FITC per FA ligand) does not automatically activate anti-FITC CAR-T cells. To study the robustness of CAR-T cell activation, 5 FR+ cell lines (KB, MDA-MB-231, HOS-FRα, THP1-FRβ, OV90) were used along with a wide range of EC17 concentration (0.1 pM to 100 μM) at an E/T ratio of 1:1 (FIG. 59A, FIG. 59B). Specific lysis (%) was quantified by Promega's LDH cytotoxicity assay kit after 24 hours of co25 culture. In all cell lines, EC17-dependent cytolysis followed a bell-shaped dose response with a somewhat broad concentration plateau (~0.1 nM to 1 mM) (FIG. 59A). When the dose response curves were fitted to the summit (up to 100 nM), half-maximal effective concentrations ($EC_{50}$) were obtained at 4.5 pM (MDA-MB-231), 5.3 pM (KB), 15 pM (THP1-FRβ), 30 pM (HOS-FRα) and 418 pM (OV90), respectively. However, maximal lysis obtained for each cell line ranked differently at 45% (MDA-MB-231), 27% (THP1-FRb), 18% (HOS-FRα), 15% (OV90) and 11% (KB) (FIG. 59B). The low EC50 values in general suggested that EC17 was highly potent in triggering FR-specific target cell lysis by activated E2-CAR-T cells.

EC17/FR-Dependent CAR-T Cell Activation and Exhaustion In Vitro

Figure 53:
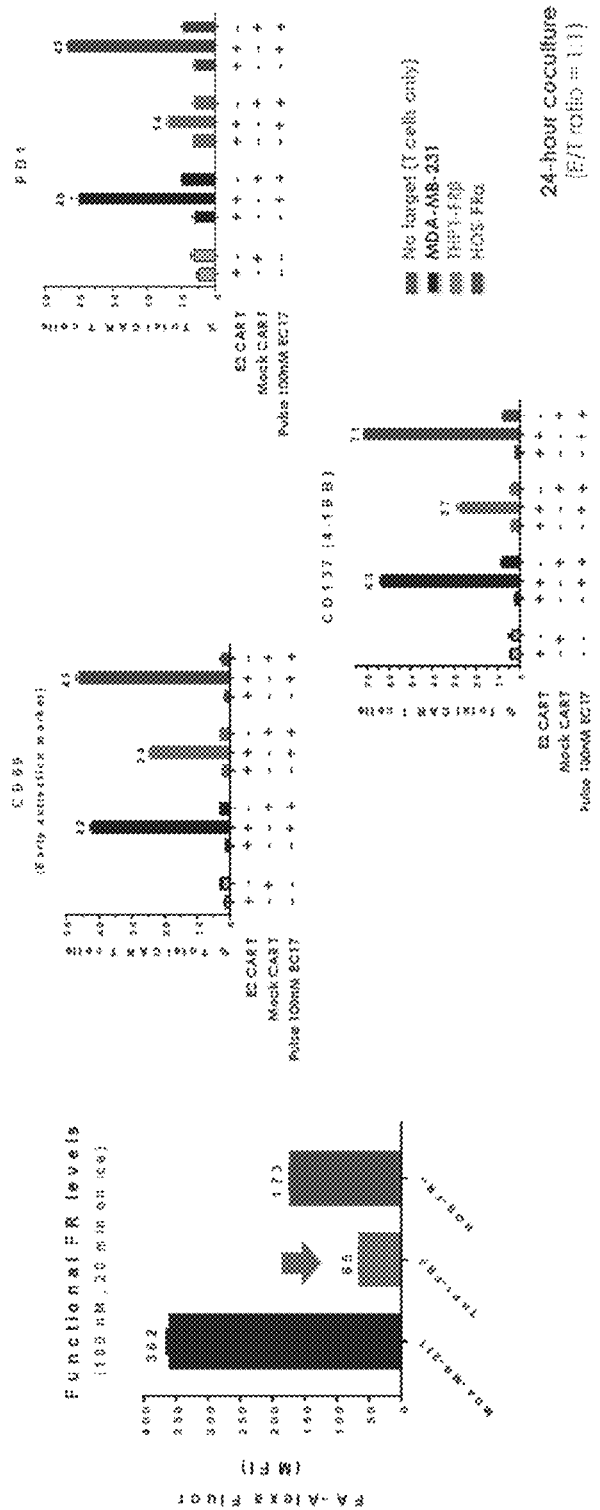
FIG. 53 shows EC17/FR-dependent CAR T cell activation and exhaustion. Expression of early (CD69), intermediate (CD137) and late (PD1) T cell activation markers detected on CAR-T cells co-cultured (E/T=1:1) with FR+ tumor cell targets pre-loaded without or with EC17 (100 nM, 30-min pulse at 37° C.) are shown. The first two open bars represent CAR-T and Mock transduced T cells only without target cells.
Figure 54:
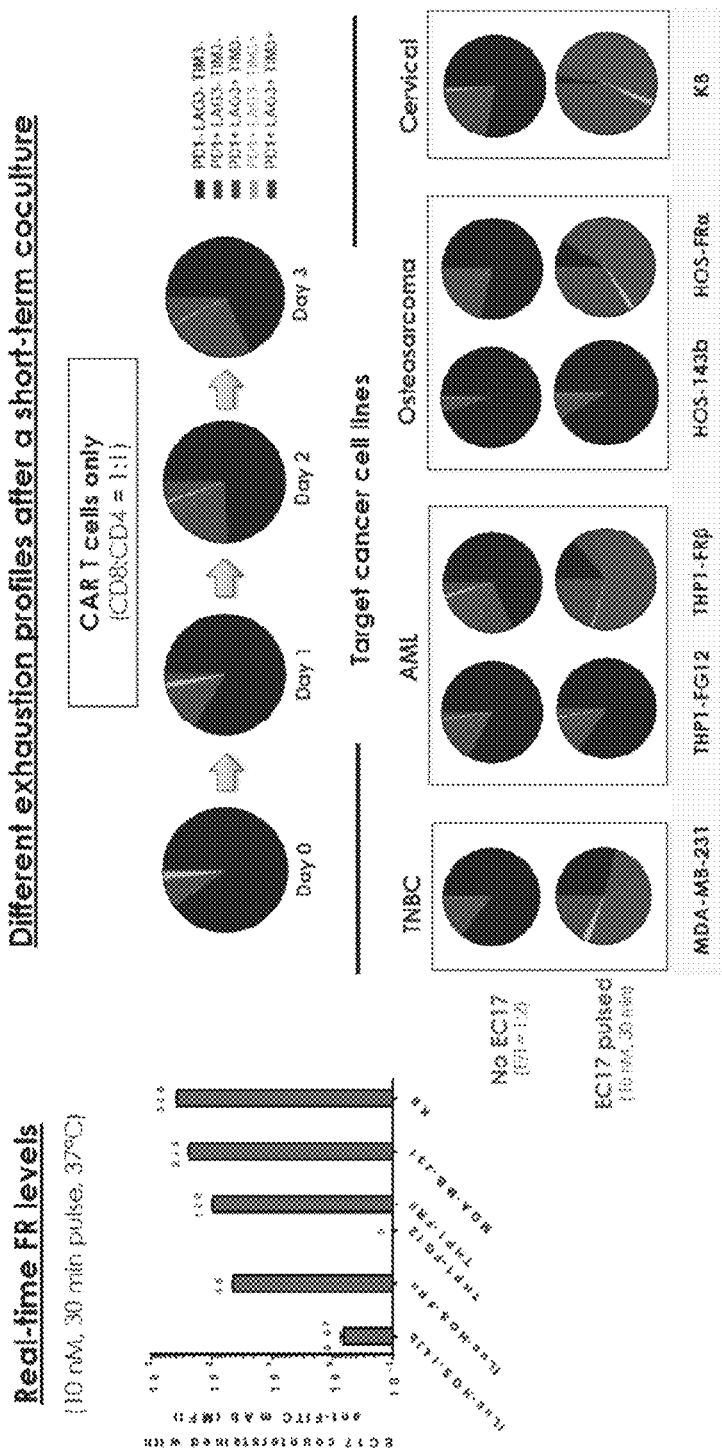
FIG. 54 shows EC17/FR-dependent CAR T cell exhaustion profiles. Top row: Colored pie charts representing change in the differentiation status of CAR-T cells in culture without target cells on days 0-3. Bottom row: Four sets of colored pie charts representing the differentiation status of CAR-T cells after 3 days of co-culture (E/T=1:2) with FR+(MDA-MB-231, THP-1FRb, HOS-FRa, KB) and FR-negative (THP1-FG12, HOS-143b) tumor cells preloaded without or with EC17 (0.1 or 10 nM, 30-min pulse at 37° C.).

To examine antigen-dependent CAR-T cell activation, MDA-MB-231, THP1-FRβ and HOS-FRα cells were pre-loaded with 100 nM EC17 over 30 min. The cells were washed and then incubated at 1:1 E/T ratio with either EGFRt-sorted E2-CAR-T cells (1:1 CD4/CD8), or mock transduced control T cells. After 24 hours of co-culture, we measured the surface expression of T cell activation markers CD69, CD137 (4-1BB) and PD1 (FIG. 53). EC17-preloaded MDA-MB-231 and HOS-FRα were strong activators of our CAR-T cells. THP1-FRb cells, which express 11-fold lower FR compared to the MDA-MB-231 cells, did trigger CAR-T cell activation, but at lower levels. Importantly, the mock controls T cells were not activated under these conditions. Some FR+ tumor types (e.g. KB) display a natural resistance to killing by EC17-directed CAR T cells (FIGS. 56, 58, 59, and 60), we studied T cell activation versus exhaustion as a mechanism of EC17 CAM action. Both FR+(KB, MDA-MB-231, HOS-FRα$^{fLuc}$, THP1-FRβ) and FR-negative (HOS-143b$^{fLuc}$, THP1-FG12) tumor cell lines were chosen for this purpose. HOS-FRα$^{fLuc}$ expressed ~5.6× lower level of functional FR than its parent HOS-FRα, and HOS-143b$^{fLuc}$ was FR-negative similar to HOS-143b (FIG. 59A). Here, FR+ and FR-negative tumor cells without or with EC17 pre-loading (0.1 or 10 nM, 30-min pulse at 37° C.) were incubated with EGFRt-sorted CAR-T cells (1:1 CD4/CD8) at an E/T ratio of 1:2 (FIG. 54 and FIG. 61B). EC17 dose-dependent pre-loading was confirmed on day 0 by counterstaining of membrane bound EC17 with an APC-conjugated anti-FITC antibody (clone NAWESLEE) (FIG. 61A). Three days later, co-cultured CAR-T cells were measured for upregulation and co-expression of T cell activation/exhaustion markers PD1, LAG3 and TIM3. In the absence of target cells, E2-CAR-T cells underwent a low-grade differentiation in culture with low frequencies of double or triple-positive cells. Interestingly, the presence of tumor cells alone (without EC17 pre-loading) appeared to "relax" the CAR-T cells to various degrees. But when encountering EC17-preloaded FR+(but not FR-negative) tumor cell targets, E2-CAR-T cells underwent significant differentiation with increased co-expression of exhaustion markers. Based on increased frequencies of triple- and double-positive cells, a more exhausted phenotype appeared on co-cultured CAR-T cells in the order of KB>HOS-FRα$^{fLuc}$>THP1-FRβ>MDA-MD-231. While EC17 dose-dependent apoptosis (Annexin V+) was seen in all FR+ tumor cell lines on day 2, high FR-expressing KB cells again showed disproportionally low apoptosis (FIG. 61B).

Example 28

Kinetics of CAR-T Cell Expansion and Tumor Uptake

Figure 62A:
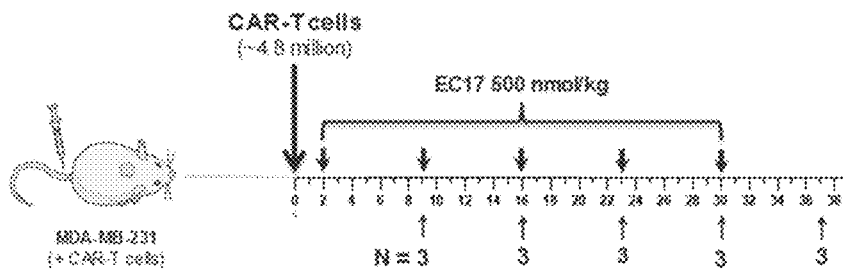
FIG. 62A, FIG. 62B, FIG. 62C, FIG. 62D and FIG. 62E show pharmacokinetics and tumor uptake of CAR-T cells in vivo.

To study CAR-T cell expansion in vivo, analysis started with 15 MDA-MB-231 tumor bearing mice having ~4.8 million EGFRt-sorted E2-CAR-T cells (1:1 CD4/CD8) injected on day 0 (FIG. 62A). When the tumor sizes averaged at ~350±60 mm³ on day 2, up to 6 weekly doses of EC17 at 500 nmol/kg were given on days 2, 9, 16, 23, and 30. For ex-vivo analysis, 3 animals were taken before the next EC17 dose on days 9, 16, 23, and 30 for a total of 4 collections. For comparison, the same EC17 dose was given to 3 CAR-T mice that had ~4.4× larger tumor sizes on day 2 (~1555±79 mm3). For each collection, fresh blood and tumor samples (if available) were analyzed for the presence of human CD3e+ EGFRt+ CAR-T cells by flow cytometry. Moreover, phenotypic changes of E2-CAR-T cells in the circulation ($T_{SCM}$, $T_{CM}$, $T_{EM}$, and $T_{EFF}$) and the activation status of tumor-infiltrating CAR-T cells (i.e., CD137/4-1BB, PD1) were analyzed.

EC17-Mediated CAR-T Cell Expansion and Tumor Uptake In Vivo

Figure 62B:
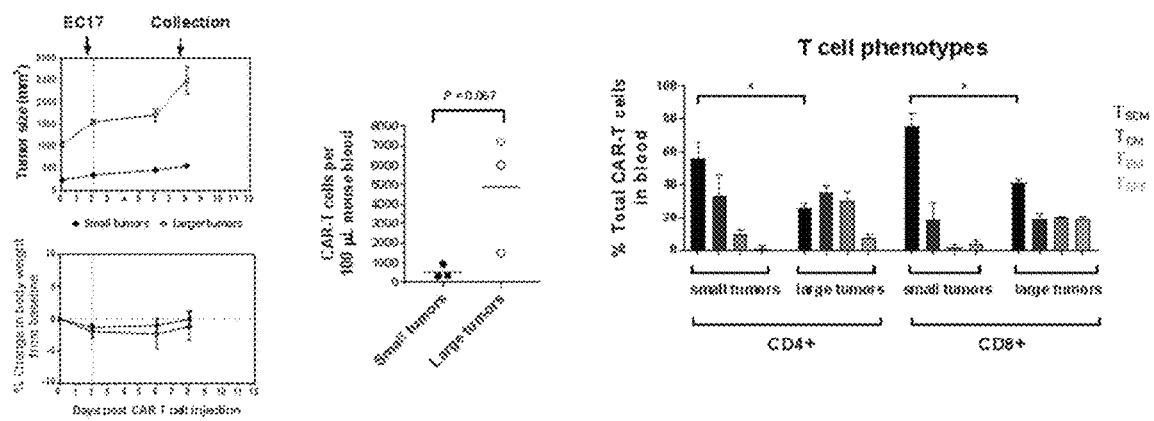
Figure 62C:
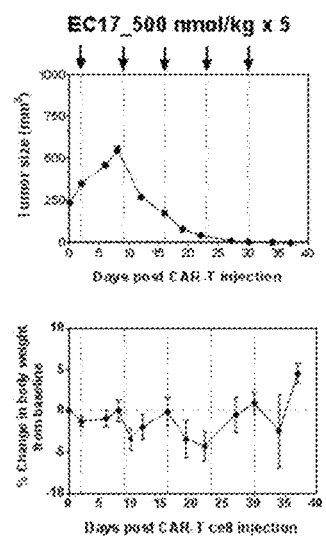
Figure 62D:
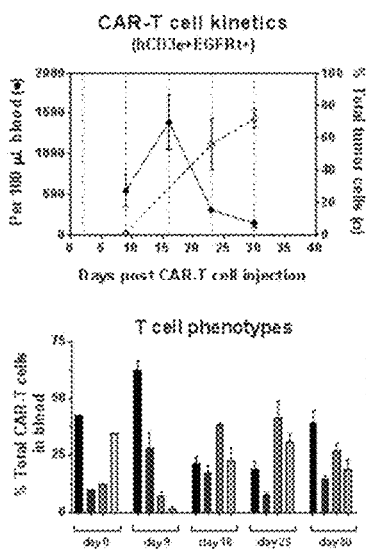
Figure 62E:
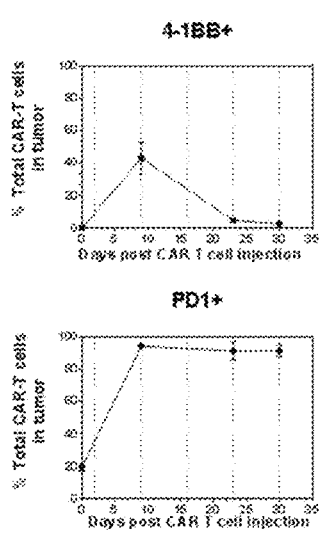

The dynamic interplay between EC17 and CAR-T cells in vivo was further analyzed using MDA-MB-231 tumor model, which was previously found to be among the highest FR expressing tumors at 103±15 pmol/mg membrane protein using a ³H-FA-based radioligand binding assay. In this study the kinetics of CAR-T cell expansion was studied in tumor-bearing mice that received ~4.8 million of EGFRt-sorted E2-CAR-T cells (FIG. 62A). Seven days following a single EC17 dose (i.e., study day 9), human CD3e+ EGFRt+ CAR-T cells were detected in the blood of mice, with elevated numbers circulating in mice bearing larger tumors (FIG. 62B). In addition to trending towards a higher expansion in vivo, these blood borne CAR-T cells also exhibited a more differentiated profile (FIG. 62B, 2504±441 mm³ versus 422±16 mm³) in mice possessing larger tumors. Mice with the smaller sized tumors continued on study to receive a total of 5 weekly EC17 doses at 500 nmol/kg. As shown in FIG. 62C, the MDA-MB-231 tumors started to respond after the second EC17 dose. Mice did experience mild body weight loss after EC17 administration, especially after the third dose. As circulating CAR-T cells peaked around day 15 and persisted for up to 30 days (last analysis by flow cytometry), a steady increase in tumor-infiltrating CAR-T cells was observed (FIG. 62D, top plot, dashed line). In addition, CAR-T cells underwent dynamic phenotypic changes in the blood from a predominantly $T_{SCM}$ phenotype on day 9, to more differentiated profiles on later days with continued EC17 treatment (FIG. 62D, bottom bar graph). Accordingly, those tumor-infiltrating CAR-T cells were activated and expressed early (CD137/4-1BB) as well as late (PD1) T cell activation markers (FIG. 62E). CD137/4-1BB expression peaked around day 9 while PD1 expression remained high from day 9 and forward. Thus, EC17 CAM dosing drives CAR-T cell activation, expansion and tumor uptake in vivo resulting a robust antitumor immunity.

Example 29

Flow Cytometry Ex-Vivo

For CAR-T cell analysis in the circulation, plasma was removed from a predetermined volume of whole blood collected into tubes containing ethylenediaminetetraacetic acid anticoagulant. After lysing red blood cells, leukocyte pellets were re-suspended in a flow cytometry staining solution comprising 1% bovine serum albumin, 50 mg/mL human IgG (Equitech Bio) and 0.9% sodium azide. The samples were stained for human leukocyte surface markers (CD3ε, CD4, CD8α, CD45RA, CD62L) and biotinylated anti-human EGFR (cetuximab) followed by a fluorophore-conjugated anti-biotin secondary antibody. For analysis of tumor-infiltrating CAR-T cells, pre-weighed fresh tumor fragments were finely minced and enzymatically digested with a digestion cocktail consisting of 0.5 mg/mL collagenase IV, 0.5 mg/mL hyaluronidase and 0.1 mg/mL DNase I in serum-free FFRPMI with vigorous shaking for one hour at 37° C. Afterwards, tumor cell pellets underwent a red blood cell lysis step, washed with cold PBS and filtered through a 40 μm nylon cell strainer. The resulting single cell suspensions were stained for EGFRt and human leukocyte markers, CD137/4-1BB and PD1. A minimum of 20,000 propidium iodide negative live cell events were collected on the Gallios flow cytometer and analyzed with the Kaluza software, version 2.1 (Beckman Coulter, Brea, Calif.). CAR-positive T cells were identified in mouse blood as human CD3ε+ EGFRt+ events and absolute numbers per volume of blood were calculated using equal numbers of Count-Bright™ beads (Invitrogen, Carlsbad, Calif.) added to each sample. The number of tumor-infiltrating CD3ε+ EGFRt+ CAR-T cells was expressed as % total viable tumor cells analyzed.

Example 30

Tumor Therapies

To study the effect of high dietary folate (FIG. 63A, FIG. 63B, FIG. 63C, FIG. 63D), two sets of NSG mice were placed on either a FA-replete diet (4 mg/kg, Envigo, Indianapolis, Ind.) or a FA-deficient diet (TestDiet, St. Louis, Mo.) upon arrival. On day 0, both sets of the mice received ~10 million of the same "clinical facsimile" CAR-T cells followed by no EC17 or EC17 SIW at 500 nmol/kg starting on day 3. On the first day of EC17 administration, MDA-MB-231 tumors size averaged around ~549±184 mm$^3$ (280-918 mm3) in FA-replete mice, and ~559±165 mm$^3$ (356-961 mm$^3$) in FA-deficient mice.

Effect of High Dietary Folate on CRS and Antitumor Activity

Figure 63A:
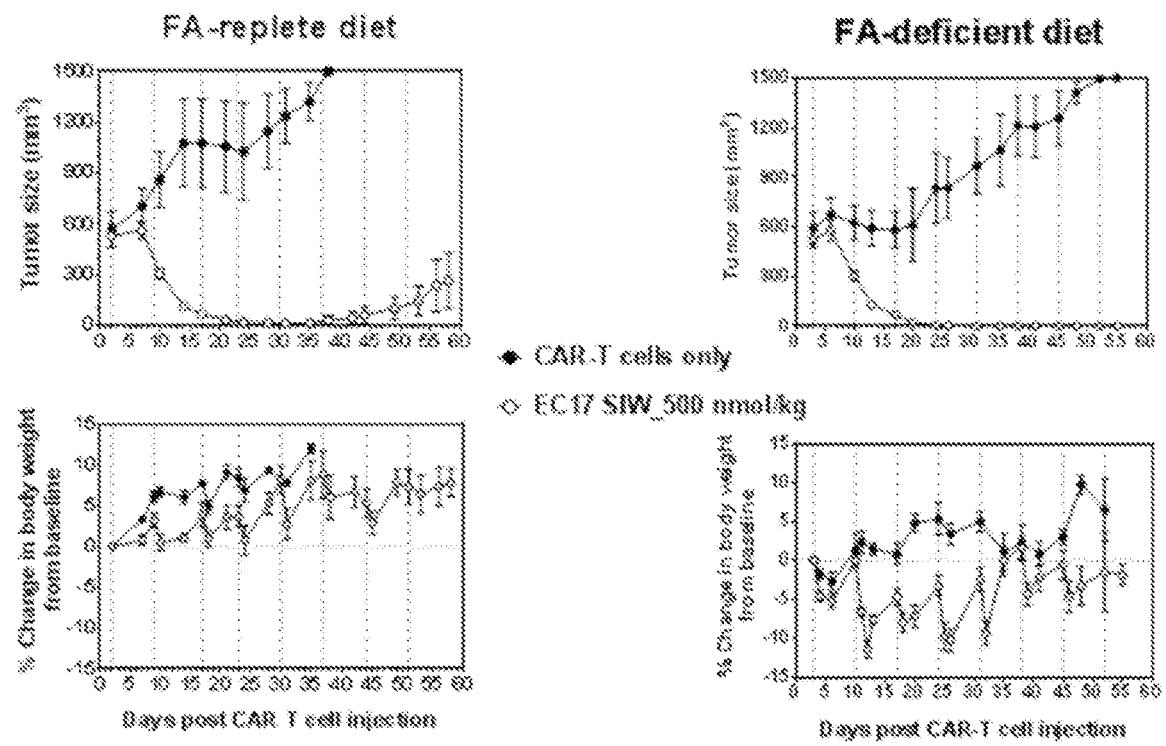
FIG. 63A, FIG. 63B, FIG. 63C, and FIG. 63D show dietary folate effect on antitumor activity and CRS toxicity.
Figure 63B:
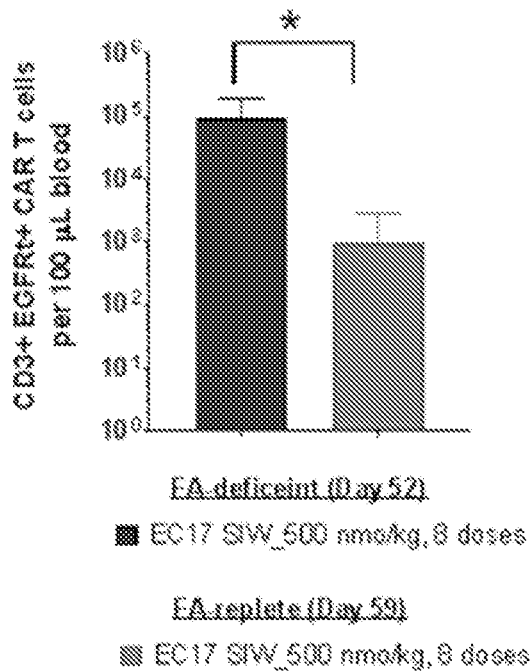
Figure 63C:
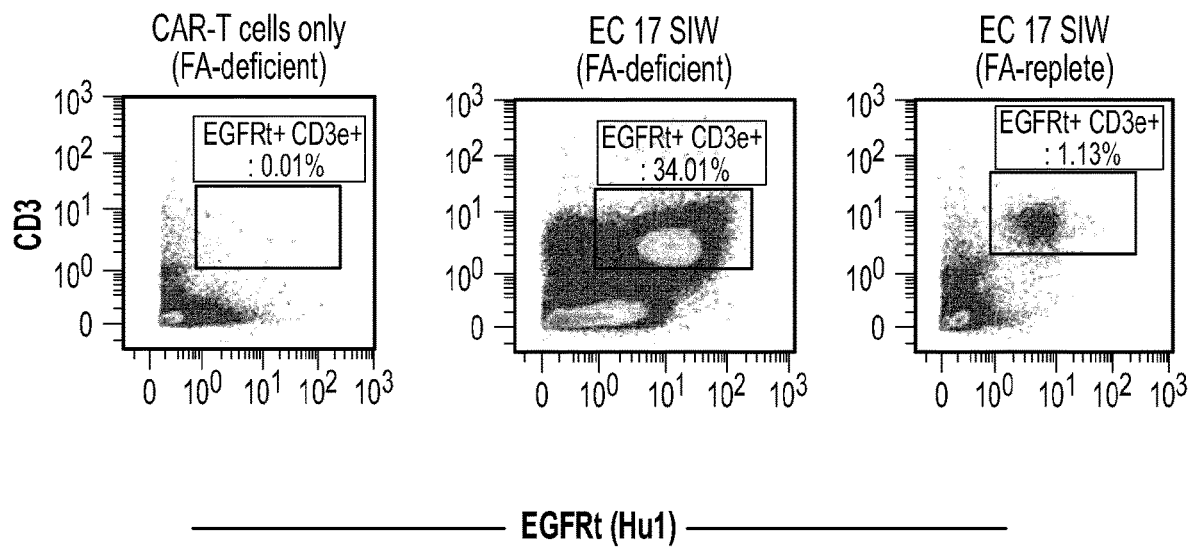

Previously, it was shown that administration of FA or a FA ligand helped reduce the severity of CRS in MDA-MB-231 tumor-bearing mice. To test the long-term effect of dietary folate, mice were maintained on defined diets for ~73 days and used when their tumors reached ~549±184 mm3 (280-918 mm$^3$) in FA-replete mice, and ~559±165 mm$^3$ (356-961 mm$^3$) in FA-deficient mice (FIG. 63A, FIG. 63B, FIG. 63C, FIG. 63D). All mice received ~10 million of the same "clinical facsimile" of E2-CAR-T cells on day 0, and EC17-treated cohorts received eight weekly doses of 500 nmol/kg starting on day 2 (FA-replete) or day 3 (FA-deficient). As seen previously, the first full dose of EC17 was generally safe and did not cause any CRS or body weight loss in mice on either diet. Actually, FA-replete animals did not show symptoms of CRS throughout EC17 treatment, whereas FA-deficient animals experienced grades 2-3 CRS and body weight loss (up to ~11.4%) with each of the subsequent EC17 doses (FIG. 63A, bottom panels). In the same duration of EC17 treatment, a much higher level of CD3e+ EGFRt+ CAR-T cells was found in mice on FA-deficient diet (1.6-20.4×10$^4$ per 100 μL blood on day 52) when compared to mice on FA-replete diet (0.027-4.3×10$^3$ per 100 μL blood on day 59) (FIG. 63B, FIG. 63C). Importantly, there was no CAR-T cell expansion detected in FA-deficient animals that did not receive EC17 treatment (FIG. 63C).

Since we started MDA-MB-231 tumors at larger sizes than previous studies, tumor regression due to alloreactivity at this 10-million "clinical facsimile" CAR-T cell dose was not apparent (FIG. 63A, top rows). Control tumors (no EC17) in FA-replete mice appeared to have faster growth kinetics compared to control tumors in FA-deficient mice; but overall, there were 2/5 cures, 2/5 complete responses, and 1/5 partial response in FA-replete mice that did receive EC17 (FIG. 63A, top left figure). A more robust in vivo T cell expansion was seen in mice on FA-deficient diet and resulted in 5/5 cures, although these animals' health deteriorated with each CRS episode (FIG. 63A, top right figure).

Figure 63D:
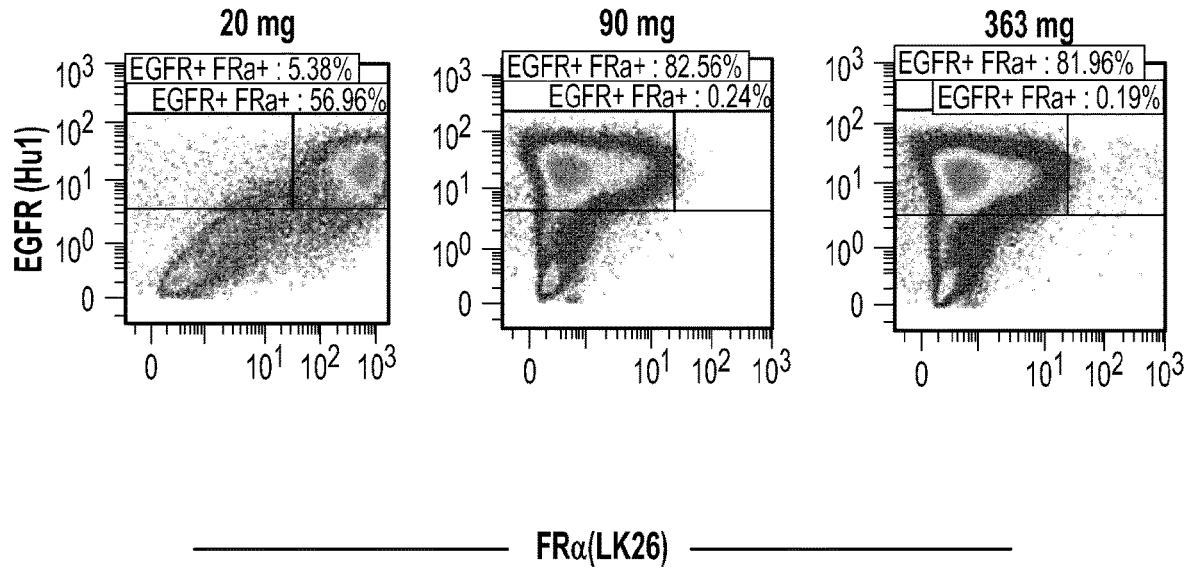

Using anti-human EGFR (clone Hu1) to identify MDA-MB-231 cancer cells within mouse tumor masses after an enzymatic digestion, we analyzed FRα protein expression (clone LK26) in three tumors recovered from mice on FA-replete diet that experienced a relapse despite continuing EC17 treatment. By flow cytometric detection, EGFR+ cancer cells isolated from the smallest tumor (21 mg) expressed FRα, while EGFR+ cancer cells isolated from the two larger tumors (90 mg and 363 mg) had completely lost their FRα expression (FIG. 63D). Using the quantitative radioligand binding assay with $^3$H-FA, the loss of functional FR levels on tissue homogenates obtained from these tumors was confirmed (~2.1 pmol/mg binding potential versus ~103 pmol/mg in tumors from untreated animals). Therefore, FA-deficiency may lead to enhanced activity and CRS toxicity; while non-physiological FA intake prevents CRS and continuous consumption may lead to reduced activity.

What is claimed is:

1. A nucleic acid encoding a chimeric antigen receptor (CAR) comprising:
   (a) a polynucleotide encoding an anti-fluorescein scFv and nucleic acid having at least about 95% sequence identity to SEQ ID NO:01, or 04; or
   (b) a polynucleotide having the sequence set forth in SEQ ID NO:01, or 04.

2. A polypeptide encoded by the nucleic acid of claim 1.

3. The polypeptide of claim 2, wherein said polypeptide comprises or consists of humanized, or human amino acid sequences.

4. A cell comprising the polypeptide of claim 3.

5. A cell comprising the polypeptide of claim 2.

6. The cell of claim 5, wherein the cell is a T lymphocyte or cytotoxic T lymphocyte.

7. A method of ameliorating or treating a folate receptor-expressing cancer in a patient comprising:
   labeling the cancer in said patient with a small molecule comprising a folate linked to a fluorescein isothiocyanate (FITC) moiety; and
   administering to said patient the cell of claim 5.

8. The method of claim 7, wherein the cell is administered before labeling the cancer with the small molecule.

9. The method of claim 7, wherein the cell is an autologous cell.

10. A vector comprising the nucleic acid of claim 1.

11. A cell comprising the vector of claim 10.

12. The vector of claim 10, wherein said vector is a lentiviral vector.

13. A cell comprising the vector of claim 12.

14. A method of ameliorating or treating a folate receptor-expressing cancer in a patient comprising:
   labeling the cancer in said patient with a small molecule comprising a folate linked to a fluorescein isothiocyanate (FITC) moiety; and
   administering to said patient a composition comprising the vector of claim 12.

15. A cell comprising the nucleic acid of claim 1.

16. The cell of claim 15, wherein the cell is a T lymphocyte or cytotoxic T lymphocyte.

17. A method of ameliorating or treating a folate receptor-expressing cancer in a patient comprising:
   labeling the cancer in said patient with a small molecule comprising a folate linked to a fluorescein isothiocyanate (FITC) moiety; and
   administering to said patient the cell of claim 15.

18. The method of claim 17, wherein the cell is a T lymphocyte or cytotoxic T lymphocyte.

19. The method of claim 18, wherein the cell is an autologous cell.

20. The method of claim 17, wherein the cell is administered before labeling the cancer with the small molecule.

21. The method of claim 17, wherein the cell is an autologous cell.

22. The nucleic acid of claim 1 comprising a polynucleotide having at least 95% sequence identity to SEQ ID NO:01.

23. The nucleic acid of claim 1 comprising a polynucleotide having at least 95% sequence identity to SEQ ID NO:04.

* * * * *